(12) United States Patent
Macielag et al.

(10) Patent No.: US 9,682,955 B2
(45) Date of Patent: Jun. 20, 2017

(54) QUINAZOLINE DERIVATIVES USEFUL AS CB-1 INVERSE AGONISTS

(71) Applicant: Janssen Pharmaceutica NV, Beerse (BE)

(72) Inventors: Mark Joseph Macielag, Gwynedd, PA (US); Yue-Mei Zhang, Belle Mead, NJ (US); Bart L. DeCorte, Southampton, PA (US); Michael N. Greco, Lansdale, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/844,309

(22) Filed: Sep. 3, 2015

(65) Prior Publication Data

US 2016/0068512 A1   Mar. 10, 2016

Related U.S. Application Data

(60) Provisional application No. 62/047,758, filed on Sep. 9, 2014.

(51) Int. Cl.

| | | |
|---|---|---|
| *C07D 401/12* | (2006.01) | |
| *C07D 417/06* | (2006.01) | |
| *C07D 417/14* | (2006.01) | |
| *C07D 239/94* | (2006.01) | |
| *C07D 401/04* | (2006.01) | |
| *C07D 401/14* | (2006.01) | |
| *C07D 239/95* | (2006.01) | |
| *C07D 409/14* | (2006.01) | |
| *C07D 403/12* | (2006.01) | |
| *C07D 403/04* | (2006.01) | |
| *C07D 403/14* | (2006.01) | |

(52) U.S. Cl.
CPC ......... *C07D 401/12* (2013.01); *C07D 239/94* (2013.01); *C07D 239/95* (2013.01); *C07D 401/04* (2013.01); *C07D 401/14* (2013.01); *C07D 403/04* (2013.01); *C07D 403/12* (2013.01); *C07D 403/14* (2013.01); *C07D 409/14* (2013.01); *C07D 417/06* (2013.01); *C07D 417/14* (2013.01)

(58) Field of Classification Search
CPC .. C07D 239/94; C07D 239/95; C07D 401/04; C07D 401/12; C07D 401/14; C07D 403/04; C07D 403/12; C07D 403/14; C07D 409/14; C07D 417/06; C07D 417/14
See application file for complete search history.

(56) References Cited

U.S. PATENT DOCUMENTS 5,985,885 A * 11/1999 Makovec ............. C07D 239/95
                                                              514/266.22
2013/0178457 A1    7/2013 Kulkarni et al.

FOREIGN PATENT DOCUMENTS

| WO | WO 2015/130444 | 9/2015 |
| WO | WO 2015/130445 | 9/2015 |

OTHER PUBLICATIONS

Felder, C. C., et al., Molecular Pharmacology, 1992, pp. 838-845, vol. 42.
Muccioli; Lambert: "Latest advances in cannabinoid receptor antagonists and inverse agonists", Expert Opin. Ther. Patents, vol. 16, No. 10, Jan. 1, 2006 (Jan. 1, 2006), pp. 1405-1423.
International Search Report re: PCT/US2015/048261 dated Nov. 27, 2015.

* cited by examiner

*Primary Examiner* — Erich A Leeser
(74) *Attorney, Agent, or Firm* — Thomas J. Dodd

(57) ABSTRACT

The present invention is directed to quinazoline derivatives, pharmaceutical compositions containing said derivatives and their use in the treatment of disorders and conditions mediated by the CB-1 receptor; more particularly, in the treatment of disorders and conditions responsive to inverse agonism of the CB-1 receptor. For example, the compounds of the present invention are useful in the treatment of metabolic disorders.

24 Claims, No Drawings

QUINAZOLINE DERIVATIVES USEFUL AS CB-1 INVERSE AGONISTS

CROSS-REFERENCE TO RELATED APPLICATIONS

This application claims priority to U.S. provisional patent application No. 62/047,758, filed Sep. 9, 2014, which is hereby incorporated by reference in its entirety.

FIELD OF THE INVENTION

The present invention is directed to quinazoline derivatives, pharmaceutical compositions containing said derivatives and their use in the treatment of disorders and conditions mediated by the CB-1 receptor; more particularly, in the treatment of disorders and conditions responsive to inverse agonism of the CB-1 receptor. For example, the compounds of the present invention are useful in the treatment of metabolic disorders.

BACKGROUND OF THE INVENTION

Centrally penetrant cannabanoid-1 receptor (CB1) inverse agonist compounds are efficacious for weight loss, glycemic control and treatment of cardiovascular risk factors associated with obesity and/or Type II diabetes mellitus. However such compounds are also associated serious adverse effects such as anxiety, depression, suicidal ideation, and others, which adverse effects preclude their use. Peripherally restricted cannabanoid-1 receptor (CB1R) inverse agonists aim to selectively inhibit the CB1R in organs/tissues outside the blood-brain barrier, for example in the liver, adipose tissue and/skeletal muscle, to avoid the adverse effects.

There remains a need for peripherally restricted cannabanoid-1 receptor (CB1R) inverse agonists for the treatment of, for example metabolic disorders, such as obesity, Type II diabetes mellitus, Syndrome X.

SUMMARY OF THE INVENTION

The present invention is directed to CB-1 inverse agonists, more particularly quinazoline derivatives, compounds of formula (I)

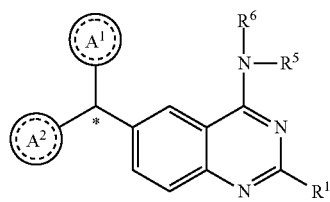

wherein

is selected from the group consisting of phenyl, furyl, thienyl, thiazolyl, pyridyl, benzothiazolyl and benzo[d][1,3]dioxolyl;
wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and $NR^AR^B$; wherein $R^A$ and $R^B$ are each independently selected from the group consisting of hydrogen, $C_{1-4}$alkyl and —($C_{2-4}$alkyl)-O—($C_{1-4}$alkyl); provided that each substituent is bound to a carbon atom of the ring;

is selected from the group consisting of phenyl, furyl, thienyl, thiazolyl, pyridyl, benzothiazolyl and benzo[d][1,3]dioxolyl;
wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and $NR^CR^D$; wherein $R^C$ and $R^D$ are each independently selected from the group consisting of hydrogen, $C_{1-4}$alkyl and —($C_{2-4}$alkyl)-O—($C_{1-4}$alkyl); provided that each substituent is bound to a carbon atom of the ring;

$R^1$ is selected from the group consisting of hydrogen, $C_{1-6}$alkyl, —CH=CH—($C_{1-4}$alkyl)-OH, —CH=CH—($C_{0-3}$alkyl)-$CO_2H$, —CH=CH—($C_{0-3}$alkyl)-C(O)O—($C_{1-4}$alkyl), —CH=CH—($C_{1-4}$alkyl)-$NH_2$, —$CH_2CH_2$—($C_{1-4}$alkyl)-OH, —$CH_2CH_2$—($C_{0-3}$alkyl)-$CO_2H$, —$CH_2CH_2$—($C_{0-3}$alkyl)-C(O)O—($C_{1-4}$alkyl), —$CH_2CH_2$—($C_{1-4}$alkyl)-$NH_2$, cyclopropyl, cyclobutyl, —$OR^2$ and —$NR^3R^4$;

$R^2$ is selected from the group consisting of hydrogen, —$C_{1-12}$alkyl, —$CH_2$-(hydroxy substituted $C_{1-11}$alkyl), —($C_{1-12}$alkyl)-$N_3$, —($C_{2-12}$alkyl)-$NR^ER^F$, —($C_{2-12}$alkyl)-O—($C_{1-12}$alkyl), —($C_{2-12}$alkyl)-O—($C_{1-12}$alkyl)-OH, —($C_{2-12}$alkyl)-O—($C_{1-12}$alkyl)-CN, —($C_{2-12}$alkyl)-O—($C_{1-12}$alkyl)-$CO_2H$, —($C_{2-12}$alkyl)-O—($C_{1-12}$alkyl)-C(O)—O—($C_{1-6}$alkyl), —($C_{2-12}$alkyl)-O—($C_{1-12}$alkyl)-C(O)—$NR^ER^F$, —($C_{1-12}$alkyl)-$CO_2H$, —($C_{1-12}$alkyl)-C(O)O—($C_{1-6}$alkyl), —($C_{2-12}$alkyl)-OC(O)—($C_{1-6}$alkyl), —($C_{2-12}$alkyl)-OC(O)—$NR^ER^F$, —($C_{1-12}$alkyl)-C(O)—$NR^ER^F$, —($C_{2-12}$alkyl)-$NR^E$—C(O)—($C_{1-6}$alkyl), —($C_{2-12}$alkyl)-$NR^E$—C(O)—($C_{1-12}$alkyl)-OH and —($C_{2-12}$alkyl)-$NR^E$—$SO_2$—($C_{1-6}$alkyl); wherein $R^E$ and $R^F$ are each independently selected from the group consisting of hydrogen, $C_{1-6}$ alkyl and —$CH_2$-(hydroxy substituted $C_{1-5}$alkyl);

$R^3$ is selected from the group consisting of hydrogen and $C_{1-4}$alkyl;

$R^4$ is selected from the group consisting of hydrogen, —$C_{1-12}$alkyl, —$CH_2$-(hydroxy substituted $C_{1-11}$alkyl), —($C_{1-12}$alkyl)-$N_3$, —($C_{2-12}$alkyl)-$NR^GR^H$, —($C_{2-12}$alkyl)-O—($C_{1-12}$alkyl), —($C_{2-12}$alkyl)-O—($C_{1-12}$alkyl)-OH, —($C_{2-12}$alkyl)-O—($C_{1-12}$alkyl)-CN, —($C_{2-12}$alkyl)-O—($C_{1-12}$alkyl)-$CO_2H$, —($C_{2-12}$alkyl)-O—($C_{1-12}$alkyl)-C(O)—O—($C_{1-6}$ alkyl), —($C_{2-12}$alkyl)-O—($C_{1-12}$alkyl)-C(O)—$NR^GR^H$, —($C_{1-12}$alkyl)-$CO_2H$, —($C_{1-12}$alkyl)-C(O)O—($C_{1-6}$alkyl), —($C_{2-12}$alkyl)-OC(O)—($C_{1-6}$alkyl), —($C_{2-12}$alkyl)-OC(O)—$NR^GR^H$, —($C_{1-12}$alkyl)-C(O)—$NR^GR^H$, —($C_{2-12}$alkyl)-$NR^G$—C(O)—($C_{1-6}$alkyl), —($C_{2-12}$alkyl)-$NR^G$—C(O)—($C_{1-12}$alkyl)-OH, —($C_{2-12}$alkyl)-$NR^G$—$SO_2$-($C_{1-6}$alkyl), —C(O)—($C_{1-4}$alkyl), —$SO_2$—($C_{1-4}$alkyl) and —$SO_2$-(halogenated $C_{1-6}$alkyl); wherein $R^G$ and $R^H$ are each independently selected from the group consisting of hydrogen, $C_{1-6}$alkyl and —$CH_2$-(hydroxy substituted $C_{1-5}$alkyl);

$R^5$ is selected from the group consisting of hydrogen and $C_{1-4}$alkyl;

$R^6$ is selected from the group consisting of

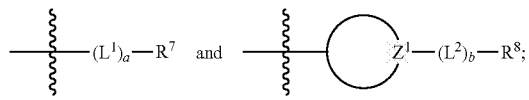

a is an integer from 0 to 1;

$L^1$ is selected from the group consisting of —$CH_2$—, —$CH(CH_3)$—, —$CH_2CH_2$— and cycloprop-1,1-diyl;

$R^7$ is selected from the group consisting of azetidin-3-yl, pyrrolidin-3-yl, piperidin-4-yl, piperazin-1-yl, morpholin-4-yl, thiomorpholin-4-yl, thiomorpholin-4-yl-1-oxide, thiomorpholin-4-yl-1,1-dioxide, phenyl, pyridin-2-yl, pyridin-3-yl, pyridin-4-yl, thien-2-yl, thien-3-yl, furan-2-yl, furan-3-yl, pyrimidin-2-yl, pyrazin-2-yl, cyclopropyl, cyclobutyl, cyclopentyl and cyclohexyl;

wherein any of the $R^7$ ring structures is optionally substituted with one substituent selected from the group consisting of halogen, hydroxy, cyano, $C_{1-4}$ alkyl, halogenated $C_{1-4}$alkyl, hydroxy substituted $C_{1-12}$alkyl, $C_{1-4}$alkoxy, halogenated $C_{1-4}$alkoxy, —($C_{1-4}$alkyl)-O—($C_{1-4}$alkyl), —($C_{1-4}$alkyl)-$CO_2H$, —($C_{1-4}$alkyl)-C(O)O—($C_{1-4}$alkyl), —($C_{1-4}$alkyl)-C(O)—$NR^JR^K$, —O—($C_{1-4}$alkyl)-O—($C_{1-4}$alkyl), —O—($C_{1-4}$alkyl)-$CO_2H$, —O—($C_{1-4}$alkyl)-C(O)O—($C_{1-4}$alkyl), —O—($C_{1-4}$alkyl)-C(O)—$NR^JR^K$, C(O)—($C_{1-4}$alkyl), —C(O)-(halogenated $C_{1-4}$alkyl), —C(O)—($C_{1-4}$alkyl)-$CO_2H$, —C(O)—($C_{1-4}$alkyl)-C(O)O—($C_{1-4}$alkyl), —C(O)—$NR^JR^K$, —C(O)—($C_{1-4}$alkyl)-C(O)—$NR^JR^K$, —$CO_2H$, —C(O)O—($C_{1-4}$alkyl), —C(O)O—($C_{1-4}$alkyl)-OC(O)O—($C_{1-4}$alkyl), —C(=$NR^J$)—$NR^K$—C(O)O—($C_{1-4}$alkyl), —C(=NH)—$NH_2$, —C(=N-Boc)-NH(Boc), —$NR^JR^K$, —$NR^J$—C(O)—($C_{1-4}$alkyl), —$NR^J$—$SO_2$—($C_{1-4}$alkyl), —$SO_2$—($C_{1-4}$alkyl), —$SO_2$-(halogenated $C_{1-4}$alkyl), —$SO_2$—($C_{1-4}$alkyl)-OH, —$SO_2$—($C_{1-4}$alkyl)-C(O)O—($C_{1-4}$alkyl), —$SO_2NR^JR^K$ and —$SO_2$—($C_{1-4}$alkyl)-C(O)—$NR^JR^K$; and wherein $R^J$ and $R^K$ are each independently selected from the group consisting of hydrogen, $C_{1-4}$alkyl and ($C_{2-4}$alkyl)-OH;

and wherein $R^7$ is phenyl; the phenyl is further optionally substituted with an additional substituent selected from the group consisting of halogen, hydroxy, cyano, $C_{1-4}$alkyl, halogenated $C_{1-4}$alkyl, $C_{1-4}$alkoxy and halogenated $C_{1-4}$alkoxy;

provided that when a is 0 ($L^1$ is absent), then $R^7$ is other than piperazin-1-yl, morpholin-4-yl, thiomorpholin-4-yl or thiomorpholin-4-yl-1-oxide;

provided further that when the substituent group on the $R^7$ ring structure is selected from the group consisting of $C_{1-4}$alkoxy, halogenated $C_{1-4}$alkoxy, —O—($C_{1-4}$alkyl)-O—($C_{1-4}$alkyl), —O—($C_{1-4}$alkyl)-$CO_2H$, —O—($C_{1-4}$alkyl)-C(O)O—($C_{1-4}$alkyl), —O—($C_{1-4}$alkyl)-C(O)—$NR^JR^K$, —$NR^JR^K$, —$NR^J$—C(O)—($C_{1-4}$alkyl) and —$NR^J$—$SO_2$—($C_{1-4}$alkyl), then said substituent group is bound to a carbon atom on the $R^7$ ring structure;

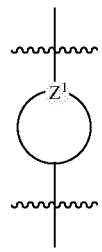

is selected from the group consisting of

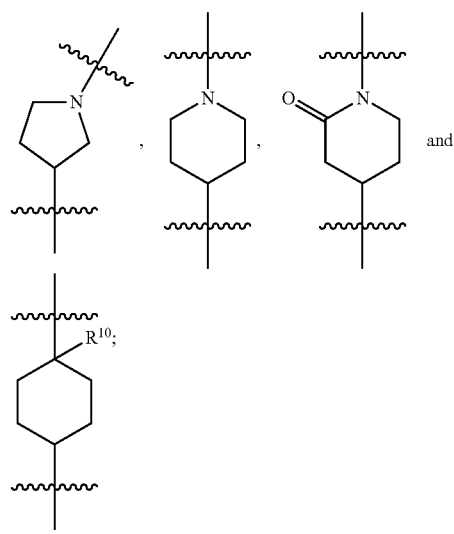

wherein $Z^1$ is selected from the group consisting of N and CH;

b is an integer from 0 to 1;

$L^2$ is selected from the group consisting of —$CH_2$—, —$CH_2CH_2$—, —$CH(CH_3)$—, —$CH(CH_2CH_3)$—, —C(O)— and —$SO_2$—;

$R^8$ is selected from the group consisting of azetidin-3-yl, pyrrolidin-1-yl, piperidin-4-yl, piperazin-1-yl, morpholin-4-yl, phenyl, pyridin-2-yl, pyridin-3-yl, pyridin-4-yl, thien-2-yl, thien-3-yl, furan-2-yl, furan-3-yl, pyrimidin-2-yl, pyrazin-2-yl, cyclopropyl, cyclobutyl, cyclopentyl and cyclohexyl;

wherein any of the $R^8$ ring structures is optionally substituted with one substituent selected from the group consisting of halogen, hydroxy, cyano, $C_{1-4}$alkyl, halogenated $C_{1-4}$alkyl, hydroxy substituted $C_{1-12}$alkyl, $C_{1-4}$alkoxy, halogenated $C_{1-4}$alkoxy, —($C_{1-4}$alkyl)-O—($C_{1-4}$alkyl), —($C_{1-4}$alkyl)-$CO_2H$, —($C_{1-4}$alkyl)-C(O)O—($C_{1-4}$alkyl), —($C_{1-4}$alkyl)-C(O)—$NR^PR^Q$, —O—($C_{1-4}$alkyl)-O—($C_{1-4}$alkyl), —O—($C_{1-4}$alkyl)-$CO_2H$, —O—($C_{1-4}$alkyl)-C(O)O—($C_{1-4}$alkyl), —O—($C_{1-4}$alkyl)-C(O)—$NR^PR^Q$, —C(O)—($C_{1-4}$alkyl), —C(O)-(halogenated $C_{1-4}$alkyl), —C(O)—($C_{1-4}$alkyl)-$CO_2H$, —C(O)—($C_{1-4}$alkyl)-C(O)O—($C_{1-4}$alkyl), —C(O)—$NR^PR^Q$, —C(O)$NR^P$—($C_{2-4}$alkyl)-O—$R^{11}$, —C(O)—($C_{1-4}$alkyl)-C(O)—$NR^PR^Q$, —$CO_2H$, —C(O)O—($C_{1-4}$alkyl), —C(O)O—($C_{1-4}$alkyl)-OC(O)O—($C_{1-4}$alkyl), —C(=$NR^P$)—$NR^Q$—C(O)O—($C_{1-6}$alkyl), —C(=NH)—$NH_2$, —C(=N-Boc)-NH(Boc), —$NR^PR^Q$, —$NR^P$—C(O)—($C_{1-4}$alkyl), —$NR^Q$—$SO_2$—($C_{1-4}$alkyl), —$SO_2$—($C_{1-4}$alkyl), —$SO_2$-(halogenated $C_{1-4}$alkyl), —$SO_2$—($C_{1-4}$alkyl)-OH, —$SO_2$—($C_{1-4}$alkyl)-C(O)O—($C_{1-4}$alkyl), —$SO_2$—$NR^PR^Q$ and —$SO_2$—($C_{1-4}$alkyl)-C(O)—$NR^PR^Q$;

wherein $R^{11}$ is phenyl; wherein the phenyl is optionally substituted at the 4-position with a substituents selected from the group consisting of halogen, hydroxymethyl, methyl, ethyl, trifluoromethyl and cyano;

wherein $R^P$ and $R^Q$ are each independently selected from the group consisting of hydrogen, $C_{1-4}$alkyl, and —$CH_2$-(hydroxy substituted $C_{1-5}$alkyl);

and when $R^8$ is phenyl; the phenyl is further optionally substituted with an additional substituent selected from the group consisting of halogen, hydroxy, cyano, $C_{1-4}$alkyl, halogenated $C_{1-4}$alkyl, $C_{1-4}$alkoxy and halogenated $C_{1-4}$alkoxy;

$R^{10}$ is selected from the group consisting of hydrogen, hydroxy and cyano;

provided that when

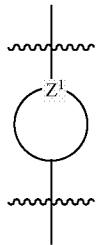

is selected from the group consisting of

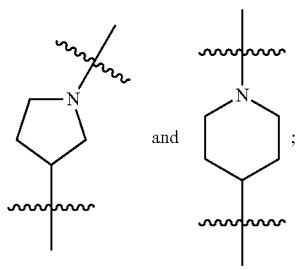 [SMILES: *C1CCN(*)C1 ; *C1CCN(*)CC1]

and the $R^8$ ring structure is bound through a nitrogen ring atom; then b is 1 and $L^2$ is selected from the group consisting of —C(O)— and —$SO_2$—;

provided further that when

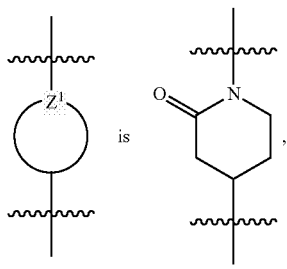

then $R^8$ is phenyl, wherein the phenyl is optionally substituted with one to two substituents independently selected from the group consisting of F, Cl, methyl, ethyl, cyano, trifluoromethyl, methoxy and ethoxy;

alternatively, $R^5$ and $R^6$ are taken together with the nitrogen atom to which they are bound to form a ring structure selected from the group consisting of

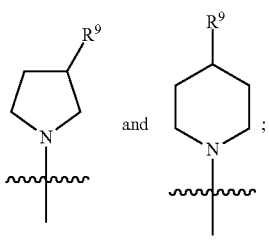

wherein $R^9$ is selected from the group consisting of $C_{1-4}$alkyl, trifluoromethyl, cyclopropyl and —$NR^SR^T$; wherein $R^S$ is selected from the group consisting of hydrogen, methyl and ethyl; and $R^T$ is selected from the group consisting of —C(O)—($C_{1-4}$alkyl), —$SO_2$—($C_{1-4}$alkyl) and —$SO_2$-(halogenated $C_{1-4}$alkyl);

and stereoisomers, tautomers and pharmaceutically acceptable salts thereof.

The present invention is further directed to processes for the preparation of the compounds of formula (I). The present invention is further directed to a product prepared according to any of the process(es) described herein.

The present invention is further directed to intermediate compounds useful in the synthesis of the compounds of formula (I), as described and defined in the synthesis schemes and examples which follow herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder mediated by the CB-1 receptor (selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain) comprising administering to a subject in need thereof a therapeutically effective amount of any of the compounds or pharmaceutical compositions described above.

In an embodiment, the present invention is directed to a compound of formula (I) or a compound of formula (II) for use as a medicament. In another embodiment, the present invention is directed to a compound of formula (I) or a compound of formula (II) for use in the treatment of a disorder mediated by the CB-1 receptor (selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain). In another embodiment, the present invention is directed to a composition comprising a compound of formula (I) for the treatment of a disorder mediated by the CB-1 receptor (selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain).

Another example of the invention is the use of any of the compounds described herein in the preparation of a medicament for treating: (a) obesity, (b) Type I diabetes, (c) Type II diabetes, (d) gestational diabetes, (e) latent autoimmune diabetes of adults (LADA), (f) pre-diabetes, (g) insulin resistance, (h) inadequate glucose tolerance, (i) dyslipidemia (including, but not limited to elevated triglycerides and LDL, and low HDL), (j) nonalcoholic steatohepatitis (NASH), (k) cirrhosis, (l) fatty liver disease, (m) atherosclerosis, (n) hypertension, (o) inflammatory bowel disease, (p) Alzheimer's disease, (q) osteoporosis, (r) multiple sclerosis, (s) traumatic brain injury, (t) arthritis, or (u) neuropathic pain, in a subject in need thereof. In another example, the present invention is directed to a compound as described herein for use in method for treating a disorder selected from the group consisting of obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain, in a subject in need thereof.

In additional embodiments the present invention is as described herein.

DETAILED DESCRIPTION OF THE INVENTION

The present invention is directed to compounds of formula (I)

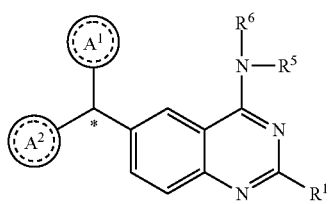

(I)

wherein

$R^1$, $R^5$ and $R^6$ are as herein defined, and stereoisomers, tautomers and pharmaceutically acceptable salts thereof.

The compounds of formula (I) of the present invention are CB-1 receptor inverse agonists, useful in the treatment of metabolic disorders, including but not limited to obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain.

In an embodiment, the present invention is directed to compounds of formula (I-A)

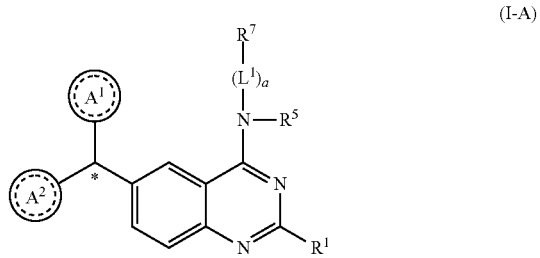

(I-A)

wherein

$R^1$, $R^5$, a, $L^1$ and $R^7$ are as herein defined, and stereoisomers, tautomers and pharmaceutically acceptable salts thereof. In another embodiment, the present invention is directed to compounds of formula (I-B)

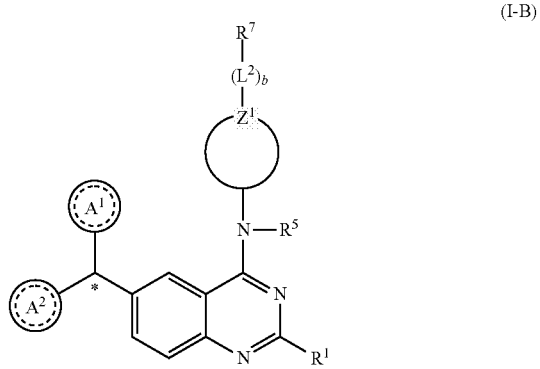

(I-B)

wherein

$R^1$, $R^5$,

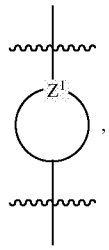

$Z^1$, b, $L^2$ and $R^8$ are as herein defined, and stereoisomers, tautomers and pharmaceutically acceptable salts thereof. In another embodiment, the present invention is directed to compounds of formula (I-C)

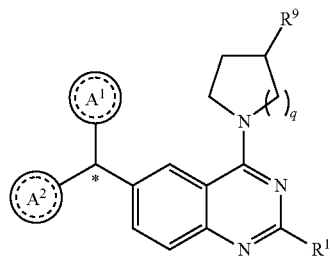

wherein

and $R^1$ are as herein defined, and wherein q is an integer from 0 to 1 (i.e. compounds of formula (I) wherein $R^5$ and $R^6$ are taken together with the nitrogen atom to which they are bound to form

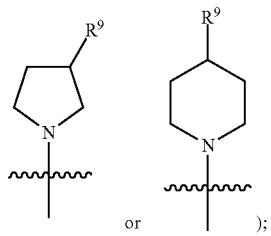

and stereoisomers, tautomers and pharmaceutically acceptable salts thereof.

In an embodiment, the present invention is directed to compounds of formula (I) wherein

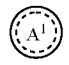

is selected from the group consisting of phenyl and thiazolyl; wherein the phenyl or thiazolyl is optionally substituted with one or more substituents independently selected from the group consisting of halogen, hydroxy, $C_{1-2}$alkyl, trifluoromethyl, $C_{1-2}$alkoxy, trifluoromethoxy, cyano, —C(O)OH, C(O)O—$C_{1-2}$alkyl and $NR^A R^B$; wherein $R^A$ and $R^B$ are each independently selected from the group consisting of hydrogen, $C_{1-2}$alkyl and —($C_{2-4}$alkyl)-O—($C_{1-4}$alkyl); provided that each substituent is bound to a carbon atom of the ring. In another embodiment, the present invention is directed to compounds of formula (I) wherein

is phenyl; wherein the phenyl is substituted with a substituent selected from the group consisting of halogen, cyano and carboxy.

In another embodiment, the present invention is directed to compounds of formula (I) wherein

is phenyl; wherein the phenyl is optionally substituted with a halogen. In another embodiment, the present invention is directed to compounds of formula (I) wherein

is selected from the group consisting of 4-chlorophenyl and 4-fluorophenyl. In another embodiment, the present invention is directed to compounds of formula (I) wherein

is 4-chlorophenyl.

In an embodiment, the present invention is directed to compounds of formula (I) wherein

is selected from the group consisting of phenyl and thiazolyl; wherein the phenyl or thiazolyl is optionally substituted with one or more substituents independently selected from the group consisting of halogen, hydroxy, $C_{1-2}$alkyl, trifluoromethyl, $C_{1-2}$alkoxy, trifluoromethoxy, cyano, —C(O)OH, C(O)O—$C_{1-2}$alkyl and $NR^A R^B$; wherein $R^A$ and $R^B$ are each independently selected from the group consisting of hydrogen, $C_{1-2}$alkyl and —($C_{2-4}$alkyl)-O—($C_{1-4}$alkyl); provided that each substituent is bound to a carbon atom of the ring. In another embodiment, the present invention is directed to compounds of formula (I) wherein

is selected from the group consisting phenyl and thiazol-2-yl; wherein the phenyl is substituted with a substituent selected from the group consisting of halogen, cyano, carbonyl and —NH—($C_2$alkyl)-O—($C_{1-2}$alkyl). In another embodiment, the present invention is directed to compounds of formula (I) wherein

is phenyl, wherein the phenyl is optionally substituted with a substituent selected from the group consisting of halogen and $C_{1-2}$alkoxy.

In another embodiment, the present invention is directed to compounds of formula (I) wherein

is selected from the group consisting of 4-chlorophenyl, 4-bromophenyl, 4-carboxyphenyl, 4-cyanophenyl, 4-(2-methoxy-ethyl-amino)phenyl and thiazol-2-yl. In another embodiment, the present invention is directed to compounds of formula (I) wherein

is selected from the group consisting of 4-chlorophenyl, 4-bromophenyl, 4-carboxyphenyl, 4-cyanophenyl, 4-(2-methoxy-ethyl-amino)-phenyl and thiazol-2-yl. In another embodiment, the present invention is directed to compounds of formula (I) wherein

is selected from the group consisting of 4-chlorophenyl, 4-bromophenyl, 4-carboxyphenyl, 4-cyanophenyl, 4-(2-methoxy-ethyl-amino)-phenyl and thiazol-2-yl. In another embodiment, the present invention is directed to compounds of formula (I) wherein

is selected from the group consisting of 4-chlorophenyl and thiazol-2-yl. In another embodiment, the present invention is directed to compounds of formula (I) wherein

is selected from the group consisting of 4-chlorophenyl, 4-fluorophenyl and 4-methoxyphenyl. In another embodiment, the present invention is directed to compounds of formula (I) wherein

is selected from the group consisting of 4-chlorophenyl and 4-fluorophenyl. In another embodiment, the present invention is directed to compounds of formula (I) wherein

is 4-chlorophenyl.

In an embodiment, the present invention is directed to compounds of formula (I) wherein $R^1$ is selected from the group consisting of hydrogen, $C_{1-2}$alkyl, —CH=CH—($C_{1-2}$alkyl)-OH, —CH=CH—($C_{0-1}$alkyl)-$CO_2$H, —CH=CH—($C_{0-1}$alkyl)-C(O)O—($C_{1-4}$alkyl), —$CH_2CH_2$—($C_{1-2}$alkyl)-OH, —$CH_2CH_2$—($C_{0-1}$alkyl)-$CO_2$H, —$CH_2CH_2$—($C_{0-1}$alkyl)-C(O)O—($C_{1-4}$alkyl), cyclopropyl, —$OR^2$ and —$NR^3R^4$. In another embodiment, the present invention is directed to compounds of formula (I) wherein $R^1$ is selected from the group consisting of hydrogen, cyclopropyl, —$OR^2$ and —$NR^3R^4$. In another embodiment, the present invention is directed to compounds of formula (I) wherein $R^1$ is selected from the group consisting of hydrogen and —$OR^2$.

In another embodiment, the present invention is directed to compounds of formula (I) wherein $R^1$ is selected from the group consisting of hydrogen, —OH, —$OCH_3$, —O—$CH_2$—$CO_2$H, —O—$CH_2CH_2$—OH, —O—$CH_2CH_2$—$OCH_3$, —O—$(CH_2)_4$—OH, —O—$CH_2CH_2$—O—$CH_2CH_2$—OH, —O—$CH_2$—CH($CH_2OH)_2$, —O—$CH_2$—C($CH_2OH)_3$, —O—$CH_2CH_2$—O—$CH_2CH_2$—$CO_2$H, —O—$CH_2CH_2$—O—$CH_2CH_2$—CN, —O—$CH_2CH_2$—$N_3$, —O—$CH_2CH_2$—$NH_2$, —O—$(CH_2)_4$—$NH_2$, —O—$(CH_2)_3$—C(O)—$NH_2$, —O—$CH_2$—C(O)—NH—$CH_2CH_2$—OH, —O—$CH_2CH_2$—NH—C(O)—$CH_3$, —$NH_2$, —$NH$—$CH_3$, —NH—C(O)—$CH_3$, —NH—$SO_2$—$CH_3$, and cyclopropyl. In another embodiment, the present invention is directed to compounds of formula (I) wherein $R^1$ is selected from the group consisting of hydrogen, —OH, —$OCH_3$, —O—$CH_2CH_2$—OH, —O—$CH_2CH_2$—$OCH_3$, —O—$(CH_2)_4$—OH, —O—$CH_2$—CH($CH_2OH)_2$, —O—$CH_2$—C($CH_2OH)_3$, —O—$CH_2CH_2$—O—$CH_2CH_2$—$CO_2$H, —O—$CH_2CH_2$—O—$CH_2CH_2$—CN, —O—$CH_2CH_2$—$N_3$, —O—$CH_2$ $CH_2$—$NH_2$, —O—$(CH_2)_4$—$NH_2$, —O—$(CH_2)_3$—C(O)—$NH_2$, —O—$CH_2$—C(O)—NH—$CH_2CH_2$—OH, —O—$CH_2CH_2$—NH—C(O)—$CH_3$, —$NH_2$, —NH—C(O)—$CH_3$ and cyclopropyl. In another embodiment, the present invention is directed to compounds of formula (I) wherein $R^1$ is selected from the group consisting of hydrogen, —OH, —$OCH_3$, —O—$CH_2CH_2$—OH, —O—$CH_2CH_2$—$OCH_3$, —O—$(CH_2)_4$—OH, —O—$CH_2$—CH($CH_2OH)_2$, —O—$CH_2$—C($CH_2OH)_3$, —O—$CH_2CH_2$—O—$CH_2CH_2$—$CO_2$H, —O—$CH_2CH_2$—O—$CH_2CH_2$—CN, —O—$CH_2CH_2$—$N_3$, —O—$(CH_2)_3$—C(O)—$NH_2$, —O—$CH_2$—C(O)—NH—$CH_2CH_2$—OH and cyclopropyl. In another embodiment, the present invention is directed to compounds of formula (I) wherein $R^1$ is selected from the group consisting of hydrogen, —$OCH_3$, —O—$CH_2$—CH($CH_2OH)_2$, —O—$CH_2CH_2$—$N_3$, —O—$(CH_2)_3$—C(O)—$NH_2$, —O—$CH_2$—C(O)—NH—$CH_2CH_2$—OH and cyclopropyl. In another embodiment, the present invention is directed to compounds of formula (I) wherein $R^1$ is selected from the group consisting of hydrogen and —O—$CH_2$—CH($CH_2OH)_2$.

In another embodiment, the present invention is directed to compounds of formula (I) wherein $R^1$ is selected from the group consisting of hydrogen, methoxy, —O—$CH_2CH$—OH and —O—$CH_2CH_2$—NH—$SO_2$—$CH_3$. In another embodiment, the present invention is directed to compounds of formula (I) wherein $R^1$ is selected from the group consisting of hydrogen, methoxy and —O—$CH_2CH$—OH. In another embodiment, the present invention is directed to compounds of formula (I) wherein $R^1$ is selected from the group consisting of hydrogen and methoxy. In another embodiment, the present invention is directed to compounds of formula (I) wherein $R^1$ is hydrogen.

In an embodiment, the present invention is directed to compounds of formula (I) wherein $R^2$ is selected from the group consisting of hydrogen, —$C_{1-6}$alkyl, —$CH_2$-(hydroxy substituted $C_{1-6}$alkyl), —($C_{1-4}$alkyl)-$N_3$, —($C_{2-4}$alkyl)-$NR^E R^F$, —($C_{2-4}$alkyl)-O—($C_{1-4}$alkyl), —($C_{2-4}$alkyl)-O—($C_{1-6}$alkyl)-OH, —($C_{2-4}$alkyl)-O—($C_{1-6}$alkyl)-CN, —($C_{2-4}$alkyl)-O—($C_{1-4}$alkyl)-$CO_2$H, —($C_{1-12}$alkyl)-$CO_2$H, —($C_{1-4}$alkyl)-C(O)—$NR^E R^F$, —($C_{2-4}$alkyl)-$NR^E$—C(O)—($C_{1-6}$alkyl) and —($C_{2-4}$alkyl)-$NR^E$—$SO_2$—($C_{1-6}$alkyl); wherein $R^E$ and $R^F$ are each independently selected from the group consisting of hydrogen, $C_{1-2}$alkyl and —$CH_2$-(hydroxy substituted $C_{1-2}$alkyl). In another embodiment, the present invention is directed to compounds of formula (I) wherein $R^2$ is selected from the group consisting of hydrogen, $C_{1-2}$alkyl, —($C_{1-2}$alkyl)-$CO_2$H, —$CH_2$-(hydroxy substituted $C_{1-4}$alkyl), —$C_{1-2}$alkyl)-$N_3$, —($C_2$alkyl)-O—($C_{1-2}$alkyl), —($C_2$-alkyl)-O—($C_2$alkyl)-OH, —($C_2$alkyl)-O—($C_2$alkyl)-$CO_2$H, —($C_2$alkyl)-O—($C_2$alkyl)-CN, —($C_{2-4}$alkyl)-$NH_2$, —($C_{1-4}$alkyl)-C(O)—$NR^E R^F$ and —($C_2$alkyl)-NH—C(O)—($C_{1-4}$alkyl); wherein $R^E$ and $R^F$ are each independently selected from the group consisting of hydrogen and —$CH_2CH_2$—OH. In another embodiment, the present invention is directed to compounds of formula (I) wherein $R^2$ is selected from the group consisting of $C_{1-2}$alkyl, —$CH_2$-(hydroxy substituted $C_{1-2}$alkyl) and —($C_2$alkyl)-NH—$SO_2$—($C_{1-2}$alkyl).

In an embodiment, the present invention is directed to compounds of formula (I) wherein $R^3$ is selected from the group consisting of hydrogen and $C_{1-2}$alkyl. In another embodiment, the present invention is directed to compounds of formula (I) wherein $R^3$ is hydrogen.

In an embodiment, the present invention is directed to compounds of formula (I) wherein $R^4$ is selected from the group consisting of hydrogen, —$C_{1-6}$alkyl, —$CH_2$-(hydroxy substituted $C_{1-4}$alkyl), —($C_{1-4}$alkyl)-$N_3$, —($C_{2-4}$alkyl)-$NR^G R^H$, —($C_2$alkyl)-O—($C_{1-4}$alkyl), —($C_{2-4}$alkyl)-O—($C_{1-4}$alkyl)-OH, —($C_{2-4}$alkyl)-O—($C_{1-4}$alkyl)-$CO_2$H, —($C_{1-4}$alkyl)-$CO_2$H, —($C_{1-4}$alkyl)-C(O)O—($C_{1-4}$alkyl), —C(O)—($C_{1-4}$alkyl), —$SO_2$—($C_{1-4}$alkyl) and —$SO_2$—(halogenated $C_{1-2}$alkyl); wherein $R^G$ and $R^H$ are each independently selected from the group consisting of hydrogen, $C_{1-2}$alkyl and —$CH_2$-(hydroxy substituted $C_{1-2}$alkyl). In another embodiment, the present invention is directed to compounds of formula (I) wherein $R^4$ is selected from the group consisting of $C_{1-2}$alkyl, —C(O)—$C_{1-2}$alkyl and —$SO_2$—$C_{1-2}$alkyl.

In an embodiment, the present invention is directed to compounds of formula (I) wherein $R^5$ is selected from the group consisting of hydrogen and $C_{1-4}$alkyl. In another embodiment, the present invention is directed to compounds of formula (I) wherein $R^5$ is selected from the group consisting of hydrogen and $C_{1-2}$alkyl. In another embodiment, the present invention is directed to compounds of formula (I) wherein $R^5$ is selected from the group consisting of hydrogen and methyl. In another embodiment, the present invention is directed to compounds of formula (I) wherein $R^5$ is hydrogen.

In an embodiment, the present invention is directed to compounds of formula (I) wherein $R^6$ is

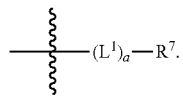

In another embodiment, the present invention is directed to compounds of formula (I) wherein $R^6$ is

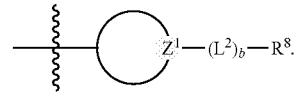

In an embodiment, the present invention is directed to compounds of formula (I) wherein a is an integer from 0 to 1. In another embodiment, the present invention is directed to compounds of formula (I) wherein a is 0. In another embodiment, the present invention is directed to compounds of formula (I) wherein a is 1.

In an embodiment, the present invention is directed to compounds of formula (I) wherein $L^1$ is selected from the group consisting of —$CH_2$—, —$CH(CH_3)$—, —$CH_2CH_2$—, and cycloprop-1,1-diyl. In another embodiment, the present invention is directed to compounds of formula (I) wherein $L^1$ is selected from the group consisting of —$CH_2$—, —$CH_2CH_2$—, —$CH(CH_3)$—, —$CH(R^*$—$CH_3)$—, —$CH(S^*$—$CH_3)$— and cycloprop-1,1-diyl. In another embodiment, the present invention is directed to compounds of formula (I) wherein $L^1$ is selected from the group consisting of —$CH_2$—, —$CH(CH_3)$— and —$CH(S^*$—$CH_3)$—. In another embodiment, the present invention is directed to compounds of formula (I) wherein $L^1$ is —$CH_2$—.

In an embodiment, the present invention is directed to compounds of formula (I) wherein $R^7$ is selected from the group consisting of piperidin-4-yl, piperazin-1-yl, morpholin-4-yl, thiomorpholin-4-yl, thiomorpholin-4-yl-1-oxide, thiomorpholin-4-yl-1,1-dioxide, phenyl, pyridin-2-yl, pyridin-3-yl, pyridin-4-yl, pyrimidin-2-yl and pyrazin-2-yl; wherein any of the $R^7$ ring structures is optionally substituted with one substituent selected from the group consisting of halogen, hydroxy, cyano, $C_{1-4}$alkyl, halogenated $C_{1-2}$alkyl, hydroxy substituted $C_{1-4}$alkyl, —($C_{1-2}$alkyl)-O—($C_{1-4}$alkyl), —($C_{1-2}$alkyl)-$CO_2$H, —($C_{1-2}$alkyl)-C(O)O—($C_{1-4}$alkyl), —C(O)-(halogenated $C_{1-2}$alkyl), —C(O)—($C_{1-4}$alkyl)-$CO_2$H, —C(O)—($C_{1-4}$alkyl)-C(O)O—($C_{1-4}$alkyl), —C(O)—$NR^J R^K$, —C(O)—($C_{1-2}$alkyl)-C(O)—$NR^J R^K$, —$CO_2$H, —C(O)O—($C_{1-4}$alkyl), —C(=$NR^J$)—$NR^K$—C(O)O—($C_{1-4}$alkyl), —C(=NH)—$NH_2$, —C(=N-Boc)-NH(Boc), —$SO_2$—($C_{1-4}$alkyl), —$SO_2$-(halogenated $C_{1-2}$alkyl), —$SO_2$—($C_{1-4}$alkyl)-OH, —$SO_2$—($C_{1-4}$alkyl)-C(O)O—($C_{1-4}$alkyl) and —$SO_2$—($C_{1-4}$alkyl)C(O)—$NR^J R^K$; and wherein $R^J$ and $R^K$ are each independently selected from the group consisting of hydrogen, $C_{1-2}$alkyl and ($C_{2-4}$alkyl)-OH; and wherein $R^7$ is phenyl; the phenyl is further optionally substituted with an additional substituent selected from the group consisting of halogen, cyano, $C_{1-4}$alkyl and halogenated $C_{1-2}$alkyl. In another embodiment, the present invention is directed to compounds of formula (I) wherein $R^7$ is selected from the group consisting of phenyl, piperidin-4-yl, pyridin-2-yl, pyridin-3-yl and thiomorpholin-2-yl-1,1-dioxide; wherein any of the $R^7$ ring structures is optionally substituted with one substituent selected from the group consisting of halogen, carboxy, halogenated $C_{1-2}$alkyl, —C(O)O—($C_{1-4}$alkyl), —C(O)—($C_{1-2}$alkyl)-$CO_2$H, —C(O)-(halogenated $C_{1-2}$alkyl), —C(O)—($C_{1-2}$alkyl)-C(O)O—($C_{1-2}$alkyl), —C(O)—$NH_2$, —C(O)—($C_{1-2}$alkyl)-C(O)—$NH_2$, —C(O)—($C_{1-2}$alkyl)-C(O)—NH—($C_2$alkyl)-OH, —$SO_2$—($C_{1-4}$alkyl), —$SO_2$-(halogenated $C_{1-2}$alkyl), —$SO_2$—($C_{1-2}$alkyl)-OH, —$SO_2$—($C_{1-2}$alkyl)-C(O)O—($C_{1-2}$alkyl) and —$SO_2$—($C_{1-2}$alkyl)-C(O)—$NH_2$; and wherein $R^7$ is phenyl; the phenyl is further optionally substituted with an additional substituent selected from the group consisting of halogen and halogenated $C_{1-2}$alkyl.

In another embodiment, the present invention is directed to compounds of formula (I) wherein R⁷ is selected from the group consisting of phenyl, 3-fluoro-phenyl, 4-fluoro-phenyl, 3-carboxy-phenyl, 4-carboxy-phenyl, 3-trifluoromethyl-phenyl, 4-trifluoromethyl-phenyl, 3-(methoxy-carbonyl)-phenyl, 4-(methoxy-carbonyl)-phenyl, 3-(amino-carbonyl)-phenyl, 4-(amino-carbonyl)-phenyl, 4-(trifluoromethyl-sulfonyl)-phenyl, 3-chloro-4-trifluoromethyl-phenyl, 1-(2,2,2-trifluoroethyl)-piperidin-4yl, 1-(t-butoxycarbonyl)-piperidin-4-yl, 1-(trifluoromethyl-sulfonyl)-piperidin-4-yl, 1-(methyl-sulfonyl)-piperidin-4-yl, 1-(ethyl-sulfonyl)-piperidin-4-yl, 1-(2,2,2-trifluoroethyl-carbonyl)-piperidin-4-yl, 1-((2-hydroxyethyl)-amino-carbonyl-ethyl-carbonyl)-piperidin-4-yl, 1-((2-hydroxyethyl)-sulfonyl)-piperidin-4-yl, 1-((2-carboxy-methyl)-carbonyl)-piperidin-4-yl, 1-((2-carboxy-ethyl)-carbonyl)-piperidin-4-yl, 1-(ethoxy-carbonyl-methyl-carbonyl)-piperidin-4-yl, 1-((2-ethoxy-carbonyl-ethyl)-carbonyl)-piperidin-4-yl, 1-((2-hydroxyethyl)-amino-carbonyl-methyl-carbonyl)-piperidin-4-yl, 1-(methoxy-carbonyl-methyl-sulfonyl)-piperidin-4-yl, 1-(amino-carbonyl-methyl-carbonyl)-piperidin-4-yl, 1-(amino-carbonyl-ethyl-carbonyl)-piperidin-4-yl, 1-(amino-carbonyl-methyl-sulfonyl)-piperidin-4-yl, 5-trifluoromethyl-pyridin-2-yl, 5-trifluoromethyl-pyridin-3-yl, 6-trifluoromethyl-pyridin-3-yl, and thiomorpholin-4-yl-1,1-dioxide. In another embodiment, the present invention is directed to compounds of formula (I) wherein R⁷ is selected from the group consisting of phenyl, 3-fluoro-phenyl, 4-fluoro-phenyl, 3-trifluoromethyl-phenyl, 4-trifluoromethyl-phenyl, 3-(methoxy-carbonyl)-phenyl, 4-(methoxy-carbonyl)-phenyl, 4-(trifluoromethyl-sulfonyl)-phenyl, 3-chloro-4-trifluoromethyl-phenyl, 1-(2,2,2-trifluoroethyl)-piperidin-4yl, 1-(trifluoromethyl-sulfonyl)-piperidin-4-yl, 1-(methyl-sulfonyl)-piperidin-4-yl, 1-(ethyl-sulfonyl)-piperidin-4-yl, 1-(2,2,2-trifluoroethyl-carbonyl)-piperidin-4-yl, 1-((2-hydroxyethyl)-sulfonyl)-piperidin-4-yl, 1-(ethoxy-carbonyl-methyl-carbonyl)-piperidin-4-yl, 1-((2-ethoxy-carbonyl-ethyl)-carbonyl)-piperidin-4-yl, 1-(methoxy-carbonyl-methyl-sulfonyl)-piperidin-4-yl, 5-trifluoromethyl-pyridin-2-yl, 5-trifluoromethyl-pyridin-3-yl, 6-trifluoromethyl-pyridin-3-yl, and thiomorpholin-4-yl-1,1-dioxide. In another embodiment, the present invention is directed to compounds of formula (I) wherein R⁷ is selected from the group consisting of phenyl, 3-fluoro-phenyl, 4-fluoro-phenyl, 3-trifluoromethyl-phenyl, 4-trifluoromethyl-phenyl, 3-(methoxy-carbonyl)-phenyl, 4-(methoxy-carbonyl)-phenyl, 3-chloro-4-trifluoromethyl-phenyl, 1-(2,2,2-trifluoroethyl)-piperidin-4yl, 1-(trifluoromethyl-sulfonyl)-piperidin-4-yl, 1-(methyl-sulfonyl)-piperidin-4-yl, 1-(ethyl-sulfonyl)-piperidin-4-yl, 1-(2,2,2-trifluoroethyl-carbonyl)-piperidin-4-yl, 1-((2-hydroxyethyl)-sulfonyl)-piperidin-4-yl, 1-(ethoxy-carbonyl-methyl-carbonyl)-piperidin-4-yl, 1-((2-ethoxy-carbonyl-ethyl)-carbonyl)-piperidin-4-yl, 1-(methoxy-carbonyl-methyl-sulfonyl)-piperidin-4-yl, 5-trifluoromethyl-pyridin-2-yl, 5-trifluoromethyl-pyridin-3-yl, 6-trifluoromethyl-pyridin-3-yl and thiomorpholin-4-yl-1,1-dioxide. In another embodiment, the present invention is directed to compounds of formula (I) wherein R⁷ is selected from the group consisting of phenyl, 3-fluoro-phenyl, 4-fluoro-phenyl, 3-trifluoromethyl-phenyl, 4-trifluoromethyl-phenyl, 1-(2,2,2-trifluoroethyl)-piperidin-4yl, 1-(trifluoromethyl-sulfonyl)-piperidin-4-yl, 1-(2,2,2-trifluoroethyl-carbonyl)-piperidin-4-yl and 1-((2-ethoxy-carbonyl-ethyl)-carbonyl)-piperidin-4-yl. In another embodiment, the present invention is directed to compounds of formula (I) wherein R⁷ is selected from the group consisting of 3-trifluoromethyl-phenyl, 4-trifluoromethyl-phenyl and 1-(2,2,2-trifluoroethyl)-piperidin-4-yl.

In an embodiment, the present invention is directed to compounds of formula (I) wherein

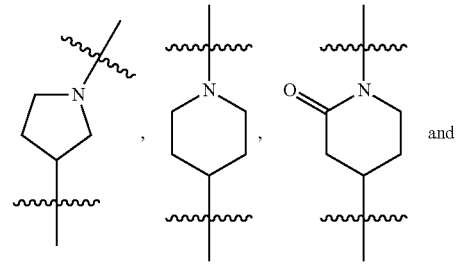

is selected from the group consisting of

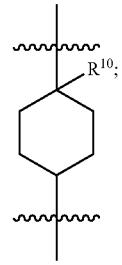

wherein Z¹ is selected from the group consisting of N and CH; and wherein R¹⁰ is selected from the group consisting of hydroxy and cyano. In another embodiment, the present invention is directed to compounds of formula (I) wherein

is selected from the group consisting of

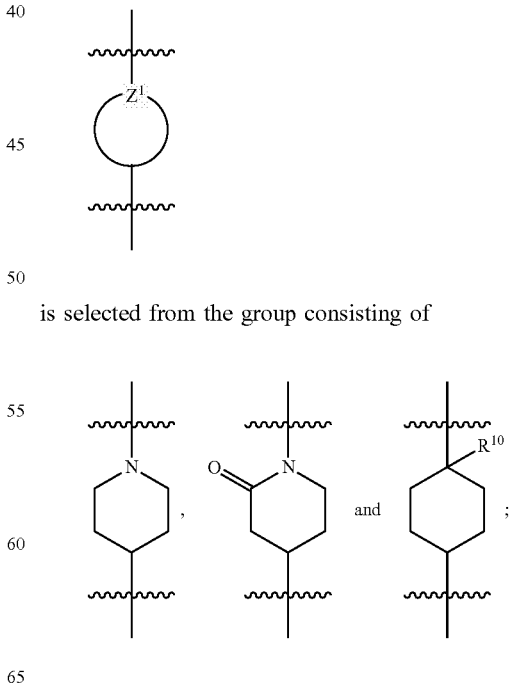

wherein Z¹ is selected from the group consisting of N and CH; and wherein R¹⁰ is selected from the group consisting of hydroxy and cyano. In another embodiment, the present invention is directed to compounds of formula (I) wherein

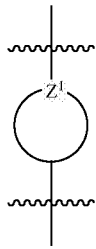

is selected from the group consisting of

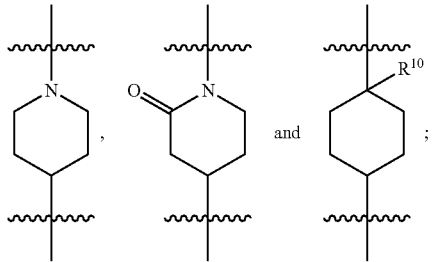

wherein $Z^1$ is selected from the group consisting of N and CH; and wherein $R^{10}$ is hydroxy. In another embodiment, the present invention is directed to compounds of formula (I) wherein

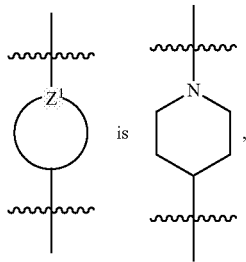

wherein $Z^1$ is N.

In an embodiment, the present invention is directed to compounds of formula (I) wherein b is an integer from 0 to 1. In another embodiment, the present invention is directed to compounds of formula (I) wherein b is 0. In another embodiment, the present invention is directed to compounds of formula (I) wherein b is 1.

In an embodiment, the present invention is directed to compounds of formula (I) wherein $L^2$ is selected from the group consisting of —CH$_2$—, —CH$_2$CH$_2$—, CH(CH$_3$)—, —C(O)— and —SO$_2$—. In another embodiment, the present invention is directed to compounds of formula (I) wherein $L^2$ is selected from the group consisting of —CH$_2$—, —CH$_2$CH$_2$—, —C(O)— and —SO$_2$—. In another embodiment, the present invention is directed to compounds of formula (I) wherein $L^2$ is selected from the group consisting of —CH$_2$—, —C(O)— and —SO$_2$—. In another embodiment, the present invention is directed to compounds of formula (I) wherein $L^2$ is selected from the group consisting of —C(O)— and —SO$_2$—. In another embodiment, the present invention is directed to compounds of formula (I) wherein $L^2$ is —SO$_2$—.

In an embodiment, the present invention is directed to compounds of formula (I) wherein $R^8$ is selected from the group consisting of azetidin-3-yl, pyrrolidin-1-yl, piperidin-4-yl, piperazin-1-yl, phenyl, pyridin-2-yl, pyridin-3-yl, pyridin-4-yl, thien-2-yl, thien-3-yl, furan-2-yl, furan-3-yl, pyrimidin-2-yl and pyrazin-2-yl; wherein any of the $R^8$ ring structures is optionally substituted with one substituent selected from the group consisting of halogen, hydroxy, cyano, halogenated C$_{1-4}$alkyl, hydroxy substituted C$_{1-4}$alkyl, —(C$_{1-4}$alkyl)-CO$_2$H, —(C$_{1-2}$alkyl)-C(O)O—(C$_{1-4}$alkyl), —(C$_{1-4}$alkyl)-C(O)—NR$^P$R$^Q$, —O—(C$_{1-2}$alkyl)-O—(C$_{1-4}$alkyl), —O—(C$_{1-4}$alkyl)-CO$_2$H, —O—(C$_{1-4}$alkyl)-C(O)O—(C$_{1-4}$alkyl), —C(O)—(C$_{1-2}$alkyl), —C(O)-(halogenated C$_{1-2}$alkyl), —C(O)—(C$_{1-4}$alkyl)-CO$_2$H, —C(O)—(C$_{1-2}$alkyl)-C(O)O—(C$_{1-4}$alkyl), —C(O)—NR$^P$R$^Q$, —C(O)—NR$^P$—(C$_{2-4}$alkyl)-O—R$^{11}$, —C(O)—(C$_{1-4}$alkyl)-C(O)—NR$^P$R$^Q$, —CO$_2$H, —C(O)O—(C$_{1-4}$alkyl), —C(O)O—(C$_{1-2}$alkyl)-OC(O)O—(C$_{1-4}$alkyl), —C(=NR$^P$)—NR$^Q$—C(O)O—(C$_{1-6}$alkyl), —C(=NH)—NH$_2$, —C(=N-Boc)-NH(Boc), —SO$_2$—(C$_{1-2}$alkyl), —SO$_2$-(halogenated C$_{1-2}$alkyl), —SO$_2$—NR$^P$R$^Q$ and —SO$_2$—(C$_{1-4}$alkyl)-C(O)—NR$^P$R$^Q$; wherein R$^P$ and R$^Q$ are each independently selected from the group consisting of hydrogen, C$_{1-2}$alkyl and —CH$_2$-(hydroxy substituted C$_{1-2}$alkyl); and wherein R$^{11}$ is phenyl; wherein the phenyl is optionally substituted at the 4-position with a substituent selected from the group consisting of halogen, hydroxymethyl, methyl and trifluoromethyl; and wherein R$^8$ is phenyl; the phenyl is further optionally substituted with an additional substituent selected from the group consisting of halogen, hydroxy, C$_{1-2}$alkyl, trifluoromethyl, C$_{1-2}$alkoxy and trifluromethoxy. In another embodiment, the present invention is directed to compounds of formula (I) wherein R$^8$ is selected from the group consisting of phenyl, pyrrolidiny-1-yl, piperidin-4-yl, thien-2-yl, pyridin-2-yl and pyrimidin-2-yl; wherein any of the R$^8$ ring structures is optionally substituted with one substituent selected from the group consisting of halogen, hydroxy, cyano, halogenated C$_{1-2}$alkyl, —O—(C$_{1-2}$alkyl)-CO$_2$H, —O—(C$_{1-2}$alkyl)-C(O)O—(C$_{1-2}$alkyl), —CO$_2$H, —(C$_{1-2}$alkyl)-CO$_2$H, —(C$_{1-2}$alkyl)-C(O)O—(C$_{1-2}$alkyl), —(C$_{1-2}$alkyl)-C(O)—NH$_2$, —C(O)O—(C$_{1-2}$alkyl), —C(O)O—(C$_{1-2}$alkyl)-OC(O)—O—(C$_{1-4}$alkyl), —C(O)—NR$^P$R$^Q$, —C(O)—NH—(C$_{1-4}$alkyl)-O—R$^{11}$, —C(O)—NH—CH$_2$-(hydroxy substituted C$_{1-5}$alkyl), —C(=NH)—NH$_2$, —C(=NH)—NH—C(O)O—(C$_{1-6}$alkyl), and —SO$_2$—NH—CH$_2$-(hydroxy substituted C$_{1-2}$alkyl); wherein R$^P$ and R$^Q$ are each independently selected from the group consisting of hydrogen and —CH$_2$-(hydroxy substituted C$_{1-2}$alkyl); and wherein R$^{11}$ is phenyl; wherein the phenyl is optionally substituted at the 4-position with a substituent selected from the group consisting of halogen and hydroxymethyl; and wherein R$^8$ is phenyl; the phenyl is further optionally substituted with an additional substituent selected from the group consisting of halogen and C$_{1-2}$alkoxy.

In another embodiment, the present invention is directed to compounds of formula (I) wherein R$^8$ is selected from the group consisting of phenyl, 3-hydroxyphenyl, 4-hydroxyphenyl, 2-fluorophenyl, 4-fluorophenyl, 4-trifluoromethylphenyl, 2-carboxyphenyl, 3-carboxyphenyl, 4-carboxyphenyl, 3-chloro-4-carboxy-phenyl, 3-methoxy-4-carboxyphenyl, 4-(carboxy-methyl)-phenyl, 3-(methoxy-carbonyl)-phenyl, 4-(methoxy-carbonyl)-phenyl, 4-(methoxy-carbonyl-methyl)-phenyl, 4-cyanophenyl, 4-amidinophenyl, 3-(amino-carbonyl)-phenyl, 4-(amino-carbonyl)-phenyl, 4-(amino-carbonyl-methyl)-phenyl, 4-(carboxy-methoxy)-phenyl, 4-(ethoxycarbonyl-methoxy)-phenyl, 4-(n-hexyloxy-carbonyl-amidino)-phenyl, 4-((4-hydroxymethyl)-phenyloxy-n-propyl-amino-carbonyl)-phenyl, 4-((4-chloromethyl)-phenyloxy-n-propyl-amino-carbonyl)-phenyl, 4-(isopropyloxy-carbonyl-oxy-methoxy-carbonyl)-phenyl, 4-(1,3-dihydroxy-2-hydroxy-methyl)-propan-2-yl-amino-carbonyl)-phenyl, 4-((2-hydroxy-ethyl)-amino-sulfonyl)-phenyl, 3-((2-hydroxy-ethyl)-amino-carbonyl)-phenyl, 4-((2-hydroxy-ethyl)-amino-carbonyl)-phenyl, pyrrolidin-1-yl, 4-carboxy-thien-2-yl, 5-carboxy-thien-2-yl, pyridin-2-yl and pyrimidin-2-yl. In another embodiment, the present invention is directed to compounds of formula (I) wherein $R^8$ is selected from the group consisting of phenyl, 3-hydroxyphenyl, 4-hydroxyphenyl, 2-fluorophenyl, 4-fluorophenyl, 4-trifluoromethyl-phenyl, 4-carboxy-phenyl, 3-chloro-4-carboxy-phenyl, 3-methoxy-4-carboxy-phenyl, 3-(methoxy-carbonyl)-phenyl, 4-(methoxy-carbonyl)-phenyl, 4-(methoxy-carbonyl-methyl)-phenyl, 4-cyanophenyl, 4-amidino-phenyl, 3-(amino-carbonyl)-phenyl, 4-(amino-carbonyl)-phenyl, 4-(ethoxycarbonyl-methoxy)-phenyl, 4-(n-hexyloxy-carbonyl-amidino)-phenyl, 4-((4-hydroxymethyl)-phenyloxy-n-propyl-amino-carbonyl)-phenyl, 4-(isopropyloxy-carbonyl-oxy-methoxy-carbonyl)-phenyl, 4-(1,3-dihydroxy-2-hydroxy-methyl)-propan-2-yl-amino-carbonyl)-phenyl, 3-((2-hydroxy-ethyl)-amino-carbonyl)-phenyl, 4-((2-hydroxy-ethyl)-amino-carbonyl)-phenyl, pyrrolidin-1-yl, 4-carboxy-thien-2-yl, 5-carboxy-thien-2-yl, pyridin-2-yl and pyrimidin-2-yl. In another embodiment, the present invention is directed to compounds of formula (I) wherein $R^8$ is selected from the group consisting of phenyl, 3-hydroxyphenyl, 4-hydroxyphenyl, 2-fluorophenyl, 4-fluorophenyl, 4-trifluoromethyl-phenyl, 4-carboxy-phenyl, 3-chloro-4-carboxy-phenyl, 3-methoxy-4-carboxy-phenyl, 4-(methoxy-carbonyl)-phenyl, 4-(methoxy-carbonyl-methyl)-phenyl, 4-cyanophenyl, 4-amidino-phenyl, 3-(amino-carbonyl)-phenyl, 4-(amino-carbonyl)-phenyl, 4-(ethoxycarbonyl-methoxy)-phenyl, 4-(n-hexyloxy-carbonyl-amidino)-phenyl, 4-((4-hydroxymethyl)-phenyloxy-n-propyl-amino-carbonyl)-phenyl, 4-(isopropyloxy-carbonyl-oxy-methoxy-carbonyl)-phenyl, 4-(1,3-dihydroxy-2-hydroxy-methyl)-propan-2-yl-amino-carbonyl)-phenyl, 4-((2-hydroxy-ethyl)-amino-carbonyl)-phenyl, pyrrolidin-1-yl, 5-carboxy-thien-2-yl, pyridin-2-yl and pyrimidin-2-yl. In another embodiment, the present invention is directed to compounds of formula (I) wherein $R^8$ is selected from the group consisting of phenyl, 4-hydroxyphenyl, 2-fluorophenyl, 4-fluorophenyl, 4-trifluoromethyl-phenyl, 4-(methoxy-carbonyl)-phenyl, 4-(methoxy-carbonyl-methyl)-phenyl, 4-amidino-phenyl, 4-(ethoxycarbonyl-methoxy)-phenyl4-(1,3-dihydroxy-2-hydroxy-methyl)-propan-2-yl-amino-carbonyl)-phenyl, pyrrolidin-1-yl, 5-carboxy-thien-2-yl, pyridin-2-yl and pyrimidin-2-yl. In another embodiment, the present invention is directed to compounds of formula (I) wherein $R^8$ is selected from the group consisting of phenyl, 4-fluorophenyl, 4-carboxy-phenyl, 4-amidino-phenyl, pyrrolidin-1-yl; and pyridin-2-yl.

In an embodiment, the present invention is directed to compounds of formula (I) wherein $R^5$ and $R^6$ are taken together with the nitrogen atom to which they are bound to form a ring structure selected from the group consisting of

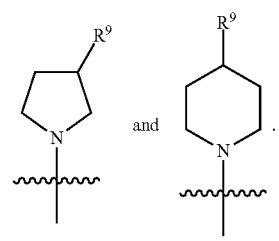

In an embodiment, the present invention is directed to compounds of formula (I) wherein $R^9$ is selected from the group consisting of $C_{1-4}$alkyl, trifluoromethyl, cyclopropyl and —$NR^SR^T$; wherein $R^S$ is selected from the group consisting of hydrogen, methyl and ethyl; and $R^T$ is selected from the group consisting of —C(O)—($C_{1-4}$alkyl), —$SO_2$—($C_{1-4}$alkyl) and —$SO_2$-(halogenated $C_{1-4}$alkyl). In another embodiment, the present invention is directed to compounds of formula (I) wherein $R^9$ is selected from the group consisting of —$NR^SR^T$; wherein $R^S$ is selected from the group consisting of hydrogen, methyl and ethyl; and wherein $R^T$ is —$SO_2$-(halogenated $C_{1-2}$alkyl). In another embodiment, the present invention is directed to compounds of formula (I) wherein $R^9$ is trifluoromethyl-sulfonyl-amino.

In an embodiment, the present invention is directed to compounds of formula (I) wherein, when a is 0 (i.e. $L^1$ is absent), then $R^7$ is other than piperazin-1-yl, morpholin-4-yl, thiomorpholin-4-yl or thiomorpholin-4-yl-1-oxide. In another embodiment, the present invention is directed to compounds of formula (I) wherein, when a is 0 (i.e. $L^1$ is absent), then $R^7$ is other than thiomorpholin-4-yl-1-oxide.

In an embodiment, the present invention is directed to compounds of formula (I) wherein when

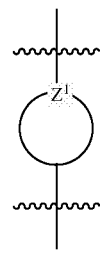

is selected from the group consisting of

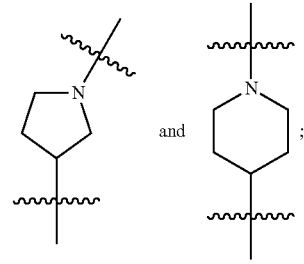 [SMILES: *C1CCN(*)C1 ; *C1CCN(*)CC1]

and the $R^8$ is selected from the group consisting of pyrrolidin-1-yl and piperazin-1-yl, then b is 1 and $L^2$ is selected from the group consisting of —C(O)— and —$SO_2$—. In an embodiment, the present invention is directed to compounds of formula (I) wherein when

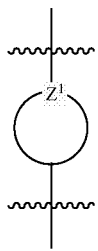

is selected from the group consisting of

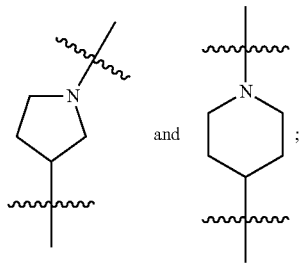 [SMILES: *C1CCN(*)C1 ; *C1CCN(*)CC1]

and the R⁸ is pyrrolidin-1-yl, then b is 1 and L² is selected from the group consisting of —C(O)— and —SO₂—. In another embodiment, the present invention is directed to compounds of formula (I) wherein when

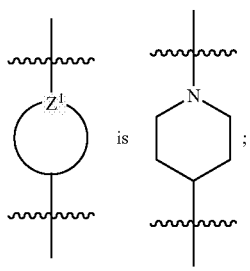

and R⁸ is pyrrolidin-1-yl, then b is 1 and L² is selected from the group consisting of —C(O)— and —SO₂—. In another embodiment, the present invention is directed to compounds of formula (I) wherein when

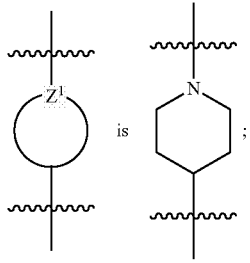

and R⁸ is pyrrolidin-1-yl, then b is 1 and L² is —SO₂—.

In an embodiment, the present invention is directed to compounds of formula (I) wherein when

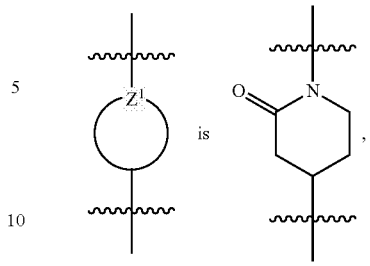

then R⁸ is phenyl, wherein the phenyl is optionally substituted with one to two substituents independently selected from the group consisting of F, Cl, cyano and trifluoromethyl. In another embodiment, the present invention is directed to compounds of formula (I) wherein provided further that when

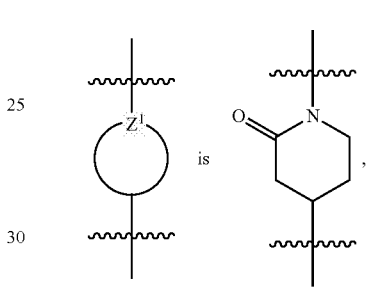

then R⁸ is selected from the group consisting of phenyl, 2-fluorophenyl, 4-fluorophenyl and 4-trifluoromethyl-phenyl.

Additional embodiments of the present invention, include those wherein the substituents selected for one or more of the variables defined herein (e.g.

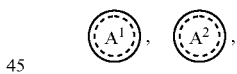

a, b, L¹, L², R¹, R², R³, R⁴, R⁵, R⁶, R⁷, R⁸, R⁹, R¹⁰,

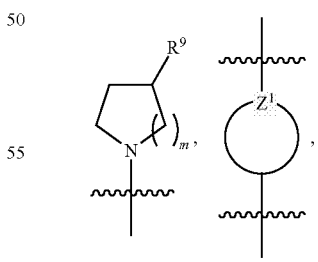

Z¹, etc.) are independently selected to be any individual substituent or any subset of substituents selected from the complete list as defined herein.

Additional embodiments of the present invention, include those wherein the substituents selected for one or more of the variables defined herein (e.g.

a, b, L$^1$, L$^2$, R$^1$, R$^2$, R$^3$, R$^4$, R$^5$, R$^6$, R$^7$, R$^8$, R$^9$, R$^{10}$,

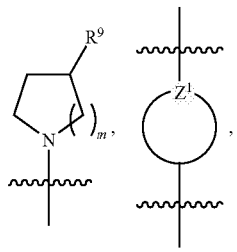

Z$^1$, etc.) are independently selected to be individual substituent or subset of substituents selected from those exemplified in the Tables which follow herein.

In additional embodiments, the present invention is directed to any single compound or subset of compounds, independently selected from the representative compounds of formula (I) listed in the Tables 1-3 which follow herein.

In the Tables which follow herein, unless otherwise noted, wherein a stereogenic center is present in the listed compound, the compound was prepared as a mixture of enantiomers. Where a stereogenic center is present, and the compound was prepared in an enantiomeric or diastereomeric excess, the S*- and R* designations are intended to indicate relative stereo-configuration (where the exact stereo-configuration of the stereogenic center has not been determined).

Representative compounds of formula (I) of the present invention are as listed in Tables 1-3 below.

TABLE 1

Representative Compounds of Formula (I)

| ID No | A$^1$ | A$^2$ | R$^1$ | NR$^5$ | (L$^1$)$_a$ | R$^7$ |
|---|---|---|---|---|---|---|
| 1 | 4-chloro-phenyl | 4-chloro-phenyl | H | NH | a = 0 | 1-(t-butoxy-carbonyl)-piperidin-4-yl |
| 2 | 4-chloro-phenyl | 4-chloro-phenyl | H | NH | —CH$_2$CH$_2$— | 3-carboxy-phenyl |
| 5 | 4-chloro-phenyl | 4-chloro-phenyl | H | NH | —CH$_2$CH$_2$— | 4-carboxy-phenyl |
| 6 | 4-chloro-phenyl | 4-chloro-phenyl | H | NH | —CH$_2$CH$_2$— | thiomorpholin-4-yl-1,1-dioxide |
| 12 | 4-chloro-phenyl | 4-chloro-phenyl | H | NH | —CH$_2$CH$_2$— | phenyl |
| 15 | 4-chloro-phenyl | 4-(2-methoxy-ethyl-amino)-phenyl | H | NH | a = 0 | 1-(trifluoromethyl-sulfonyl)-piperidin-4-yl |
| 16 | 4-chloro-phenyl | 4-carboxy-phenyl | H | NH | a = 0 | 1-(trifluoromethyl-sulfonyl)-piperidin-4-yl |
| 19 | 4-chloro-phenyl | 4-cyano-phenyl | H | NH | a = 0 | 1-(trifluoromethyl-sulfonyl)-piperidin-4-yl |
| 20 | 4-chloro-phenyl | 4-bromo-phenyl | H | NH | a = 0 | 1-(trifluoromethyl-sulfonyl)-piperidin-4-yl |
| 31 | 4-chloro-phenyl | 4-chloro-phenyl | —O(CH$_2$)$_4$—NH$_2$— | NH | —CH$_2$— | 3-trifluoromethyl-phenyl |
| 35 | 4-chloro-phenyl | 4-chloro-phenyl | —O—CH$_2$CH$_2$—O—CH$_2$CH$_2$—OH | NH | —CH$_2$— | 3-trifluoromethyl-phenyl |
| 40 | 4-chloro-phenyl | 4-chloro-phenyl | —OCH$_2$—C(O)—NH—(CH$_2$)$_2$—OH | NH | —CH$_2$— | 3-trifluoromethyl-phenyl |
| 48 | 4-chloro-phenyl | 4-chloro-phenyl | —O—CH$_2$CH$_2$—O—CH$_2$CH$_2$—CO$_2$H | NH | —CH$_2$— | 3-trifluoromethyl-phenyl |
| 49 | 4-chloro-phenyl | 4-chloro-phenyl | —OCH$_2$—CH(CH$_2$OH)$_2$ | NH | —CH$_2$— | 3-trifluoromethyl-phenyl |

TABLE 1-continued

Representative Compounds of Formula (I)

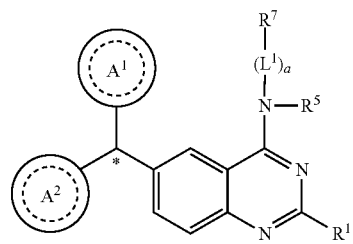

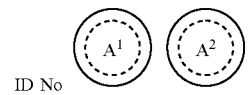

| ID No | A¹ | A² | R¹ | NR⁵ | (L¹)ₐ | R⁷ |
|---|---|---|---|---|---|---|
| 50 | 4-chloro-phenyl | 4-chloro-phenyl | —O—CH₂CH₂—O—CH₂CH₂—CN | NH | —CH₂— | 3-trifluoromethyl-phenyl |
| 51 | 4-chloro-phenyl | 4-chloro-phenyl | —O—CH₂—CO₂H | NH | —CH₂— | 3-trifluoromethyl-phenyl |
| 53 | 4-chloro-phenyl | 4-chloro-phenyl | —O—(CH₂)₄—OH | NH | —CH₂— | 3-trifluoromethyl-phenyl |
| 54 | 4-chloro-phenyl | 4-chloro-phenyl | —O—CH₂—C(CH₂OH)₃ | NH | —CH₂— | 3-trifluoromethyl-phenyl |
| 55 | 4-chloro-phenyl | 4-chloro-phenyl | —O—CH₂CH₂—OH | NH | —CH₂— | 3-trifluoromethyl-phenyl |
| 56 | 4-chloro-phenyl | 4-chloro-phenyl | H | NH | —CH₂— | 4-(amino-carbonyl)-pheenyl |
| 57 | 4-chloro-phenyl | 4-chloro-phenyl | H | NH | —CH₂— | 3-(amino-carbonyl)-phenyl |
| 59 | 4-chloro-phenyl | 4-chloro-phenyl | H | NH | —CH₂— | 3-carboxy-phenyl |
| 60 | 4-chloro-phenyl | 4-chloro-phenyl | H | NH | —CH₂— | 4-carboxy-phenyl |
| 61 | 4-chloro-phenyl | 4-chloro-phenyl | H | NH | —CH₂— | 4-(methoxy-carbonyl)-phenyl |
| 62 | 4-chloro-phenyl | 4-chloro-phenyl | H | NH | —CH₂— | 3-(methoxy-carbonyl)-phenyl |
| 63 | 4-chloro-phenyl | 4-chloro-phenyl | H | NH | —CH₂— | 3-fluoro-phenyl |
| 65 | 4-chloro-phenyl | 4-chloro-phenyl | H | NH | —CH₂— | 4-fluoro-phenyl |
| 66 | 4-chloro-phenyl | 4-chloro-phenyl | —O—(CH₂)₃—C(O)—NH₂ | NH | —CH₂— | 4-trifluoromethyl-phenyl |
| 69 | 4-chloro-phenyl | 4-chloro-phenyl | —O—(CH₂)₂—NH—C(O)—CH₃ | NH | —CH₂— | 4-trifluoromethyl-phenyl |
| 71 | 4-chloro-phenyl | 4-chloro-phenyl | —O—(CH₂)₄—OH | NH | —CH₂— | 4-trifluoromethyl-phenyl |
| 72 | 4-chloro-phenyl | 4-chloro-phenyl | —O—CH₂CH₂—NH₂ | NH | —CH₂— | 4-trifluoromethyl-phenyl |
| 75 | 4-chloro-phenyl | 4-chloro-phenyl | —O—CH₂CH₂—N₃ | NH | —CH₂— | 4-trifluoromethyl-phenyl |
| 76 | 4-chloro-phenyl | 4-chloro-phenyl | H | NH | a = 0 | 1-((2-hydroxyethyl)-amino-carbonyl-ethyl-carbonyl)-piperidin-4-yl |
| 78 | 4-chloro-phenyl | 4-chloro-phenyl | H | NH | a = 0 | 1-((2-hydroxyethyl)-sulfonyl)-piperidin-4-yl |
| 80 | 4-chloro-phenyl | 4-chloro-phenyl | H | NH | a = 0 | 1-((2-carboxy-ethyl)-carbonyl)-piperidin-4-yl |
| 81 | 4-chloro-phenyl | 4-chloro-phenyl | H | NH | a = 0 | 1-((2-ethoxy-carbonyl-ethyl)-carbonyl)-piperidin-4-yl |
| 82 | 4-chloro-phenyl | 4-chloro-phenyl | H | NH | a = 0 | 1-((2-hydroxy-ethyl)-amino-carbonyl-methyl-carbonyl)-piperidin-4-yl |
| 85 | 4-chloro-phenyl | 4-chloro-phenyl | —OCH₃ | NH | —CH₂— | 4-trifluoromethyl-phenyl |
| 86 | 4-chloro-phenyl | 4-chloro-phenyl | H | NH | a = 0 | 1-(amino-carbonyl-ethyl-carbonyl)-piperidin-4-yl |

TABLE 1-continued

Representative Compounds of Formula (I)

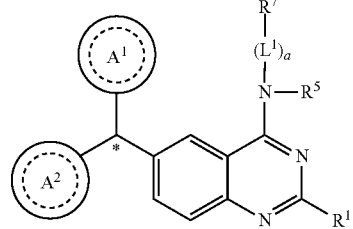

| ID No | A¹ | A² | R¹ | NR⁵ | (L¹)ₐ | R⁷ |
|---|---|---|---|---|---|---|
| 87 | 4-chloro-phenyl | 4-chloro-phenyl | H | NH | a = 0 | 1-(amino-carbonyl-methyl-carbonyl)-piperidin-4-yl |
| 88 | 4-chloro-phenyl | 4-chloro-phenyl | H | NH | a = 0 | 1-(carboxy-methyl-carbonyl)-piperidin-4-yl |
| 89 | 4-chloro-phenyl | 4-chloro-phenyl | H | NH | a = 0 | 1-(ethoxy-carbonyl-methyl-carbonyl)-piperidin-4-yl |
| 91 | 4-chloro-phenyl | 4-chloro-phenyl | —O—CH₂CH₂—OCH₃ | NH | —CH₂— | 4-trifluoromethyl-phenyl |
| 98 | 4-chloro-phenyl | 4-chloro-phenyl | H | NH | a = 0 | 1-(amino-carbonyl-methyl-sulfonyl)-piperidin-4-yl |
| 100 | 4-chloro-phenyl | 4-chloro-phenyl | —NH—SO₂—CH₃ | NH | a = 0 | 1-(trifluoromeethyl-sulfonyl)-piperidin-4-yl |
| 103 | 4-chloro-phenyl | 4-chloro-phenyl | —OCH₃ | NH | a = 0 | 1-(trifluoromeethyl-sulfonyl)-piperidin-4-yl |
| 106 | 4-chloro-phenyl | 4-chloro-phenyl | —NH—C(O)—CH₃ | NH | a = 0 | 1-(trifluoromeethyl-sulfonyl)-piperidin-4-yl |
| 107 | 4-chloro-phenyl | 4-chloro-phenyl | NH₂ | NH | a = 0 | 1-(trifluoromeethyl-sulfonyl)-piperidin-4-yl |
| 108 | 4-chloro-phenyl | 4-chloro-phenyl | cyclo-propyl | NH | a = 0 | 1-(trifluoromeethyl-sulfonyl)-piperidin-4-yl |
| 110 | 4-chloro-phenyl | 4-chloro-phenyl | H | NH | a = 0 | 1-(methoxy-carbonyl-meethyl-sulfonyl)-piperidin-4-yl |
| 112 | 4-chloro-phenyl | 4-chloro-phenyl | H | NH | —CH(S*—CH₃)— | 3-trifluoromethyl-phenyl |
| 113 | 4-chloro-phenyl | 4-chloro-phenyl | —NH—CH₃ | NH | a = 0 | 1-(trifluoromethyl-sulfonyl)-piepridin-4-yl |
| 114 | 4-chloro-phenyl | 4-chloro-phenyl | OH | NH | a = 0 | 1-(trifluoromethyl-sulfonyl)-piepridin-4-yl |
| 115 | 4-chloro-phenyl | 4-chloro-phenyl | H | NH | —CH(R*—CH₃)— | 3-trifluoromethyl-phenyl |
| 116 | 4-chloro-phenyl | 4-chloro-phenyl | H | NH | —CH(CH₃)— | 4-trifluoromethyl-phenyl |
| 122 | 4-chloro-phenyl | 4-chloro-phenyl | H | NH | a = 0 | 3-chloro-4-trifluoromethyl-phenyl |
| 123 | 4-chloro-phenyl | 4-chloro-phenyl | H | NH | a = 0 | 1-(2,2,2-trifluoroethyl)-piperidin-4-yl |
| 125 | 4-chloro-phenyl | 4-chloro-phenyl | H | NH | cycloprop-1,1-diyl | 4-trifluoromethyl-phenyl |

TABLE 1-continued

Representative Compounds of Formula (I)

| ID No | A¹ | A² | R¹ | NR⁵ | (L¹)ₐ | R⁷ |
|---|---|---|---|---|---|---|
| 126 | 4-chloro-phenyl | 4-chloro-phenyl | H | NH | —CH₂— | 5-trifluoromeethyl-pyridin-3-yl |
| 127 | 4-chloro-phenyl | 4-chloro-phenyl | H | NH | —CH₂— | 5-trifluoromethyl-pyridin-2-yl |
| 128 | 4-chloro-phenyl | 4-chloro-phenyl | H | NH | —CH(CH₃)— | 3-trifluoromethyl-phenyl |
| 131 | 4-chloro-phenyl | 4-chloro-phenyl | H | NH | —CH₂— | 6-trifluoromethyl-pyridin-3-yl |
| 132 | 4-chloro-phenyl | 4-chloro-phenyl | H | NCH₃ | —CH₂— | 4-trifluoromethyl-phenyl |
| 133 | 4-chloro-phenyl | 4-chloro-phenyl | H | NH | a = 0 | 1-(2,2,2-trifluoroethyl-carbonyl)-piperidin-4-yl |
| 134 | 4-chloro-phenyl | 4-chloro-phenyl | H | NH | a = 0 | 4-(trifluoromethyl-sulfonyl)-phenyl |
| 135 | 4-chloro-phenyl | 4-chloro-phenyl | H | NH | —CH₂— | 1-(trifluoromethyl-sulfonyl)-piperidin-4-yl |
| 136 | 4-chloro-phenyl | 4-chloro-phenyl | H | NH | —CH₂— | 3-trifluoromethyl-phenyl |
| 138 | 4-chloro-phenyl | 4-chloro-phenyl | H | NH | —CH₂— | 4-trifluoromethyl-phenyl |
| 140 | 4-chloro-phenyl | 4-chloro-phenyl | H | NH | a = 0 | 1-(methyl-sulfonyl)-piperidin-4-yl |
| 141 | 4-chloro-phenyl | 4-chloro-phenyl | H | NH | a = 0 | 1-(ethyl-sulfonyl)-piperidin-4-yl |
| 142 | 4-chloro-phenyl | thiazol-2-yl | H | NH | a = 0 | 4-(trifluoromethyl-sulfonyl)-phenyl |
| 143 | 4-chloro-phenyl | 4-chloro-phenyl | H | NH | a = 0 | 4-trifluoromethyl-phenyl |
| 144 | 4-chloro-phenyl | thiazol-2-yl | H | NH | a = 0 | 4-trifluoromethyl-phenyl |
| 145 | 4-chloro-phenyl | 4-chloro-phenyl | H | NH | a = 0 | 1-(trifluoromethyl-sulfonyl)-piperidin-4-yl |
| 146 | 4-chloro-phenyl | thiazol-2-yl | H | NH | a = 0 | 1-(trifluoromethyl-sulfonyl)-piperidin-4-yl |

TABLE 2

Representative Compounds of Formula (I)

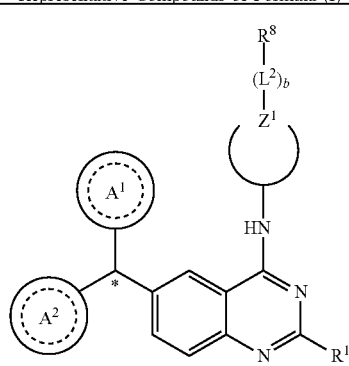

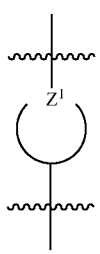

| ID No | A¹ | A² | R¹ | Z¹ | $(L^2)_b$ | R⁸ |
|---|---|---|---|---|---|---|
| 3 | 4-chloro-phenyl | 4-chloro-phenyl | H | piperidin-1,4-diyl | —SO₂— | 4-(carboxy-methoxy)-phenyl |
| 4 | 4-chloro-phenyl | 4-chloro-phenyl | H | piperidin-1,4-diyl | —SO₂— | 4-(ethoxycarbonyl-methoxy)-phenyl |
| 7 | 4-chloro-phenyl | 4-chloro-phenyl | H | piperidin-1,4-diyl | —SO₂— | 4-(n-hexyloxy-carbonyl-amidino)-phenyl |
| 8 | 4-chloro-phenyl | 4-chloro-phenyl | H | piperidin-1,4-diyl | —SO₂— | 4-hydroxy-phenyl |
| 10 | 4-chloro-phenyl | 4-chloro-phenyl | H | piperidin-1,4-diyl | —CH₂CH₂— | 4-carboxyphenyl |
| 11 | 4-chloro-phenyl | 4-chloro-phenyl | H | piperidin-1,4-diyl | —CH₂CH₂— | phenyl |
| 13 | 4-chloro-phenyl | 4-chloro-phenyl | H | piperidin-1,4-diyl | —CH₂CH₂— | 3-carboxy-phenyl |
| 14 | 4-chloro-phenyl | 4-chloro-phenyl | H | pyrrolidin-1,3-diyl | —CH₂— | 4-carboxy-phenyl |
| 17 | 4-chloro-phenyl | 4-chloro-phenyl | H | pyrrolidin-1,3-diyl | —CH₂— | 3-carboxy-phenyl |
| 18 | 4-chloro-phenyl | 4-chloro-phenyl | H | piperidin-1,4-diyl | —CH₂— | 4-carboxy-thien-2-yl |
| 21 | 4-chloro-phenyl | 4-chloro-phenyl | H | piperidin-1,4-diyl | —CH₂— | 2-carboxy-phenyl |
| 22 | 4-chloro-phenyl | 4-chloro-phenyl | H | piperidin-1,4-diyl | —SO₂— | 3-methoxy-4-carboxy-phenyl |
| 23 | 4-chloro-phenyl | 4-chloro-phenyl | H | piperidin-1,4-diyl | —SO₂— | 3-chloro-4-carboxy-phenyl |
| 25 | 4-chloro-phenyl | 4-chloro-phenyl | H | piperidin-1,4-diyl | —SO₂— | 5-carboxy-thien-2-yl |
| 26 | 4-chloro-phenyl | 4-chloro-phenyl | H | piperidin-1,4-diyl | —SO₂— | 4-((4-hydroxymethyl)-phenyl-oxy-n-propyl-amino-carbonyl)-phenyl |

TABLE 2-continued

Representative Compounds of Formula (I)

| ID No | A¹ | A² | R¹ | Z¹ | (L²)_b | R⁸ |
|---|---|---|---|---|---|---|
| 27 | 4-chloro-phenyl | 4-chloro-phenyl | H | piperidin-1,4-diyl | —CH₂— | 4-hydroxy-phenyl |
| 28 | 4-chloro-phenyl | 4-chloro-phenyl | H | piperidin-1,4-diyl | —CH₂— | 3-hydroxy-phenyl |
| 30 | 4-chloro-phenyl | 4-chloro-phenyl | H | piperidin-1,4-diyl | —SO₂— | 4-((4-chloromethyl)-phenyl-oxy-n-propyl-amino-carbonyl)-phenyl |
| 32 | 4-chloro-phenyl | 4-chloro-phenyl | H | piperidin-1,4-diyl | b = 0 | 4-hydroxy-phenyl |
| 33 | 4-chloro-phenyl | 4-chloro-phenyl | —O—(CH₂)₂—NH—SO₂—CH₃ | piperidin-1,4-diyl | —SO₂— | 4-carboxy-phenyl |
| 34 | 4-chloro-phenyl | 4-chloro-phenyl | H | piperidin-1,4-diyl | —CH₂— | 5-carboxy-thien-2-yl |
| 36 | 4-chloro-phenyl | 4-chloro-phenyl | H | piperidin-1,4-diyl | —CH₂— | 3-(amino-carbonyl)-phenyl |
| 37 | 4-chloro-phenyl | 4-chloro-phenyl | H | piperidin-1,4-diyl | —CH₂— | 3-carboxy-phenyl |
| 38 | 4-chloro-phenyl | 4-chloro-phenyl | H | piperidin-1,4-diyl | —CH₂— | 4-(amino-carbonyl)-phenyl |
| 39 | 4-chloro-phenyl | 4-chloro-phenyl | —O—CH₂—CH₂—OH | piperidin-1,4-diyl | —SO₂— | 4-carboxy-phenyl |
| 41 | 4-chloro-phenyl | 4-chloro-phenyl | H | piperidin-1,4-diyl | —SO₂— | 4-(1,3-dihydroxy-2-(hydroxy-methyl)-propan-2-yl)-amino-carbonyl)-phenyl |
| 42 | 4-chloro-phenyl | 4-chloro-phenyl | H | piperidin-1,4-diyl | b = 0 | 4-(1,3-dihydroxy-2-(hydroxy-methyl)-propan-2-yl-amino-carbonyl)-phenyl |
| 43 | 4-chloro-phenyl | 4-chloro-phenyl | H | piperidin-1,4-diyl | —CH₂— | 4-(methoxy-carbonyl)-phenyl |
| 44 | 4-chloro-phenyl | 4-chloro-phenyl | H | piperidin-1,4-diyl | —CH₂— | 4-carboxy-phenyl |

TABLE 2-continued

Representative Compounds of Formula (I)

| ID No | A¹ | A² | R¹ | (Z¹) | (L²)ᵦ | R⁸ |
|---|---|---|---|---|---|---|
| 45 | 4-chloro-phenyl | 4-chloro-phenyl | H | piperidin-1,4-diyl | —C(O)— | (4-((2-hydroxy-ethyl)-amino-sulfonyl)-phenyl |
| 46 | 4-chloro-phenyl | 4-chloro-phenyl | —OCH₃ | piperidin-1,4-diyl | —SO₂— | 4-carboxy-phenyl |
| 47 | 4-chloro-phenyl | 4-chloro-phenyl | H | piperidin-1,4-diyl | —SO₂— | 4-amidino-phenyl |
| 52 | 4-chloro-phenyl | 4-chloro-phenyl | H | piperidin-1,4-diyl | —SO₂— | 4-cyano-phenyl |
| 58 | 4-chloro-phenyl | 4-methoxy-phenyl | H | piperidin-1,4-diyl | b = 0 | phenyl |
| 64 | 4-chloro-phenyl | 4-chloro-phenyl | H | piperidin-1,4-diyl | —SO₂— | 4-(isopropyloxy-carbonyl-oxy-methoxy-carbonyl)-phenyl |
| 67 | 4-fluoro-phenyl | 4-fluoro-phenyl | H | piperidin-1,4-diyl | b = 0 | phenyl |
| 68 | 4-chloro-phenyl | 4-chloro-phenyl | H | piperidin-1,4-diyl | —C(O)— | 4-carboxy-phenyl |
| 73 | 4-chloro-phenyl | 4-chloro-phenyl | H | piperidin-1,4-diyl | —C(O)— | 4-(methoxy-carbonyl)-phenyl |
| 74 | 4-chloro-phenyl | 4-chloro-phenyl | H | piperidin-1,4-diyl | b = 0 | 4-(amino-carbonyl-methyl)-phenyl |
| 77 | 4-chloro-phenyl | 4-chloro-phenyl | H | piperidin-1,4-diyl | b = 0 | 4-(carboxy-methyl)-phenyl |
| 79 | 4-chloro-phenyl | 4-chloro-phenyl | H | piperidin-1,4-diyl | b = 0 | 4-(methoxy-carbonyl-methyl)-phenyl |
| 83 | 4-chloro-phenyl | 4-chloro-phenyl | H | piperidin-1,4-diyl | b = 0 | 3-((2-hydroxy-ethyl)-amino-carbonyl)-phenyl |
| 84 | 4-chloro-phenyl | 4-chloro-phenyl | H | piperidin-1,4-diyl | b = 0 | 4-((2-hydroxy-ethyl)-amino-carbonyl)-phenyl |
| 90 | 4-chloro-phenyl | 4-chloro-phenyl | H | piperidin-1,4-diyl | b = 0 | 4-(amino-carbonyl)-phenyl |

TABLE 2-continued

Representative Compounds of Formula (I)

| ID No | A¹ | A² | R¹ | Z¹ | $(L^2)_b$ | R⁸ |
|---|---|---|---|---|---|---|
| 92 | 4-chloro-phenyl | 4-chloro-phenyl | H | piperidin-1,4-diyl | b = 0 | 4-carboxy-phenyl |
| 93 | 4-chloro-phenyl | 4-chloro-phenyl | H | piperidin-1,4-diyl | —SO₂— | 4-carboxy-phenyl- |
| 94 | 4-chloro-phenyl | 4-chloro-phenyl | H | piperidin-1,4-diyl | b = 0 | 4-(methoxy-carbonyl)-phenyl |
| 95 | 4-chloro-phenyl | 4-chloro-phenyl | H | piperidin-1,4-diyl | b = 0 | 3-carboxy-phenyl |
| 96 | 4-chloro-phenyl | 4-chloro-phenyl | H | piperidin-1,4-diyl | b = 0 | 3-(amino-carbonyl)-phenyl |
| 97 | 4-chloro-phenyl | 4-chloro-phenyl | H | piperidin-1,4-diyl | b = 0 | 3-(methoxy-carbonyl)-phenyl |
| 99 | 4-chloro-phenyl | 4-chloro-phenyl | H | 4-hydroxy-cyclohex-1,4-diyl | b = 0 | phenyl |
| 101 | 4-chloro-phenyl | 4-chloro-phenyl | H | piperidin-1,4-diyl | —SO₂— | 3-carboxy-phenyl |
| 102 | 4-chloro-phenyl | 4-chloro-phenyl | H | piperidin-1,4-diyl | b = 0 | phenyl |
| 109 | 4-chloro-phenyl | 4-chloro-phenyl | H | piperidin-1,4-diyl | —SO₂— | phenyl- |
| 111 | 4-chloro-phenyl | 4-chloro-phenyl | H | piperidin-1,4-diyl | —SO₂— | pyridin-2-yl |
| 118 | 4-chloro-phenyl | 4-chloro-phenyl | H | piperidin-1,4-diyl | b = 0 | phenyl |
| 119 | 4-chloro-phenyl | 4-chloro-phenyl | H | piperidin-1,4-diyl | —C(O)— | phenyl |
| 120 | 4-chloro-phenyl | 4-chloro-phenyl | H | piperidin-1,4-diyl | —SO₂— | pyrrolidin-1-yl |
| 121 | 4-chloro-phenyl | 4-chloro-phenyl | H | piperidin-1,4-diyl | —SO₂— | 4-fluoro-phenyl |

TABLE 2-continued

Representative Compounds of Formula (I)

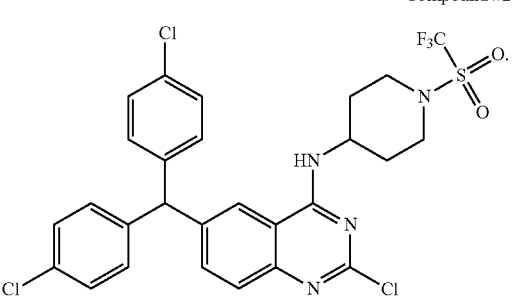

| ID No | A¹ | A² | R¹ | (L²)_b | | R⁸ |
|---|---|---|---|---|---|---|
| 124 | 4-chloro-phenyl | 4-chloro-phenyl | H | piperidin-1,4-diyl | —SO₂— | 2-fluoro-phenyl |
| 129 | 4-chloro-phenyl | 4-chloro-phenyl | H | piperidin-1,4-diyl | b = 0 | 4-trifluoromethyl-phenyl |
| 130 | 4-chloro-phenyl | 4-chloro-phenyl | H | piperidin-1,4-diyl | b = 0 | pyridin-2-yl |
| 137 | 4-chloro-phenyl | 4-chloro-phenyl | H | piperidin-1,4-diyl | b = 0 | phenyl |
| 139 | 4-chloro-phenyl | 4-chloro-phenyl | H | piperidin-1,4-diyl | b = 0 | pyrimidin-2-yl |

TABLE 3

Representative Compounds of Formula (I)

| ID No | A¹ | A² | R¹ | R⁵ and R⁶ taken together with N to which they are bound |
|---|---|---|---|---|
| 9 | 4-chloro-phenyl | 4-chloro-phenyl | H | 3-(trifluoromethyl-sulfonyl-amino)-pyrrolidin-1-yl |
| 104 | 4-chloro-phenyl | 4-chloro-phenyl | H | 4-(trifluoromethyl-sulfonyl-amino)-pyrrolidin-1-yl |

The following is an example of a representative intermediate compound in the synthesis of one or more compounds of formula (I) of the present invention Compound #200

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Unless otherwise noted, "$C_{X-Y}$alkyl" wherein X and Y are integers, shall mean a carbon chain composition of between X and Y carbon atoms. For example, "$C_{1-4}$alkyl" shall mean any straight or branched chain composition of between 1 and 4 carbon atoms (including methyl, ethyl, n-propyl, isopropyl, n-butyl, isobutyl and t-butyl).

One skilled in the art will recognize that the term "—($C_{X-Y}$alkyl)—" shall denote any $C_{X-Y}$alkyl straight or branched chain composition as defined above, wherein said $C_{X-Y}$alkyl straight or branched chain composition is divalent and is therefore bound through two points of attachment, preferably through two terminal carbon atoms.

As used herein, unless otherwise noted, the term "halogenated $C_{1-4}$alkyl" shall mean any $C_{1-4}$alkyl group as defined above substituted with at least one halogen atom, preferably substituted with a least one fluoro atom. Suitable examples include but are not limited to —$CH_2F$, —$CH_2I$, —$CH_2Br$, —$CH_2Cl$, —$CF_3$, —$CCl_3$, —$CH_2$—$CF_3$, $CH_2$—$CCl_3$, —$CF_2$—$CF_2$—$CF_2$—$CF_3$, and the like. Similarly, the term "fluorinated $C_{1-4}$alkyl" shall mean any $C_{1-4}$alkyl group as defined above substituted with at least one fluoro atom, preferably one to three fluoro atoms. Suitable examples include but are not limited to —$CF_3$, —$CH_2$—$CF_3$, —$CF_2$—$CF_2$—$CF_2$—$CF_3$, and the like.

As used herein, unless otherwise noted, the term "hydroxy substituted $C_{X-Y}$alkyl" shall mean any $C_{X-Y}$alkyl group as defined above, substituted with at least one hydroxy group, preferably one to two hydroxy groups, more preferably one hydroxy group. Suitable examples include but are not limited to —$CH_2OH$, —$CH_2CH_2OH$, —$CH(OH)CH_3$, —$CH_2CH_2CH_2OH$, —$CH_2CH(OH)CH_3$, —$CH_2CH_2CH_2CH_2OH$, and the like. In an embodiment, the $C_{X-Y}$alkyl is substituted with the hydroxy group at a terminal carbon atom.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Unless otherwise noted, "$C_{X-Y}$alkoxy" wherein X and Y are integers, shall mean an oxygen ether radical of the above described straight or branched chain carbon chain composition of between X and Y carbon atoms. For example, "$C_{1-4}$alkoxy" shall mean any oxygen ether radical of the above described straight or branched chain composition of between 1 and 4 carbon atoms.

As used herein, unless otherwise noted, the term "halogenated $C_{1-4}$alkoxy" shall mean any $C_{1-4}$alkoxy group as defined above substituted with at least one halogen atom, preferably substituted with a least one fluoro atom. Suitable examples include but are not limited to —$OCH_2F$, —$OCH_2I$, —$OCH_2Br$, —$OCH_2Cl$, —$OCF_3$, —$OCCl_3$, —$OCH_2$—$CF_3$, —$OCH_2$—$CCl_3$, —$OCF_2$—$CF_2$—$CF_2$—$CF_3$, and the like. Similarly, the term "fluorinated $C_{1-4}$alkoxy" shall mean any $C_{1-4}$alkoxy group as defined above substituted with at least one fluoro atom, preferably one to three fluoro atoms. Suitable examples include but are not limited to —$OCF_3$, —$OCH_2$—$CF_3$, —$OCF_2$—$CF_2$—$CF_2$—$CF_3$, and the like.

When a particular group is "substituted" (e.g., alkyl, phenyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at a diastereomeric excess of greater than or equal to about 80%, more preferably, at a diastereomeric excess of greater than or equal to about 90%, more preferably still, at a diastereomeric excess of greater than or equal to about 95%, more preferably still, at a diastereomeric excess of greater than or equal to about 98%, most preferably, at a diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

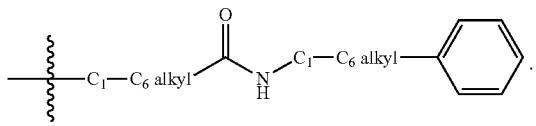

Abbreviations used in the specification, particularly the Schemes and Examples, are as follows:
aq.=Aqueous
BINAP=(2,2'-Bis(diphenylphosphino)-1,1'-binaphthyl)
BLOQ=Below Limit of Quantitation
Boc or BOC=tert-butoxycarbonyl
BSA=Bovine Serum Albumin
cAMP=Cyclic Adenosine Monophosphate
CB1 or CB1R or $CB_1R$=Cannabanoid 1 Receptor
CB2 or CB2R or $CB_2R$=Cannabanoid 2 Receptor
CBz of Cbz=Carboxybenzyl
DCC=N,N'-Dicyclohexylcarbodiimide
DCE=1,1-Dichloroethane
DCM=Dichloromethane
DIPEA or DIEA or =Diisopropylethylamine
Hunig's Base
DMA=Dimethylacetamide
DME=Dimethoxyethane
DMEM=Dulbecco's Modified Eagle Medium
DMF=N,N-Dimethylformamide
DMI=1,3-Dimethyl-2-imidazolidinone
DMSO=Dimethylsulfoxide dppf=1,1'-Bis(diphenylphosphino)ferrocene
EDCl=1-Ethyl-3-(3-dimethylaminopropyl)carbodiimide
EDTA=Ethylene Diamine Tetraacetic Acid
$Et_2O$=Diethyl ether
EtOAc or EA=Ethyl acetate
EtOH=Ethanol
$Et_3SiH$=Triethylsilane
FBS=Fetal Bovine Serum
GPCR=G-coupled Receptor
HATU=O-(7-Azabenzotriazol-1-yl)-N,N,N",N"-Tetramethyl Uronium Hexafluorophosphate
HBSS=Hank's Balanced Salt Solution
HBTU=N N,N,N',N'-Tetramethyl-O-(1H-benzotriazol-1-yl)uronium hexafluorophosphate
HDL=High Density Lipoprotein
HEPES=4-(2-Hydroxyethyl)-1-Piperazine Ethane Sulfonic Acid
HEX=Hexanes
HPLC=High Performance Liquid Chromatography
HOBT or HOBt=Hydroxybenzotriazole
KOt-Bu or t-BuOK or $KOBu^t$ =Potassium t-butoxide
LADA=Latent Autoimmune Diabetes of Adults
LCMS or LC-MS=Liquid Cromatography-Mass Spectrometry
LDA=Lithium diisopropylamide
LDL=Low Density Lipoprotein
LiHMDS=Lithium bis(trimethylsilyl)amide
MeCN=Acetonitrile
MeOH=Methanol
Mesyl=Methylsulfonyl
MTBE=Methyl t-butyl ether
n-BuLi=n-Buttyl Lithium
$NaBH(OAc)_3$=Sodium triacetoxyborohydride
NaHMDS=Sodium bis(trimethylsilyl)amide
NaOAc=Sodium acetate
NaOMe=Sodium methoxide
NaOt-Bu=Sodium t-butoxide
NASH=NonAlcoholic Steatohepatitis
NMR=Nuclear magnetic Resonance
NSB=Non-Specific Binding
OTf=Triflate
PBS=Phosphate Buffered Saline
$PBu_3$=Tributylphosphine
$PCy_3HBF_4$=Tricyclohexylphosphine Tetrafluoroborate
PDC=Pyridinium dichromate
$Pd_2(OAc)_2$=Palladium(II)acetate
$Pd_2(dba)_3$=Tris(dibenzylidene acetone)dipalladium(0)
$Pd(dppf)_2Cl_2$=[1,1'-Bis(diphenylphosphino) ferrocene]dichloropalladium(II)
$Pd(OAc)_2(PPh_3)_2$=Bis(triphenylphosphine)palladium(II) diacetate
$Pd(PPh_3)_4$=Tetrakistriphenylphosphine palladium (0)
PE=Petroleum Ether
$PPh_3$=Triphenyl phosphine
QPhos=1,2,3,4,5-Pentaphenyl-1'-(di-tert-butylphosphino)ferrocene
Ra-Ni=Raney Nickel
RT or rt=Room temperature
sat.=Saturated
sec-BuLi=sec-Butyl lithium
SPhos=2-Dicyclohexylphosphino-2',6'-dimethoxybiphenyl
TBAF=Tetrabutylamonium fluoride hydrate
TBDMS=tert-Butyl dimethylsilyl
t-BuLi=tert-Butyl lithium
TEA=Triethylamine
TFA=Trifluoroacetic Acid
THF=Tetrahydrofuran
THP=Tetrahydropyranyl
TLC=Thin Layer Chromatography
Tosyl=p-Toluenesulfonyl
Tris HCl or Tris-Cl=Tris[hydroxymethyl]aminomethyl hydrochloride
XantPhos=4,5-Bis(diphenylphosphino)-9,9-dimethylxanthene
XPhos=2-Dicyclohexylphosphino-2',4',6'-triisopropylbiphenyl The compounds of the present invention are CB-1 inverse agonists useful for the treatment and/or prevention of metabolic disorders, including obesity, Type I diabetes, Type II diabetes, gestational diabetes, latent autoimmune diabetes of adults (LADA), pre-diabetes, insulin resistance, inadequate glucose tolerance, dyslipidemias (including, but not limited to elevated triglycerides and LDL, and low HDL), nonalcoholic steatohepatitis (NASH), cirrhosis, fatty liver disease, atherosclerosis, hypertension, inflammatory bowel disease, Alzheimer's disease, osteoporosis, multiple sclerosis, traumatic brain injury, arthritis, and neuropathic pain. Preferably, the metabolic disorder is selected from the group consisting of obesity, Type II diabetes, and dyslipidemias. More preferably, the metabolic disorder is obesity or Type II diabetes.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of one or more additional symptoms; and/or (d) delay or avoidance of the development or progression of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named. One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same or different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems. Examples of suitable solvents, bases, reaction temperatures, and other reaction parameters and components are provided in the detailed descriptions which follow herein. One skilled in the art will recognize that the listing of said examples is not intended, and should not be construed, as limiting in any way the invention set forth in the claims which follow thereafter.

As used herein, unless otherwise noted, the term "aprotic solvent" shall mean any solvent that does not yield a proton. Suitable examples include, but are not limited to DMF, 1,4-dioxane, THF, acetonitrile, pyridine, dichloroethane, dichloromethane, MTBE, toluene, acetone, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

One skilled in the art will recognize that during any of the processes for preparation of the compounds of the present invention, as herein described I more detail, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2=CH—CH_2—$, and the like; amides—groups of the formula —C(O)—R' wherein R' is for example methyl, phenyl, trifluoromethyl, and the like; N-sulfonyl derivatives-groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles-Smoles)/(Rmoles+Smoles)]\times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha\text{-obs}]/[\alpha\text{-max}])\times 100.$$

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "*Design of Prodrugs*", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

Compounds of formula (I) wherein $R^1$ is hydrogen may be prepared according to the process outlined in Scheme 1, below.

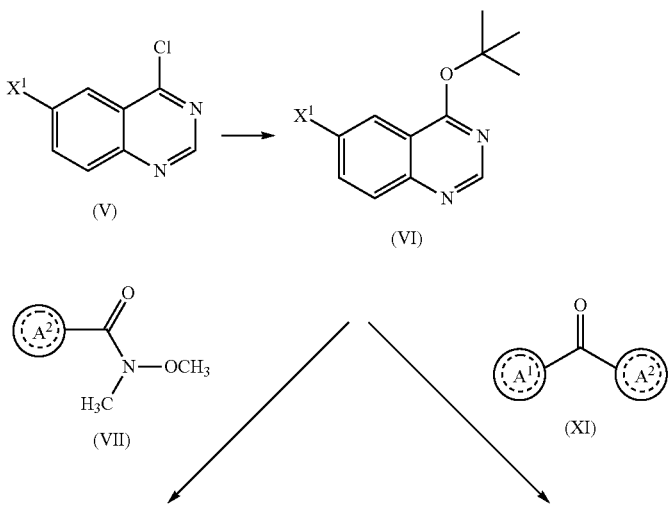

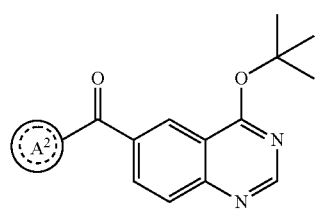 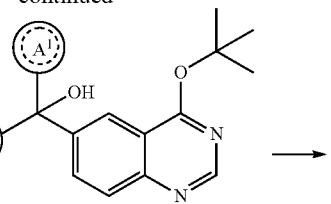

(VIII) (X)

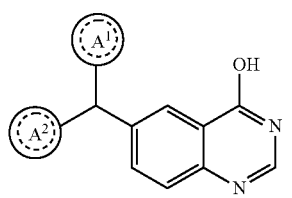 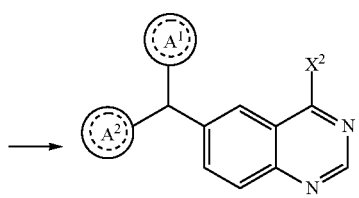 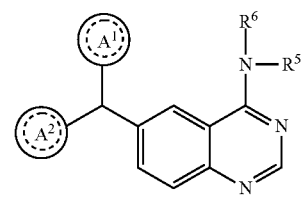

(XII) (XIII) (Ia)

Accordingly, a suitably substituted compound of formula (V), wherein $X^1$ is a suitably selected group such as Br, I, and the like, preferably Br; a known compound or compound prepared by known methods, is reacted with KOt-Bu or NaOt-Bu, and the like; in a suitably selected organic solvent such as toluene, THF, and the like; to yield the corresponding compound of formula (VI).

The compound of formula (VI) is reacted with a suitably selected organolithium reagent such as n-BuLi, sec-BuLi, t-BuLi, and the like; in a suitably selected solvent such as THF, diethyl ether, and the like; at a temperature of about −78° C. (to yield in situ, the corresponding compound where the Br or I is converter to the corresponding Li species); and then reacted with a suitably substituted compound of formula (VII), a known compound or compound prepared by known methods; wherein the reaction mixture is allowed to warm to a temperature in the range of from about 0° C. to about room temperature; to yield the corresponding compound of formula (VIII).

The compound of formula (VIII) is reacted with a suitably substituted compound of formula (IX), wherein $W^1$ is Li, MgBr, MgCl, and the like, a known compound or compound prepared by known methods, to yield the corresponding compound of formula (X). Wherein $W^1$ is Li, the compound of formula (VIII) is reacted with the compound of formula (IX); in a suitably selected organic solvent such as THF, diethyl ether, and the like; at a temperature of about 0° C. Wherein $W^1$ is MgBr or MgCl, the compound of formula (VIII) is reacted with the compound of formula (IX) under Grignard conditions; in a suitably selected anhydrous organic solvent such as THF, diethyl ether, and the like.

Alternatively, the compound of formula (VI) is reacted with a suitably selected organo-lithium reagent such as n-BuLi, sec-BuLi, t-BuLi, and the like; in a suitably selected solvent such as THF, diethyl ether, and the like; at a temperature of about −78° C. (to yield in situ, the corresponding compound where the Br or I is converter to the corresponding Li species); and then reacted with a suitably substituted compound of formula (XI), a known compound or compound prepared by known methods, in a suitably selected organic solvent such as THF, diethyl ether, and the like; to yield the corresponding compound of formula (X).

The compound of formula (X) is reacted $SnC_2.HCl$, $Et_3SiH$ in combination with TFA, or $TiCl_4$ in combination with $Et_3SiH$; in a suitably selected solvent such as DCM, DCE, and the like; to yield the corresponding compound of formula (XII).

The compound of formula (XII) is reacted with a suitably selected chlorinating, brominating or triflating agent such $POCl_3$, oxalylchloride in the presence of a catalytic DMF, $POBr_3$, triflic anhydride in the presence of an organic base (such as TEA, DIPEA, and the like), and the like; neat (for example with $POCl_3$ or $POBr_3$) or in a suitably selected organic solvent such as toluene, benzene, methylene chloride, DCE, and the like; to yield the corresponding compound of formula (XIII), wherein $X^2$ is the corresponding Cl, Br or triflate.

The compound of formula (XIII) is reacted with a suitably substituted compound of formula (XIV), a known compound or compound prepared by known methods; in the presence of a suitably selected base such as Hunig's base, TEA, $Cs_2CO_3$, and the like; in a suitably selected solvent such as DMF, ethanol, isopropanol, and the like; to yield the corresponding compound of formula (Ia).

Alternatively, the compound of formula (XIII) is reacted with a suitably substituted compound of formula (XIV), a known compound or compound prepared by known methods, in the presence of a suitably selected catalyst such as $Pd_2(dba)_3$, $Pd(OAc)_2$, and the like; in the presence of a suitably selected ligand such as dppf, XantPhos, XPhos, and the like; in the presence of a suitably selected base such as $Cs_2CO_3$, $K_2CO_3$, $K_3PO_4$, and the like; in a suitably selected organic solvent such as 1,4-dioxane, toluene, DME, THF, and the like; to yield the corresponding compound of formula (Ia).

Compounds of formula (I) wherein $R^1$ is hydrogen, $R^6$ is

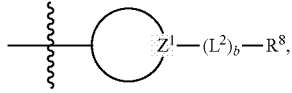

$Z^1$ is N and

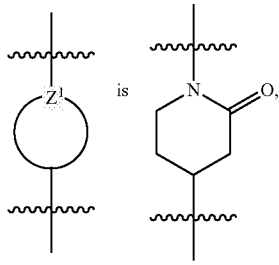

may be prepared according to the procedure as described in Scheme 1 above, reacting the compound of formula (XIII) with a suitably substituted compound of formula (XIVa)

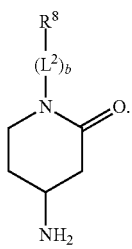
(XVIa)

Compounds of formula (I) wherein $R^1$ is hydrogen, $R^6$ is

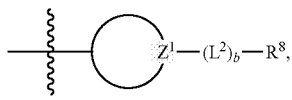

$Z^1$ is C and

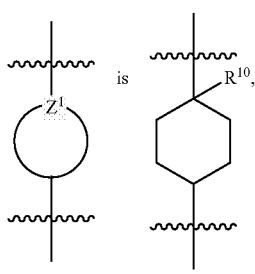

may be prepared according to the process as outlined in Scheme 1, reacting the compound of formula (XIII) with a suitably substituted compound of formula (XIVb)

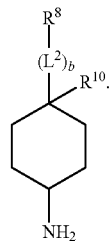
(XIVb)

Compounds of formula (I) wherein $R^1$ is hydrogen, $R^6$ is

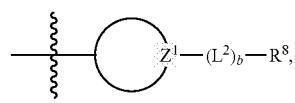

$Z^1$ is N and

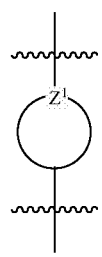

is selected from the group consisting of

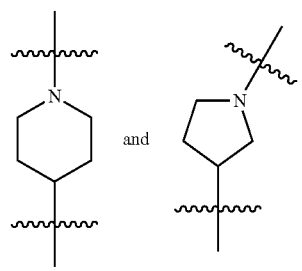 [SMILES: *C1CCN(*)CC1 ; *C1CCN(*)C1]

may alternatively be prepared according to the process as outlined in Scheme 2, below.

Scheme 2

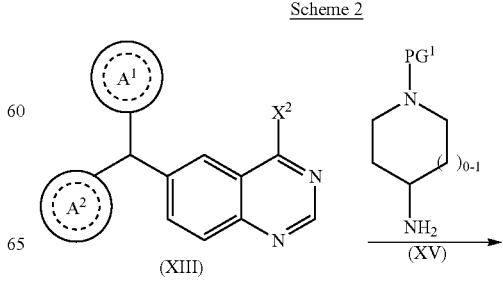

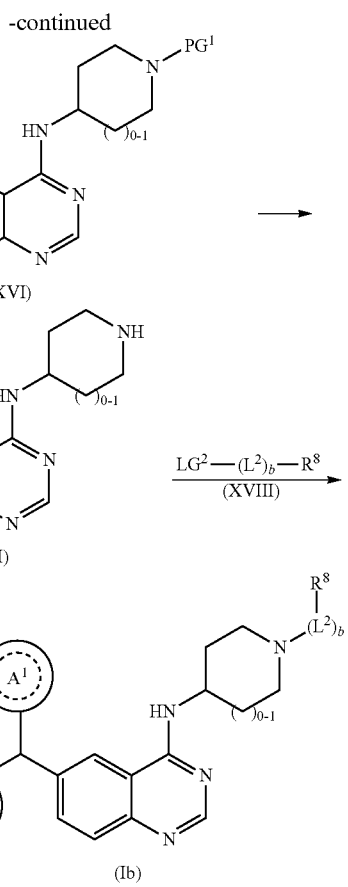

Accordingly, a suitably substituted compound of formula (XIII), prepared for example as described in Scheme 1 above, is reacted with a suitably substituted compound of formula (XV), wherein $PG^1$ is a suitably selected nitrogen protecting group, such as BOC, Cbz, ethoxycarbonyl, and the like, a known compound or compound prepared by known methods; in the presence of a suitably selected base such as Hunig's base, TEA, $Cs_2CO_3$, and the like; in a suitably selected solvent such as DMF, ethanol, isopropanol, and the like; to yield the corresponding compound of formula (XVI).

Alternatively, a suitably substituted compound of formula (XIII), prepared for example as described in Scheme 1 above, is reacted with a suitably substituted compound of formula (XV), wherein $PG^1$ is a suitably selected nitrogen protecting group, such as BOC, Cbz, ethoxycarbonyl, and the like, a known compound or compound prepared by known methods; in the presence of a suitably selected catalyst such as $Pd_2(dba)_3$, Pd(OAc), and the like; in the presence of a suitably selected ligand such as dppf, Xant-Phos, XPhos, and the like; in the presence of a suitably selected base such as $Cs_2CO_3$, $K_2CO_3$, $K_3PO_4$, and the like; in a suitably selected organic solvent such as 1,4-dioxane, toluene, DME, THF, and the like; to yield the corresponding compound of formula (XVI).

The compound of formula (XVI) is de-protected according to known methods, to yield the corresponding compound of formula (XVII). For example, wherein $PG^1$ is BOC, the compound of formula (XVI) is de-protected by reacting with a suitably selected acid such as TFA, HCl, and the like.

The compound of formula (XVII) is reacted with a suitably substituted compound of formula (XVIII), wherein $LG^2$ is a suitably selected leaving group such as Cl, Br, I, tosylate, mesylate, and the like; to yield the corresponding compound of formula (Ib).

In an example, the compound of formula (XVII) is reacted with a suitably substituted compound of formula (XVIII) wherein $L^2$ is selected from the group consisting of —$CH_2$—, —$CH_2CH_2$—, —$CH(CH_3)$— and —$CH(CH_2CH_3)$—, and wherein $LG^2$ is a suitably selected leaving group such as Cl, Br, I, tosylate, mesylate, and the like; in the presence of a suitably selected base such as TEA, Hunig's base, $Na_2CO_3$, and the like; in a suitably selected solvent such as DMF, acetonitrile, DCM, and the like; to yield the corresponding compound of formula (Ib) wherein $L^2$ is the corresponding —$CH_2$—, —$CH_2CH_2$—, —$CH(CH_3)$— or —$CH(CH_2CH_3)$—.

One skilled in the art will recognize that the compound of formula (Ib) wherein $L^2$ is selected from the group consisting of —$CH_2$—, —$CH(CH_3)$— and —$CH(CH_2CH_3)$— may alternatively be prepared by reacting the compound of formula (XVII) with a compound of the formula $R^8$—C(O)H or compound of formula $R^8$—C(O)—$CH_3$ or compound of formula $R^8$—C(O)—$CH_2CH_3$; in the presence of a suitably selected reducing agent such as $NaCNBH_3$, sodium triacetoxyborohydride, and the like; in a suitably selected organic solvent such as DCE, methanol, ethanol, and the like; to yield the corresponding compound of formula (IIa) wherein $L^2$ is the corresponding —$CH_2$—, —$CH(CH_3)$— or —$CH(CH_2CH_3)$—.

In another example, the compound of formula (XVII) is reacted with a suitably substituted compound of formula (XVIII) wherein $L^2$ is —C(O)— or —$SO_2$— and wherein $LG^2$ is for example, Cl; in the presence of a suitably selected tertiary organic base such as TEA, Hunig's base, and the like; in a suitably selected solvent such as DCM, THF, and the like; to yield the corresponding compound of formula (IIa) wherein $L^2$ is the corresponding —C(O)— or —$SO_2$—. Preferably, wherein $R^8$-$L^3$ is $CF_3$—$SO_2$—, the compound of formula (XXVIII) is reacted with triflic anhydride, a known compound, in the presence of TEA, in methylene chloride; to yield the corresponding compound of formula (IIa) wherein $L^2$ is —$SO_2$—.

In another example, the compound of formula (XVII) is reacted with a suitably substituted compound of formula (XVIII) wherein $L^2$ is —C(O)— and wherein $LG^2$ is —OH; in the presence of a suitably selected peptide coupling agent such as DCC, HATU, HBTU, EDCl, and the like; optionally in the presence of a suitably selected base such as Hunig's base, TEA, and the like; in a suitably selected solvent such as DMF, DCM, and the like; to yield the corresponding compound of formula (Ib) wherein $L^2$ is —C(O)—.

In another example, wherein $L^2$ is absent (b is 0) and $R^8$ is selected from, for example, the group consisting of phenyl, pyridin-2-yl, pyridin-3-yl, pyridin-4-yl, thien-2-yl, thien-3-yl, furan-2-yl, furan-3-yl, pyrimidin-2-yl and pyrazin-2-yl; the compound of formula (XVII) is reacted with a suitably substituted compound of formula (XVIII) wherein $L^2$ is absent (i.e. b is 0) and wherein $LG^2$ is suitably selected group such as Cl, Br, I, triflate, and the like; in the presence of a suitably selected catalyst such as $Pd_2(dba)_3$, $Pd(OAc)_2$, and the like; in the presence of a suitably selected ligand such as BINAP, dppf, XantPhos, XPhos, and the like; in the presence of a suitably selected base such as $Cs_2CO_3$, $K_2CO_3$, $K_3PO_4$, and the like; in a suitably selected organic solvent such as 1,4-dioxane, toluene, THF, DME, and the like; to yield the corresponding compound of formula (Ib) wherein $L^2$ is absent (i.e. c is 0).

In another example, wherein L² is absent (b is 0) and R⁸ is selected from the group consisting of cyclopropyl, cyclobutyl, cyclopentyl and cyclohexyl; the compound of formula (XVII) is reacted with a suitably substituted compound of formula (XVIII), wherein L² is absent (i.e. b is 0) and wherein LG² is suitably selected group such as Cl, Br, I, mesylate, tosylate, and the like; in the presence of a suitably selected base such as TEA, Hunig's base, Na₂CO₃, and the like; in a suitably selected solvent such as DMF, acetonitrile, DCM, and the like; to yield the corresponding compound of formula (Ib) wherein L² is absent (i.e. c is 0).

Alternatively, wherein L² is absent (b is 0) and R⁸ is selected from the group consisting of cyclopropyl, cyclobutyl, cyclopentyl and cyclohexyl; the compound of formula (XVII) is reacted with cyclobutanone, cyclopentanone or cyclohexanone, respectively; in the presence of a suitably selected reducing agent such as NaCNBH₃, sodium triacetoxyborohydride, and the like; in a suitably selected organic solvent such as DCE, methanol, ethanol, and the like; to yield the corresponding compound of formula (Ib) wherein L² is absent (i.e. c is 0).

Compounds of formula (I) wherein R¹ is hydrogen, R⁶ is

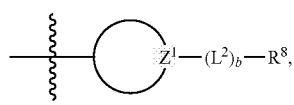

Z¹ is C,

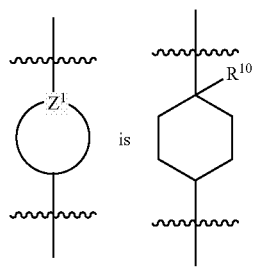

and R¹⁰ is OH may be prepared according to the process as outlined in Scheme 2, by reacting a suitably substituted compound of formula (XIII) with 4-aminocyclohexanone, a known compound, to yield the corresponding compound of formula (XVII-A2)

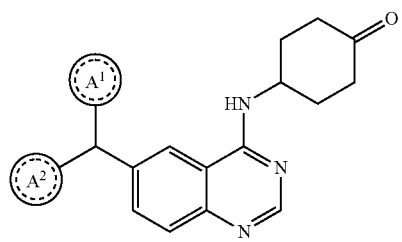

which compound is then reacted with a suitably substituted compound of formula (XVIII), wherein LG² is MgBr or MgCl, under Grignard conditions.

Compounds of formula (XXI) and (XXIII) useful as intermediates in the synthesis of the compounds of formula (I) of the present invention may be prepared according to the process as outlined in Scheme 3, below.

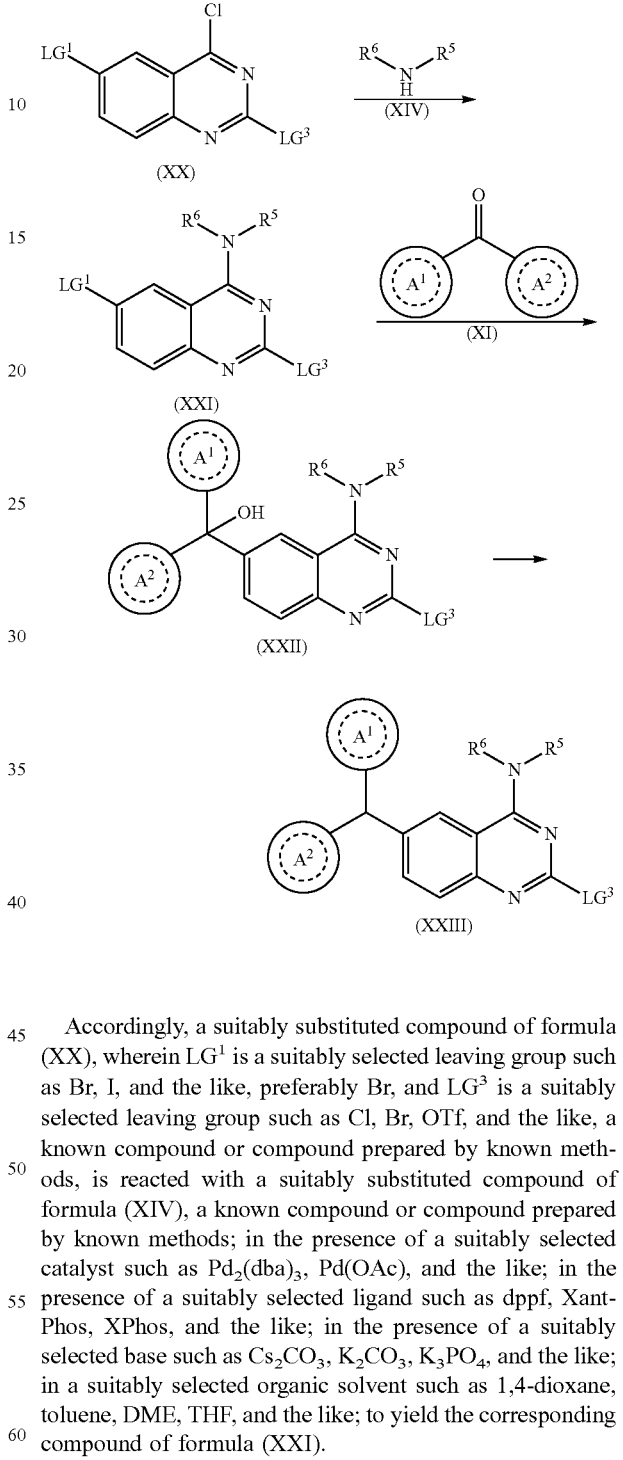

Accordingly, a suitably substituted compound of formula (XX), wherein LG¹ is a suitably selected leaving group such as Br, I, and the like, preferably Br, and LG³ is a suitably selected leaving group such as Cl, Br, OTf, and the like, a known compound or compound prepared by known methods, is reacted with a suitably substituted compound of formula (XIV), a known compound or compound prepared by known methods; in the presence of a suitably selected catalyst such as Pd₂(dba)₃, Pd(OAc), and the like; in the presence of a suitably selected ligand such as dppf, XantPhos, XPhos, and the like; in the presence of a suitably selected base such as Cs₂CO₃, K₂CO₃, K₃PO₄, and the like; in a suitably selected organic solvent such as 1,4-dioxane, toluene, DME, THF, and the like; to yield the corresponding compound of formula (XXI).

The compound of formula (XXI) is reacted with a suitably substituted compound of formula (XI), a known compound or compound prepared by known methods, to yield the corresponding compound of formula (XXII). More particularly, wherein the compound of formula (XI), R⁵ is hydrogen, the compound of formula (XXI) is reacted with a suitably selected first base such as LiHMDS, LDA, and the like; and then reacted with a suitably substituted compound of formula (XI); in the presence of with a suitably selected lithium exchange reagent such as n-BuLi, sec-BuLi, and the like; in a a suitably selected organic solvent such as THF, diethyl ether, 1,4-dioxane, and the like; to yield the corresponding compound of formula (XXII). Alternatively, wherein the compound of formula (XI), $R^5$ is other than hydrogen, the compound of formula (XXI) is reacted with the compound of formula (XI); in the presence of a suitably substituted lithium exchange reagent such as n-BuLi, sec-BuLi, and the like; in a a suitably selected organic solvent such as THF, diethyl ether, 1,4-dioxane, and the like; to yield the corresponding compound of formula (XXII).

The compound of formula (XXII) is reacted with $SnCl_2 \cdot HCl$, $Et_3SiH$ in combination with TFA, or $TiCl_4$ in combination with $Et_3SiH$; in a suitably selected solvent such as DCM, DCE, and the like; to yield the corresponding compound of formula (XXIII).

Compounds of formula (I) wherein $R^1$ is selected from the group consisting of hydroxy, $C_{1-6}$alkyl, cyclopropyl and cyclobutyl may be prepared according to the process as outlined in Scheme 4, below.

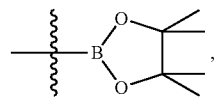

a known compound or compound prepared by known methods; in the presence of a suitably selected catalyst such as $Pd_2(dba)_3$, Pd(OAc), $Pd(dppf)_2C_{1-2}$, and the like; in the presence of a suitably selected ligand such as SPhos, XPhos, QPhos, and the like; in the presence of a suitably selected base such as $Cs_2CO_3$, $K_2CO_3$, $K_3PO_4$, and the like; in a suitably selected organic solvent such as 1,4-dioxane, toluene, DME, THF, and the like; to yield the corresponding compound of formula (Ic).

Alternatively, a suitably substituted compound of formula (XXIII), prepared for example, as described in Scheme 3 above, is reacted with a suitably substituted alkoxide such as $NaOA^2$, $KOA^2$, and the like, wherein A2 is selected from $C_{1-6}$alkyl; in a suitably selected solvent such as THF, toluene, 1,4-dioxane, and the like; to yield the corresponding compound of formula (XXV), wherein $A^2$ is the corresponding $C_{1-6}$alkyl.

The compound of formula (XXV) is reacted with a suitably selected acid, such as HCl (for example 6NHCl), Scheme 4

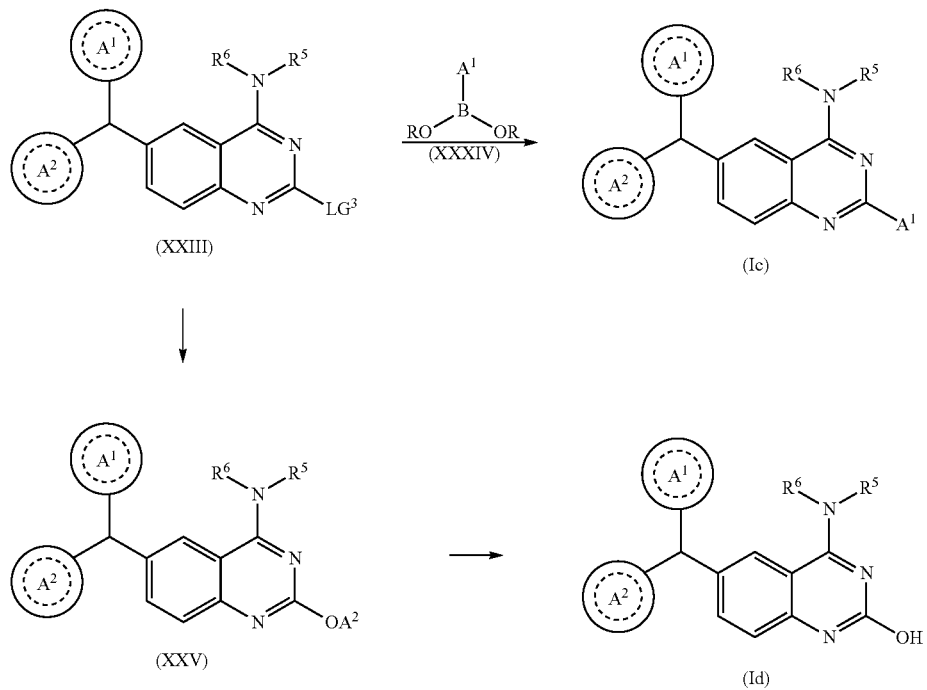

Accordingly, a suitably substituted compound of formula (XXIII), prepared for example, as described in Scheme 3 above, is reacted with a suitably substituted compound of formula (XXIV), wherein $A^1$ is selected from the group consisting of $C_{1-6}$alkyl, cyclopropyl and cyclobutyl, and wherein the two R groups are the same and are selected from the group consisting of hydrogen and $C_{1-4}$alkyl; or the two R groups are taken together with the oxygen atoms to which they are bound to form $H_2SO_4$, TFA, and the like; optionally in the presence of a suitably selected alcohol such as ethanol, and the like; neat or in the presence of a suitably selected DCM, DCE; to yield the corresponding compound of formula (Id).

Compounds of formula (I) wherein $R^1$ is selected from the group consisting of —CH=CH—($C_{1-4}$alkyl)-OH, —CH=CH—($C_{0-3}$alkyl)-$CO_2H$, —CH=CH—($C_{0-3}$alkyl)-C(O)O—($C_{1-4}$alkyl), —CH=CH—($C_{1-4}$alkyl)-$NH_2$, —$CH_2CH_2$—($C_{1-4}$alkyl)-OH, —$CH_2CH_2$—($C_{0-3}$alkyl)-$CO_2H$, —$CH_2CH_2$—($C_{0-3}$alkyl)-C(O)O—($C_{1-4}$alkyl), —CH$_2$CH$_2$—(C$_{1-4}$alkyl)-NH$_2$, may be prepared according to the process as outlined in Scheme 5, below.

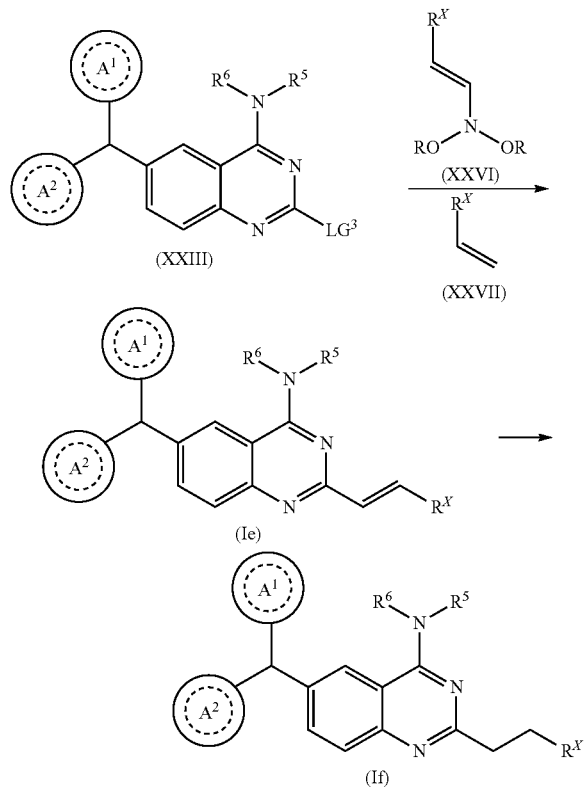

Scheme 5

Accordingly, a suitably substituted compound of formula (XXIII), prepared for example, as described in Scheme 3 above, is reacted with a suitably substituted compound of formula (XXVI), wherein R$^X$ is selected from the group consisting of —(C$_{1-4}$alkyl)-OH, —(C$_{0-3}$alkyl)-CO$_2$PG$^2$, —(C$_{0-3}$alkyl)-C(O)O—(C$_{1-4}$alkyl) and —(C$_{1-4}$alkyl)-NH-PG$^3$, wherein PG$^2$ is a suitably selected oxygen protecting group such as TBDMS, THP, and the like, wherein PG$^3$ is a suitably selected nitrogen protecting group such as BOC, CBz, and the like, and wherein the two R groups are the same and are selected from the group consisting of hydrogen and C$_{1-4}$alkyl; or the two R groups are taken together with the oxygen atoms to which they are bound to form

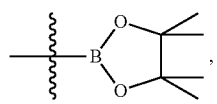

a known compound or compound prepared by known methods; in the presence of a suitably selected catalyst such as Pd(OAc)$_2$, Pd(PPh$_3$)$_4$, Pd$_2$(dba)$_3$·CH$_2$Cl$_2$, and the like; in the presence of a suitably selected ligand such as SPhos, PPh$_3$, dppf, and the like; in the presence of a suitably selected base such as Cs$_2$CO$_3$, K$_2$CO$_3$, K$_3$PO$_4$, and the like; in a suitably selected organic solvent such as 1,4-dioxane, toluene, DME, THF, and the like; to yield the corresponding compound of formula (Ie).

Alternatively, a suitably substituted compound of formula (XXIII), prepared for example, as described in Scheme 3 above, is reacted with a suitably substituted compound of formula (XXVII), wherein R$^X$ is selected from the group consisting of —(C$_{1-4}$alkyl)-OH, —(C$_{0-3}$alkyl)-CO$_2$—PG$^2$, —(C$_{0-3}$alkyl)-C(O)O—(C$_{1-4}$alkyl) and —(C$_{1-4}$alkyl)-NH-PG$^3$, wherein PG$^2$ is a suitably selected oxygen protecting group such as TBDMS, THP, and the like, wherein PG$^3$ is a suitably selected nitrogen protecting group such as BOC, CBz, and the like, in the presence of a suitably selected base such as sodium acetate, TEA, Hunig base, Cs$_2$CO$_3$, and the like; in the presence of a suitably selected palladium catalyst such as Pd(OAc)$_2$(PPh$_3$)$_2$, mixture of Pd(OAc)$_2$ and PBu$_3$, Pd(PPh$_3$)$_4$, and the like; in a suitably selected solvent such as DMF, DMA, DME, and the like; to yield the corresponding compound of formula (Ie).

The compound of formula (Ie) is reacted with a suitably substituted selected reducing agent such as hydrogen gas in the presence of Pd/C, PtO$_2$, Ra-Ni, and the like; in a suitably selected solvent such as methanol, ethanol, ethyl acetate, and the like; to yield the corresponding compound of formula (If).

One skilled in the art will recognize that wherein the compound of formula (If), R$^X$ is —(C$_{1-4}$alkyl)-NH-PG$^3$, the nitrogen protecting group PG$^3$ is removed during the reaction of the compound of formula (Ie) with a suitably selected reducing agent. One skilled in the art will further recognize that therein the compound of formula (If), R$^X$ is selected from the group consisting of —(C$_{0-3}$alkyl)-CO$_2$—PG$^2$, —(C$_{0-3}$alkyl)-C(O)O—(C$_{1-4}$alkyl) and, then the compound of formula (If) is further reacted according to known methods (for example, wherein PG$^2$ is TBDMS (tetrabutyldimethylsilyl), by reacting with TBAF, or wherein —OPG$^2$ is THP (tetrahydropyranyl), by reacting with a suitably selected acid such as HCl), to remove the oxygen protecting group, PG$^2$.

Compounds of formula (I) wherein R$^1$ is —OR$^2$ and wherein R$^2$ is selected from the group consisting of —C$_{1-12}$alkyl, -(hydroxy substituted C$_{2-12}$alkyl), —(C$_{1-12}$alkyl)-N$_3$, —(C$_{2-12}$alkyl)-NR$^E$R$^F$, —(C$_{2-12}$alkyl)-O—(C$_{1-12}$alkyl), —(C$_{2-12}$alkyl)-O—(C$_{1-12}$alkyl)-OH, —(C$_{2-12}$alkyl)-O—(C$_{1-12}$alkyl)-CN, —(C$_{2-12}$alkyl)-O—(C$_{1-12}$alkyl)-CO$_2$H, —(C$_{2-12}$alkyl)-O—(C$_{1-12}$alkyl)-C(O)—O—(C$_{1-6}$alkyl), —(C$_{2-12}$alkyl)-O—(C$_{1-12}$alkyl)-C(O)—NR$^E$R$^F$, —(C$_{1-12}$alkyl)-CO$_2$H, —(C$_{1-12}$alkyl)-C(O)O—(C$_{1-16}$alkyl), —(C$_{2-12}$alkyl)-OC(O)—(C$_{1-6}$alkyl), —(C$_{2-12}$alkyl)-OC(O)—NR$^E$R$^F$, —(C$_{1-12}$alkyl)-C(O)—NR$^E$R$^F$, —(C$_{2-12}$alkyl)-NR$^E$—C(O)—(C$_{1-6}$alkyl), —(C$_{2-12}$alkyl)-NR$^E$—C(O)—(C$_{1-12}$alkyl)-OH and —(C$_{2-12}$alkyl)-NR$^E$—SO$_2$—(C$_{1-6}$alkyl) may be prepared according to the process as outlined in Scheme 6, below.

Scheme 6

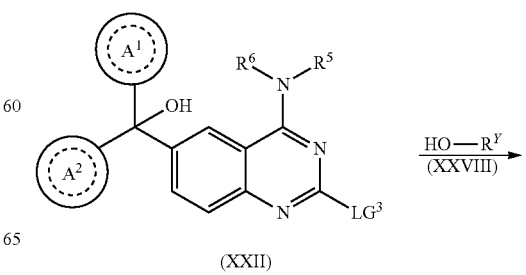

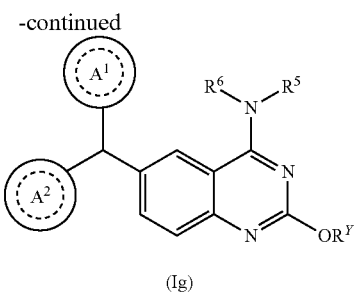

(Ig)

Accordingly, a suitably substituted compound of formula (XXII), prepared for example, as described in Scheme 3 above, is reacted with a suitably substituted compound of formula (XXVI), wherein $R^Y$ is —$C_{1-12}$alkyl, -(hydroxy substituted $C_{2-12}$alkyl), —($C_{1-12}$alkyl)-$N_3$, —($C_{2-12}$alkyl)-$NR^E R^F$, —($C_{2-12}$alkyl)-O—($C_{1-12}$alkyl), —($C_{2-12}$alkyl)-O—($C_{1-12}$alkyl)-OH, —($C_{2-12}$alkyl)-O—($C_{1-12}$alkyl)-CN, —($C_{2-12}$alkyl)-O—($C_{1-12}$alkyl)-$CO_2H$, —($C_{2-12}$alkyl)-O—($C_{1-12}$alkyl)-C(O)—O—($C_{1-6}$alkyl), —($C_{2-12}$alkyl)-O—($C_{1-12}$alkyl)-C(O)—$NR^E R^F$, —($C_{1-12}$alkyl)-$CO_2H$, —($C_{1-12}$alkyl)-C(O)—$NR^E R^F$, —($C_{2-12}$alkyl)-OC(O)—($C_{1-6}$alkyl), —($C_{2-12}$alkyl)-OC(O)O—($C_{1-6}$alkyl), —($C_{2-12}$alkyl)-OC(O)—$NR^E R^F$, —($C_{1-12}$alkyl)-C(O)—$NR^E R^F$, —($C_{2-12}$alkyl)-$NR^E$—C(O)—($C_{1-6}$alkyl), —($C_{2-12}$alkyl)-$NR^E$—C(O)—($C_{1-12}$alkyl)-OH and —($C_{2-12}$alkyl)-$NR^E$—$SO_2$—($C_{1-6}$alkyl), a known compound of compound prepared by known methods; in the presence of a suitably selected base such as NaH, NaHMDS, and the like; in a suitably selected organic solvent such as THF, DMF, DMA, and the like; to yield the corresponding compound of formula (Ig).

Compounds of formula (I) wherein $R^1$ is —$NR^3 R^4$ may be prepared according to the process as outlined in Scheme 7, below.

selected organic solvent such as 1,4-dioxane, DMF, isopropanol, and the like; to yield the corresponding compound of formula (Ig).

Optionally, wherein $R^3$ and/or $R^4$ are hydrogen, the compound of formula (XXIII) is reacted with the compound of formula (XXIX) in the presence of a suitably selected catalyst such as CuI, and the like.

Alternatively, wherein $R^4$ is selected from the group consisting of —C(O)—($C_{1-4}$alkyl), —$SO_2$—($C_{1-4}$alkyl) and —$SO_2$-(halogenated $C_{1-6}$alkyl), a suitably substituted compound of formula (XXIII) is reacted with a suitably substituted compound of formula (XXIX), a known compound or compound prepared by known methods; in the presence of a suitably selected catalysts such as $Pd_2(dba)_3$ or $Pd(OAc)_2$, and the like; in the presence of a suitably selected ligand such as XantPhos, and the like; in a suitably selected solvent such as DMF, DMA, 14,4-dioxane, and the like; to yield the corresponding compound of formula (Ig).

One skilled in the art will recognize that when $R^1$ is —$OR^2$ or —$NR^3 R^4$ and $R^2$, $R^3$ and/or $R^4$ are long, heteroatom containing straight or branched chain substituent groups, then the $R^1$ group may be incorporated into the compound of formula (I) as a single piece (e.g. via a direct coupling reaction); or may be incorporated into the compound of formula (I) via multiple, sequential coupling reactions, each of which serves to build up the long chain substituent group(s), according to known reaction methods; for example as described in the Examples which follow herein.

For example, wherein $R^1$ is —O—$CH_2$—C(O)—NH—$(CH_2)_2$—OH, the $R^1$ group may be incorporated into the compound of formula (I) as described in Scheme 8, below.

Scheme 7

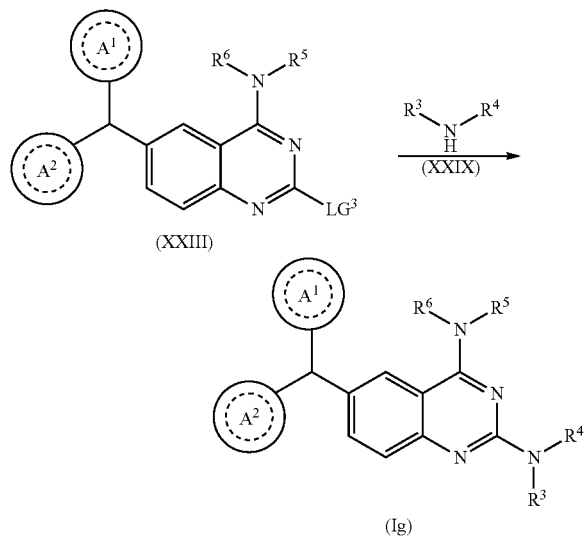

Accordingly, a suitably substituted compound of formula (XXIII), prepared for example, as described in Scheme 3 above, is reacted with a suitably substituted compound of formula (XXIX), a known compound or compound prepared by known methods; in the presence of a suitably selected base such as TEA, DIPEA, and the like; in a suitably Scheme 8

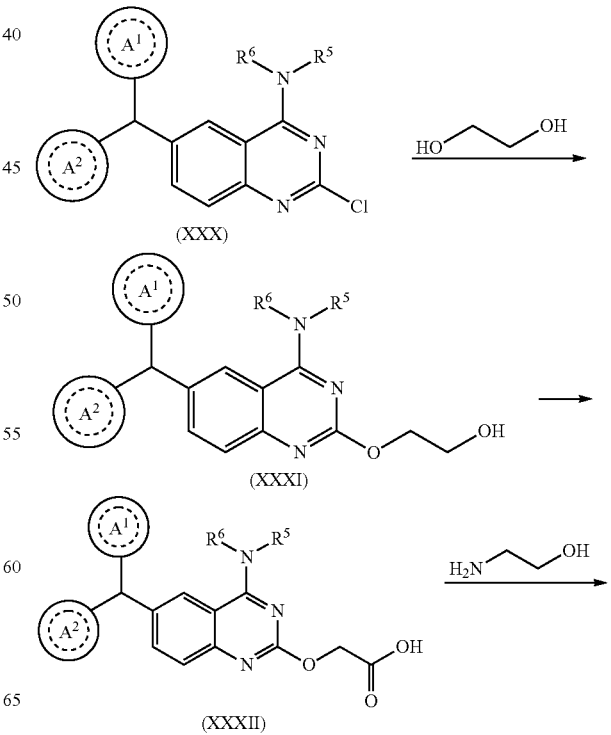

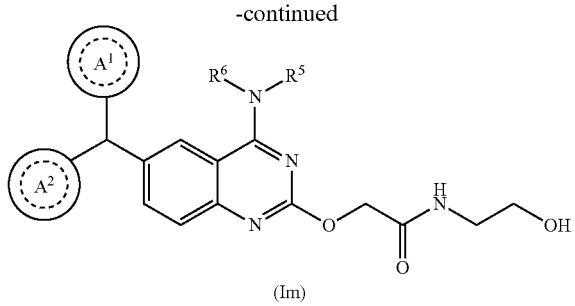

(Im)

Accordingly, a suitably substituted compound of formula (XXX), prepared for example as described in Scheme 3 above, is reacted with ethylene glycol, a known compound; in the presence of a suitably selected base such as NaH, Na, and the like; in a suitably selected organic solvent such as THF, diethyl ether, 1,4-dioxane, and the like; to yield the corresponding compound of formula (XXXI).

The compound of formula (XXXI) is reacted with a suitably selected oxidizing agent such as PDC, sodium periodate/ruthenium (Ill) chloride, and the like; in a suitably selected organic solvent such as DMF, DCE/acetonitrile, and the like; to yield the corresponding compound of formula (XXXII).

The compound of formula (XXXII) is reacted with ethanolamine, a known compound; in the presence of a suitably selected coupling agent such as HATU, EDCl/HOBt, and the like; in the presence of a suitably selected organic base such as DIPEA, TEA, and the like; in a suitably selected organic solvent such as DMF, DCM, DCE, and the like; to yield the corresponding compound of formula (Im).

In another example, wherein $R^1$ is —O(CH$_2$)$_2$—O (CH$_2$)$_2$—CO$_2$H, the $R^1$ group may be incorporated into the compound of formula (I) as described in Scheme 9, below.

Scheme 9

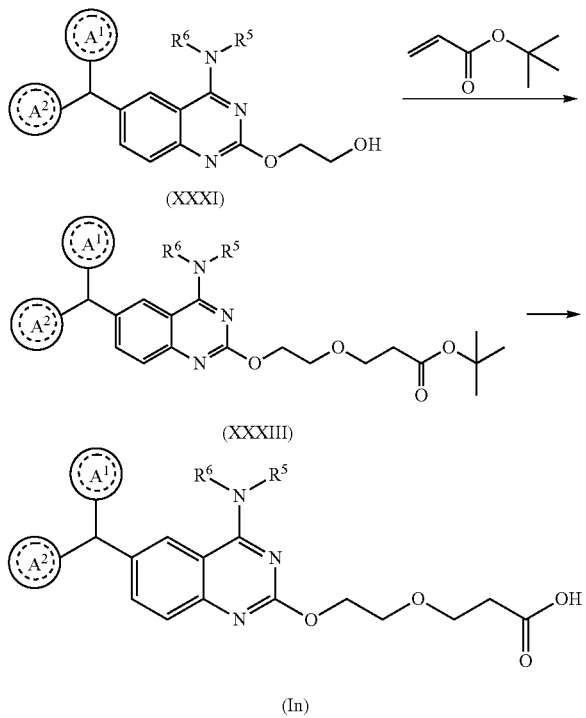

Accordingly, a suitably substituted compound of formula (XXXI), prepared for example as described in Scheme 8 above, is reacted with tert-butyl acrylate, a known compound; in the presence of a suitably selected base such as NaH, KOt-Bu, NaHDMS, and the like; in a suitably selected organic solvent such as THF, DMF, 1,4-dioxane, and the like; to yield the corresponding compound of formula (XXXIII).

The compound of formula (XXXIII) is reacted with a suitably selected acid such as TFA, HCl, and the like; in a suitably selected organic solvent such as DCM, DCE, 1,4-dioxane, and the like; to yield the corresponding compound of formula (In).

One skilled in the art will recognize that in any of the processes described herein, the

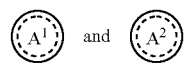

rings (as substituent groups or in reagents containing said substituent groups) may be interchanged, and the synthesis completed as described, to yield the corresponding desired compound.

One skilled in the art will further recognize that additional substitutions and/or substituent transformations (to yield the desired intermediates or compound(s) of the present invention) may be effected according to the procedures as described herein (in the general synthesis schemes and examples) or according to methods known to those skilled in the art.

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.01 mg/kg/day to about 300 mg/kg/day, or any amount or range therein, preferably from about 0.1 mg/kg/day to about 50 mg/kg/day, or any amount or range therein, preferably from about 0.5 mg/kg/day to about 15 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders described herein may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably from about 1.0 mg to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may contain suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of the present invention may be administered in any of the foregoing compositions and according to dosage regimens established in the art whenever treatment of metabolic disorders is required.

The daily dosage of the products may be varied over a wide range from about 0.01 mg to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day, or any amount or range therein. Preferably, the range is from about 0.01 to about 50.0 mg/kg of body weight per day, or any amount or range therein. More preferably, from about 0.05 to about 15.0 mg/kg of body weight per day, or any amount or range therein. More preferably, from about 0.07 to about 7.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

SYNTHESIS EXAMPLES

The following Examples are set forth to aid in the understanding of the invention, and are not intended and should not be construed to limit in any way the invention set forth in the claims which follow thereafter.

In the Synthesis Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

6-((4-chlorophenyl)(thiazol-2-yl)methyl)-N-(1-((trifluoromethyl)sulfonyl)piperidin-4-yl)quinazolin-4-amine (Compound #146)

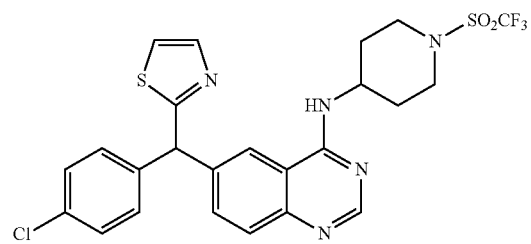

Step 1: tert-butyl N-[1-(trifluoromethane)sulfonylpiperidin-4-yl]carbamate

Into a 1-L round-bottom flask, was placed tert-butyl N-(piperidin-4-yl)carbamate (50 g, 249.65 mmol, 1.00 equiv), dichloromethane (500 mL) and TEA (75 g, 741.18 mmol, 3.00 equiv). This was followed by the addition of (CF$_3$SO$_2$)$_2$O (100 g, 354.61 mmol, 1.40 equiv) dropwise with stirring at 0° C. The resulting solution was stirred overnight at room temperature. The resulting mixture was washed with water (1×500 mL) and then concentrated under vacuum to yield tert-butyl N-[1-(trifluoromethane)sulfonylpiperidin-4-yl]carbamate as a brown solid.

Step 2: 1-(trifluoromethane)sulfonylpiperidin-4-amine hydrochloride

Into a 1-L round-bottom flask, was placed tert-butyl N-[1-(trifluoromethane)sulfonylpiperidin-4-yl]carbamate (70 g, 210.63 mmol, 1.00 equiv), 1,4-dioxane (200 mL) and hydrogen chloride (100 mL, 3.00 equiv, 6M). The resulting solution was stirred overnight at 60° C. in an oil bath. The resulting mixture was then concentrated under vacuum. The resulting residue was re-crystallized from DCM to yield 1-(trifluoromethane)sulfonylpiperidin-4-amine hydrochloride as a light brown solid. $^1$HNMR (400 MHz, DMSO) δ 8.278 (s, 2H), 3.854 (d, J=13.6 Hz, 2H), 3.302 (m, 2H), 2.064 (d, J=10.8 Hz, 2H), 1.543-1.635 (m, 2H)

Step 3: Methyl 4-(1-(trifluoromethylsulfonyl)piperidin-4-ylamino)quinazoline-6-carboxylate Into a 100-mL round-bottom flask, was placed methyl 4-chloroquinazoline-6-carboxylate (1.5 g, 6.74 mmol, 1.00 equiv), 1-(trifluoromethane)sulfonylpiperidin-4-amine hydrochloride (2.44 g, 8.04 mmol, 1.20 equiv), propan-2-ol (50 mL) and TEA (5 mL). The resulting solution was stirred overnight at 25° C. in an oil bath. The resulting mixture was then concentrated under vacuum. The residue was applied onto a silica gel column with dichloromethane/methanol (10:1) to yield methyl 4-[[1-(trifluoromethane)sulfonylpiperidin-4-yl]amino]quinazoline-6-carboxylate as an off-white solid. LC-MS (ES, m/z) 419 [M+H]+

Step 4: 4-(1-(Trifluoromethylsulfonyl)piperidin-4-ylamino)quinazoline-6-carboxylic acid Into a 50-mL round-bottom flask, was placed methyl 4-[[1-(trifluoromethane)sulfonylpiperidin-4-yl]amino]quinazoline-6-carboxylate (1.5 g, 3.59 mmol, 1.00 equiv), methanol (10 mL) and potassium hydroxide (1 M, 10 mL). The resulting solution was stirred overnight at 29° C. in an oil bath. The pH value of the solution was adjusted to pH2 with hydrogen chloride (1 M). The resulting solid was collected by filtration and dried in an oven to yield 4-[[1-(trifluoromethane)sulfonylpiperidin-4-yl]amino]quinazoline-6-carboxylic acid as a yellow solid. (ES, m/z) 405 [M+H]+

Step 5: N-methoxy-N-methyl-4-(1-(trifluoromethylsulfonyl)piperidin-4-ylamino)quinazoline-6-carboxamide Into a 50-mL vial, was placed 4-[[1-(trifluoromethane)sulfonylpiperidin-4-yl]amino]quinazoline-6-carboxylic acid (850 mg, 2.10 mmol, 1.00 equiv), methoxy(methyl)amine hydrochloride (810 mg, 8.30 mmol, 4.00 equiv), HATU (960 mg, 2.52 mmol, 1.20 equiv) and dichloromethane (20 mL). This was followed by the addition of TEA (1.16 g, 11.46 mmol, 5.00 equiv) dropwise with stirring at 0° C. The resulting solution was stirred for 3 h at room temperature. The resulting mixture was washed with water (1×20 mL) and then concentrated. The residue was applied onto a silica gel column with dichloromethane/methanol (15:1) to yield N-methoxy-N-methyl-4-[[1-(trifluoromethane)sulfonylpiperidin-4-yl]amino]quinazoline-6-carboxamide as a yellow solid. LC-MS (ES, m/z) 448 [M+H]+

Step 6: (4-Chlorophenyl)(4-(1-(trifluoromethylsulfonyl)piperidin-4-ylamino)quinazolin-6-yl)methanone Into a 8-mL vial, was placed N-methoxy-N-methyl-4-[[1-(trifluoromethane)sulfonylpiperidin-4-yl]amino]quinazoline-6-carboxamide (200 mg, 0.45 mmol, 1.00 equiv) in tetrahydrofuran (3.0 mL). This was followed by the addition of bromo(4-chlorophenyl)magnesium (1.1 mL, 2.50 equiv) dropwise with stirring at 0° C. The resulting solution was stirred for 3 h at room temperature. The reaction was then quenched by the addition of water (1 mL). The resulting solution was extracted with ethyl acetate (2×10 mL) and the organic layers combined. The residue was applied onto a silica gel column with ethyl acetate/petroleum ether (1:1) to yield 6-[(4-chlorophenyl)carbonyl]-N-[1-(trifluoromethane)sulfonylpiperidin-4-yl]quinazolin-4-amine as a yellow solid. (ES, m/z) 499 [M+H]+

Step 7: (4-Chlorophenyl)(thiazol-2-yl)(4-(1-(trifluoromethylsulfonyl)piperidin-4-ylamino)quinazolin-6-yl)methanol Into a 20-mL vial purged and maintained with an inert atmosphere of nitrogen, was placed 1,3-thiazole (107 mg, 1.26 mmol, 3.00 equiv), tetrahydrofuran (8 mL). This was followed by the addition of n-BuLi (0.5 mL, 3.00 equiv) dropwise with stirring at −78° C. The resulting solution was stirred for 30 min at −78° C. in a liquid nitrogen bath. To the resulting mixture was then added a solution of 6-[(4-chlorophenyl)carbonyl]-N-[1-(trifluoromethane)sulfonylpiperidin-4-yl]quinazolin-4-amine (210 mg, 0.42 mmol, 1.00 equiv) in tetrahydrofuran (2 mL) dropwise with stirring at −78° C. The resulting solution was allowed to react with stirring for an additional 30 min at −78° C. in a liquid nitrogen bath and stirred for 20 min at 0° C. The reaction was then quenched by the addition of water (10 mL). The resulting solution was extracted with ethyl acetate (2×20 mL) acetate and the organic layers combined and concentrated. The residue was applied onto a silica gel column with dichloromethane/methanol (15:1) to yield (4-chlorophenyl)(1,3-thiazol-2-yl)(4-[[1-(trifluoromethane) sulfonylpiperidin-4-yl]amino]quinazolin-6-yl)methanol as a yellow solid. (ES, m/z) 584 [M+H]+

Step 8: 6-((4-Chlorophenyl)(thiazol-2-yl)methyl)-N-(1-(trifluoromethylsulfonyl)piperidin-4-yl)quinazolin-4-amine Into a 8-mL vial, was placed a solution of (4-chlorophenyl)(1,3-thiazol-2-yl)(4-[[1-(trifluoromethane)sulfonylpiperidin-4-yl]amino]quinazolin-6-yl)methanol (200 mg, 0.34 mmol, 1.00 equiv) in acetic acid (3 mL), $SnCl_2 \cdot 2H_2O$ (387 mg, 1.71 mmol, 5.00 equiv) and hydrochloric acid (0.5 mL). The resulting solution was stirred for 3 h at 100° C. in an oil bath. The pH value of the solution was adjusted to pH8 with aqueous sodium bicarbonate. The resulting solution was extracted with ethyl acetate (2×20 mL) and the organic layers combined and concentrated. The residue was applied onto a silica gel column with dichloromethane/methanol (15:1). The resulting residue was purified by re-crystallization from ethyl acetate/petroleum ether, to yield 6-[(4-chlorophenyl)(1,3-thiazol-2-yl)methyl]-N-[1-(trifluoromethane)sulfonylpiperidin-4-yl]quinazolin-4-amine as a white solid. LC-MS (ES, m/z) 568 [M+H]+

$^1$H-NMR (300 MHz, DMSO) δ 8.476 (s, 1H), 8.329 (s, 1H), 8.066-8.041 (m, 1H), 7.847-7.836 (m, 1H), 7.722-7.687 (m, 3H), 7.449-7.421 (m, 2H), 7.376-7.347 (m, 2H), 6.085 (s, 1H), 4.504-4.482 (m, 1H), 3.909-3.865 (m, 2H), 3.455-3.373 (m, 2H), 2.114-2.077 (m, 2H), 1.733-1.617 (m, 2H)

Example 2

6-((4-chlorophenyl)(thiazol-2-yl)methyl)-N-(4-((trifluoromethyl)sulfonyl)phenyl)quinazolin-4-amine (Compound #142)

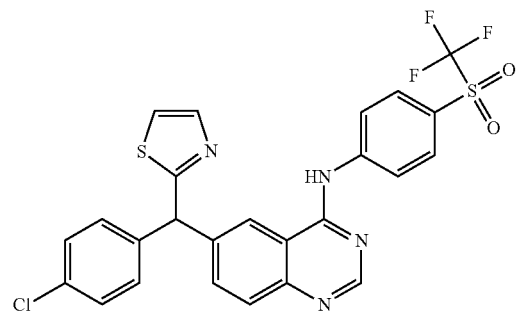 [SMILES: O=S(=O)(c1ccc(Nc2ncnc3ccc(C(c4ccc(Cl)cc4)c4nccs4)cc23)cc1)C(F)(F)F]

Step 1: 6-Bromo-4-tert-butoxyquinazoline

Into a 500-mL round-bottom flask, was placed tetrahydrofuran (300 mL) 6-bromo-4-chloroquinazoline (6 g, 24.64 mmol, 1.00 equiv). The solution was cooled to 0° C. To the cooled solution was then added (tert-butoxy)potassium (30 mL, 1.20 equiv) dropwise over 10 min at 0° C. The resulting solution was allowed to react, with stirring, for an additional 3 h at room temperature. The reaction was then quenched by the addition of water (100 mL). The resulting solution was extracted with ethyl acetate (2×200 mL) and the organic layers combined and dried over anhydrous sodium sulfate, then concentrated under vacuum. The residue was applied onto a silica gel column with ethyl acetate/petroleum ether (15:85), to yield 6-bromo-4-(tert-butoxy)quinazoline as a white solid. (ES, m/z) 282 [M+H]+

Step 2: (4-tert-Butoxyquinazolin-6-yl)(4-chlorophenyl)methanone

Into a 250-mL round-bottom flask purged and maintained with an inert atmosphere of nitrogen, was placed a solution of 6-bromo-4-(tert-butoxy)quinazoline (2.5 g, 8.89 mmol, 1.00 equiv) in tetrahydrofuran (100 mL). This was followed by the addition of n-BuLi (4.25 mL, 1.20 equiv) dropwise with stirring at −78° C. After 40 mins, to the mixture was added a solution of 4-chloro-N-methoxy-N-methylbenzamide (2.17 g, 10.87 mmol, 1.20 equiv) in tetrahydrofuran (20 mL). The resulting solution was stirred for another 30 min at 0° C. in a water/ice bath. The reaction was then quenched by the addition of water (10 mL), and concentrated under vacuum. The residue was applied onto a silica gel column with ethyl acetate/petroleum ether (1:5), to yield of 4-(tert-butoxy)-6-[(4-chlorophenyl)carbonyl]quinazoline as a white solid.

Step 3: (4-tert-Butoxyquinazolin-6-yl)(4-chlorophenyl)(thiazol-2-yl)methanol Into a 250-mL round-bottom flask purged and maintained with an inert atmosphere of nitrogen, was placed a solution of 1,3-thiazole (500 mg, 5.87 mmol, 2.00 equiv) in tetrahydrofuran (60 mL). This was followed by the addition of n-BuLi (2.3 mL, 2.00 equiv) dropwise with stirring at −78° C. After 40 mins, to the mixture was added a solution of 4-(tert-butoxy)-6-[(4-chlorophenyl)carbonyl]quinazoline (1.0 g, 2.93 mmol, 1.00 equiv) in tetrahydrofuran (10 mL) dropwise with stirring at −78° C. The resulting solution was stirred for 30 min at 0° C. in a water/ice bath. The reaction was then quenched by the addition of water (5 mL). The resulting mixture was concentrated under vacuum. The residue was applied onto a silica gel column with ethyl acetate/petroleum ether (3:2), to yield [4-(tert-butoxy)quinazolin-6-yl](4-chlorophenyl)1,3-thiazol-2-ylmethanol as a white solid. (ES, m/z) 426 [M+H]+

Step 4: 6-[(4-Chlorophenyl)(1,3-thiazol-2-yl)methyl]quinazolin-4-ol

Into a 50-mL round-bottom flask, was placed [4-(tert-butoxy)quinazolin-6-yl](4-chlorophenyl)1,3-thiazol-2-ylmethanol (600 mg, 1.41 mmol, 1.00 equiv), SnCl$_2$.2H$_2$O (640 mg, 2.84 mmol, 2.01 equiv), acetic acid (20 mL) and hydrogen chloride (2 mL). The resulting solution was stirred for 1 h at 120° C. The pH value of the solution was adjusted to pH6 with sodium bicarbonate (aq.). The resulting solution was extracted with ethyl acetate (2×50 mL) and the organic layers combined and concentrated under vacuum. The residue was applied onto a silica gel column with dichloromethane/methanol (15:1), to yield 6-[(4-chlorophenyl)(1,3-thiazol-2-yl)methyl]quinazolin-4-ol as a white solid. (ES, m/z) 354 [M+H]+

Step 5: 4-Chloro-6-[(4-chlorophenyl)(1,3-thiazol-2-yl)methyl]quinazoline

Into a 100-mL round-bottom flask, was placed 6-[(4-chlorophenyl)(1,3-thiazol-2-yl)methyl]quinazolin-4-ol (400 mg, 1.13 mmol, 1.00 equiv). POCl$_3$ (15 mL) was then added. The resulting solution was stirred for 3 h at 120° C. in an oil bath. The resulting mixture was concentrated under vacuum. The residue was applied onto a silica gel column with ethyl acetate/petroleum ether (1:1), to yield 4-chloro-6-[(4-chlorophenyl)(1,3-thiazol-2-yl)methyl]quinazoline as a yellow solid. (ES, m/z) 372 [M+H]+

Step 6: 6-((4-Chlorophenyl)(thiazol-2-yl)methyl)-N-(4-(trifluoromethylsulfonyl)phenyl)quinazolin-4-amine Into a 8-mL vial, was placed 4-chloro-6-[(4-chlorophenyl)(1,3-thiazol-2-yl)methyl]quinazoline (100 mg, 0.27 mmol, 1.00 equiv), 4-(trifluoromethane)sulfonylaniline (72 mg, 0.32 mmol, 1.20 equiv), isopropanol (5 mL) and TEA (0.5 mL). The resulting solution was stirred overnight at 100° C. in an oil bath. The resulting mixture was concentrated under vacuum. The residue was applied onto a silica gel column with ethyl acetate/petroleum ether (1:1). The resulting residue was purified by re-crystallization from petroleum ether/ethyl acetate, to yield 6-[(4-chlorophenyl)(1,3-thiazol-2-yl)methyl]-N-[4-(trifluoromethane)sulfonylphenyl]quinazolin-4-amine as an off-white solid. LC-MS (ES, m/z) 561 [M+H]+

$^1$H-NMR (300 MHz, DMSO) δ 10.453 (s, 1H), 8.807 (s, 1H), 8.622 (s, 1H), 8.379-8.357 (m, 2H), 8.152-8.130 (m, 2H), 7.894-7.862 (m, 3H), 7.746-7.739 (m, 1H), 7.465-7.401 (m, 4H), 6.225 (s, 1H),

Example 3

6-((4-chlorophenyl)(thiazol-2-yl)methyl)-N-(4-(trifluoromethyl)phenyl)quinazolin-4-amine (Compound #144)

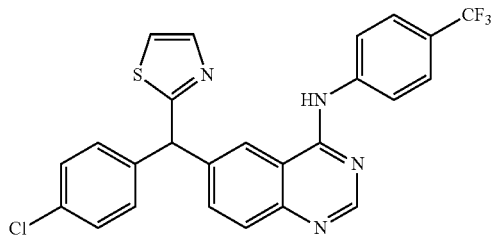 [SMILES: FC(F)(F)c1ccc(Nc2ncnc3ccc(C(c4ccc(Cl)cc4)c4nccs4)cc23)cc1]

Into a 8-mL vial, was placed 4-chloro-6-[(4-chlorophenyl)(1,3-thiazol-2-yl)methyl]quinazoline (100 mg, 0.27 mmol, 1.00 equiv), 4-(trifluoromethyl)aniline (52 mg, 0.32 mmol, 1.20 equiv), isopropanol (5 mL) and TEA (0.5 mL). The resulting solution was stirred overnight at 80° C. in an oil bath. The resulting mixture was concentrated under vacuum. The residue was applied onto a silica gel column with ethyl acetate/petroleum ether (1:1). The resulting residue was purified by re-crystallization from PE/EA, to yield 6-[(4-chlorophenyl)(1,3-thiazol-2-yl)methyl]-N-[4-(trifluoromethyl)phenyl]quinazolin-4-amine as a brown solid LC-MS (ES, m/z) 497 [M+H]+

$^1$H-NMR (300 MHz, DMSO) δ 10.119 (s, 1H), 8.691 (s, 1H), 8.622 (s, 1H), 8.122-8.094 (m, 2H), 7.881-7.746 (m, 6H), 7.481-7.410 (m, 4H), 6.205 (s, 1H)

Example 4

6-(bis(4-chlorophenyl)methyl)-N-(1-((trifluoromethyl)sulfonyl)piperidin-4-yl)quinazolin-4-amine (Compound #145)

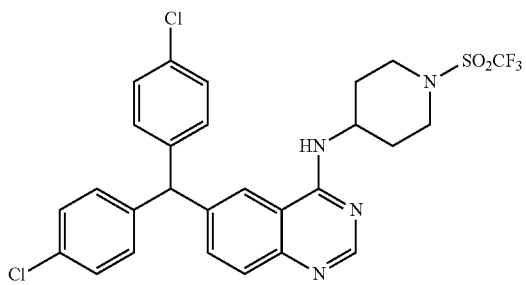

Step 1: Bis(4-chlorophenyl)(4-(1-(trifluoromethylsulfonyl)piperidin-4-ylamino)quinazolin-6-yl)methanol Into a 20-mL vial, was placed a solution of methyl 4-[[1-(trifluoromethane)sulfonylpiperidin-4-yl]amino]quinazoline-6-carboxylate (100 mg, 0.24 mmol, 1.00 equiv) in tetrahydrofuran (8 mL). This was followed by the addition of bromo(4-chlorophenyl)magnesium (1.2 mL, 5.00 equiv) dropwise with stirring at 0° C. The resulting solution was stirred overnight at room temperature. The reaction was then quenched by the addition of water (5 mL). The resulting solution was extracted with ethyl acetate (2×20 mL) and the organic layers combined and concentrated. The residue was applied onto a silica gel column with dichloromethane/methanol (15:1), to yield bis(4-chlorophenyl)(4-[[1-(trifluoromethane)sulfonylpiperidin-4-yl]amino]quinazolin-6-yl)methanol as a yellow solid. (ES, m/z) 611 [M+H]+

Step 2: 6-(Bis(4-chlorophenyl)methyl)-N-(1-(trifluoromethylsulfonyl)piperidin-4-yl)quinazolin-4-amine Into a 8-mL vial, was placed bis(4-chlorophenyl)(4-[[1-(trifluoromethane)sulfonylpiperidin-4-yl]amino]quinazolin-6-yl)methanol (100 mg, 0.16 mmol, 1.00 equiv), acetic acid (3 mL), SnCl$_2$ (181 mg, 0.95 mmol, 5.00 equiv) and hydrochloric acid (0.5 mL). The resulting solution was stirred for 3 h at 100° C. in an oil bath. The pH value of the solution was adjusted to pH8 with sodium bicarbonate. The resulting solution was extracted with ethyl acetate (2×20 mL) and the organic layers combined. The residue was applied onto a silica gel column with dichloromethane/methanol (10:1). The resulting residue was purified by re-crystallization from ethyl acetate/petroleum ether, to yield 47.3 mg (46%) of 6-[bis(4-chlorophenyl)methyl]-N-[1-(trifluoromethane)sulfonylpiperidin-4-yl]quinazolin-4-amine as a white solid.

LC-MS (ES, m/z) 595 [M+H]+

$^1$H-NMR (300 MHz, DMSO) δ 8.466 (s, 1H), 8.211 (s, 1H), 8.026-8.001 (m, 1H), 7.680-7.652 (m, 1H), 7.489-7.398 (m, 5H), 7.178-7.150 (m, 4H), 5.779 (s, 1H), 4.494-4.481 (m, 1H), 3.900-3.855 (m, 2H), 3.448-3.405 (m, 2H), 2.100-2.004 (m, 2H), 1.723-1.601 (m, 2H)

Example 5

6-(bis(4-chlorophenyl)methyl)-N-(4-((trifluoromethyl)sulfonyl)phenyl)quinazolin-4-amine (Compound #134)

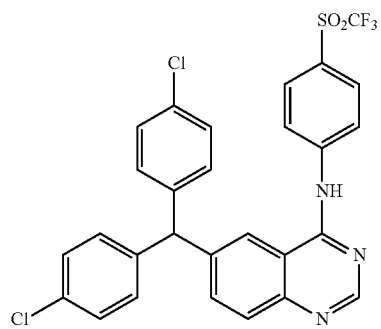

Step 1: [4-(tert-Butoxy)quinazolin-6-yl]bis(4-chlorophenyl)methanol

Into a 100-mL round-bottom flask, was placed a solution of 4-(tert-butoxy)-6-[(4-chlorophenyl)carbonyl]quinazoline (2.8 g, 8.22 mmol, 1.00 equiv) in tetrahydrofuran (40 mL). This was followed by the addition of bromo(4-chlorophenyl)magnesium (41 mL, 5.00 equiv) dropwise with stirring at 0° C. The resulting solution was stirred for 3 h at room temperature. The reaction was then quenched by the addition of water (20 mL). The resulting solution was extracted with ethyl acetate (2×50 mL) and the organic layers combined and concentrated under vacuum. The residue was applied onto a silica gel column with ethyl acetate/petroleum ether (1:1), to yield [4-(tert-butoxy)quinazolin-6-yl]bis(4-chlorophenyl)methanol as a white solid LC-MS (ES, m/z) 453 [M+H]+

Step 2: 6-[Bis(4-chlorophenyl)methyl]quinazolin-4-ol

Into a 250-mL round-bottom flask, was placed [4-(tert-butoxy)quinazolin-6-yl]bis(4-chlorophenyl)methanol (3.0 g, 6.62 mmol, 1.00 equiv), dichloromethane (120 mL), Et$_3$SiH (3.1 g, 26.66 mmol, 4.00 equiv) and trifluoroacetic acid (10 mL). The resulting solution was stirred overnight at room temperature. The resulting mixture was concentrated under vacuum. The residue was applied onto a silica gel column with dichloromethane/methanol (7:1), to yield 6-[bis(4-chlorophenyl)methyl]quinazolin-4-ol as a white solid. LC-MS (ES, m/z) 381 [M+H]+

Step 3: 6-[Bis(4-chlorophenyl)methyl]-4-chloroquinazoline

Into a 100-mL round-bottom flask, was placed 6-[bis(4-chlorophenyl)methyl]quinazolin-4-ol (1.0 g, 2.62 mmol, 1.00 equiv), POCl$_3$ (41.3 g, 269.35 mmol, 102.69 equiv). The resulting solution was stirred for 4 h at 110° C. in an oil bath. The resulting mixture was concentrated under vacuum. The reaction was then quenched by the addition of water (10 mL). The resulting solution was extracted with dichloromethane (2×100 mL) and the organic layers combined and concentrated under vacuum, to yield 6-[bis(4-chlorophenyl)methyl]-4-chloroquinazoline as a brown solid. LC-MS (ES, m/z) 399 [M+H]+

Step 4: 6-[Bis(4-chlorophenyl)methyl]-N-[4-(trifluoromethane)sulfonylphenyl]quinazolin-4-amine Into a 8-mL vial, was placed 6-[bis(4-chlorophenyl)methyl]-4-chloroquinazoline (100 mg, 0.25 mmol, 1.00 equiv), 4-(trifluoromethane)sulfonylaniline (84.8 mg, 0.38 mmol, 1.50 equiv), DMI (5 mL) and $CH_3SO_3H$ (48 mg, 2.00 equiv). The resulting solution was stirred overnight at 80° C. in an oil bath. The resulting solution was diluted with ethyl acetate (50 mL). The resulting mixture was washed with water (2×50 mL). The resulting mixture was concentrated under vacuum. The residue was applied onto a silica gel column with ethyl acetate/petroleum ether (1:3). The resulting residue was purified by re-crystallization from methanol, to yield 6-[bis(4-chlorophenyl)methyl]-N-[4-(trifluoromethane)sulfonylphenyl]quinazolin-4-amine as a white solid. LC-MS (ES, m/z) 588 [M+H]+

$^1$H-NMR (300 MHz, DMSO) δ 10.403 (s, 1H), 8.798 (s, 1H), 8.490 (s, 1H), 8.364-8.342 (m, 2H), 8.144-8.122 (m, 2H), 7.891-7.870 (m, 1H), 7.694-7.673 (m, 1H), 7.440-7.420 (m, 4H), 7.222-7.201 (m, 4H), 5.900 (s, 1H)

Example 6

6-(bis(4-chlorophenyl)methyl)-N-(4-(trifluoromethyl)phenyl)quinazolin-4-amine (Compound #143)

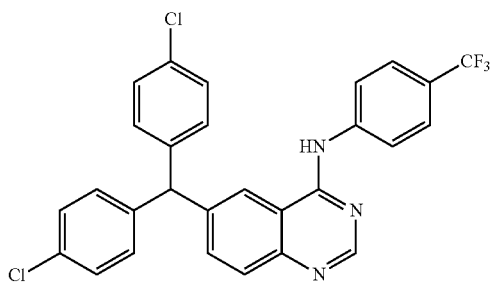 [SMILES: FC(F)(F)c1ccc(Nc2ncnc3ccc(C(c4ccc(Cl)cc4)c4ccc(Cl)cc4)cc23)cc1]

Step 1: Methyl 4-(4-(trifluoromethyl)phenylamino)quinazoline-6-carboxylate

Into a 100-mL round-bottom flask, was placed methyl 4-chloroquinazoline-6-carboxylate (500 mg, 2.25 mmol, 1.00 equiv), 4-(trifluoromethyl)aniline (346 mg, 2.15 mmol, 1.00 equiv) and propan-2-ol (30 mL). This was followed by the addition of TEA (5 mL) dropwise with stirring. The resulting solution was stirred for 4 days at 25° C. in an oil bath. The resulting mixture was concentrated under vacuum. The residue was applied onto a silica gel column with dichloromethane/methanol (15:1), to yield methyl 4-[[4-(trifluoromethyl)phenyl]amino]quinazoline-6-carboxylate as a white solid. (ES, m/z) 348 [M+H]+

Step 2: Bis(4-chlorophenyl)(4-(4-(trifluoromethyl)phenylamino)quinazolin-6-yl)methanol Into a 50-mL round-bottom flask, was placed a solution of methyl 4-[[4-(trifluoromethyl)phenyl]amino]quinazoline-6-carboxylate (150 mg, 0.43 mmol, 1.00 equiv) in tetrahydrofuran (20 mL). This was followed by the addition of bromo(4-chlorophenyl)magnesium (2.2 mL, 5.00 equiv) dropwise with stirring at 0° C. The resulting solution was stirred overnight at 25° C. in an oil bath. The reaction was then quenched by the addition of water (1 mL). The resulting mixture was concentrated under vacuum. The residue was applied onto a silica gel column with dichloromethane/methanol (15:1), to yield bis(4-chlorophenyl)(4-[[4-(trifluoromethyl)phenyl]amino]quinazolin-6-yl)methanol as a brown solid.

Step 3: 6-(Bis(4-chlorophenyl)methyl)-N-(4-(trifluoromethyl)phenyl)quinazolin-4-amine Into a 50-mL round-bottom flask, was placed a solution of bis(4-chlorophenyl)(4-[[4-(trifluoromethyl)phenyl]amino]quinazolin-6-yl)methanol (140 mg, 0.26 mmol, 1.00 equiv) in dichloromethane (10 mL), $Et_3SiH$ (120 mg, 1.03 mmol, 4.00 equiv) and trifluoroacetic acid (1 mL). The resulting solution was stirred overnight at room temperature. The reaction was then quenched by the addition of water (10 mL). The resulting solution was extracted with dichloromethane (2×20 mL) and the organic layers combined and concentrated. The residue was applied onto a silica gel column with ethyl acetate/petroleum ether (1:1). The resulting residue was purified by re-crystallization from MeCN, to yield 6-[bis(4-chlorophenyl)methyl]-N-[4-(trifluoromethyl)phenyl]quinazolin-4-amine as a white solid. LC-MS (ES, m/z) 524 [M+H]+

$^1$H-NMR (300 MHz, DMSO) δ 10.075 (s, 1H), 8.682 (s, 1H), 8.489 (s, 1H), 8.102-8.076 (m, 2H), 7.847-7.757 (m, 3H), 7.661-7.633 (m, 1H), 7.457-7.429 (m, 4H), 7.239-7.211 (m, 4H), 5.888 (s, 1H).

Example 7

6-(bis(4-chlorophenyl)methyl)-N-(1-(2,2,2-trifluoroethyl)piperidin-4-yl)quinazolin-4-amine (Compound #123)

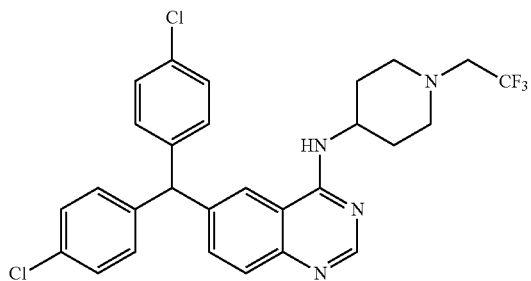 [SMILES: FC(F)(F)CN1CCC(Nc2ncnc3ccc(C(c4ccc(Cl)cc4)c4ccc(Cl)cc4)cc23)CC1]

Into a 25-mL round-bottom flask, was placed 6-[bis(4-chlorophenyl)methyl]-4-chloroquinazoline (60 mg, 0.15 mmol, 1.00 equiv), 1-(2,2,2-trifluoroethyl)piperidin-4-amine (33 mg, 0.18 mmol, 1.20 equiv), propan-2-ol (10 mL) and triethylamine (0.2 mL). The resulting solution was stirred overnight at 25° C. The resulting mixture was concentrated under vacuum. The residue was applied onto a silica gel column with ethyl acetate/petroleum ether (1:2), to yield 6-[bis(4-chlorophenyl)methyl]-N-[1-(2,2,2-trifluoroethyl)piperidin-4-yl]quinazolin-4-amine as a white solid. LC-MS: (ES, m/z): 545 [M+H]+

¹H-NMR: (300 MHz, DMSO, ppm) δ 8.429 (s, 1H), 8.221 (s, 1H), 7.890 (d, J=6.9 Hz, 1H), 7.637 (d, J=8.4 Hz, 1H), 7.472-7.349 (m, 5H), 7.181 (m, 4H), 5.766 (s, 1H), 4.229-4.169 (m, 1H), 3.275-3.139 (m, 2H), 2.989-2.949 (m, 2H), 2.505-2.400 (m, 2H), 1.904-1.870 (m, 2H), 1.705-1.639 (m, 2H).

Example 8

1-(4-((6-(bis(4-chlorophenyl)methyl)quinazolin-4-yl)amino)piperidin-1-yl)-3,3,3-trifluoropropan-1-one (Compound #133)

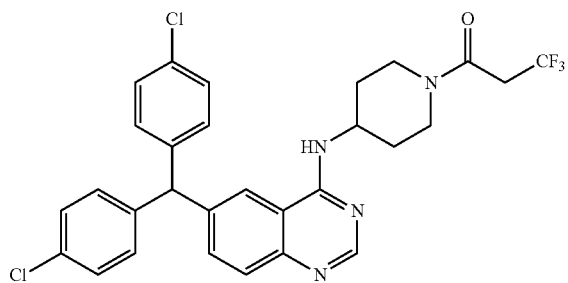 [SMILES: O=C(CC(F)(F)F)N1CCC(Nc2ncnc3ccc(C(c4ccc(Cl)cc4)c4ccc(Cl)cc4)cc23)CC1]

Step 1: tert-Butyl 1-(3,3,3-trifluoropropanoyl)piperidin-4-ylcarbamate

Into a 100-mL round-bottom flask, was placed tert-butyl N-(piperidin-4-yl)carbamate (600 mg, 3.00 mmol, 1.00 equiv), dichloromethane (30 mL) and TEA (606 mg, 5.99 mmol, 2.00 equiv). This was followed by the addition of 3,3,3-trifluoropropanoyl chloride (481.8 mg, 3.29 mmol, 1.10 equiv) dropwise with stirring at −10° C. The resulting solution was stirred for 3 h at room temperature. The resulting mixture was washed with water (2×30 mL). The resulting mixture was concentrated under vacuum. The residue was applied onto a silica gel column with ethyl acetate/petroleum ether (1:3), to yield tert-butyl N-[1-(3,3,3-trifluoropropanoyl)piperidin-4-yl]carbamate as a yellow solid.

Step 2: 1-(4-aminopiperidin-1-yl)-3,3,3-trifluoropropan-1-one hydrochloride

Into a 50-mL round-bottom flask, was placed tert-butyl N-[1-(3,3,3-trifluoropropanoyl)piperidin-4-yl]carbamate (580 mg, 1.87 mmol, 1.00 equiv), 1,4-dioxane (10 mL) and hydrogen chloride (5 mL). The resulting solution was stirred overnight at 60° C. in an oil bath. The resulting mixture was concentrated under vacuum. The resulting residue was purified by re-crystallization from ether, to yield 1-(4-aminopiperidin-1-yl)-3,3,3-trifluoropropan-1-one hydrochloride as a light yellow solid. (ES, m/z) 211 [M+H]+

Step 3: 1-(4-(6-(Bis(4-chlorophenyl)methyl)quinazolin-4-ylamino)piperidin-1-yl)-3,3,3-trifluoropropan-1-one Into a 8-mL vial, was placed 6-[bis(4-chlorophenyl)methyl]-4-chloroquinazoline (50 mg, 0.13 mmol, 1.00 equiv), 1-(4-aminopiperidin-1-yl)-3,3,3-trifluoropropan-1-one hydrochloride (46.3 mg, 0.19 mmol, 1.50 equiv), i-propanol (5 mL) and TEA (38 mg, 0.38 mmol, 3.00 equiv). The resulting solution was stirred overnight at 40° C. in an oil bath. The resulting mixture was concentrated under vacuum. The residue was applied onto a silica gel column with ethyl acetate/petroleum ether (1:1). The resulting residue was purified by re-crystallization from petroleum ether/ethyl acetate, to yield 1-[4-([6-[bis(4-chlorophenyl)methyl]quinazolin-4-yl]amino)piperidin-1-yl]-3,3,3-trifluoropropan-1-one as an off-white solid. LC-MS (ES, m/z) 573 [M+H]+

¹H-NMR: (300 MHz, DMSO) δ 8.481 (s, 1H), 8.225 (s, 1H), 8.052-8.034 (m, 1H), 7.668-7.647 (m, 1H), 7.491-7.469 (m, 1H), 7.417-7.396 (m, 4H), 7.172-7.151 (m, 4H), 5.768 (s, 1H), 4.490-4.413 (m, 2H), 3.930-3.896 (m, 1H), 3.768-3.611 (m, 2H), 3.211-3.149 (m, 1H), 2.775-2.714 (m, 1H), 1.977-1.950 (m, 2H), 1.613-1.490 (m, 2H)

Example 9

6-(bis(4-chlorophenyl)methyl)-N-(1-(pyrimidin-2-yl)piperidin-4-yl)quinazolin-4-amine (Compound #139)

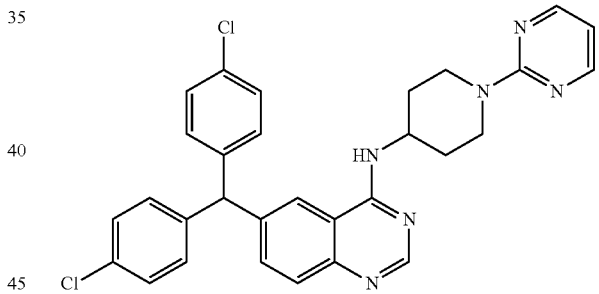

Into a 8-mL vial, was placed 6-[bis(4-chlorophenyl)methyl]-4-chloroquinazoline (50 mg, 0.13 mmol, 1.00 equiv), 1-(pyrimidin-2-yl)piperidin-4-amine dihydrochloride (47 mg, 0.19 mmol, 1.50 equiv), isopropanol (5 mL) and TEA (63 mg, 0.62 mmol, 5.00 equiv). The resulting solution was stirred overnight at 60° C. in an oil bath. The resulting mixture was concentrated under vacuum. The resulting solution was diluted with DCM (5 mL). The solids were filtered out. The resulting residue was purified by re-crystallization from methanol, to yield 6-[bis(4-chlorophenyl)methyl]-N-[1-(pyrimidin-2-yl)piperidin-4-yl]quinazolin-4-amine as a white solid. LC-MS (ES, m/z) 541 [M+H]+

¹H-NMR (300 MHz, DMSO) δ 8.477 (s, 1H), 8.398-8.382 (m, 2H), 8.210 (s, 1H), 7.929-7.904 (m, 1H), 7.675-7.646 (m, 1H), 7.488-7.397 (m, 5H), 7.182-7.154 (m, 4H), 6.650-6.619 (m, 1H), 5.759 (s, 1H), 4.758-4.712 (m, 2H), 4.650-4.500 (m, 1H), 3.087-3.006 (m, 2H), 2.011-1.979 (m, 2H), 1.572-1.532 (m, 2H)

Example 10

6-(bis(4-chlorophenyl)methyl)-N-(1-phenylpiperidin-4-yl)quinazolin-4-amine Dihydrochloride Salt (Compound #137)

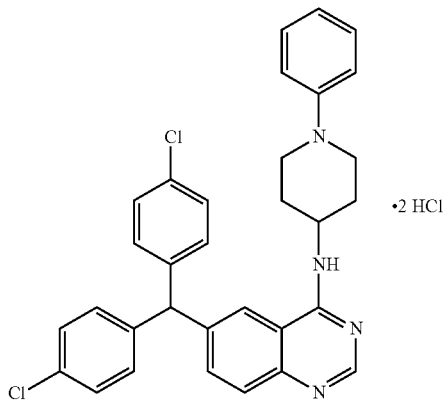 [SMILES: Clc1ccc(C(c2ccc(Cl)cc2)c2ccc3ncnc(NC4CCN(c5ccccc5)CC4)c3c2)cc1]

Step 1: 6-(Bis(4-chlorophenyl)methyl)-N-(1-phenylpiperidin-4-yl)quinazolin-4-amine Into a 8-mL vial, was placed 6-[bis(4-chlorophenyl)methyl]-4-chloroquinazoline (50 mg, 0.13 mmol, 1.00 equiv), 1-phenylpiperidin-4-amine (33 mg, 0.19 mmol, 1.50 equiv), i-propanol (5 mL) and TEA (25 mg, 0.25 mmol, 2.00 equiv). The resulting solution was stirred overnight at 40° C. in an oil bath. The resulting mixture was concentrated under vacuum. The residue was applied onto a silica gel column with dichloromethane/methanol (20:1). The resulting residue was purified by re-crystallization from methanol, to yield 6-[bis(4-chlorophenyl)methyl]-N-(1-phenylpiperidin-4-yl)quinazolin-4-amine as a white solid. (ES, m/z) 539 [M+H]+

Step 2: 6-(Bis(4-chlorophenyl)methyl)-N-(1-phenylpiperidin-4-yl)quinazolin-4-amine Into a 100-mL round-bottom flask, was placed 6-[bis(4-chlorophenyl)methyl]-N-(1-phenylpiperidin-4-yl)quinazolin-4-amine (200 mg, 0.37 mmol, 1.00 equiv), hydrogen chloride/Et$_2$O (50 mL). The resulting solution was stirred overnight at 25° C. The resulting mixture was concentrated under vacuum, to yield 6-[bis(4-chlorophenyl)methyl]-N-(1-phenylpiperidin-4-yl)quinazolin-4-amine dihydrochloride as a yellow solid. LC-MS: (ES, m/z): 539 [M+H]+

$^1$H-NMR: (300 MHz, DMSO, ppm) δ: 9.888 (d, J=7.6 Hz, 1H), 8.895 (s, 1H), 8.608 (s, 1H), 7.864-7.774 (m, 1H), 7.769-7.741 (m, 1H), 7.437-7.409 (m, 4H), 7.314-7.157 (m, 6H), 7.047-7.030 (m, 1H), 6.810 (brs, 1H), 5.840 (s, 1H), 4.740-4.550 (m, 1H), 3.867-3.826 (m, 2H), 3.050-2.855 (m, 2H), 2.040-1.830 m (m, 2H).

Example 11

6-(bis(4-chlorophenyl)methyl)-N-(3-(trifluoromethyl)benzyl)quinazolin-4-amine Dihydrochloride Salt (Compound #136)

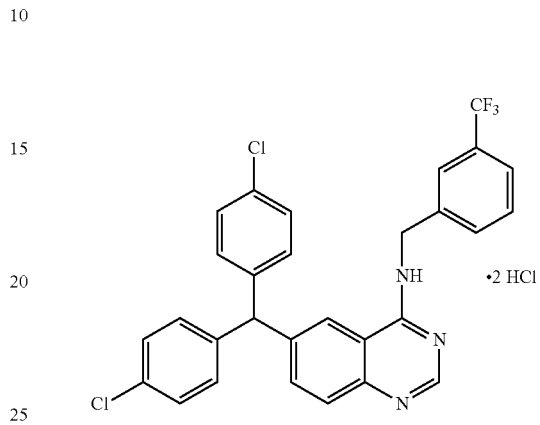

Step 1: 6-(Bis(4-chlorophenyl)methyl)-N-(3-(trifluoromethyl)benzyl)quinazolin-4-amine Into a 25-mL round-bottom flask, was placed 6-[bis(4-chlorophenyl)methyl]-4-chloroquinazoline (200 mg, 0.50 mmol, 1.00 equiv), [3-(trifluoromethyl)phenyl]methanamine (132 mg, 0.75 mmol, 1.50 equiv), isopropanol (10 mL) and TEA (0.3 ml). The resulting solution was stirred overnight at 40° C. The resulting mixture was concentrated under vacuum. The residue was applied onto a silica gel column with dichloromethane/methanol (20:1), to yield 6-[bis(4-chlorophenyl)methyl]-N-[[3-(trifluoromethyl)phenyl]methyl]quinazolin-4-amine as a white solid. (ES, m/z) 538 [M+H]+

Step 2: 6-(Bis(4-chlorophenyl)methyl)-N-(3-(trifluoromethyl)benzyl)quinazolin-4-amine Into a 100-mL round-bottom flask, was placed 6-[bis(4-chlorophenyl)methyl]-N-[[3-(trifluoromethyl)phenyl]methyl]quinazolin-4-amine (200 mg, 0.37 mmol, 1.00 equiv) and hydrogen chloride/Et$_2$O (50 mL). The resulting solution was stirred overnight at 25° C. The resulting mixture was concentrated under vacuum, to yield 6-[bis(4-chlorophenyl)methyl]-N-[[3-(trifluoromethyl)phenyl]methyl]quinazolin-4-amine hydrochloride as a white solid. LC-MS: (ES, m/z): 538 [M+H]+

$^1$H-NMR: (300 MHz, DMSO, ppm) δ 10.805 (m, 1H), 8.907 (s, 1H), 8.508 (d, J=1.9 Hz, 1H), 7.919-7.749 (m, 3H), 7.746-7.518 (m, 3H), 7.471-7.357 (m, 4H), 7.247-7.133 (m, 4H), 5.867 (s, 1H), 5.008 (m, 2H).

Example 12

6-(bis(4-chlorophenyl)methyl)-2-chloro-N-(1-((trifluoromethyl)sulfonyl)piperidin-4-yl)quinazolin-4-amine (Intermediate Compound #200)

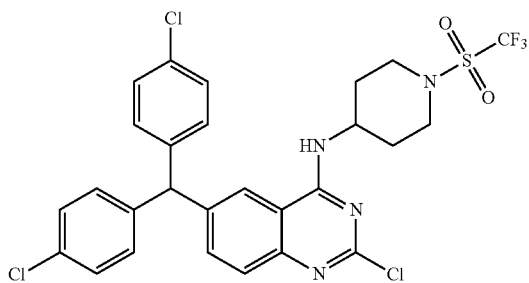 [SMILES: O=S(=O)(N1CCC(Nc2nc(Cl)nc3ccc(C(c4ccc(Cl)cc4)c4ccc(Cl)cc4)cc23)CC1)C(F)(F)F]

Step 1: 6-Bromo-2-chloro-N-(1-(trifluoromethylsulfonyl)piperidin-4-yl)quinazolin-4-amine Into a 250-mL round-bottom flask, was placed a solution of 6-bromo-2,4-dichloroquinazoline (4 g, 14.39 mmol, 1.00 equiv) in tetrahydrofuran (120 mL) and 1-(trifluoromethane)sulfonylpiperidin-4-amine hydrochloride (7.74 g, 28.81 mmol, 2.00 equiv). This was followed by the addition of DIPEA (12.5 g, 96.72 mmol, 5.00 equiv) dropwise with stirring at 0° C. The resulting solution was stirred for 3 h at room temperature. The resulting solution was quenched with sat. NaHCO$_3$ (100 mL) and extracted with ethyl acetate (3×100 mL) and the organic layers combined, dried over anhydrous sodium sulfate and concentrated under vacuum. The residue was applied onto a silica gel column with ethyl acetate/petroleum ether (15:85), to yield 6-bromo-2-chloro-N-[1-(trifluoromethane)sulfonylpiperidin-4-yl]quinazolin-4-amine as a light yellow solid. (ES, m/z) 474 [M+H]+

Step 2: (2-Chloro-4-(1-(trifluoromethylsulfonyl)piperidin-4-ylamino)quinazolin-6-yl)bis(4-chlorophenyl)methanol Into a 500-mL 3-necked round-bottom flask, was placed a solution of 6-bromo-2-chloro-N-[1-(trifluoromethane)sulfonylpiperidin-4-yl]quinazolin-4-amine (4 g, 8.44 mmol, 1.00 equiv) in tetrahydrofuran (200 mL), under nitrogen atmosphere. This was followed by the addition of LiHMDS (18.57 mL, 2.50 equiv, 1 M) dropwise with stirring at 0° C. The resulting solution was stirred for 40 min at 0° C. Then the reaction was cooled to −78° C. To the reaction mixture was added n-BuLi (14.07 mL, 4.00 equiv) dropwise with stirring at −78° C. To the mixture was then added bis(4-chlorophenyl)methanone (4.24 g, 16.89 mmol, 2.00 equiv) dropwise with stirring at −78° C. The reaction was then warmed to rt and quenched by the addition of sat. NaHCO$_3$ (100 mL). The resulting solution was extracted with ethyl acetate (2×200 mL) and the organic layers combined, dried over anhydrous sodium sulfate and concentrated under vacuum. The residue was applied onto a silica gel column with ethyl acetate/petroleum ether (15:85), to yield (2-chloro-4-[[1-(trifluoromethane)sulfonylpiperidin-4-yl]amino]quinazolin-6-yl)bis(4-chlorophenyl)methanol as a white solid. (ES, m/z) 646 [M+H]+

Step 3: 6-(Bis(4-chlorophenyl)methyl)-2-chloro-N-(1-(trifluoromethylsulfonyl)piperidin-4-yl)quinazolin-4-amine Into a 250-mL round-bottom flask, was placed a solution of (2-chloro-4-[[1-(trifluoromethane)sulfonylpiperidin-4-yl]amino]quinazolin-6-yl)bis(4-chlorophenyl)methanol (3 g, 4.64 mmol, 1.00 equiv) in dichloromethane (100 mL). This was followed by the addition of Et$_3$SiH (3.0 mL, 4.00 equiv) dropwise with stirring at 0° C. To the resulting mixture was added trifluoroacetic acid (8.9 mL, 25.00 equiv) dropwise with stirring at 0° C. The resulting solution was stirred for 3 h at room temperature. The reaction was then quenched by the addition of sat. sodium bicarbonate (50 mL). The resulting solution was extracted with ethyl acetate (2×200 mL) and the organic layers combined, dried over anhydrous sodium sulfate and concentrated under vacuum. The residue was applied onto a silica gel column with ethyl acetate/petroleum ether (10:90), to yield 6-[bis(4-chlorophenyl)methyl]-2-chloro-N-[1-(trifluoromethane)sulfonylpiperidin-4-yl]quinazolin-4-amine as a white solid. LCMS (ES, m/z) 631[M+H]+

$^1$H-NMR (400 MHz, DMSO) δ 8.42 (d, J=8.0 Hz, 1H), 8.24 (s, 1H), 7.61 (d, J=8.8 Hz, 1H), 7.51 (d, J=10 Hz, 1H), 7.42 (d, J=8.4 Hz, 4H), 7.16 (d, J=8.4 Hz, 4H), 5.78 (s, 1H), 4.42 (br, 1H), 3.89-3.86 (m, 2H), 3.43-3.32 (m, 2H), 2.09-2.06 (m, 2H), 1.72-1.64 (m, 2H).

Example 13

6-(bis(4-chlorophenyl)methyl)-4-((1-(((trifluoromethyl)sulfonyl)piperidin-4-yl)amino)quinazolin-2-ol (Compound #114)

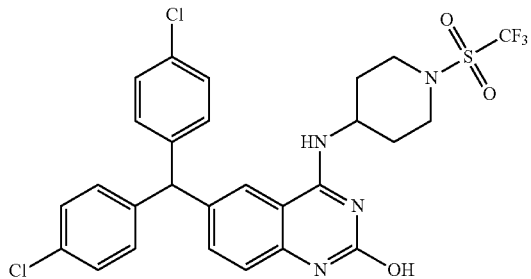 [SMILES: O=S(=O)(N1CCC(Nc2nc(O)nc3ccc(C(c4ccc(Cl)cc4)c4ccc(Cl)cc4)cc23)CC1)C(F)(F)F]

Step 1: 6-(Bis(4-chlorophenyl)(hydroxy)methyl)-4-(1-(trifluoromethylsulfonyl)piperidin-4-ylamino)quinazolin-2-ol Into a 25-mL round-bottom flask, was placed a solution of (2-chloro-4-[[1-(trifluoromethane)sulfonylpiperidin-4-yl]amino]quinazolin-6-yl)bis(4-chlorophenyl)methanol (300 mg, 0.46 mmol, 1.00 equiv) in toluene (10 mL) and KOt-Bu (1.12 mL, 2.40 equiv). The resulting solution was stirred overnight at 85° C. The reaction was then quenched by the addition of water (2 mL). The resulting solution was extracted with ethyl acetate (2×20 mL) and the organic layers combined, dried over anhydrous sodium sulfate and concentrated under vacuum. The residue was applied onto a silica gel column with ethyl acetate/petroleum ether (50:50). This resulted in 6-(bis(4-chlorophenyl)(hydroxy)methyl)-4-(1-(trifluoromethylsulfonyl)piperidin-4-ylamino)quinazolin-2-ol as a colorless oil.

Step 2: 6-(Bis(4-chlorophenyl)methyl)-4-(1-(trifluoromethylsulfonyl)piperidin-4-ylamino)quinazolin-2-ol Into a 25-mL round-bottom flask, was placed a solution of 6-[bis(4-chlorophenyl)(hydroxy)methyl]-4-[[1-(trifluoromethane)sulfonylpiperidin-4-yl]amino]quinazolin-2-ol (288 mg, 0.46 mmol, 1.00 equiv) in dichloromethane (10 mL). This was followed by the addition of Et$_3$SiH (0.294 mL, 4.00 equiv) dropwise with stirring at 0° C. To the resulting mixture was added trifluoroacetic acid (0.88 mL, 25.00 equiv) dropwise with stirring at 0° C. The resulting solution was stirred for 3 h at room temperature. The reaction was then quenched by the addition of sat. NaHCO$_3$ (5 mL). The resulting solution was extracted with ethyl acetate (2×10 mL) and the organic layers combined, dried over anhydrous sodium sulfate and concentrated under vacuum. The residue was applied onto a silica gel column with ethyl acetate/petroleum ether (85:15). The resulting residue was purified again by prep-TLC, used 10% methanol/DCM as eluent, to yield 6-[bis(4-chlorophenyl)methyl]-4-[[1-(trifluoromethane)sulfonylpiperidin-4-yl]amino]quinazolin-2-ol as a white solid. LCMS (ES, m/z) 611 [M+H]$^+$ $^1$H-NMR (300 MHz, DMSO) δ 10.68 (s, 1H), 7.99 (br, 2H), 7.39 (d, J=8.7 Hz, 4H), 7.25 (d, J=8.4 Hz, 1H), 7.14-7.09 (m, 5H), 5.610 (s, 1H), 4.40 (br, 1H), 3.88-3.84 (m, 2H), 3.42-3.32 (m, 2H), 2.05-2.012 (m, 2H), 1.68-1.57 (m, 2H).

Example 14

6-(bis(4-chlorophenyl)methyl)-2-cyclopropyl-N-(1-((trifluoromethyl)sulfonyl)piperidin-4-yl)quinazolin-4-amine (Compound #108)

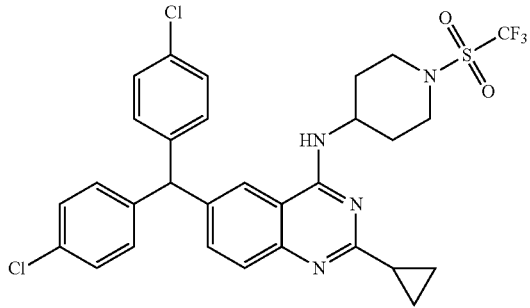 [SMILES: O=S(=O)(N1CCC(Nc2nc(C3CC3)nc3ccc(C(c4ccc(Cl)cc4)c4ccc(Cl)cc4)cc23)CC1)C(F)(F)F]

Into a 50-mL 3-necked round-bottom flask, was placed 6-[bis(4-chlorophenyl)methyl]-2-chloro-N-[1-(trifluoromethane)sulfonylpiperidin-4-yl]quinazolin-4-amine (540 mg, 0.86 mmol, 1.00 equiv), Pd(OAc)$_2$ (10 mg, 0.04 mmol, 0.05 equiv), PCy$_3$HBF$_4$ (tricyclohexylphosphine tetrafluoroborate) (32 mg, 0.10 equiv), K$_3$PO$_4$ (446 mg, 2.10 mmol, 2.40 equiv), cyclopropylboronic acid (148 mg, 1.72 mmol, 2.00 equiv), toluene, (20 mL) and water (1 mL). The resulting solution was heated to reflux (110° C.) for 4 hr, under nitrogen atmosphere. The reaction was then quenched by the addition of sat. NaHCO$_3$ (20 mL). The resulting solution was extracted with ethyl acetate (2×50 mL) and the organic layers combined, dried over anhydrous sodium sulfate and concentrated under vacuum. The resulting residue was purified by Prep-TLC with 1:2 ethyl acetate:hexane as eluent, to yield 6-[bis(4-chlorophenyl)methyl]-2-cyclopropyl-N-[1-(trifluoromethane)sulfonylpiperidin-4-yl]quinazolin-4-amine as a white solid. LCMS (ES, m/z) 635[M+H]$^+$ $^1$H-NMR (400 MHz, DMSO) δ 8.13 (s, 1H), 7.82 (d, J=7.2 Hz, 1H), 7.53 (d, J=8.4 Hz, 1H), 7.41-7.36 (m, 5H), 7.15 (d, J=8.4 Hz, 4H), 5.73 (s, 1H), 4.36 (br, 1H), 3.89-3.86 (m, 2H), 3.43-3.39 (m, 2H), 2.09-1.99 (m, 3H), 1.68-1.64 (m, 2H), 1.02-1.02 (m, 2H), 1.00-0.91 (m, 2H).

Example 15

6-(bis(4-chlorophenyl)methyl)-2-methoxy-N-(1-((trifluoromethyl)sulfonyl)piperidin-4-yl)quinazolin-4-amine (Compound #103)

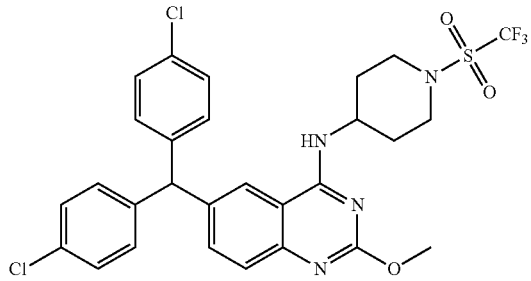 [SMILES: COc1nc(NC2CCN(S(=O)(=O)C(F)(F)F)CC2)c2cc(C(c3ccc(Cl)cc3)c3ccc(Cl)cc3)ccc2n1]

Into a 50-mL sealed tube, was placed 6-[bis(4-chlorophenyl)methyl]-2-chloro-N-[1-(trifluoromethane)sulfonylpiperidin-4-yl]quinazolin-4-amine (100 mg, 0.16 mmol, 1.00 equiv), NaOMe/MeOH (30 mL). The resulting solution was stirred overnight at 120° C. The reaction was then quenched by the addition of water (20 mL). The resulting solution was extracted with ethyl acetate (2×50 mL) and the organic layers combined, dried over anhydrous sodium sulfate and concentrated under vacuum. The resulting residue was purified by Prep-TLC with 10% methanol/DCM as eluent, to yield 6-[bis(4-chlorophenyl)methyl]-2-methoxy-N-[1-(trifluoromethane)sulfonylpiperidin-4-yl]quinazolin-4-amine as a white solid. LCMS (ES, m/z) 625[M+H]$^+$ $^1$H-NMR (300 MHz, DMSO) δ 8.13 (s, 1H), 8.00-7.98 (m, 1H), 7.49-7.33 (m, 6H), 7.15 (d, J=8.4 Hz, 4H), 5.71 (s, 1H), 4.39 (br, 1H), 3.93-3.86 (m, 5H), 3.43-3.39 (m, 2H), 2.09-2.05 (m, 2H), 1.71-1.59 (m, 2H).

Example 16

6-(bis(4-chlorophenyl)methyl)-N4-(1-((trifluoromethyl)sulfonyl)piperidin-4-yl)quinazoline-2,4-diamine (Compound #107)

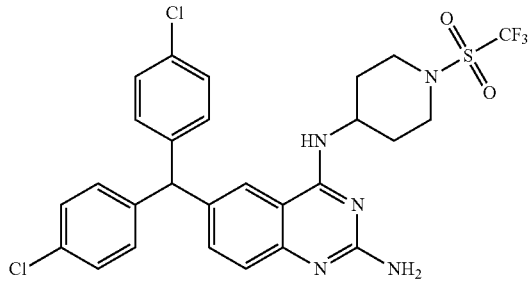 [SMILES: Nc1nc(NC2CCN(S(=O)(=O)C(F)(F)F)CC2)c2cc(C(c3ccc(Cl)cc3)c3ccc(Cl)cc3)ccc2n1]

Into a 30-mL sealed tube, was placed 6-[bis(4-chlorophenyl)methyl]-2-chloro-N-[1-(trifluoromethane)sulfonylpiperidin-4-yl]quinazolin-4-amine (300 mg, 0.48 mmol, 1.00 equiv), NH$_3$/methanol (30 mL) and CuI (91 mg, 0.48 mmol, 1.00 equiv). The resulting solution was stirred overnight at 120° C. The reaction was then quenched by the addition of sat. NaHCO$_3$ (20 mL). The resulting solution was extracted with ethyl acetate (2×30 mL) and the organic layers combined, dried over anhydrous sodium sulfate and concentrated under vacuum. The resulting residue was purified by prep-TLC, with 10% methanol/DCM as eluent, to yield 6-[bis(4-chlorophenyl)methyl]-4-N-[1-(trifluoromethane)sulfonylpiperidin-4-yl]quinazoline-2,4-diamine as a white solid. LCMS (ES, m/z) 610[M+H]$^+$ $^1$H-NMR (400 MHz, DMSO) δ 7.95 (s, 1H), 7.57-7.55 (m, 1H), 7.39 (d, J=8.8 Hz, 4H), 7.18-7.13 (m, 6H), 6.06 (s, 2H), 5.61 (s, 1H), 4.35 (br, 1H), 3.90-3.87 (m, 2H), 3.36-3.31 (m, 2H), 2.08-2.05 (m, 2H), 1.69-1.63 (m, 2H).

Example 17

6-(bis(4-chlorophenyl)methyl)-N2-methyl-N4-(1-((trifluoromethyl)sulfonyl)piperidin-4-yl)quinazoline-2,4-diamine (Compound #113)

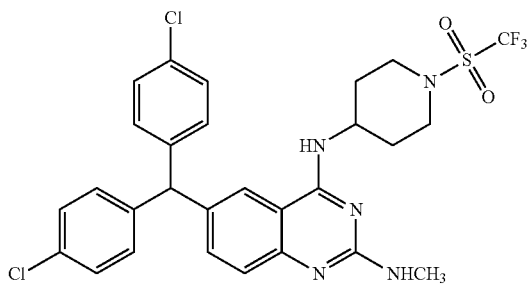 [SMILES: CNc1nc(NC2CCN(S(=O)(=O)C(F)(F)F)CC2)c2cc(C(c3ccc(Cl)cc3)c3ccc(Cl)cc3)ccc2n1]

Into a 30-mL sealed tube, was placed a solution of 6-[bis(4-chlorophenyl)methyl]-2-chloro-N-[1-(trifluoromethane)sulfonylpiperidin-4-yl]quinazolin-4-amine (150 mg, 0.24 mmol, 1.00 equiv) in methanol (20 mL), CH$_3$NH$_2$HCl (163 mg, 10.00 equiv) and triethylamine (0.334 mL, 10.00 equiv). The resulting solution was stirred for 3 days at 50° C. The reaction was then quenched by the addition of sat. sodium bicarbonate (10 mL). The resulting solution was extracted with ethyl acetate (2×50 mL) and the organic layers combined, dried over anhydrous sodium sulfate and concentrated under vacuum. Prep-TLC, used 10% methanol/DCM as eluent to yield 6-[bis(4-chlorophenyl)methyl]-2-N-methyl-4-N-[1-(trifluoromethane)sulfonylpiperidin-4-yl]quinazoline-2,4-diamine as a yellow solid. LCMS (ES, m/z) 624[M+H]$^+$ $^1$H-NMR (300 MHz, DMSO) δ 7.94 (s, 1H), 7.53 (br, 1H), 7.39 (d, J=8.4 Hz, 4H), 7.24-7.18 (m, 2H), 7.14 (d, J=8.4 Hz, 4H), 6.43 (br, 1H), 5.61 (s, 1H), 4.33 (br, 1H), 3.90-3.86 (m, 2H), 3.37-3.33 (m, 2H), 2.81 (d, J=4.5 Hz, 3H), 2.10-2.06 (m, 2H), 1.71-1.59 (m, 2H).

Example 18

N-(6-(bis(4-chlorophenyl)methyl)-4-((1-(((trifluoromethyl)sulfonyl)piperidin-4-yl)amino)quinazolin-2-yl)acetamide (Compound #106)

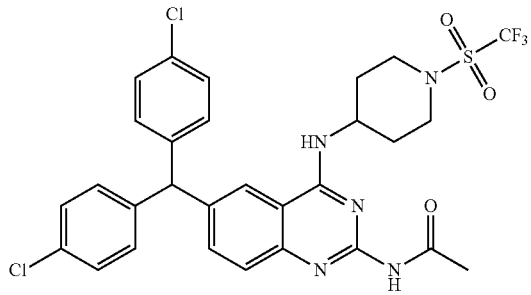 [SMILES: CC(=O)Nc1nc(NC2CCN(S(=O)(=O)C(F)(F)F)CC2)c2cc(C(c3ccc(Cl)cc3)c3ccc(Cl)cc3)ccc2n1]

Into a 25-mL round-bottom flask, was placed a solution of 6-[bis(4-chlorophenyl)methyl]-2-chloro-N-[1-(trifluoromethane)sulfonylpiperidin-4-yl]quinazolin-4-amine (100 mg, 0.16 mmol, 1.00 equiv) in 1,4-dioxane (10 mL), under nitrogen atmosphere. To this solution was then added Pd$_2$(dba)$_3$ (15 mg, 0.02 mmol, 0.10 equiv), XantPhos (28 mg, 0.05 mmol, 0.30 equiv) and Cs$_2$CO$_3$ (73 mg, 0.22 mmol, 1.40 equiv). The resulting solution was heated to reflux for hr. The reaction was then quenched by the addition of sat. NaHCO$_3$ (20 mL). The resulting solution was extracted with ethyl acetate (2×20 mL) and the organic layers combined, dried over anhydrous sodium sulfate and concentrated under vacuum. The resulting residue was purified by Prep-TLC, with 10% methanol/DCM as eluent to yield N-[6-[bis(4-chlorophenyl)methyl]-4-[[1-(trifluoromethane)sulfonylpiperidin-4-yl]amino]quinazolin-2-yl]acetamide as a yellow solid. LCMS (ES, m/z) 652[M+H]$^+$ $^1$H-NMR (300 MHz, DMSO) δ 9.86 (s, 1H), 8.12 (s, 1H), 8.03-8.01 (m, 1H), 7.485-7.36 (m, 6H), 7.15 (d, J=8.4 Hz, 4H), 5.71 (s, 1H), 4.34 (br, 1H), 3.91-3.87 (m, 2H), 3.31-3.29 (m, 2H), 2.29 (s, 3H), 2.17-2.12 (m, 2H), 1.66-1.62 (m, 2H).

Example 19

N-(1-(6-(bis(4-chlorophenyl)methyl)quinazolin-4-yl)piperidin-4-yl)-1,1,1-trifluoromethanesulfonamide (Compound #104)

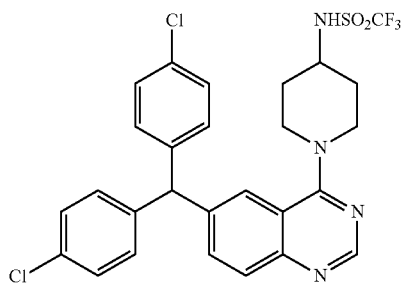

Into a 25-mL round-bottom flask, was placed 6-[bis(4-chlorophenyl)methyl]-4-chloroquinazoline (60 mg, 0.15 mmol, 1.00 equiv), 1,1,1-trifluoro-N-(piperidin-4-yl)methanesulfonamide (45 mg, 0.19 mmol, 1.30 equiv) and propan-2-ol (10 mL), triethylamine (0.2 mL). The resulting solution was stirred overnight at 40° C. The resulting mixture was concentrated under vacuum. The residue was applied onto a silica gel column with dichloromethane:CH$_3$OH (20:1), to yield N-(1-[6-[bis(4-chlorophenyl)methyl]quinazolin-4-yl]piperidin-4-yl)-1,1,1-trifluoromethanesulfonamide as a white solid. LC-MS: (ES, m/z): 595 [M+H]+

$^1$H-NMR: (400 MHz, DMSO, ppm) δ: 9.552 (d, J=8.0 Hz, 1H), 8.620 (s, 1H), 7.784 (d, J=8.8 HZ, 1H), 7.594 (d, J=8.8 Hz, 1H), 7.428 (d, J=8.4 Hz, 4H), 7.325 (s, 1H), 7.188 (d, J=8.4 Hz, 4H), 5.945 (s, 1H), 4.026-3.992 (m, 2H), 3.641 (br, 1H), 3.163-3.102 (m, 2H), 1.857-1.829 (m, 2H), 1.526-1.499 (m, 2H).

Example 20

6-(bis(4-chlorophenyl)methyl)-N-methyl-N-(4-(trifluoromethyl)benzyl)quinazolin-4-amine (Compound #132)

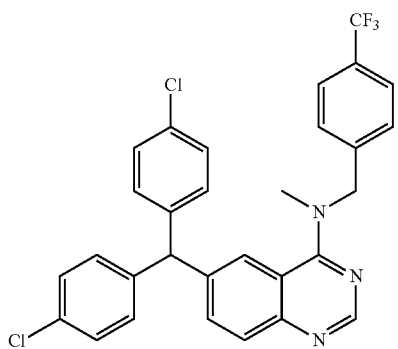 [SMILES: CN(Cc1ccc(C(F)(F)F)cc1)c1ncnc2ccc(C(c3ccc(Cl)cc3)c3ccc(Cl)cc3)cc12]

Into a 8-mL vial, was placed 6-[bis(4-chlorophenyl)methyl]-4-chloroquinazoline (70 mg, 0.18 mmol, 1.00 equiv), methyl([[4-(trifluoromethyl)phenyl]methyl])amine (40 mg, 0.21 mmol, 1.50 equiv), i-propanol (4 mL) and TEA (0.5 mL). The resulting solution was stirred overnight at 40° C. in an oil bath. The resulting mixture was concentrated under vacuum. The residue was applied onto a silica gel column with dichloromethane/methanol (20:1). The resulting residue was purified by re-crystallization from petroleum ether/ethyl acetate, to yield 6-[bis(4-chlorophenyl)methyl]-N-methyl-N-[[4-(trifluoromethyl)phenyl]methyl]quinazolin-4-amine as a white solid. LC-MS (ES, m/z) 552 [M+H]+

$^1$H-NMR (300 MHz, DMSO) δ 8.543 (s, 1H), 7.769-7.581 (m, 5H), 7.443-7.422 (m, 2H), 7.314-7.287 (m, 4H), 7.058-7.031 (m, 4H), 5.789 (s, 1H), 4.925 (s, 2H), 3.136 (s, 3H)

Example 21

6-(bis(4-chlorophenyl)methyl)-N-(3-chloro-4-(trifluoromethyl)phenyl)quinazolin-4-amine (Compound #122)

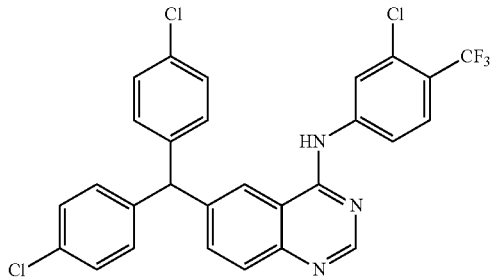 [SMILES: FC(F)(F)c1ccc(Nc2ncnc3ccc(C(c4ccc(Cl)cc4)c4ccc(Cl)cc4)cc23)cc1Cl]

Into a 25-mL round-bottom flask, was placed 6-[bis(4-chlorophenyl)methyl]-4-chloroquinazoline (100 mg, 0.25 mmol, 1.00 equiv), 3-chloro-4-(trifluoromethyl)aniline (59 mg, 0.30 mmol, 1.20 equiv), propan-2-ol (10 mL) and triethylamine (0.1 mL). The resulting solution was stirred overnight at 25° C. The resulting mixture was concentrated under vacuum. The residue was applied onto a silica gel column with ethyl acetate/petroleum ether (2:1), to yield 6-[bis(4-chlorophenyl)methyl]-N-[3-chloro-4-(trifluoromethyl)phenyl]quinazolin-4-amine as a white solid. LC-MS (ES, m/z): 558 [M+H]+

$^1$H-NMR: (400 MHz, DMSO, ppm) δ 10.127 (s, 1H), 8.745 (s, 1H), 8.464 (s, 1H), 8.357 (s, 1H), −8.031 (m, 1H), 7.889-7.832 (m, 2H), 7.652 (d, J=7.5 Hz, 1H), 7.442-7.414 (m, 4H), 7.219-7.191 (m, 4H).

Example 22

(S)-6-(bis(4-chlorophenyl)methyl)-N-(1-(3-(trifluoromethyl)phenyl)ethyl)quinazolin-4-amine (Compound #112)

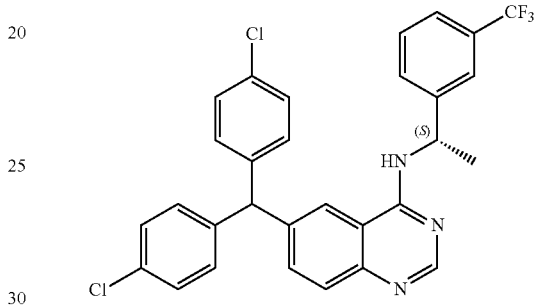

Into a 25-mL round-bottom flask, was placed 6-[bis(4-chlorophenyl)methyl]-4-chloroquinazoline (70 mg, 0.18 mmol, 1.00 equiv), (1S)-1-[3-(trifluoromethyl)phenyl]ethan-1-amine (51 mg, 0.27 mmol, 1.30 equiv), propan-2-ol (8 mL), triethylamine (0.1 mL). The resulting solution was stirred overnight at 25° C. The resulting mixture was concentrated under vacuum. The residue was applied onto a silica gel column with ethyl acetate/petroleum ether (2:3), to yield 6-[bis(4-chlorophenyl)methyl]-N-[(1S)-1-[3-(trifluoromethyl)phenyl]ethyl]quinazolin-4-amine as a white solid. LC-MS (ES, m/z): 552 [M+H]+

$^1$H-NMR (300 MHz, DMSO, ppm) δ 8.554 (d, J=7.5 HZ, 1H), 8.409-8.391 (m, 2H), 7.776-7.656 (m, 6H), 7.487-7.407 (m, 4H), 7.208 (m, 4H), 5.813 (s, 1H), 5.664 (m, 1H), 1.613 (d, J=6.9 Hz, 3H).

Example 23

6-(bis(4-chlorophenyl)methyl)-N-(1-(pyrrolidin-1-ylsulfonyl)piperidin-4-yl)quinazolin-4-amine (Compound #120)

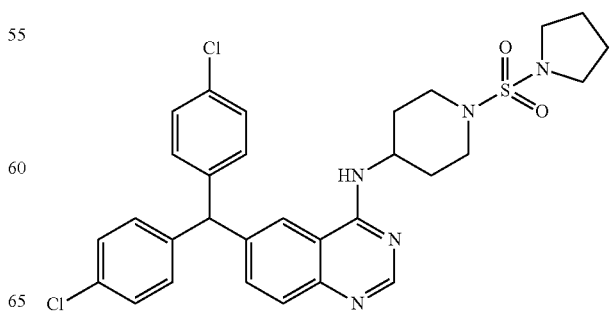

Step 1: tert-Butyl 4-([6-[bis(4-chlorophenyl)methyl] quinazolin-4-yl]amino)piperidine-1-carboxylate Into a 250-mL round-bottom flask, was placed 6-[bis(4-chlorophenyl)methyl]-4-chloroquinazoline (3 g, 7.51 mmol, 1.00 equiv), propan-2-ol (80 mL), triethylamine (5 ml), tert-butyl 4-aminopiperidine-1-carboxylate (2 g, 9.99 mmol, 1.30 equiv). The resulting solution was stirred overnight at 25° C. The resulting mixture was concentrated under vacuum. The residue was applied onto a silica gel column with dichloromethane:CH$_3$OH (20:1), to yield tert-butyl 4-([6-[bis(4-chlorophenyl)methyl]quinazolin-4-yl]amino) piperidine-1-carboxylate as a white solid. (ES, m/z) 563 [M+H]+

Step 2: 6-[bis(4-chlorophenyl)methyl]-N-(piperidin-4-yl)quinazolin-4-amine

Into a 250-mL round-bottom flask, was placed tert-butyl 4-([6-[bis(4-chlorophenyl)methyl]quinazolin-4-yl]amino) piperidine-1-carboxylate (3.6 g, 6.39 mmol, 1.00 equiv), dichloromethane (150 mL) and CF$_3$COOH (15 mL). The resulting solution was stirred overnight at 25° C. The resulting mixture was concentrated under vacuum. The resulting solution was diluted with ethyl acetate (500 mL). The resulting mixture was washed with aqueous sodium bicarbonate (3×300 mL). The mixture was dried over sodium sulfate. The solids were filtered out. The resulting mixture was concentrated under vacuum, to yield 6-[bis(4-chlorophenyl)methyl]-N-(piperidin-4-yl)quinazolin-4-amine as a white solid. (ES, m/z) 463 [M+H]+

Step 3: 6-[Bis(4-chlorophenyl)methyl]-N-[1-(pyrrolidine-1-sulfonyl)piperidin-4-yl]quinazolin-4-amine Into a 25-mL round-bottom flask, was placed 6-[bis(4-chlorophenyl)methyl]-N-(piperidin-4-yl)quinazolin-4-amine (50 mg, 0.11 mmol, 1.00 equiv), dichloromethane (10 mL), triethylamine (0.2 mL), pyrrolidine-1-sulfonyl chloride (20 mg, 0.12 mmol, 1.10 equiv). The resulting solution was stirred overnight at 25° C. The resulting solution was diluted with DCM (10 mL). The resulting mixture was washed with water (2×10 mL). The mixture was dried over anhydrous sodium sulfate. The solids were filtered out. The resulting mixture was concentrated under vacuum. The residue was applied onto a silica gel column with ethyl acetate/petroleum ether (2:1), to yield 6-[bis(4-chlorophenyl)methyl]-N-[1-(pyrrolidine-1-sulfonyl)piperidin-4-yl] quinazolin-4-amine as a white solid. LC-MS (ES, m/z): 596 [M+H]+

$^1$H-NMR (300 MHz, DMSO, ppm) δ: 8.452 (s, 1H), 8.236 (s, 1H), 7.978 (d, J=7.2 Hz, 1H), 7.666-7.637 (d, J=8.7 Hz, 1H), 7.477-7.394 (m, 5H), 7.178-7.150 (m, 4H), 5.768 (s, 1H), 4.348 (br, 1H), 3.667-3.627 (m, 2H), 3.244-3.200 (m, 4H), 2.989-2.910 (m, 2H), 1.999-1.962 (m, 2H), 1.894-1.892 (m, 4H), 1.662-1.584 (m, 2H).

Example 24

6-(bis(4-chlorophenyl)methyl)-N-(1-(pyridin-2-yl) piperidin-4-yl)quinazolin-4-amine (Compound #130)

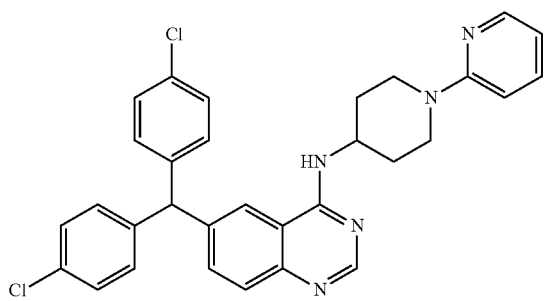 [SMILES: Clc1ccc(C(c2ccc(Cl)cc2)c2ccc3ncnc(NC4CCN(c5ccccn5)CC4)c3c2)cc1]

Into a 8-mL vial, was placed 6-[bis(4-chlorophenyl) methyl]-4-chloroquinazoline (70 mg, 0.18 mmol, 1.00 equiv), 1-(pyridin-2-yl)piperidin-4-amine hydrochloride (50 mg, 0.23 mmol, 1.20 equiv), isopropanol (4 mL) and TEA (0.5 mL). The resulting solution was stirred overnight at 40° C. in an oil bath. The resulting mixture was concentrated under vacuum. The residue was applied onto a silica gel column with dichloromethane/methanol (20:1). The resulting residue was purified by re-crystallization from petroleum ether/ethyl acetate, to yield 6-[bis(4-chlorophenyl)methyl]-N-[1-(pyridin-2-yl)piperidin-4-yl]quinazolin-4-amine as a white solid. LC-MS (ES, m/z) 540 [M+H]+

$^1$H-NMR (300 MHz, DMSO) δ 8.497 (s, 1H), 8.205 (s, 1H), 8.129-8.124 (m, 1H), 7.943-7.913 (m, 1H), 7.656-7.627 (m, 1H), 7.552-7.378 (m, 6H), 7.163-7.135 (m, 4H), 6.900-6.871 (m, 1H), 6.624-6.585 (m, 1H), 5.735 (s, 1H), 4.535-4.484 (m, 1H), 4.407-4.363 (m, 2H), 2.996-2.916 (m, 2H), 1.990-1.925 (m, 2H), 1.632-1.522 (m, 2H)

Example 25

4-((6-(bis(4-chlorophenyl)methyl)quinazolin-4-yl) amino)piperidin-2-one (Intermediate Compound)

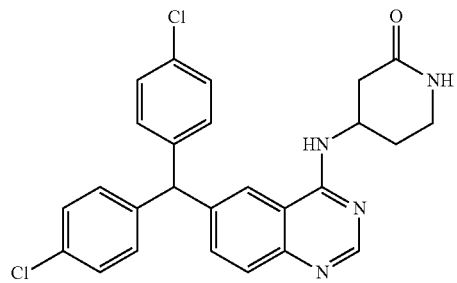 [SMILES: O=C1CC(Nc2ncnc3ccc(C(c4ccc(Cl)cc4)c4ccc(Cl)cc4)cc23)CCN1]

Into a 50-mL round-bottom flask, was placed 6-[bis(4-chlorophenyl)methyl]-4-chloroquinazoline (150 mg, 0.38 mmol, 1.00 equiv), 4-aminopiperidin-2-one (55.6 mg, 0.49 mmol, 1.30 equiv), propan-2-ol (20 mL) and triethylamine (0.2 mL). The resulting solution was stirred overnight at 40° C. The resulting mixture was concentrated under vacuum. The residue was applied onto a silica gel column with dichloromethane:CH$_3$OH (10:1), to yield 4-([6-[bis(4-chlorophenyl)methyl]quinazolin-4-yl]amino)piperidin-2-one as a white solid. LC-MS (ES, m/z): 477 [M+H]$^+$ $^1$H-NMR (400 MHz, DMSO-d6) δ 8.472 (s, 1H), 8.258 (d, J=1.8 Hz, 1H), 8.044 (d, J=7.1 Hz, 1H), 7.678-7.656 (m, 1H), 7.615 (s, 1H), 7.449-7.402 (m, 4H), 7.175-7.158 (m, 4H), 5.781 (s, 1H), 4.569 (br, 1H), 3.221-3.181 (m, 2H), 2.675-2.581 (m, 1H), 2.382-2.315 (m, 1H), 2.090-2.059 (m, 1H), 1.837-1.740 (m, 1H).

Example 26

4-((6-(bis(4-chlorophenyl)methyl)quinazolin-4-yl)amino)-1-phenylpiperidin-2-one (Compound #102)

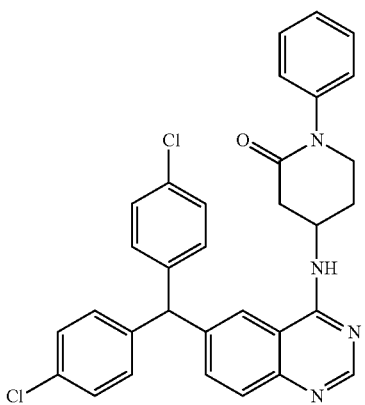 [SMILES: O=C1CC(Nc2ncnc3ccc(C(c4ccc(Cl)cc4)c4ccc(Cl)cc4)cc23)CCN1c1ccccc1]

Into a 25-mL 3-necked round-bottom flask purged and maintained with an inert atmosphere of nitrogen, was placed 4-([6-[bis(4-chlorophenyl)methyl]quinazolin-4-yl]amino)piperidin-2-one (60 mg, 0.13 mmol, 1.00 equiv), bromobenzene (40 mg, 0.25 mmol, 2.00 equiv), Pd$_2$(dba)$_3$ (12 mg, 0.01 mmol, 0.10 equiv), XantPhos (22 mg, 0.04 mmol, 0.30 equiv), Cs$_2$CO$_3$ (82 mg, 0.25 mmol, 2.00 equiv) and 1,4-dioxane (15 mL). The resulting solution was heated to reflux overnight. The reaction mixture was cooled with a water/ice bath. The resulting solution was diluted with ethyl acetate (30 mL). The resulting mixture was washed with water (2×20 mL). The mixture was dried over anhydrous sodium sulfate. The solids were filtered out. The resulting mixture was concentrated under vacuum. The residue was applied onto a silica gel column with dichloromethane/methanol (30:1), to yield 4-([6-[bis(4-chlorophenyl)methyl]quinazolin-4-yl]amino)-1-phenylpiperidin-2-one as a white solid. LC-MS (ES, m/z): 553 [M+H]$^+$ $^1$H-NMR (400 MHz, DMSO, ppm) δ: 8.580 (s, 1H), 8.550 (brs, 1H), 8.309 (s, 1H), 7.691 (d, J=8.4 Hz, 1H), 7.530 (d, J=8.4 Hz, 1H), 7.413-7.310 (m, 6H), 7.292-7.224 (m, 3H), 7.173-7.147 (m, 4H), 5.800 (s, 1H), 4.785-4.776 (m, 1H), 3.784-3.729 (m, 2H), 2.882-2.826 (m, 1H), 2.651-2.608 (m, 1H), 2.487-2.310 (m, 1H), 2.133-2.095 (m, 1H).

Example 27

Methyl 2-((4-(((6-(bis(4-chlorophenyl)methyl)quinazolin-4-yl)amino)piperidin-1-yl)sulfonyl)acetate (Compound #110)

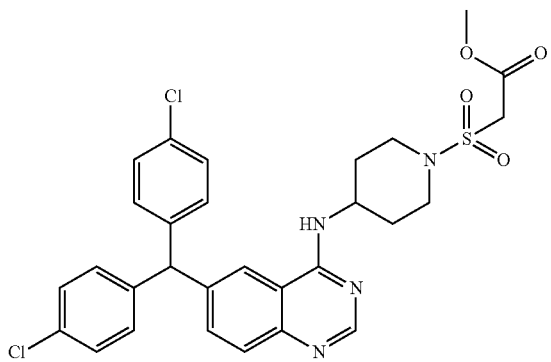 [SMILES: COC(=O)CS(=O)(=O)N1CCC(Nc2ncnc3ccc(C(c4ccc(Cl)cc4)c4ccc(Cl)cc4)cc23)CC1]

Into a 25-mL round-bottom flask, was placed 6-[bis(4-chlorophenyl)methyl]-N-(piperidin-4-yl)quinazolin-4-amine (200 mg, 0.43 mmol, 1.00 equiv), dichloromethane (20 mL), triethylamine (0.2 mL) and methyl 2-(chlorosulfonyl)acetate (82 mg, 0.48 mmol, 1.10 equiv). The resulting solution was stirred overnight at 25° C. The resulting mixture was concentrated under vacuum. The residue was applied onto a silica gel column with dichloromethane:CH$_3$OH (30:1), to yield methyl 2-[4-([6-[bis(4-chlorophenyl)methyl]quinazolin-4-yl]amino)piperidine-1-sulfonyl]acetate as a white solid. LC-MS (ES, m/z): 599 [M+H]$^+$ $^1$H-NMR (300 MHz, DMSO, ppm) δ 8.462 (s, 1H), 8.231 (s, 1H), 8.022 (br, 1H), 7.655 (d, J=8.7 Hz, 1H), 7.484-7.393 (m, 5H), 7.177-7.149 (m, 4H), 5.773 (s, 1H), 4.314 (overlapping m, 3H), 3.720-3.685 (m, 5H), 3.041-2.965 (m, 2H), 2.047-2.008 (m, 2H), 1.694-1.661 (m, 2H).

Example 28

2-((4-(((6-(bis(4-chlorophenyl)methyl)quinazolin-4-yl)amino)piperidin-1-yl)sulfonyl)ethanol (Compound #78)

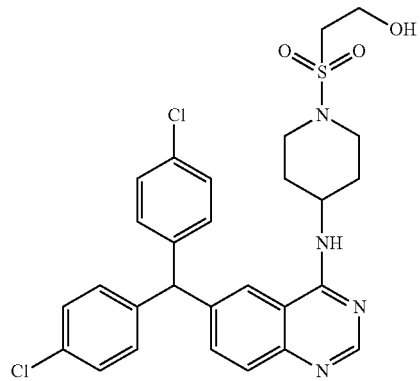 [SMILES: O=S(=O)(CCO)N1CCC(Nc2ncnc3ccc(C(c4ccc(Cl)cc4)c4ccc(Cl)cc4)cc23)CC1]

Step 1: Methyl 2-(4-(tert-butoxycarbonylamino)piperidin-1-ylsulfonyl)acetate Into a 50-mL 3-necked round-bottom flask, was placed tert-butyl N-(piperidin-4-yl)carbamate (440 mg, 2.20 mmol, 1.00 equiv), dichloromethane (20 mL) and triethylamine (1 mL). To the resulting mixture was then added methyl 2-(chlorosulfonyl)acetate (400 mg, 2.32 mmol, 1.20 equiv) dropwise with stirring at 0° C. The resulting solution was stirred overnight at 25° C. The resulting mixture was the washed with water (2×20 mL), dried over anhydrous sodium sulfate and the solids filtered out. The filtrate was then concentrated under vacuum to yield methyl 2-(4-[[(tert-butoxy)carbonyl]amino]piperidine-1-sulfonyl)acetate as a yellow solid.

Step 2: Methyl 2-(4-aminopiperidin-1-ylsulfonyl)acetate

Into a 100-mL round-bottom flask, was placed methyl 2-(4-[[(tert-butoxy)carbonyl]amino]piperidine-1-sulfonyl)acetate (350 mg, 1.04 mmol, 1.00 equiv) and hydrogen chloride/EtOH (40 mL). The resulting solution was stirred overnight at 25° C. The resulting mixture was then concentrated under vacuum to yield methyl 2-(4-aminopiperidine-1-sulfonyl)acetate hydrochloride as a white solid. (ES, m/z) 237 [M+H]+

Step 3: Ethyl 2-[4-([6-[bis(4-chlorophenyl)methyl]quinazolin-4-yl]amino)piperidine-1-sulfonyl]acetate Into a 50-mL round-bottom flask, was placed 6-[bis(4-chlorophenyl)methyl]-4-chloroquinazoline (300 mg, 0.75 mmol, 1.00 equiv), 2-(4-aminopiperidine-1-sulfonyl)acetate hydrochloride (213 mg, 0.90 mmol, 1.20 equiv), triethylamine (0.5 mL) and propan-2-ol (15 mL). The resulting solution was stirred overnight at 40° C. The resulting mixture was concentrated under vacuum. The residue was applied onto a silica gel column with dichloromethane:$CH_3OH$ (30:1), to yield ethyl 2-[4-([6-[bis(4-chlorophenyl)methyl]quinazolin-4-yl]amino)piperidine-1-sulfonyl]acetate as a yellow solid. (ES (m/z) 599 [M+H]+

Step 4: 2-[4-([6-[Bis(4-chlorophenyl)methyl]quinazolin-4-yl]amino)piperidine-1-sulfonyl]ethan-1-ol Into a 100-mL round-bottom flask, was placed methyl 2-(4-(6-(bis(4-chlorophenyl)methyl)quinazolin-4-ylamino)piperidin-1-ylsulfonyl)acetate (100 mg, 0.16 mmol, 1.00 equiv), tetrahydrofuran (20 mL) and a solution of LiOH (12 mg, 0.50 mmol, 3.00 equiv) in water (2 ml). The resulting solution was stirred overnight at 25° C. The resulting mixture was concentrated under vacuum. The residue was applied onto a silica gel column with dichloromethane:$CH_3OH$ (10:1), to yield 2-[4-([6-[bis(4-chlorophenyl)methyl]quinazolin-4-yl]amino)piperidine-1-sulfonyl]ethan-1-ol as a white solid. LC-MS (ES, m/z): 571 [M+H]+.

1H-NMR (300 MHz, DMSO, ppm) δ 8.445 (s, 1H), 8.220 (s, 1H), 7.987 (d, J=7.5 Hz, 1H), 7.644 (d, J=8.7 Hz, 1H), 7.470-7.385 (m, 5H), 7.169-7.141 (m, 4H), 5.764 (s, 1H), 5.033-4.997 (m, 1H), 4.330 (br, 1H), 3.787-3.728 (m, 4H), 3.331-3.289 (m, 2H), 2.965-2.928 (m, 2H), 2.018-1.981 (m, 2H), 1.686-1.634 (m, 2H),

Example 29

2-((4-(((6-(bis(4-chlorophenyl)methyl)quinazolin-4-yl)amino)piperidin-1-yl)sulfonyl)acetamide (Compound #98)

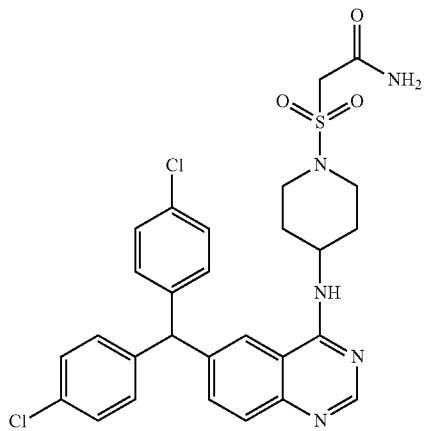 [SMILES: NC(=O)CS(=O)(=O)N1CCC(Nc2ncnc3ccc(C(c4ccc(Cl)cc4)c4ccc(Cl)cc4)cc23)CC1]

Into a 30-mL sealed tube, was placed methyl 2-[4-([6-[bis(4-chlorophenyl)methyl]quinazolin-4-yl]amino)piperidine-1-sulfonyl]acetate (100 mg, 0.17 mmol, 1.00 equiv), $NH_3/CH_3OH$ (15 mL). The resulting solution was stirred overnight at 70° C. The reaction mixture was cooled with a water/ice bath. The resulting mixture was concentrated under vacuum. The residue was applied onto a silica gel column with dichloromethane/methanol (10:1), to yield 2-[4-([6-[bis(4-chlorophenyl)methyl]quinazolin-4-yl]amino)piperidine-1-sulfonyl]acetamide as a white solid. LC-MS (ES, m/z): 584 [M+H]+

1H-NMR (300 MHz, DMSO, ppm) δ 8.448 (s, 1H), 8.220 (d, J=1.9 Hz, 1H), 7.974 (d, J=7.5 Hz, 1H), 7.645 (d, J=8.5 Hz, 2H), 7.506-7.340 (m, 6H), 7.214-7.100 (m, 4H), 5.763 (s, 1H), 4.297 (br, 1H), 3.936 (s, 2H), 3.683 (d, J=12.2 Hz, 2H), 3.018 (dd, J=13.2, 10.7 Hz, 2H), 2.013 (d, J=10.7 Hz, 2H), 1.699-1.563-(m, 2H).

Example 30

4-((6-(bis(4-chlorophenyl)methyl)quinazolin-4-yl)amino)-1-phenylcyclohexanol (Compound #99)

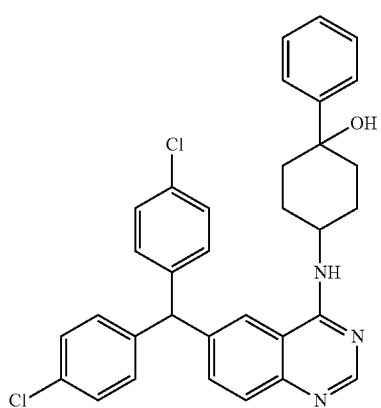 [SMILES: OC1(c2ccccc2)CCC(Nc2ncnc3ccc(C(c4ccc(Cl)cc4)c4ccc(Cl)cc4)cc23)CC1]

Step 1: 4-([6-[Bis(4-chlorophenyl)methyl]quinazolin-4-yl]amino)cyclohexan-1-one Into a 25-mL round-bottom flask, was placed 6-[bis(4-chlorophenyl)methyl]-4-chloroquinazoline (120 mg, 0.30 mmol, 1.00 equiv), 4-aminocyclohexan-1-one hydrochloride (80 mg, 0.53 mmol, 1.50 equiv), propan-2-ol (10 mL) and triethylamine (0.2 mL). The resulting solution was stirred overnight at 40° C. The resulting mixture was concentrated under vacuum. The residue was applied onto a silica gel column with dichloromethane:CH$_3$OH (30:1), to yield 4-([6-[bis(4-chlorophenyl)methyl]quinazolin-4-yl]amino)cyclohexan-1-one as a white solid. (ES (m/z) 476 [M+H]+

Step 2: 4-([6-[Bis(4-chlorophenyl)methyl]quinazolin-4-yl]amino)-1-phenylcyclohexan-1-ol Into a 25-mL round-bottom flask, was placed 4-([6-[bis(4-chlorophenyl)methyl]quinazolin-4-yl]amino)cyclohexan-1-one (100 mg, 0.21 mmol, 1.00 equiv), tetrahydrofuran (10 mL) and bromo(phenyl)magnesium (0.2 mL). The resulting solution was stirred overnight at 25° C. The reaction was then quenched by the addition of water (5 mL). The resulting solution was extracted with ethyl acetate (2×20 mL) and the organic layers combined and dried over sodium sulfate. The solids were filtered out. The resulting mixture was concentrated under vacuum, purified by going through a silica gel column with DCM/MeOH (30:1), to yield 4-([6-[bis(4-chlorophenyl)methyl]quinazolin-4-yl]amino)-1-phenylcyclohexan-1-ol as a white solid. LC-MS (ES, m/z): 554 [M+H]$^+$ $^1$H-NMR (400 MHz, DMSO, ppm) 8.446 (s, 1H), 8.335 (s, 1H), 8.056 (d, J 10=7.2 Hz, 1H), 7.635 (d, J=8.4 Hz, 1H), 7.561-7.542 (m, 2H), 7.479-7.409 (m, 5H), 7.340-7.302 (m, 2H), 7.222-7.179 (m, 5H), 5.758 (s, 1H), 4.885 (s, 1H), 4.361-4.345 (m, 1H), 2.043-1.905 (m, 4H), 1.870-1.705 (m, 4H).

Example 31

4-((6-(bis(4-chlorophenyl)methyl)quinazolin-4-yl)amino)-1-phenylcyclohexanecarbonitrile (Compound #118)

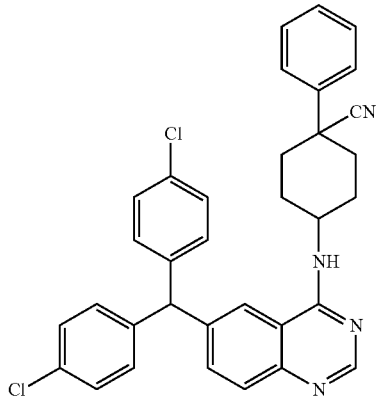 [SMILES: N#CC1(c2ccccc2)CCC(Nc2ncnc3ccc(C(c4ccc(Cl)cc4)c4ccc(Cl)cc4)cc23)CC1]

Step 1: 4-Amino-1-phenylcyclohexanecarbonitrile

Into a 100-mL 3-necked round-bottom flask, was placed a solution of 4-oxo-1-phenylcyclohexane-1-carbonitrile (600 mg, 3.01 mmol, 1.00 equiv) in methanol (20 mL), CH$_3$COONH$_4$ (2.3 g) and NaBH$_3$(CN) (0.19 g). The resulting solution was stirred for 4 h at 25° C. The reaction was then quenched by the addition of sodium bicarbonate (aq) (30 mL). The resulting solution was extracted with ethyl acetate (3×30 mL) and the organic layers combined and dried over anhydrous sodium sulfate. The solids were filtered out. The resulting mixture was concentrated under vacuum, to yield 4-amino-1-phenylcyclohexane-1-carbonitrile as light yellow oil.

Step 2: 4-(6-(Bis(4-chlorophenyl)methyl)quinazolin-4-ylamino)-1-phenylcyclohexanecarbonitrile Into a 25-mL round-bottom flask, was placed 6-[bis(4-chlorophenyl)methyl]-4-chloroquinazoline (70 mg, 0.18 mmol, 1.00 equiv), 4-amino-1-phenylcyclohexane-1-carbonitrile (41 mg, 0.20 mmol, 1.20 equiv), propan-2-ol (8 mL) and triethylamine (0.1 mL). The resulting solution was stirred overnight at 40° C. The resulting mixture was concentrated under vacuum. The residue was applied onto a silica gel column with dichloromethane: CH$_3$OH (30:1), to yield 4-([6-[bis(4-chlorophenyl)methyl]quinazolin-4-yl]amino)-1-phenylcyclohexane-1-carbonitrile as a white solid. LC-MS (ES, m/z): 563 [M+H]$^+$ $^1$H-NMR (300 MHz, DMSO, ppm) δ: 8.462 (s, 1H), 8.317 (s, 1H), 8.144 (d, J=7.8 Hz, 1H), 7.671-7.598 (m, 3H), 7.481-7.342 (m, 8H), 7.192-7.165 (m, 4H), 5.776 (s, 1H), 4.406-4.363 (m, 1H), 2.272-2.079 (m, 6H), 1.954-1.845 (m, 2H).

Example 32

N-(6-(bis(4-chlorophenyl)methyl)-4-((1-((trifluoromethyl)sulfonyl)piperidin-4-yl)amino)quinazolin-2-yl)methanesulfonamide (Compound #100)

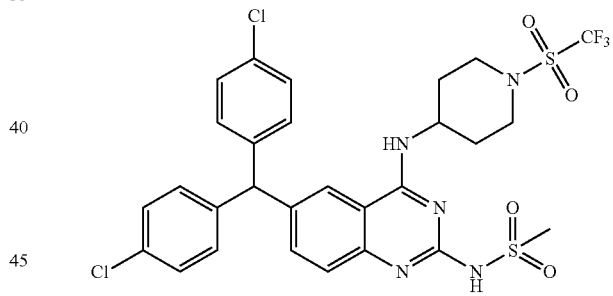

Into a 50-mL 3-necked round-bottom flask, was placed a solution of 6-[bis(4-chlorophenyl)methyl]-2-chloro-N-[1-(trifluoromethane)sulfonylpiperidin-4-yl]quinazolin-4-amine (200 mg, 0.32 mmol, 1.00 equiv) in 1,4-dioxane (20 mL), Cs$_2$CO$_3$ (146 mg, 0.45 mmol, 1.40 equiv), Pd$_2$(dba)$_3$ (29 mg, 0.03 mmol, 0.10 equiv), XantPhos (56 mg, 0.10 mmol, 0.30 equiv) and methanesulfonamide (36 mg, 0.38 mmol, 1.20 equiv). The resulting solution was heated to reflux for 3 hr, under nitrogen atmosphere. The reaction was then quenched by the addition of sat. NaHCO$_3$ (30 mL). The resulting solution was extracted with ethyl acetate (3×30 mL) and the organic layers combined, dried over anhydrous sodium sulfate and concentrated under vacuum. The resulting residue was purified by Prep-TLC with 10% methanol/DCM as eluent, to yield N-[6-[bis(4-chlorophenyl)methyl]-4-[[1-(trifluoromethane)sulfonylpiperidin-4-yl]amino]quinazolin-2-yl]methanesulfonamide as a white solid. LCMS (ES, m/z) 688[M+H]$^+$ $^1$H-NMR (300 MHz, DMSO) δ 11.85 (br, 1H), 8.66 (br, 1H), 8.13 (s, 1H), 7.42-7.39 (m, 5H), 7.30-7.27 (m, 1H), 7.13 (d, J=8.4 Hz, 4H), 5.68 (s, 1H), 4.29 (br, 1H), 3.91-3.87 (m, 2H), 3.36-3.31 (m, 2H), 3.04 (s, 3H), 2.27-2.21 (m, 2H), 1.73-1.61 (m, 2H),

Example 33

6-(bis(4-chlorophenyl)methyl)-2-(2-methoxyethoxy)-N-(4-(trifluoromethyl)benzyl)quinazolin-4-amine (Compound #91)

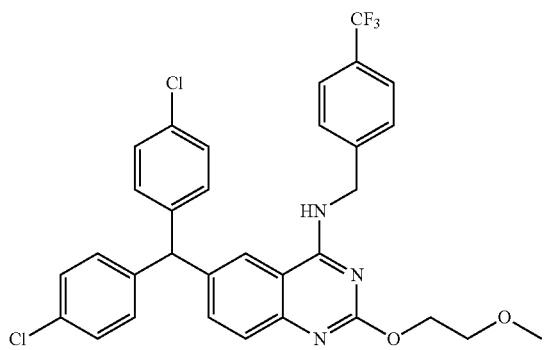 [SMILES: COCCOc1nc(NCc2ccc(C(F)(F)F)cc2)c2cc(C(c3ccc(Cl)cc3)c3ccc(Cl)cc3)ccc2n1]

Into a 50-mL sealed tube, was placed 6-[bis(4-chlorophenyl)methyl]-2-chloro-N-[[4-(trifluoromethyl)phenyl]methyl]quinazolin-4-amine (100 mg, 0.17 mmol, 1.00 equiv), NaOCH$_2$CH$_2$OCH$_3$ (333 mg, 3.40 mmol, 20.00 equiv) and HOCH$_2$CH$_2$OCH$_3$ (30 mL). The resulting solution was stirred overnight at 130° C. The reaction was then quenched by the addition of sat. sodium bicarbonate (30 mL). The resulting solution was extracted with ethyl acetate (2×50 mL) and the organic layers combined, dried over anhydrous sodium sulfate and concentrated under vacuum. The resulting residue was purified with Prep-TLC, used 1:2 EA/PE as eluent, to yield 6-[bis(4-chlorophenyl)methyl]-2-(2-methoxyethoxy)-N-[[4-(trifluoromethyl)phenyl]methyl] quinazolin-4-amine as a white solid. LCMS (ES, m/z) 612[M+H]$^+$ $^1$H-NMR (400 MHz, DMSO) δ 8.91 (br, 1H), 8.09 (s, 1H), 7.69 (d, J=8.4 Hz, 2H), 7.53 (d, J=8 Hz, 2H), 7.49-7.42 (m, 6H), 7.18 (d, J=8.4 Hz, 4H), 5.74 (s, 1H), 4.80-4.79 (m, 2H), 4.35-4.328 (m, 2H), 3.58-3.56 (m, 2H), 3.24 (s, 3H).

Example 34

2-(2-azidoethoxy)-6-(bis(4-chlorophenyl)methyl)-N-(4-(trifluoromethyl)benzyl)quinazolin-4-amine (Compound #75)

Step 1: 2-Azidoethanol

Into a 50-mL round-bottom flask, was placed 2-bromoethan-1-ol (7.51 g, 60.10 mmol, 1.00 equiv), NaN$_3$ (5.13 g, 78.91 mmol, 1.30 equiv) and Bu$_4$NBr (500 mg, 0.03 equiv). The resulting solution was stirred for 15 h at 110° C. After the mixture had cooled, diethyl ether (20 mL) was added, and the resulting precipitate (consisting of NaBr, unreacted NaN$_3$, and phase-transfer catalyst) was removed by filtration. The precipitate was washed with Et$_2$O (~20 mL). Evaporation of the combined organic solvents yielded a yellow residue that was purified by distillation (b.p. 35° C./1 Torr) to yield 2-azidoethanol as a colorless liquid. $^1$HNMR (300 mHz, DMSO) δ 4.974 (brs, 1H), 3.581-3.516 (m, 4H)

Step 2: 2-(2-Azidoethoxy)-6-[bis(4-chlorophenyl) methyl]-N-[[4-(trifluoromethyl)phenyl]methyl]quinazolin-4-amine Into a 250-mL round-bottom flask purged and maintained with an inert atmosphere of nitrogen, was placed a solution of 2-azidoethan-1-ol (1.218 g, 13.99 mmol, 40.00 equiv) in tetrahydrofuran (80 mL). This was followed by the addition of sodium hydride (280 mg, 11.67 mmol, 20.00 equiv), in portions. To the resulting mixture was added 6-[bis(4-chlorophenyl)methyl]-2-chloro-N-[[4-(trifluoromethyl)phenyl]methyl]quinazolin-4-amine (200 mg, 0.35 mmol, 1.00 equiv), in portions at 70° C. The resulting solution was stirred for 30 min at room temperature. The resulting solution was allowed to react, with stirring, for an additional 1 overnight at 70° C. The reaction was then quenched by the addition of sat. sodium bicarbonate (30 mL). The resulting solution was extracted with ethyl acetate (2×50 mL) and the organic layers combined, dried over anhydrous sodium sulfate and concentrated under vacuum. The resulting residue was purified by Prep-TLC, with 1:2 ethyl acetate/ petroleum ether as eluent, to yield 2-(2-azidoethoxy)-6-[bis (4-chlorophenyl)methyl]-N-[[4-(trifluoromethyl)phenyl] methyl]quinazolin-4-amine as a white solid. LCMS (ES, m/z) 623[M+H]$^+$ $^1$H-NMR (300 MHz, DMSO) δ 8.94 (br, 1H), 8.08 (s, 1H), 7.67 (d, J=8.1 Hz, 2H), 7.55-7.47 (m, 3H), 7.43-7.38 (m, 5H), 7.17 (d, J=8.4 Hz, 4H), 5.73 (s, 1H), 4.78-4.77 (m, 2H), 4.40-4.37 (m, 2H), 3.62-3.58 (m, 2H).

Example 35

2-(2-aminoethoxy)-6-(bis(4-chlorophenyl)methyl)-N-(4-(trifluoromethyl)benzyl)quinazolin-4-amine (Compound #72)

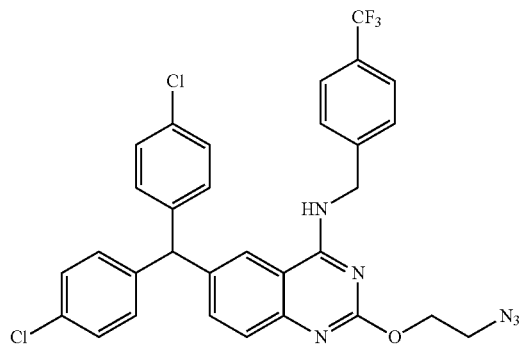 [SMILES: [N-]=[N+]=NCCOc1nc(NCc2ccc(C(F)(F)F)cc2)c2cc(C(c3ccc(Cl)cc3)c3ccc(Cl)cc3)ccc2n1]

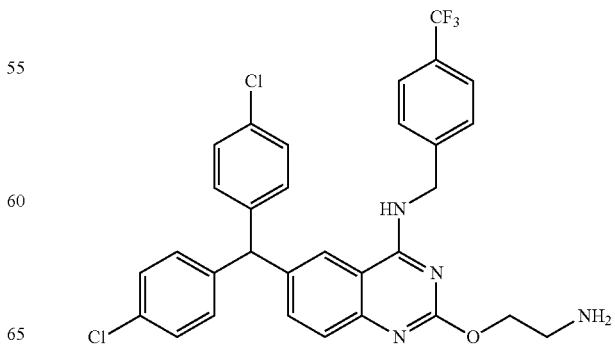

Into a 50-mL round-bottom flask, was placed 2-(2-azidoethoxy)-6-[bis(4-chlorophenyl)methyl]-N-[[4-(trifluoromethyl)phenyl]methyl]quinazolin-4-amine (50 mg, 0.08 mmol, 1.00 equiv), triphenylphosphane (25 mg, 0.10 mmol, 1.20 equiv) in NaOH aqueous (0.1 M, 1.5 mL) and THF (20 mL). The resulting solution was stirred overnight at 50° C. The reaction was then quenched by the addition of sat. sodium bicarbonate (10 mL). The resulting solution was extracted with ethyl acetate (2×30 mL) and the organic layers combined, dried over anhydrous sodium sulfate and concentrated under vacuum. The resulting residue was purified by Prep-TLC with ethyl acetate as eluent, to yield 2-(2-aminoethoxy)-6-[bis(4-chlorophenyl)methyl]-N-[[4-(trifluoromethyl)phenyl]methyl]quinazolin-4-amine as a white solid. LCMS (ES, m/z) 597[M+H]$^+$ $^1$H-NMR (300 MHz, DMSO) δ 8.46 (br, 1H), 7.88 (s, 1H), 7.68-7.53 (m, 6H), 7.38 (d, J=8.4 Hz, 4H), 7.24-7.14 (m, 5H), 6.38 (br, 1H), 5.62 (s, 1H), 4.74-4.72 (m, 2H), 3.45 (br, 2H), 3.31-3.28 (m, 2H).

Example 36

N-(2-((6-(bis(4-chlorophenyl)methyl)-4-((4-(trifluoromethyl)benzyl)amino)quinazolin-2-yl)oxy)ethyl)acetamide (Compound #69)

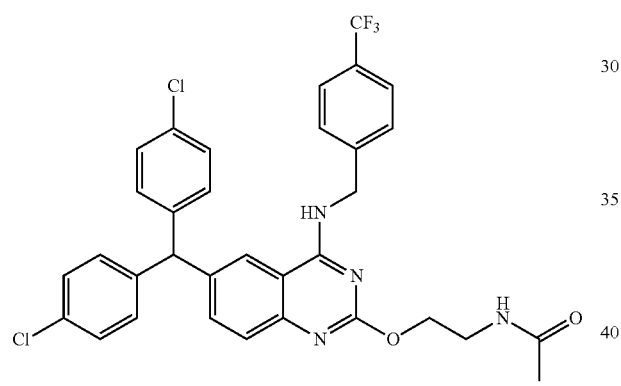

Into a 5-mL round-bottom flask, was placed a solution of HATU (20 mg, 0.05 mmol, 1.20 equiv) in N,N-dimethylformamide (2 mL), DIPEA (11 mg, 0.09 mmol, 2.00 equiv) and acetic acid (3 mg, 0.05 mmol, 1.20 equiv). The resulting solution was stirred for 20 min at room temperature. This was followed by the addition of 2-(2-aminoethoxy)-6-[bis(4-chlorophenyl)methyl]-N-[[4-(trifluoromethyl)phenyl]methyl]quinazolin-4-amine (26 mg, 0.04 mmol, 1.00 equiv), in portions at room temperature. The resulting solution was allowed to react overnight at room temperature with stirring. The reaction was then quenched by the addition of ice/salt (10 mL). The resulting solution was extracted with ethyl acetate (2×30 mL) and the organic layers combined, dried over anhydrous sodium sulfate and concentrated under vacuum. The resulting residue was purified with Prep-TLC, using 1:1 ethyl acetate/petroleum ether as eluent to yield N-[2-([6-[bis(4-chlorophenyl)methyl]-4-([[4-(trifluoromethyl)phenyl]methyl]amino)quinazolin-2-yl]oxy)ethyl]acetamide as a yellow solid. LCMS (ES, m/z) 639[M+H]$^+$ $^1$H-NMR (400 MHz, DMSO) δ 8.48 (br, 1H), 7.91 (s, 1H), 7.67 (d, J=8 Hz, 2H), 7.55 (d, J=8 Hz, 2H), 7.40 (d, J=8.4 Hz, 4H), 7.25 (s, 2H), 7.17 (d, J=8.4 Hz, 4H), 6.68 (br, 1H), 5.65 (s, 1H), 4.76-4.74 (m, 2H), 4.03 (br, 2H), 3.46 (br, 2H), 1.91 (s, 3H).

Example 37

4-((6-(bis(4-chlorophenyl)methyl)-4-((4-(trifluoromethyl)benzyl)amino)quinazolin-2-yl)oxy)butan-1-ol (Compound #71)

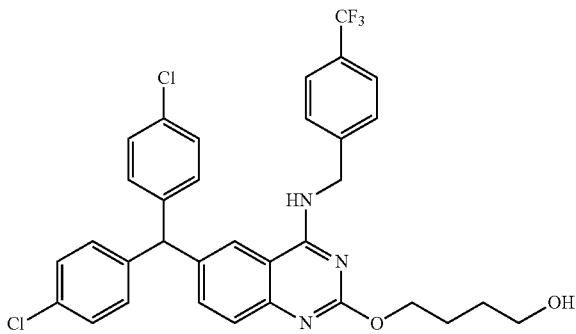 [SMILES: OCCCCOc1nc(NCc2ccc(C(F)(F)F)cc2)c2cc(C(c3ccc(Cl)cc3)c3ccc(Cl)cc3)ccc2n1]

Into a 250-mL round-bottom flask, was placed a solution of butane-1,4-diol (20 mL) in tetrahydrofuran (50 mL). This was followed by the addition of sodium hydride (420 mg, 10.50 mmol, 30.00 equiv), in portions. The resulting solution was stirred for 30 min at room temperature. To the resulting mixture was added 6-[bis(4-chlorophenyl)methyl]-2-chloro-N-[[4-(trifluoromethyl)phenyl]methyl]quinazolin-4-amine (200 mg, 0.35 mmol, 1.00 equiv). The resulting solution was allowed to react overnight at 70° C. with stirring. The reaction was then quenched by the addition of sat. sodium bicarbonate (120 mL). The resulting solution was extracted with ethyl acetate (2×100 mL) and the organic layers combined, dried over anhydrous sodium sulfate and concentrated under vacuum. The residue was applied onto a silica gel column with ethyl acetate/petroleum ether (50:50), to yield 4-([6-[bis(4-chlorophenyl)methyl]-4-([[4-(trifluoromethyl)phenyl]methyl]amino)quinazolin-2-yl]oxy)butan-1-ol as a light yellow solid. LCMS (ES, m/z) 626[M+H]$^+$ $^1$H-NMR (300 MHz, DMSO) δ 8.88 (br, 1H), 8.07 (s, 1H), 7.67 (d, J=8.1 Hz, 2H), 7.54-7.38 (m, 8H), 7.17 (d, J=8.4 Hz, 4H), 5.72 (s, 1H), 4.79-4.77 (m, 2H), 4.41-4.37 (m, 1H), 4.24-4.19 (m, 2H), 3.43-3.37 (m, 2H), 1.71-1.62 (m, 2H), 1.52-1.43 (m, 2H).

Example 38

4-((6-(bis(4-chlorophenyl)methyl)-4-((4-(trifluoromethyl)benzyl)amino)quinazolin-2-yl)oxy)butanamide (Compound #66)

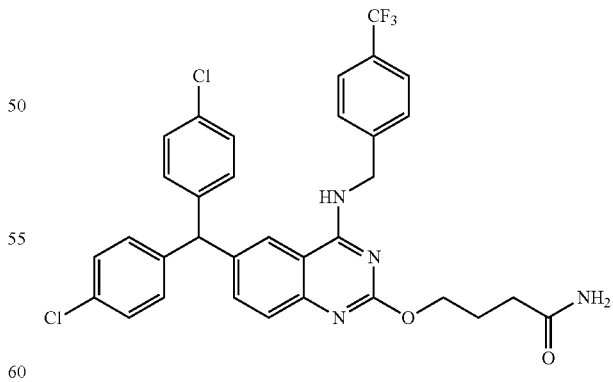

Step 1: 4-(6-(Bis(4-chlorophenyl)methyl)-4-(4-(trifluoromethyl)benzylamino)quinazolin-2-yloxy)butanoic acid Into a 25-mL round-bottom flask, was placed a solution of 4-([6-[bis(4-chlorophenyl)methyl]-4-([[4-(trifluoromethyl)

phenyl]methyl]amino)quinazolin-2-yl]oxy)butan-1-ol (116 mg, 0.19 mmol, 1.00 equiv) in N,N-dimethylformamide (10 mL) and PDC (714 mg, 1.90 mmol, 10.00 equiv). The resulting solution was stirred overnight at room temperature. The reaction was then quenched by the addition of sat. NH$_4$Cl (20 mL). The resulting solution was extracted with chloroform (2×30 mL) first and extracted again with ethyl acetate (2×20 mL), and the organic layers combined, dried over anhydrous sodium sulfate and concentrated under vacuum. All these process were complete under room temperature. The resulting residue was purified by Prep-TLC, with methanol/DCM (1/10) as eluent, to yield 4-([6-[bis(4-chlorophenyl)methyl]-4-([[4-(trifluoromethyl)phenyl] methyl]amino)quinazolin-2-yl]oxy)butanoic acid as a yellow solid.

Step 2: 4-(6-(Bis(4-chlorophenyl)methyl)-4-(4-(trifluoromethyl)benzylamino)quinazolin-2-yloxy)butanamide Into a 25-mL round-bottom flask purged and maintained with an inert atmosphere of nitrogen, was placed a solution of 4-([6-[bis(4-chlorophenyl)methyl]-4-([[4-(trifluoromethyl)phenyl]methyl]amino)quinazolin-2-yl]oxy)butanoic acid (32.3 mg, 0.05 mmol, 1.00 equiv) in N,N-dimethylformamide (2.5 mL), NH$_4$Cl (21 mg, 0.39 mmol, 8.00 equiv), HATU (29 mg, 0.08 mmol, 1.50 equiv) and DIPEA (52 mg, 0.40 mmol, 8.00 equiv). The resulting solution was stirred overnight at room temperature. The resulting solution was diluted with water (20 mL). The resulting solution was extracted with ethyl acetate (2×30 mL) and the organic layers combined, dried over anhydrous sodium sulfate and concentrated under vacuum. The resulting residue was purified by Prep-TLC, with methanol/DCM=1/20 as eluent, to yield 4-([6-[bis(4-chlorophenyl)methyl]-4-([[4-(trifluoromethyl)phenyl]methyl]amino)quinazolin-2-yl]oxy)butanamide as an off-white solid. LCMS (ES, m/z) 639 [M+H]$^+$ $^1$H-NMR (300 MHz, DMSO) δ 8.88 (br, 1H), 8.07 (s, 1H), 7.68 (d, J=8.1 Hz, 2H), 7.54 (d, J=8.1 Hz, 2H), 7.48-7.38 (m, 6H), 7.28 (s, 1H), 7.16 (d, J=8.4 Hz, 4H), 6.75 (s, 1H), 5.72 (s, 1H), 4.79-4.78 (m, 2H), 4.23-4.19 (m, 2H), 2.17-2.13 (m, 2H), 1.90-1.81 (m, 2H).

Example 39 methyl 4-(4-((6-(bis(4-chlorophenyl)methyl)quinazolin-4-yl)amino)piperidin-1-yl)benzoate (Compound #94)

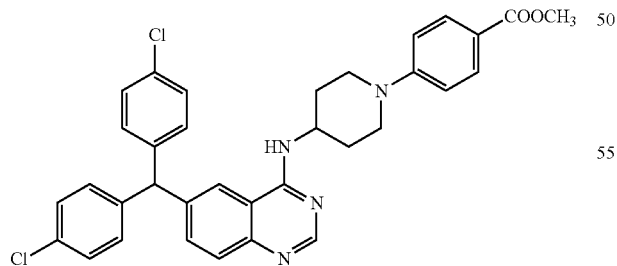

Step 1: Methyl 4-(4-(tert-butoxycarbonylamino)piperidin-1-yl)benzoate

Into a 100-mL 3-necked round-bottom flask purged and maintained with an inert atmosphere of nitrogen, was placed tert-butyl N-(piperidin-4-yl)carbamate (2 g, 9.99 mmol, 1.00 equiv), methyl 4-bromobenzoate (2.6 g, 12.09 mmol, 1.21 equiv), 1,4-dioxane (50 mL), Cs$_2$CO$_3$ (5 g, 15.35 mmol, 1.54 equiv), Pd$_2$(dba)$_3$ (23 mg, 0.03 mmol) and XantPhos (43 mg, 0.07 mmol, 0.01 equiv). The resulting solution was stirred overnight at 100° C. The reaction mixture was cooled with a water/ice bath. The resulting solution was diluted with ethyl acetate (100 mL). The resulting mixture was washed with water (3×50 mL). The mixture was dried over anhydrous sodium sulfate. The resulting mixture was concentrated under vacuum. The residue was applied onto a silica gel column with ethyl acetate:petroleum ether (1:3), to yield methyl 4-(4-[[(tert-butoxy)carbonyl]amino]piperidin-1-yl)benzoate as a yellow solid. (ES (m/z) 335 [M+H]+

Step 2: Methyl 4-(4-aminopiperidin-1-yl)benzoate

Into a 100-mL 3-necked round-bottom flask, was placed hydrogen chloride/CH$_3$OH (50 mL), methyl 4-(4-[[(tert-butoxy)carbonyl]amino]piperidin-1-yl)benzoate (1.5 g, 4.49 mmol, 1.00 equiv). The resulting solution was stirred overnight at 25° C. The resulting mixture was concentrated under vacuum. The resulting solution was diluted with ethyl acetate (50 mL). The solids were collected by filtration, to yield methyl 4-(4-aminopiperidin-1-yl)benzoate dihydrochloride as a white solid. (ES (m/z) 235 [M+H]+

Step 3: Methyl 4-[4-([6-[bis(4-chlorophenyl)methyl] quinazolin-4-yl]amino)piperidin-1-yl]benzoate Into a 25-mL round-bottom flask, was placed 6-[bis(4-chlorophenyl)methyl]-4-chloroquinazoline (300 mg, 0.75 mmol, 1.00 equiv), methyl 4-(4-aminopiperidin-1-yl)benzoate dihydrochloride (300 mg, 0.98 mmol, 1.30 equiv), propan-2-ol (15 mL) and triethylamine (0.5 mL). The resulting solution was stirred overnight at 30° C. The solids were collected by filtration, to yield methyl 4-[4-([6-[bis(4-chlorophenyl)methyl]quinazolin-4-yl]amino)piperidin-1-yl]benzoate as an off-white solid. LC-MS (ES, m/z): 597 [M+H]$^+$ $^1$H-NMR (300 MHz, DMSO, ppm) δ: 8.457 (s, 1H), 8.198 (d, J=1.2 Hz, 1H), 7.919 (d, J=7.5 Hz, 1H), 7.805-7.775 (m, 2H), 7.657-7.628 (m, 1H), 7.472-7.368 (m, 5H), 7.160-7.132 (m, 4H), 7.035-7.005 (m, 2H), 5.734 (s, 1H), 4.528-4.491 (m, 1H), 4.055-4.010 (m, 2H), 3.774 (s, 3H), 3.085-3.004 (m, 2H), 1.998-1.955 (m, 2H), 1.656-1.584 (m, 2H).

Example 40

4-(4-((6-(bis(4-chlorophenyl)methyl)quinazolin-4-yl)amino)piperidin-1-yl)benzoic acid (Compound #92)

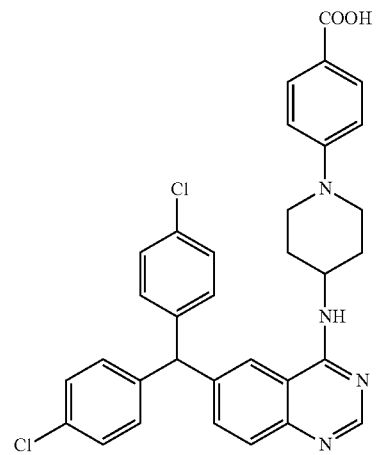 [SMILES: O=C(O)c1ccc(N2CCC(Nc3ncnc4ccc(C(c5ccc(Cl)cc5)c5ccc(Cl)cc5)cc34)CC2)cc1]

103

Into a 100-mL 3-necked round-bottom flask, was placed methyl 4-[4-([6-[bis(4-chlorophenyl)methyl]quinazolin-4-yl]amino)piperidin-1-yl]benzoate (280 mg, 0.47 mmol, 1.00 equiv), methanol (20 mL), sodium hydroxide (10 mL, 1M). The resulting solution was heated to reflux for 5 hr. The reaction mixture was cooled with a water/ice bath. The pH value of the solution was adjusted to pH 5-6 with 10% HCl. The solids were collected by filtration, to yield 230 mg (81%) of 4-[4-([6-[bis(4-chlorophenyl)methyl]quinazolin-4-yl]amino)piperidin-1-yl]benzoic acid as a light yellow solid. LC-MS (ES, m/z): 583 [M+H]$^+$ $^1$H-NMR (400 MHz, DMSO, ppm) δ: 8.89 (brs, 1H), 8.68 (s, 1H), 8.39 (s, 1H), 7.79-7.74 (m, 3H), 7.61 (d, J=8.8 HZ, 1H), 7.40 (d, J=8.4 Hz, 4H), 7.16 (d, J=8.4 Hz, 4H), 7.01 (d, J=8.8 Hz, 2H), 5.78 (s, 1H), 4.62-4.59 9m, 1H), 4.06-4.02 (m, 2H), 3.07-3.00 9m, 2H), 1.97-1.95 (m, 2H), 1.76-1.68 (m, 1H)

Example 41

4-(4-((6-(bis(4-chlorophenyl)methyl)quinazolin-4-yl)amino)piperidin-1-yl)benzamide (Compound #90)

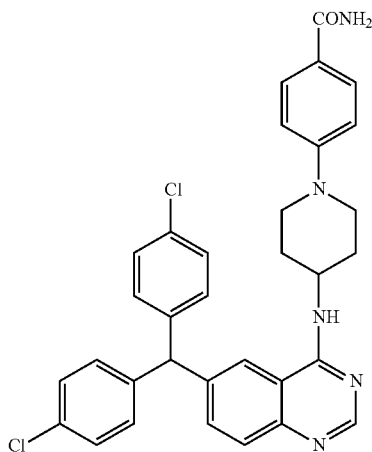 [SMILES: NC(=O)c1ccc(N2CCC(Nc3ncnc4ccc(C(c5ccc(Cl)cc5)c5ccc(Cl)cc5)cc34)CC2)cc1]

Into a 25-mL round-bottom flask, was placed 4-[4-([6-[bis(4-chlorophenyl)methyl]quinazolin-4-yl]amino)piperidin-1-yl]benzoic acid (100 mg, 0.17 mmol, 1.00 equiv), HATU (98 mg, 0.26 mmol, 1.50 equiv), NH$_4$Cl (46 mg, 0.86 mmol, 5.00 equiv), N,N-dimethylformamide (10 mL) and DIPEA (0.25 mL). The resulting solution was stirred overnight at 25° C. The resulting solution was diluted with ethyl acetate (30 mL). The resulting mixture was washed with water (2×20 mL). The mixture was dried over anhydrous sodium sulfate. The solids were filtered out. The resulting mixture was concentrated under vacuum. The residue was applied onto a silica gel column with dichloromethane/methanol (10:1), to yield 4-[4-([6-[bis(4-chlorophenyl)methyl]quinazolin-4-yl]amino)piperidin-1-yl]benzamide as a light yellow solid. LC-MS (ES, m/z): 582. [M+H]$^+$ $^1$H-NMR (300 MHz, DMSO, ppm) δ: 8.469 (s, 1H), 8.220 (s, 1H), 7.984-7.959 (d, J=7.5 Hz, 1H), 7.769-7.632 (m, 4H), 7.479-7.372 (m, 5H), 7.164-7.136 (m, 4H), 6.698-6.957 (m, 3H), 5.739 (s, 1H), 4.473 (br, 1H), 3.999-3.956 (m, 2H), 3.014-2.892 (m, 2H), 1.977-1.944 (m, 2H), 1.721-1.610 (m, 2H).

104

Example 42

Ethyl 4-(4-((6-(bis(4-chlorophenyl)methyl)quinazolin-4-yl)amino)piperidin-1-yl)-4-oxobutanoate (Compound #81)

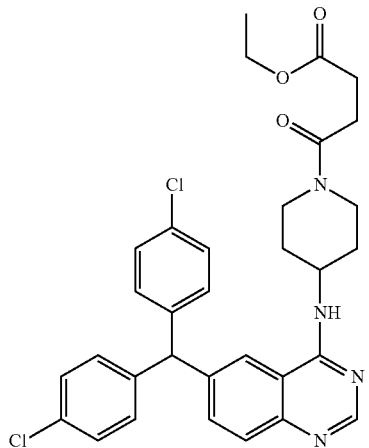 [SMILES: CCOC(=O)CCC(=O)N1CCC(Nc2ncnc3ccc(C(c4ccc(Cl)cc4)c4ccc(Cl)cc4)cc23)CC1]

Step 1: Ethyl 4-(4-(tert-butoxycarbonylamino)piperidin-1-yl)-4-oxobutanoate

Into a 250-mL 3-necked round-bottom flask, was placed tert-butyl N-(piperidin-4-yl)carbamate (5 g, 24.97 mmol, 1.00 equiv), dichloromethane (100 mL), triethylamine (11 mL). This was followed by the addition of ethyl 4-chloro-4-oxobutanoate (6.4 g, 38.89 mmol, 1.50 equiv) dropwise with stirring at 0° C. The resulting solution was stirred overnight at 25° C. The resulting mixture was washed with water (3×80 mL). The mixture was dried over anhydrous sodium sulfate. The solids were filtered out. The resulting mixture was concentrated under vacuum, to yield ethyl 4-(4-[[(tert-butoxy)carbonyl]amino]piperidin-1-yl)-4-oxobutanoate as a yellow solid.

Step 2: Ethyl 4-(4-aminopiperidin-1-yl)-4-oxobutanoate

Into a 250-mL 3-necked round-bottom flask, was placed ethyl 4-(4-[[(tert-butoxy)carbonyl]amino]piperidin-1-yl)-4-oxobutanoate (5 g, 15.23 mmol, 1.00 equiv), hydrogen chloride/EtOH (80 mL). The resulting solution was stirred overnight at 25° C. The resulting mixture was concentrated under vacuum. The resulting solution was diluted with diethyl ether (150 mL). The solids were collected by filtration, to yield 3 g (62%) of ethyl 4-(4-aminopiperidin-1-yl)-4-oxobutanoate dihydrochloride as a white solid.

Step 3: Ethyl 4-[4-([6-[bis(4-chlorophenyl)methyl]quinazolin-4-yl]amino)piperidin-1-yl]-4-oxobutanoate Into a 50-mL round-bottom flask, was placed 6-[bis(4-chlorophenyl)methyl]-4-chloroquinazoline (300 mg, 0.75 mmol, 1.00 equiv), ethyl 4-(4-aminopiperidin-1-yl)-4-oxobutanoate dihydrochloride (294 mg, 0.98 mmol, 1.30 equiv), triethylamine (0.6 mL) and propan-2-ol (20 mL). The resulting solution was stirred overnight at 40° C. The resulting solution was diluted with methanol (20 mL). The solids were collected by filtration, to yield ethyl 4-[4-([6-[bis(4-chlorophenyl)methyl]quinazolin-4-yl]amino)piperidin-1-yl]-4-oxobutanoate as a white solid. LC-MS (ES, m/z): 591 [M+H]$^+$ ¹H-NMR (300 MHz, DMSO, ppm) δ: 8.547 (s, 1H), 8.318 (brs, 1H), 8.266 (s, 1H), 7.701-7.675 (m, 1H), 7.535-7.507 (m, 1H), 7.418-7.390 (m, 4H), 7.170-7.142 (m, 4H), 5.776 (s, 1H), 4.494-4.392 (m, 2H), 4.070-4.000 (m, 3H), 3.141-3.101 (m, 1H), 2.722-2.495 (m, 5H), 1.995-1.904 (m, 2H), 1.611-1.381 (m, 2H), 1.173-1.149 (m, 3H).

Example 43

4-(4-((6-(bis(4-chlorophenyl)methyl)quinazolin-4-yl)amino)piperidin-1-yl)-4-oxobutanoic acid (Compound #80)

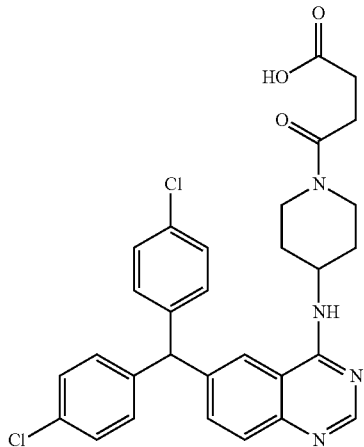 [SMILES: O=C(O)CCC(=O)N1CCC(Nc2ncnc3ccc(C(c4ccc(Cl)cc4)c4ccc(Cl)cc4)cc23)CC1]

Into a 50-mL round-bottom flask, was placed a solution of ethyl 4-[4-([6-[bis(4-chlorophenyl)methyl]quinazolin-4-yl]amino)piperidin-1-yl]-4-oxobutanoate (100 mg, 0.17 mmol, 1.00 equiv) in ethanol (15 ml), 2M NaOH (20 mL). The resulting solution was stirred overnight at 60° C. The pH value of the solution was adjusted to pH 5-6 with 10% HCl. The solids were collected by filtration. This resulted in 4-[4-([6-[bis(4-chlorophenyl)methyl]quinazolin-4-yl] amino)piperidin-1-yl]-4-oxobutanoic acid as a white solid. LC-MS (ES, m/z): 567 [M+H]⁺

¹H-NMR (300 MHz, DMSO, ppm) δ: 12.02 (brs, 1H), 9.27 (brs, 1H), 8.72 (s, 1H), 8.55 (s, 1H), 7.80 (d, J=8.7 Hz, 1H), 7.66 (d, J=8.1 Hz, 1H), 7.42 (d, J=8.4 hz, 4H), 7.18 (d, J=8.4 Hz, 4H), 5.81 (s, 1H), 4.59-4.56 (m, 1H), 4.47-4.43 (m, 1H), 4.06-3.97 (m, 1H), 3.19-3.10 (m, 1H), 2.73-2.65 (m, 1H), 2.59-2.55 (m, 2H), 2.50-2.42 (m, 2H), 1.99-1.90 (m, 2H), 1.84-1.64 (m, 2H)

Example 44

4-(4-((6-(bis(4-chlorophenyl)methyl)quinazolin-4-yl)amino)piperidin-1-yl)-4-oxobutanamide (Compound #86)

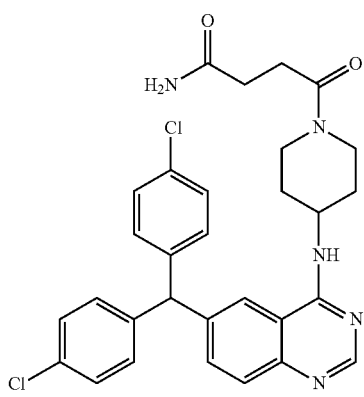 [SMILES: NC(=O)CCC(=O)N1CCC(Nc2ncnc3ccc(C(c4ccc(Cl)cc4)c4ccc(Cl)cc4)cc23)CC1]

Into a 10-mL round-bottom flask, was placed 6-[bis(4-chlorophenyl)methyl]-N-(piperidin-4-yl)quinazolin-4-amine (64 mg, 0.14 mmol, 1.00 equiv), 3-carbamoylpropanoic acid (21 mg, 0.18 mmol, 1.30 equiv), HATU (70 mg, 0.18 mmol, 1.30 equiv), N,N-dimethylformamide (5 mL) and DIPEA (0.1 mL). The resulting solution was stirred overnight at 25° C. The resulting solution was diluted with ethyl acetate (20 mL). The resulting mixture was washed with water (2×20 mL). The mixture was dried over anhydrous sodium sulfate. The solids were filtered out. The resulting mixture was concentrated under vacuum. The residue was applied onto a silica gel column with dichloromethane/methanol (20:1), to yield 4-[4-([6-[bis(4-chlorophenyl)methyl]quinazolin-4-yl]amino)piperidin-1-yl]-4-oxobutanamide as a white solid. LC-MS (ES, m/z): 562 [M+H]⁺

¹H-NMR (400 MHz, DMSO, ppm) δ 8.464 (s, 1H), 8.224 (s, 1H), 7.968 (d, J=7.6 Hz, 1H), 7.652 (d, J=8.6 Hz, 1H), 7.483-7.398 (m, 5H), 7.279 (s, 1H), 7.164 (d, J=8.8 Hz, 4H), 6.711 (s, 1H), 5.766 (s, 1H), 4.489-4.381 (m, 2H), 3.967 (d, J=13.6 Hz, 1H), 3.171-3.110 (m, 1H), 2.707-2.646 (m, 1H), 2.558-2.545 (m, 2H), 2.327-2.292 (m, 2H), 1.997-1.914 (m, 2H), 1.557-1.528 (m, 1H), 1.443-1.404 (m, 1H).

Example 45

4-((4-(((6-(bis(4-chlorophenyl)methyl)quinazolin-4-yl)amino)piperidin-1-yl)sulfonyl)benzoic acid (Compound #93)

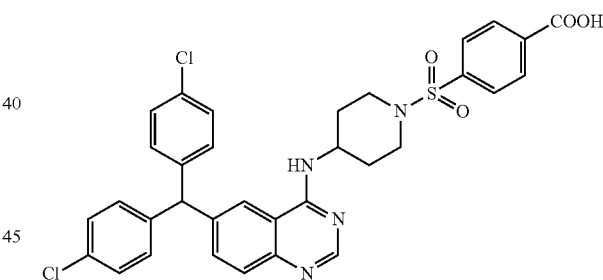

Into a 100-mL 3-necked round-bottom flask, was placed 6-[bis(4-chlorophenyl)methyl]-N-(piperidin-4-yl)quinazolin-4-amine (80 mg, 0.17 mmol, 1.00 equiv), dichloromethane (20 mL), triethylamine (0.3 mL) and 4-(chlorosulfonyl)benzoic acid (46 mg, 0.21 mmol, 1.20 equiv). The resulting solution was stirred overnight at 25° C. The resulting mixture was concentrated under vacuum. The residue was applied onto a silica gel column with dichloromethane/methanol (1:3), to yield 4-[4-([6-[bis(4-chlorophenyl)methyl]quinazolin-4-yl]amino)piperidine-1-sulfonyl]benzoic acid as a white solid. LC-MS (ES, m/z): 647 [M–H]⁻

¹H-NMR (300 MHz, DMSO, ppm) δ 8.382 (s, 1H), 8.185-8.157 (m, 3H), 7.971 (d, J=6.9 Hz, 1H), 7.884 (d, J=8.4 Hz, 2H) 7.628 (d, J=8.4 Hz, 1H), 7.4617.380 (m, 5H), 7.158-7.130 (m, 4H), 5.753 (s, 1H), 4.174 (br, 1H), 3.742 (d, J=11.6 Hz, 2H), 2.490-2.450 (m, 2H), 2.001 (d, J=11.9 Hz, 2H), 1.694-1.589 (m, 2H),

Example 46

6-(bis(4-chlorophenyl)methyl)-2-methoxy-N-(4-(trifluoromethyl)benzyl)quinazolin-4-amine (Compound #85)

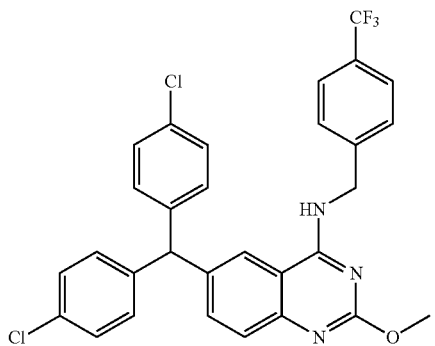 [SMILES: COc1nc(NCc2ccc(C(F)(F)F)cc2)c2cc(C(c3ccc(Cl)cc3)c3ccc(Cl)cc3)ccc2n1]

Into a 50-mL sealed tube, was placed 6-[bis(4-chlorophenyl)methyl]-2-chloro-N-[[4-(trifluoromethyl)phenyl]methyl]quinazolin-4-amine (200 mg, 0.35 mmol, 1.00 equiv) and a mixture of NaOCH$_3$/CH$_3$OH (30 mL, 30% wt). The resulting solution was stirred overnight at 120° C. The reaction was then quenched by the addition of sat. sodium bicarbonate (50 mL). The resulting solution was extracted with ethyl acetate (2×100 mL) and the organic layers combined, dried over anhydrous sodium sulfate and concentrated under vacuum. The residue was applied onto a silica gel column with ethyl acetate/petroleum ether (1:2), to yield 6-[bis(4-chlorophenyl)methyl]-2-methoxy-N-[[4-(trifluoromethyl)phenyl]methyl]quinazolin-4-amine as a white solid. LCMS (ES, m/z) 568[M+H]$^+$ $^1$H-NMR (300 MHz, DMSO) δ 8.90 (br, 1H), 8.08 (s, 1H), 7.68 (d, J=8.1 Hz, 2H), 7.55-7.48 (m, 3H), 7.42-7.39 (m, 5H), 7.18 (d, J=8.4 Hz, 4H), 5.73 (s, 1H), 4.78-4.76 (m, 2H), 3.81 (s, 3H).

Example 47

Methyl 2-(4-(4-((6-(bis(4-chlorophenyl)methyl)quinazolin-4-yl)amino)piperidin-1-yl)phenyl)acetate (Compound #79)

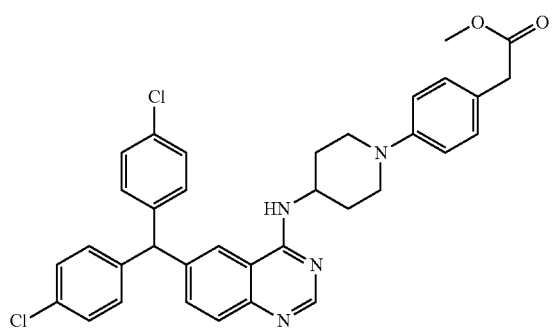 [SMILES: COC(=O)Cc1ccc(N2CCC(Nc3ncnc4ccc(C(c5ccc(Cl)cc5)c5ccc(Cl)cc5)cc34)CC2)cc1]

Step 1: Methyl 2-(4-(4-(tert-butoxycarbonylamino)piperidin-1-yl)phenyl)acetate

Into a 100-mL 3-necked round-bottom flask purged and maintained with an inert atmosphere of nitrogen, was placed tert-butyl N-(piperidin-4-yl)carbamate (1.5 g, 7.49 mmol, 1.20 equiv), methyl 2-(4-bromophenyl)acetate (1.4 g, 6.11 mmol, 1.00 equiv), 1,4-dioxane (30 mL), Cs$_2$CO$_3$ (3.01 g), Pd(OAc)$_2$ (101 mg) and X-PHOS (300 mg). The resulting solution was stirred overnight at 100° C. The reaction mixture was cooled with a water/ice bath. The resulting solution was diluted with ethyl acetate (100 mL). The resulting mixture was washed with water (3×50 mL). The mixture was dried over anhydrous sodium sulfate. The resulting mixture was concentrated under vacuum. The residue was applied onto a silica gel column with ethyl acetate: petroleum ether (1:3), to yield methyl 2-[4-(4-[[(tert-butoxy)carbonyl]amino]piperidin-1-yl)phenyl]acetate as a yellow solid.

Step 2: Methyl 2-(4-(4-aminopiperidin-1-yl)phenyl)acetate

Into a 100-mL 3-necked round-bottom flask, was placed methyl 2-[4-(4-[[(tert-butoxy)carbonyl]amino]piperidin-1-yl)phenyl]acetate (600 mg, 1.72 mmol, 1.00 equiv) and hydrogen chloride/CH$_3$OH (20 mL). The resulting solution was stirred overnight at 25° C. The resulting mixture was concentrated under vacuum, to yield methyl 2-[4-(4-aminopiperidin-1-yl)phenyl]acetate dihydrochloride as a white solid. (ES (m/z) 248 [M+H]+

Step 3: Methyl 2-[4-[4-([6-[bis(4-chlorophenyl)methyl]quinazolin-4-yl]amino)piperidin-1-yl]phenyl]acetate Into a 50-mL round-bottom flask, was placed 6-[bis(4-chlorophenyl)methyl]-4-chloroquinazoline (300 mg, 0.75 mmol, 1.00 equiv), methyl 2-[4-(4-aminopiperidin-1-yl)phenyl]acetate dihydrochloride (290 mg, 0.90 mmol, 1.20 equiv), propan-2-ol (30 mL) and triethylamine (0.5 mL). The resulting solution was stirred overnight at 40° C. The resulting mixture was concentrated under vacuum. The residue was applied onto a silica gel column with dichloromethane:CH$_3$OH (10:1), to yield methyl 2-[4-[4-([6-[bis(4-chlorophenyl)methyl]quinazolin-4-yl]amino)piperidin-1-yl]phenyl]acetate as a white solid. LC-MS (ES, m/z): 612 [M+H]$^+$ $^1$H-NMR (300 MHz, DMSO, ppm) δ 8.442 (s, 1H), 8.217 (s, 1H), 7.920 (d, J=7.8 Hz, 1H), 7.631 (d, J=8.7 Hz, 1H), 7.460-7.403 (m, 5H), 7.375-7.074 (m, 6H), 6.980-6.896 (m, 2H), 5.735 (s, 1H), 4.402-4.380 (m, 1H), 3.804-3.762 (m, 2H), 3.589 (s, 3H), 3.532 (s, 2H), 2.878-2.719 (m, 2H), 1.963-1.930 (m, 2H), 1.748-1.640 (m, 2H).

Example 48

2-(4-(4-((6-(bis(4-chlorophenyl)methyl)quinazolin-4-yl)amino)piperidin-1-yl)phenyl)acetic acid (Compound #77)

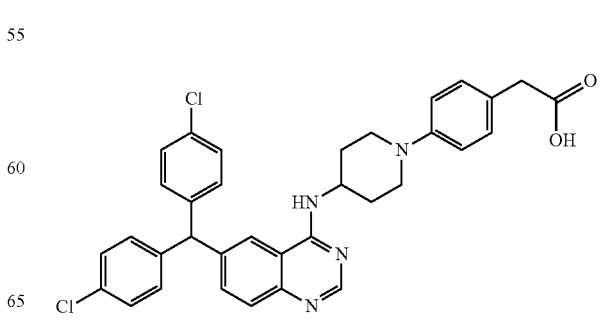

Into a 100-mL round-bottom flask, was placed a solution of methyl 2-[4-[4-([6-[bis(4-chlorophenyl)methyl]quinazolin-4-yl]amino)piperidin-1-yl]phenyl]acetate (300 mg, 0.49 mmol, 1.00 equiv) in methanol (20) and 2MN aOH (20 mL). The resulting solution was stirred overnight at 60° C. The pH value of the solution was adjusted to pH 5-6 with 10% HCl solution. The solids were collected by filtration, to yield 2-[4-[4-([6-[bis(4-chlorophenyl)methyl]quinazolin-4-yl]amino)piperidin-1-yl]phenyl]acetic acid as a white solid. LC-MS (ES, m/z): 598 [M+H]$^+$ $^1$H-NMR (300 MHz, DMSO, ppm) δ 8.791 (s, 1H), 8.438 (s, 1H), 7.781-7.751 (m, 2H), 7.396-7.367 (m, 4H), 7.222-7.129 (m, 7H), 5.800 (s, 1H), 4.648 (br, 1H), 3.782-3.739 (m, 2H), 3.490 (s, 2H), 3.172-3.096 (m, 2H), 2.062-1.925 (m, 4H).

Example 49

2-(4-(4-((6-(bis(4-chlorophenyl)methyl)quinazolin-4-yl)amino)piperidin-1-yl)phenyl)acetamide (Compound #74)

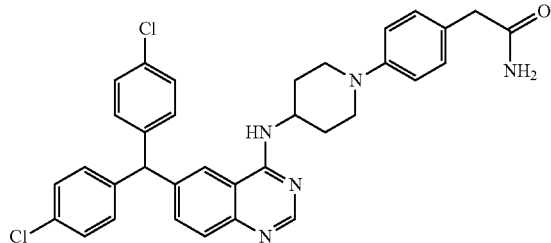 [SMILES: O=C(O)Cc1ccc(N2CCC(Nc3ncnc4ccc(C(c5ccc(Cl)cc5)c5ccc(Cl)cc5)cc34)CC2)cc1]

Into a 25-mL round-bottom flask, was placed 2-[4-[4-([6-[bis(4-chlorophenyl)methyl]quinazolin-4-yl]amino)piperidin-1-yl]phenyl]acetic acid (100 mg, 0.17 mmol, 1.00 equiv), HATU (95 mg, 0.25 mmol, 1.50 equiv), NH$_4$Cl (50 mg, 0.93 mmol, 5.00 equiv), N,N-dimethylformamide (10 mL), and DIEA (0.25 mL). The resulting solution was stirred overnight at 25° C. The resulting solution was diluted with water (100 mL). The solids were collected by filtration. The residue was applied onto a silica gel column with dichloromethane/methanol (10:1), to yield 2-[4-[4-([6-[bis(4-chlorophenyl)methyl]quinazolin-4-yl]amino)piperidin-1-yl]phenyl]acetamide as a light yellow solid. LC-MS (ES, m/z): 596 [M+H]$^+$ $^1$H-NMR (300 MHz, DMSO, ppm) δ: 8.446 (s, 1H), 8.222 (s 1H), 7.943 (d, J=7.7 Hz, 1H), 7.631 (d, J=8.6 Hz, 1H), 7.504-7.306 (m, 6H), 7.124 (m, 6H), 6.894 (d, J=8.3 Hz, 2H), 6.775 (brs, 1H), 5.735 (s, 1H), 4.387 (br, 1H), 3.774 (d, J=12.6 Hz, 2H), 3.231 9s, 2H), 2.872-2.792 (m, 2H), 1.935 (dd, J=11.9, 4.1 Hz, 2H), 1.751-1.644 (m, 2H).

Example 50

4-(4-((6-(bis(4-chlorophenyl)methyl)quinazolin-4-yl)amino)piperidin-1-yl)-N-(2-hydroxyethyl)benzamide (Compound #84)

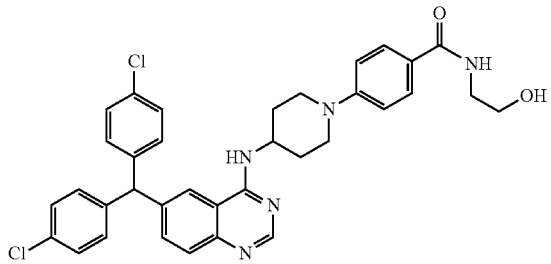 [SMILES: O=C(NCCO)c1ccc(N2CCC(Nc3ncnc4ccc(C(c5ccc(Cl)cc5)c5ccc(Cl)cc5)cc34)CC2)cc1]

Into a 25-mL round-bottom flask, was placed 4-[4-([6-[bis(4-chlorophenyl)methyl]quinazolin-4-yl]amino)piperidin-1-yl]benzoic acid (100 mg, 0.17 mmol, 1.00 equiv), 2-aminoethan-1-ol (30 mg, 0.49 mmol, 2.87 equiv), HATU (98 mg, 0.26 mmol, 1.50 equiv), N,N-dimethylformamide (10 mL) and DIPEA (0.2 mL). The resulting solution was stirred overnight at 25° C. The resulting solution was diluted with ethyl acetate (30 mL). The resulting mixture was washed with water (3×20 mL). The mixture was dried over anhydrous sodium sulfate. The solids were filtered out. The resulting mixture was concentrated under vacuum. The residue was applied onto a silica gel column with dichloromethane/methanol (10:1), to yield 4-[4-([6-[bis(4-chlorophenyl)methyl]quinazolin-4-yl]amino)piperidin-1-yl]-N-(2-hydroxyethyl)benzamide as a white solid. LC-MS (ES, m/z): 626. [M+H]$^+$ $^1$H-NMR (300 MHz, DMSO, ppm) δ 8.450 (s, 1H), 8.207 (d, J=2.0 Hz, 1H), 8.121-8.083 (m, 1H), 7.918 (d, J=7.7 Hz, 1H), 7.732 (d, J=8.7 Hz, 2H), 7.636 (d, J=8.6 Hz, 1H), 7.499-7.330 (m, 5H), 7.157-7.129 (m, 4H), 6.976 (d, J=8.8 Hz, 2H), 5.731 (s, 1H), 4.699-4.662 (m, 1H), 4.453 (br, 1H), 3.964 (d, J=13.1 Hz, 2H), 3.511-3.451 (m, 2H), 3.354-3.227 (m, 2H), 3.001-2.920 (m, 2H), 1.964 (d, J=11.6 Hz, 2H), 1.192-1.084 (m, 2H).

Example 51

3-(4-(4-((6-(bis(4-chlorophenyl)methyl)quinazolin-4-yl)amino)piperidin-1-yl)phenyl)-N-(2-hydroxyethyl)propanamide (Compound #76)

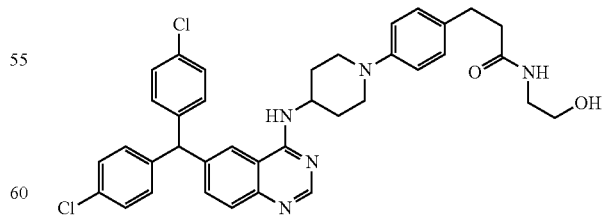

Into a 25-mL round-bottom flask, was placed 4-[4-([6-[bis(4-chlorophenyl)methyl]quinazolin-4-yl]amino)piperidin-1-yl]-4-oxobutanoic acid (100 mg, 0.18 mmol, 1.00 equiv), 2-aminoethan-1-ol (54 mg, 0.88 mmol, 5.00 equiv), HATU (101 mg, 0.27 mmol, 1.50 equiv), N,N-dimethylformamide (10 mL) and DIPEA (0.25 mL). The resulting solution was stirred overnight at 25° C. The resulting mixture was concentrated under vacuum. The residue was applied onto a silica gel column with dichloromethane/ CH$_3$OH (10:1), to yield 4-[4-([6-[bis(4-chlorophenyl) methyl]quinazolin-4-yl]amino)piperidin-1-yl]-N-(2-hydroxyethyl)-4-oxobutanamide as a white solid. LC-MS (ES, m/z): 606 [M+H]$^+$ $^1$H-NMR (300 MHz, DMSO, ppm) δ 8.459 (s, 1H), 8.215 (d, J=1.9 Hz, 1H), 7.977 (d, J=7.5 Hz, 1H), 7.793-7.775 (m, 1H), 7.643 (d, J=8.6 Hz, 1H), 7.479-7.381 (m, 5H), 7.199-7.141 (m, 4H), 5.755 (s, 1H), 4.615-4.580 (m, 1H), 4.433-4.388 (m, 2H), 3.952 (d, J=13.9 Hz, 1H), 3.388-3.348 (m, 2H), 3.125-3.065 (m, 3H), 2.750-2.656 (m, 1H), 2.574-2.526 (m, 2H), 2.343-2.296 (m, 2H), 1.991-1.900 (m, 2H), 1.541-1.389 (m, 2H), Example 52 methyl 4-(4-((6-(bis(4-chlorophenyl)methyl)quinazolin-4-yl)amino)piperidine-1-carbonyl)benzoate (Compound #73)

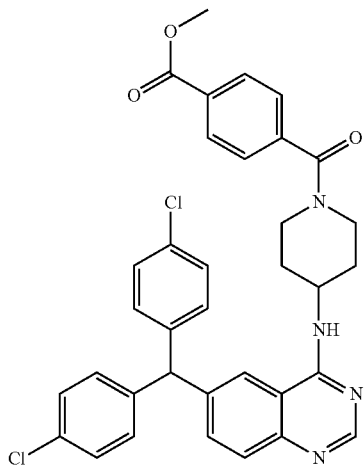 [SMILES: COC(=O)c1ccc(C(=O)N2CCC(Nc3ncnc4ccc(C(c5ccc(Cl)cc5)c5ccc(Cl)cc5)cc34)CC2)cc1]

Step 1: Methyl 4-(4-(tert-butoxycarbonylamino) piperidine-1-carbonyl)benzoate

Into a 250-mL 3-necked round-bottom flask, was placed tert-butyl N-(piperidin-4-yl)carbamate (5 g, 24.97 mmol, 1.00 equiv), dichloromethane (100 mL), triethylamine (10 mL) and methyl 4-(carbonochloridoyl)benzoate (6 g, 30.21 mmol, 1.20 equiv). The resulting solution was stirred overnight at 25° C. The resulting mixture was washed with water (2×200 mL). The mixture was dried over anhydrous sodium sulfate. The solids were collected by filtration. The resulting mixture was concentrated under vacuum, to yield methyl 4-[(4-[[(tert-butoxy)carbonyl]amino]piperidin-1-yl)carbonyl]benzoate as a white solid.

Step 2: Methyl 4-(4-aminopiperidine-1-carbonyl)benzoate

Into a 250-mL 3-necked round-bottom flask, was placed methyl 4-[(4-[[(tert-butoxy)carbonyl]amino]piperidin-1-yl) carbonyl]benzoate (9 g, 24.83 mmol, 1.00 equiv) and hydrogen chloride/CH$_3$OH (100 mL). The resulting solution was stirred overnight at 25° C. The resulting mixture was concentrated under vacuum, to yield methyl 4-[(4-aminopiperidin-1-yl)carbonyl]benzoate dihydrochloride as a white solid.

Step 3: Methyl 4-(4-(6-(bis(4-chlorophenyl)methyl) quinazolin-4-ylamino)piperidine-1-carbonyl)benzoate Into a 25-mL round-bottom flask, was placed 6-[bis(4-chlorophenyl)methyl]-4-chloroquinazoline (200 mg, 0.50 mmol, 1.00 equiv), methyl 4-[(4-aminopiperidin-1-yl)carbonyl]benzoate dihydrochloride (220 mg, 0.66 mmol, 1.30 equiv), propan-2-ol (10 mL) and triethylamine (0.5 mL). The resulting solution was stirred overnight at 40° C. The resulting mixture was concentrated under vacuum. The resulting mixture was washed with water (10 mL). The solids were collected by filtration, to yield methyl 4-[[4-([6-[bis(4-chlorophenyl)methyl]quinazolin-4-yl]amino)piperidin-1-yl]carbonyl]benzoate as a white solid. LC-MS (ES, m/z): 625. [M+H]$^+$ $^1$H-NMR (300 MHz, DMSO, ppm) δ 8.445 (s, 1H), 8.210 (s, 1H), 8.046-7.938 (m, 3H), 7.642 (d, J=8.7 Hz, 1H), 7.530-7.471 (m, 3H), 7.447-7.386 (m, 4H), 7.174-7.146 (m, 4H), 5.760 (s, 1H), 4.509 (br, 2H), 3.872 (s, 3H), 3.558-3.525 (m, 1H), 3.301-2.960 (m, 2H), 2.264-1.913 (m, 2H), 1.504 (br, 2H).

Example 53

4-(4-((6-(bis(4-chlorophenyl)methyl)quinazolin-4-yl)amino)piperidine-1-carbonyl)benzoic acid (Compound #68)

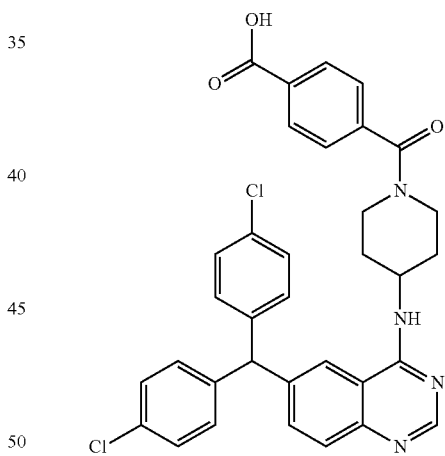

Into a 100-mL 3-necked round-bottom flask, was placed methyl 4-[[4-([6-[bis(4-chlorophenyl)methyl]quinazolin-4-yl]amino)piperidin-1-yl]carbonyl]benzoate (210 mg, 0.34 mmol, 1.00 equiv), methanol (20 mL) and 1M NaOH (20 mL). The resulting solution was heated to reflux for 5 hr. The reaction mixture was cooled with a water/ice bath. The pH value of the solution was adjusted to pH 5-6 with 10% HCl. The solids were collected by filtration, to yield 4-[[4-([6-[bis(4-chlorophenyl)methyl]quinazolin-4-yl]amino)piperidin-1-yl]carbonyl]benzoic acid as a light yellow solid. LC-MS (ES, m/z): 611 [M+H]$^+$ $^1$H-NMR (300 MHz, DMSO, ppm) δ: 9.597 (s, 1H), 8.826 (s, 1H), 8.516 (s, 1H), 8.031-8.003 (m, 2H), 7.811-7.692 (m, 2H), 7.511-7.408 (m, 6H), 7.184-7.155 (m, 4H), 5.838 (s, 1H), 4.701-4.504 (m, 2H), 3.711-3.574 (m, 1H), 3.314-3.150 (m, 1H), 2.964 (br, 1H), 2.133-1.886 (m 2H), 1.683 (br, 2H)

Example 54

4-((4-((6-(Bis(4-chlorophenyl)methyl)quinazolin-4-yl)amino)piperidin-1-yl)sulfonyl)-N-(1,3-dihydroxy-2-(hydroxymethyl)propan-2-yl)benzamide (Compound #41

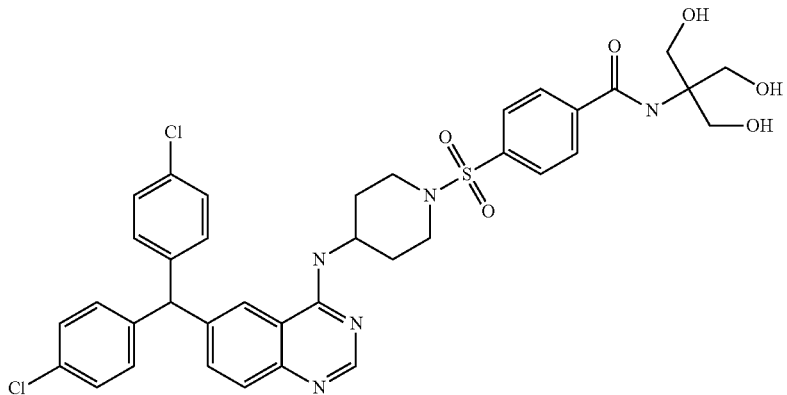 [SMILES: O=C(NC(CO)(CO)CO)c1ccc(S(=O)(=O)N2CCC(Nc3ncnc4ccc(C(c5ccc(Cl)cc5)c5ccc(Cl)cc5)cc34)CC2)cc1]

A mixture of 4-((4-((6-(bis(4-chlorophenyl)methyl)quinazolin-4-yl)amino)piperidin-1-yl)sulfonyl)benzoic acid (50 mg, 0.077 mmol), 2-amino-2-(hydroxymethyl)propane-1,3-diol (14.03 mg, 0.116 mmol), HATU (38.2 mg, 0.1 mmol) and TEA (0.0322 mL, 0.232 mmol) in DMF (2 mL) was stirred at room temperature for 3 hr. The resulting mixture was then diluted with DCM and water. The organics were concentrated and purified by silica gel column (8% MeOH/CH$_2$Cl$_2$) to yield 4-((4-((6-(bis(4-chlorophenyl)methyl)quinazolin-4-yl)amino)piperidin-1-yl)sulfonyl)-N-(1,3-dihydroxy-2-(hydroxymethyl)propan-2-yl)benzamide. LCMS (ES, m/z) 750.2, 752.1 [M+H]$^+$ $^1$H NMR (CH$_3$OD) d: 8.36 (s, 1H), 8.07 (s, 1H), 7.99-8.05 (m, J=8.6 Hz, 2H), 7.84-7.92 (m, J=8.6 Hz, 2H), 7.63 (d, J=8.6 Hz, 1H), 7.52 (dd, J=8.6, 2.0 Hz, 1H), 7.26-7.36 (m, 4H), 7.03-7.17 (m, 4H), 5.74 (s, 1H), 4.16 (m, 1H), 3.81-3.94 (m, 8H), 2.36-2.58 (m, 2H), 2.08 (d, J=10.1 Hz, 2H), 1.72 (qd, J=12.3, 4.0 Hz, 2H)

Example 55

6-(bis(4-fluorophenyl)methyl)-N-(1-phenylpiperidin-4-yl)quinazolin-4-amine (Compound #67)

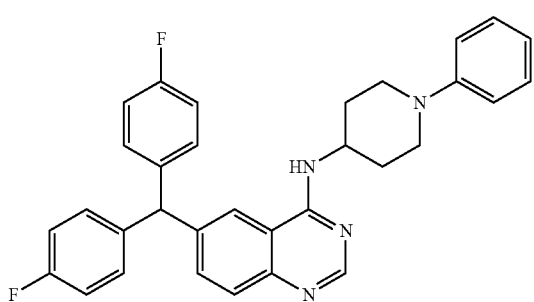 [SMILES: Fc1ccc(C(c2ccc(F)cc2)c2ccc3ncnc(NC4CCN(c5ccccc5)CC4)c3c2)cc1]

Step 1: Methyl 4-(1-phenylpiperidin-4-ylamino)quinazoline-6-carboxylate

Into a 25-mL round-bottom flask, was placed methyl 4-chloroquinazoline-6-carboxylate (150 mg, 0.67 mmol, 1.00 equiv), 4-phenylcyclohexan-1-amine (142 mg, 0.81 mmol, 1.30 equiv), propan-2-ol (10 mL) and triethylamine (0.3 mL). The resulting solution was stirred overnight at 30° C. The resulting mixture was concentrated under vacuum. The residue was applied onto a silica gel column with ethyl acetate/petroleum ether (1:5), to yield methyl 4-[(1-phenylpiperidin-4-yl)amino]quinazoline-6-carboxylate as a light yellow solid. (ES (m/z) 363 [M+H]+

Step 2: Bis(4-fluorophenyl)(4-(1-phenylpiperidin-4-ylamino)quinazolin-6-yl)methanol Into a 50-mL 3-necked round-bottom flask, was placed methyl 4-[(1-phenylpiperidin-4-yl)amino]quinazoline-6-carboxylate (150 mg, 0.41 mmol, 1.00 equiv) and tetrahydrofuran (15 mL). This was followed by the addition of bromo(4-fluorophenyl)magnesium (1.65 mL, 10.00 equiv) dropwise with stirring at 0° C. The resulting solution was stirred overnight at 25° C. The reaction was then quenched by the addition of water (30 mL). The resulting solution was extracted with ethyl acetate (3×50 mL) and the organic layers combined and dried over anhydrous sodium sulfate. The solids were filtered out. The resulting mixture was concentrated under vacuum. The residue was applied onto a silica gel column with ethyl acetate/petroleum ether (1:5), to yield of bis(4-fluorophenyl)([4-[(1-phenylpiperidin-4-yl)amino]quinazolin-6-yl])methanol as a light yellow solid.

Step 3: 6-(Bis(4-fluorophenyl)methyl)-N-(1-phenylpiperidin-4-yl)quinazolin-4-amine Into a 100-mL round-bottom flask, was placed bis(4-fluorophenyl)([4-[(1-phenylpiperidin-4-yl)amino]quinazolin-6-yl])methanol (120 mg, 0.23 mmol, 1.00 equiv), triethylsilane (107 mg, 0.92 mmol, 4.00 equiv), dichloromethane (30 mL) and trifluoroacetic acid (3 mL). The resulting solution was stirred overnight at 25° C. The resulting solution was diluted with DCM (100 mL). The resulting mixture was washed with aqueous sodium bicarbonate (3×60 mL). The mixture was dried over anhydrous sodium sulfate. The solids were filtered out. The resulting mixture was concentrated under vacuum. The residue was applied onto a silica gel column with dichloromethane/methanol (20:1), to yield 6-[bis(4-fluorophenyl)methyl]-N-(1-phenylpiperidin-4-yl)quinazolin-4-amine as a white solid. LC-MS (ES, m/z): 507 [M+H]$^+$.

$^1$H-NMR (300 MHz, DMSO, ppm) δ, 8.466 (s, 1H), 8.228 (s, 1H), 7.941 (d, J=7.5 Hz, 1H), 7.647-7.618 (m, 1H), 7.469-7.435 (m, 1H), 7.228-7.142 (m, 10H), 6.974-6.900 (m, 2H), 6.757-6.709 (m, 1H), 5.739 (s, 1H), 4.440 (br, 1H), 2.884-2.720 (m, 2H), 1.981-1.944 (m, 2H), 1.757-1.601 (m, 2H).

Example 56

6-((4-chlorophenyl)(4-methoxyphenyl)methyl)-N-(1-phenylpiperidin-4-yl)quinazolin-4-amine (Compound #58)

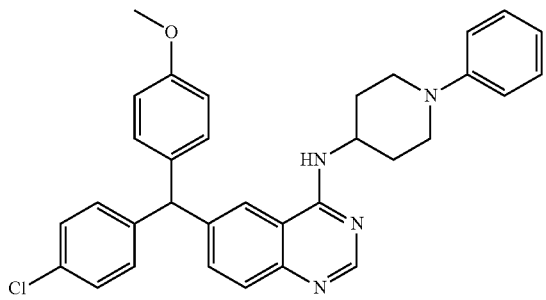 [SMILES: COc1ccc(C(c2ccc(Cl)cc2)c2ccc3ncnc(NC4CCN(c5ccccc5)CC4)c3c2)cc1]

Step 1: 4-(1-Phenylpiperidin-4-ylamino)quinazoline-6-carboxylic acid

Into a 100-mL round-bottom flask, was placed methyl 4-[(1-phenylpiperidin-4-yl)amino]quinazoline-6-carboxylate (200 mg, 0.55 mmol, 1.00 equiv), methanol (20 mL), 1M NaOH (20 mL). The resulting solution was stirred overnight at 50° C. The pH value of the solution was adjusted to pH 5-6 with 10% HCl. The solids were collected by filtration, to yield 4-[(1-phenylpiperidin-4-yl)amino]quinazoline-6-carboxylic acid as a light yellow solid. (ES (m/z) 347 [M−H]+

Step 2: N-methoxy-N-methyl-4-(1-phenylpiperidin-4-ylamino)quinazoline-6-carboxamide Into a 50-mL 3-necked round-bottom flask, was placed 4-[(1-phenylpiperidin-4-yl)amino]quinazoline-6-carboxylic acid (150 mg, 0.43 mmol, 1.00 equiv), methoxy(methyl)amine hydrochloride (86 mg, 0.88 mmol, 2.00 equiv), HATU (245 mg, 0.64 mmol, 1.50 equiv), N,N-dimethylformamide (20 mL) and triethylamine (0.5 mL). The resulting solution was stirred overnight at 25° C. The resulting solution was diluted with water (200 mL). The solids were collected by filtration, to yield N-methoxy-N-methyl-4-[(1-phenylpiperidin-4-yl)amino]quinazoline-6-carboxamide as a yellow solid. (ES (m/z) 392 [M+H]+

Step 3: (4-chlorophenyl)(4-(1-phenylpiperidin-4-ylamino)quinazolin-6-yl)methanone Into a 100-mL 3-necked round-bottom flask, was placed N-methoxy-N-methyl-4-[(1-phenylpiperidin-4-yl)amino]quinazoline-6-carboxamide (150 mg, 0.38 mmol, 1.00 equiv), tetrahydrofuran (30 mL). This was followed by the addition of bromo(4-chlorophenyl)magnesium (2.8 mL, 10.00 equiv) dropwise with stirring at 0° C. The resulting solution was stirred overnight at 25° C. The reaction was then quenched by the addition of water (80 mL). The resulting solution was extracted with ethyl acetate (3×80 mL) and the organic layers combined and dried over anhydrous sodium sulfate. The solids were filtered out. The resulting mixture was concentrated under vacuum. The residue was applied onto a silica gel column with ethyl acetate:petroleum ether (1:5), to yield 6-[(4-chlorophenyl)carbonyl]-N-(1-phenylpiperidin-4-yl)quinazolin-4-amine as a light yellow solid. (ES (m/z) 443 [M+H]+

Step 4: (4-chlorophenyl)(4-methoxyphenyl)(4-(1-phenylpiperidin-4-ylamino)quinazolin-6-yl)methanol Into a 100-mL 3-necked round-bottom flask, was placed 6-[(4-chlorophenyl)carbonyl]-N-(1-phenylpiperidin-4-yl)quinazolin-4-amine (130 mg, 0.29 mmol, 1.00 equiv) and tetrahydrofuran (30 mL). This was followed by the addition of bromo(4-methoxyphenyl)magnesium (2.9 mL, 10.00 equiv) dropwise with stirring at 0° C. The resulting solution was stirred overnight at 25° C. The reaction was then quenched by the addition of water (80 mL). The resulting solution was extracted with ethyl acetate (3×80 mL) and the organic layers combined and dried over anhydrous sodium sulfate. The solids were filtered out. The resulting mixture was concentrated under vacuum. The residue was applied onto a silica gel column with ethyl acetate:petroleum ether (1:5), to yield (4-chlorophenyl)(4-methoxyphenyl)[4-[(1-phenylpiperidin-4-yl)amino]quinazolin-6-yl]methanol as a light yellow solid.

Step 5: 6-((4-Chlorophenyl)(4-methoxyphenyl)methyl)-N-(1-phenylpiperidin-4-yl)quinazolin-4-amine Into a 100-mL 3-necked round-bottom flask, was placed (4-chlorophenyl)(4-methoxyphenyl)[4-[(1-phenylpiperidin-4-yl)amino]quinazolin-6-yl]methanol (100 mg, 0.18 mmol, 1.00 equiv), triethylsilane (84 mg, 0.72 mmol, 4.00 equiv), dichloromethane (30 mL) and trifluoroacetic acid (3 mL). The resulting solution was stirred overnight at 25° C. The resulting solution was diluted with DCM (100 mL). The resulting mixture was washed with aqueous sodium bicarbonate (3×80 mL). The mixture was dried over anhydrous sodium sulfate. The solids were filtered out. The resulting mixture was concentrated under vacuum. The residue was applied onto a silica gel column with dichloromethane/methanol (20:1), to yield 6-[(4-chlorophenyl)(4-methoxyphenyl)methyl]-N-(1-phenylpiperidin-4-yl)quinazolin-4-amine as a white solid. LC-MS (ES, m/z): 535 [M+H]$^+$ $^1$H-NMR (300 MHz, DMSO, ppm) δ: 8.402 (s, 1H), 8.194 (s, 1H), 7.852 (d, J=7.5 Hz, 1H), 7.600-7.571 (m, 1H), 7.420-7.385 (m, 1H), 7.385-7.327 (m, 2H), 7.193-7.108 (m, 4H), 7.7.079-7.022 (m, 2H), 6.993-6.940 (m, 2H), 6.874-6.835 (m, 2H), 6.723-6.675 (m, 1H), 5.618 (s, 1H), 4.368-4.355 (m, 1H), 3.788-3.746 (m, 2H), 3.677 (s, 3H), 2.848-2.807 (m, 2H), 1.943-1.909 (m, 2H), 1.737-1.646 (m, 2H).

Example 57

Methyl 3-(((6-(bis(4-chlorophenyl)methyl)quinazolin-4-yl)amino)methyl)benzoate (Compound #62)

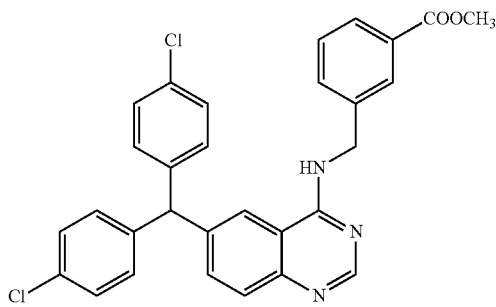 [SMILES: COC(=O)c1cccc(CNc2ncnc3ccc(C(c4ccc(Cl)cc4)c4ccc(Cl)cc4)cc23)c1]

Into a 100-mL round-bottom flask, was placed 6-[bis(4-chlorophenyl)methyl]-4-chloroquinazoline (300 mg, 0.75 mmol, 1.00 equiv), propan-2-ol (10 mL, 10.00 equiv), triethylamine (303 mg, 2.99 mmol, 4.00 equiv) and methyl 3-(aminomethyl)benzoate hydrochloride (197 mg, 0.98 mmol, 1.30 equiv). The resulting solution was stirred overnight at 50° C. The reaction was then quenched by the addition of water (100 mL). The resulting solution was extracted with ethyl acetate (3×100 mL) and the organic layers combined and dried over anhydrous sodium sulfate. The solids were filtered out. The resulting mixture was concentrated under vacuum. The resulting residue was purified by re-crystallization from n-hexane, to yield of methyl 3-[([6-[bis(4-chlorophenyl)methyl]quinazolin-4-yl]amino)methyl]benzoate as a white solid. LC-MS (ES, m/z) 528 [M+H]+

$^1$H-NMR (DMSO-d$_6$, 300 MHz) δ 8.84 (t, J=5.7 Hz, 1H), 8.42 (s, 1H), 8.15 (s, 1H), 7.94 (s, 1H), 7.84-7.81 (m, 1H), 7.68-7.61 (m, 2H), 7.53-7.38 (m, 6H), 7.18 (d, J=8.4 Hz, 4H), 5.79 (s, 1H), 4.81-4.79 (m, 2H), 3.82 (s, 3H).

Example 58

3-(((6-(bis(4-chlorophenyl)methyl)quinazolin-4-yl)amino)methyl)benzoic acid (Compound #59)

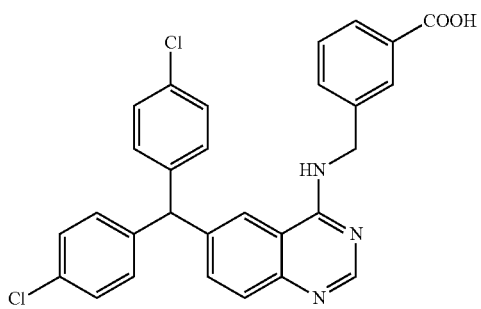 [SMILES: O=C(O)c1cccc(CNc2ncnc3ccc(C(c4ccc(Cl)cc4)c4ccc(Cl)cc4)cc23)c1]

Into a 100-mL round-bottom flask, was placed methyl 3-[([6-[bis(4-chlorophenyl)methyl]quinazolin-4-yl]amino)methyl]benzoate (250 mg, 0.47 mmol, 1.00 equiv, 98.6%), methanol (20 mL, 20.00 equiv) and sodium hydroxide (20 mL, 1M). The resulting solution was stirred overnight at 60° C. in an oil bath. The resulting mixture was concentrated under vacuum. The reaction was then quenched by the addition of water (300 mL). The solids were collected by filtration. The solid was dried in an oven under reduced pressure, to yield 3-[([6-[bis(4-chlorophenyl)methyl]quinazolin-4-yl]amino)methyl]benzoic acid as a white solid. LC-MS (ES, m/z): 514 [M+H]+

$^1$H-NMR (DMSO-d$_6$, 400 MHz): δ 8.85 (t, J=6.0 Hz, 1H), 8.43 (s, 1H), 8.18 (s, 1H), 7.91 (s, 1H), 7.80-7.78 (m, 1H), 7.68-7.66 (m, 1H), 7.53-7.49 (m, 2H), 7.41-7.35 (m, 5H), 7.19 (d, J=8.4 Hz, 4H), 5.80 (s, 1H), 4.80-4.78 (m, 2H).

Example 59

3-(((6-(bis(4-chlorophenyl)methyl)quinazolin-4-yl)amino)methyl)benzamide (Compound #57)

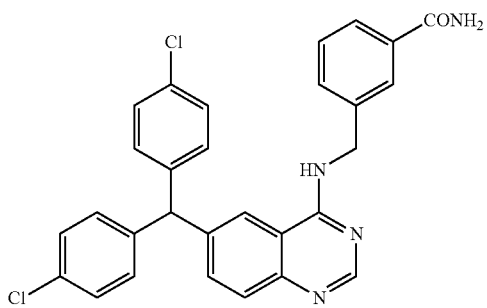 [SMILES: NC(=O)c1cccc(CNc2ncnc3ccc(C(c4ccc(Cl)cc4)c4ccc(Cl)cc4)cc23)c1]

Into a 100-mL round-bottom flask, was placed 3-[([6-[bis(4-chlorophenyl)methyl]quinazolin-4-yl]amino)methyl]benzoic acid (100 mg, 0.19 mmol, 1.00 equiv, 98.6%), N,N-dimethylformamide (2 mL, 10.00 equiv), HATU (111 mg, 0.29 mmol, 1.50 equiv), DIPEA (151 mg, 1.17 mmol, 6.00 equiv) and ammonium chloride (52 mg, 0.97 mmol, 5.00 equiv). The resulting solution was stirred overnight at room temperature. The reaction was then quenched by the addition of water (300 mL). The solid was collected by filtration. The solid was dried in an oven under reduced pressure, to yield 3-[([6-[bis(4-chlorophenyl)methyl]quinazolin-4-yl]amino)methyl]benzamide as a white solid. LC-MS (ES, m/z): 513 [M+H]+

$^1$H-NMR (DMSO-d$_6$, 300 MHz): δ 8.84 (t, J=5.7 Hz, 1H), 8.43 (s, 1H), 8.17 (s, 1H), 7.93 (s, 1H), 7.84 (s, 1H), 7.74-7.65 (m, 2H), 7.54-7.32 (m, 8H), 7.18 (d, J=8.4 Hz, 4H), 5.79 (s, 1H), 4.79-4.78 (m, 2H).

Example 60

2-((6-(bis(4-chlorophenyl)methyl)-4-((3-(trifluoromethyl)benzyl)amino)quinazolin-2-yl)oxy)ethanol (Compound #55)

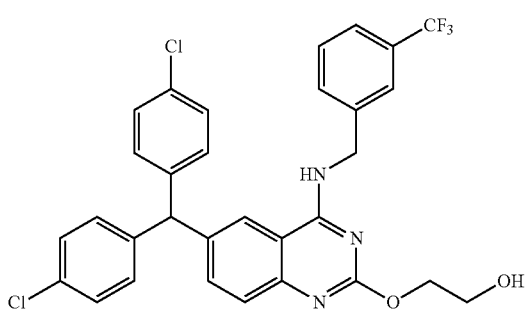 [SMILES: OCCOc1nc(NCc2cccc(C(F)(F)F)c2)c2cc(C(c3ccc(Cl)cc3)c3ccc(Cl)cc3)ccc2n1]

Step 1: 6-Bromo-2-chloro-N-(3-(trifluoromethyl)benzyl)quinazolin-4-amine

Into a 500-mL round-bottom flask, was placed a solution of 6-bromo-2,4-dichloroquinazoline (10 g, 35.98 mmol, 1.00 equiv) in tetrahydrofuran (300 mL). This was followed by the addition of DIPEA (31.27 mL, 5.00 equiv) dropwise with stirring at 0° C. To the resulting mixture was added [3-(trifluoromethyl)phenyl]methanamine (7.55 g, 43.11 mmol, 1.20 equiv) dropwise with stirring at 0° C. The resulting solution was stirred for 3 h at room temperature. The resulting solution was diluted with water (100 mL). The resulting solution was extracted with ethyl acetate (2×200 mL) and the organic layers combined, dried over anhydrous sodium sulfate and concentrated under vacuum. The residue was applied onto a silica gel column with ethyl acetate/petroleum ether (15:85), to yield 6-bromo-2-chloro-N-[[3-(trifluoromethyl)phenyl]methyl]quinazolin-4-amine as a yellow solid. (ES (m/z) 416 [M+H]+

Step 2: (2-Chloro-4-(3-(trifluoromethyl)benzylamino)quinazolin-6-yl)bis(4-chlorophenyl)methanol Into a 2-L 3-necked round-bottom flask purged and maintained with an inert atmosphere of nitrogen, was placed a solution of 6-bromo-2-chloro-N-[[3-(trifluoromethyl)phenyl]methyl]quinazolin-4-amine (7.68 g, 18.43 mmol, 1.00 equiv) in tetrahydrofuran (1.1 L). This was followed by the addition of LiHMDS (73.68 mL, 4.00 equiv, 1 M) dropwise with stirring at 0° C. The resulting solution was stirred for 30 min at 0° C. To the resulting mixture was then added n-BuLi (115 mL, 10.00 equiv, 1.6M) dropwise with stirring at −78° C. To the mixture was added bis(4-chlorophenyl)methanone (36.99 g, 147.31 mmol, 8.00 equiv), dissolved in a minimum volume of THF dropwise with stirring at −78° C. The reaction was then warmed to room temperature slowly and quenched by the addition of sat. sodium bicarbonate (500 mL). The resulting solution was extracted with ethyl acetate (2×500 mL) and the organic layers combined, dried over anhydrous sodium sulfate and concentrated under vacuum. The residue was applied onto a silica gel column with ethyl acetate/petroleum ether (15:85), to yield [2-chloro-4-([[3-(trifluoromethyl)phenyl]methyl]amino)quinazolin-6-yl]bis(4-chlorophenyl)methanol as a yellow solid, which was used in the next step without further purification. (ES (m/z) 588 [M+H]+

Step 3: 6-(Bis(4-chlorophenyl)methyl)-2-chloro-N-(3-(trifluoromethyl)benzyl)quinazolin-4-amine Into a 1-L round-bottom flask purged and maintained with an inert atmosphere of nitrogen, was placed a solution of [2-chloro-4-([[3-(trifluoromethyl)phenyl]methyl]amino)quinazolin-6-yl]bis(4-chlorophenyl)methanol (20 g, 33.97 mmol, 1.00 equiv) in dichloromethane (500 mL). This was followed by the addition of Et₃SiH (22 mL, 4.00 equiv) dropwise with stirring at 0° C. To the resulting mixture was added trifluoroacetic acid (65 mL, 25.00 equiv) dropwise with stirring at 0° C. The resulting solution was stirred for 3 h at room temperature. The reaction was then quenched by the addition of sat. sodium bicarbonate (500 mL). The resulting solution was extracted with ethyl acetate (2×500 mL) and the organic layers combined, dried over anhydrous sodium sulfate and concentrated under vacuum. The residue was applied onto a silica gel column with ethyl acetate/petroleum ether (15:85), to yield 6-[bis(4-chlorophenyl)methyl]-2-chloro-N-[[3-(trifluoromethyl)phenyl]methyl]quinazolin-4-amine as a yellow solid.

Step 4: 2-(6-(Bis(4-chlorophenyl)methyl)-4-(3-(trifluoromethyl)benzylamino)quinazolin-2-yloxy)ethanol Into a 500-mL round-bottom flask purged and maintained with an inert atmosphere of nitrogen, was placed a solution of ethane-1,2-diol (39 mL, 200.00 equiv) in tetrahydrofuran (250 mL). This was followed by the addition of sodium hydride (4.2 g, 175.00 mmol, 30.00 equiv), in portions. The resulting solution was stirred for 20 min at room temperature. To the resulting mixture was then added 6-[bis(4-chlorophenyl)methyl]-2-chloro-N-[[3-(trifluoromethyl)phenyl]methyl]quinazolin-4-amine (2 g, 3.49 mmol, 1.00 equiv), in portions. The resulting solution was allowed to react overnight at 70° C. with stirring. The reaction was then quenched by the addition of sat. sodium bicarbonate (200 mL). The resulting solution was extracted with ethyl acetate (2×200 mL) and the organic layers combined, dried over anhydrous sodium sulfate and concentrated under vacuum. The resulting residue was purified by Prep-TLC with 4:2 EA/PE as eluent, to yield 2-([6-[bis(4-chlorophenyl)methyl]-4-([[3-(trifluoromethyl)phenyl]methyl]amino)quinazolin-2-yl]oxy)ethan-1-ol as a yellow solid. LCMS (ES, m/z) 598[M+H]⁺

¹H-NMR (400 MHz, DMSO) δ 8.85 (br, 1H), 8.08 (s, 1H), 7.70 (s, 1H), 7.64-7.54 (m, 3H), 7.48-7.46 (m, 1H), 7.42-7.39 (m, 5H), 7.18 (d, J=8.4 Hz, 4H), 5.73 (s, 1H), 4.83-4.78 (m, 3H), 4.27-4.24 (m, 2H), 3.68-3.64 (m, 2H).

Example 61

2-((6-(bis(4-chlorophenyl)methyl)-4-((3-(trifluoromethyl)benzyl)amino)quinazolin-2-yl)oxy)acetic acid (Compound

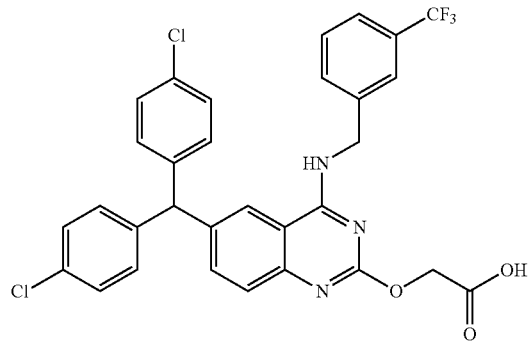 [SMILES: O=C(O)COc1nc(NCc2cccc(C(F)(F)F)c2)c2cc(C(c3ccc(Cl)cc3)c3ccc(Cl)cc3)ccc2n1]

Into a 50-mL round-bottom flask, was placed a solution of 2-([6-[bis(4-chlorophenyl)methyl]-4-([[3-(trifluoromethyl)phenyl]methyl]amino)quinazolin-2-yl]oxy)ethan-1-ol (100 mg, 0.17 mmol, 1.00 equiv) in N,N-dimethylformamide (20 mL) and PDC (1.28 g, 3.40 mmol, 20.00 equiv). The resulting solution was stirred overnight at 50° C. The reaction was then quenched by the addition of NH₄Cl (30 mL). The resulting solution was extracted with ethyl acetate (2×50 mL) and then extracted with DCM (2×50 mL). The organic layers combined, dried over anhydrous sodium sulfate and concentrated under vacuum. The resulting residue was purified by Prep-TLC with ethyl acetate as eluent, to yield 2-([6-[bis(4-chlorophenyl)methyl]-4-([[3-(trifluoromethyl)phenyl]methyl]amino)quinazolin-2-yl]oxy)acetic acid; trifluoroacetic acid as a white solid. LCMS (ES, m/z) 612[M+H]⁺

¹H-NMR (300 MHz, DMSO-d₆) δ 8.16 (s, 1H), 7.74 (s, 1H), 7.67-7.59 (m, 2H), 7.59-7.48 (m, 3H), 7.40 (d, J=8.4 Hz, 4H), 7.16 (d, J=8.8 Hz, 4H), 5.77 (s, 1H), 4.886-4.756 (m, 4H).

Example 62

2-((6-(bis(4-chlorophenyl)methyl)-4-((3-(trifluoromethyl)benzyl)amino)quinazolin-2-yl)oxy)-N-(2-hydroxyethyl)acetamide (Compound #40)

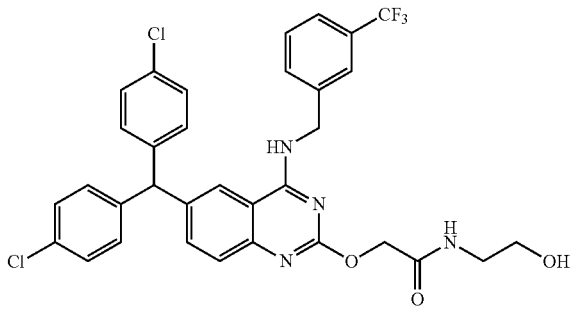 [SMILES: O=C(COc1nc(NCc2cccc(C(F)(F)F)c2)c2cc(C(c3ccc(Cl)cc3)c3ccc(Cl)cc3)ccc2n1)NCCO]

Into a 25-mL round-bottom flask purged and maintained with an inert atmosphere of nitrogen, was placed a solution of 2-([6-[bis(4-chlorophenyl)methyl]-4-([[3-(trifluoromethyl)phenyl]methyl]amino)quinazolin-2-yl]oxy)acetic acid (160 mg, 0.26 mmol, 1.00 equiv) in N,N-dimethylformamide (10 mL), 2-aminoethan-1-ol (0.124 mL, 8.00 equiv), HATU (148 mg, 0.39 mmol, 1.50 equiv) and DIPEA (0.362 mL, 8.00 equiv). The resulting solution was stirred overnight at 70° C. The reaction was then quenched by the addition of sat. sodium bicarbonate (30 mL). The resulting solution was extracted with ethyl acetate (3×50 mL) and the organic layers combined, dried over anhydrous sodium sulfate and concentrated under vacuum. The resulting residue was purified by Prep-TLC with methanol/DCM=2/8 as eluent, to yield 2-([6-[bis(4-chlorophenyl)methyl]-4-([[3-(trifluoromethyl)phenyl]methyl]amino)quinazolin-2-yl]oxy)-N-(2-hydroxyethyl)acetamide as a white solid. LCMS (ES, m/z) 655 [M+H]⁺

¹H-NMR (300 MHz, DMSO-d₆) δ 9.01 (br, 1H), 8.09 (s, 1H), 7.88 (br, 1H), 7.71 (s, 1H), 7.66-7.53 (m, 3H), 7.49-7.37 (m, 6H), 7.16 (d, J=8.4 Hz, 4H), 5.74 (s, 1H), 4.89-4.53 (m, 5H), 3.54-3.38 (m, 2H), 3.13-3.03 (m, 2H).

Example 63

2-(2-((6-(bis(4-chlorophenyl)methyl)-4-((3-(trifluoromethyl)benzyl)amino)quinazolin-2-yl)oxy)ethoxy)ethanol (Compound #35)

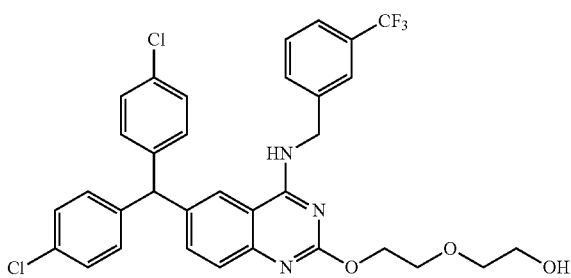

Into a 500-mL round-bottom flask, was placed a solution of 2-(2-hydroxyethoxy)ethan-1-ol (25 mL, 100.00 equiv) in tetrahydrofuran (250 mL). This was followed by the addition of sodium hydride (3.1 g, 129.17 mmol, 30.00 equiv) in several batches. The resulting solution was stirred for 20 min at room temperature. To the resulting mixture was added 6-[bis(4-chlorophenyl)methyl]-2-chloro-N-[[3-(trifluoromethyl)phenyl]methyl]quinazolin-4-amine (1.5 g, 2.62 mmol, 1.00 equiv), in portions. The resulting solution was allowed to react overnight at 70° C. with stirring. The reaction was then quenched by the addition of sat. sodium bicarbonate (100 mL). The resulting solution was extracted with ethyl acetate (2×200 mL) and the organic layers combined and concentrated under vacuum. The resulting solution was diluted with water (100 mL). The resulting solution was extracted with DCM (200 mL) and the organic layers combined, dried over anhydrous sodium sulfate and concentrated under vacuum. The residue was applied onto a silica gel column with ethyl acetate/petroleum ether (60:40), to yield 2-[2-([6-[bis(4-chlorophenyl)methyl]-4-([[3-(trifluoromethyl)phenyl]methyl]amino)quinazolin-2-yl]oxy)ethoxy]ethan-1-ol as a yellow solid. LCMS (ES, m/z) 642 [M+H]⁺

¹H-NMR (400 MHz, DMSO-d₆) δ 8.88 (s, 1H), 8.08 (s, 1H), 7.71 (s, 1H), 7.64-7.54 (m, 3H), 7.49-7.47 (m, 1H), 7.42-7.39 (m, 5H), 7.18 (d, J=8.4 Hz, 4H), 5.74 (s, 1H), 4.80-4.79 (m, 2H), 4.61-4.58 (m, 1H), 4.36-4.34 (m, 2H), 3.69-3.66 (m, 2H), 3.51-3.43 (m, 4H).

Example 64

3-(2-((6-(bis(4-chlorophenyl)methyl)-4-((3-(trifluoromethyl)benzyl)amino)quinazolin-2-yl)oxy)ethoxy)propanoic acid (Compound #48)

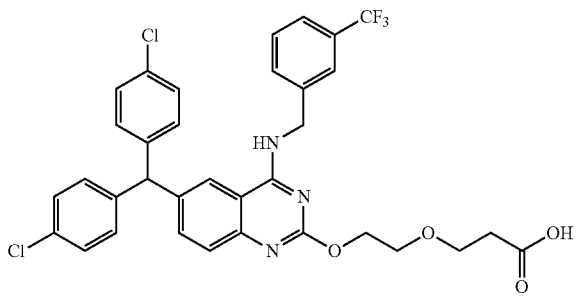

Step 1: tert-Butyl 3-(2-(6-(bis(4-chlorophenyl)methyl)-4-(3-(trifluoromethyl)benzylamino)quinazolin-2-yloxy)ethoxy)propanoate Into a 25-mL round-bottom flask purged and maintained with an inert atmosphere of nitrogen, was placed a solution of 2-([6-[bis(4-chlorophenyl)methyl]-4-([[3-(trifluoromethyl)phenyl]methyl]amino)quinazolin-2-yl]oxy)ethan-1-ol (827 mg, 1.38 mmol, 1.00 equiv) in tetrahydrofuran (10 mL). This was followed by the addition of sodium hydride (28 mg, 1.17 mmol, 0.50 equiv, 60%), in portions. To the resulting mixture was then added tert-Butyl prop-2-enoate (1.59 g, 12.41 mmol, 9.00 equiv) dropwise with stirring. The resulting solution was stirred overnight at room temperature. The reaction was then quenched by the addition of sat. sodium bicarbonate (30 mL). The resulting solution was extracted with ethyl acetate (2×30 mL) and the organic layers combined, dried over anhydrous sodium sulfate and concentrated under vacuum, to yield tert-butyl 3-[2-([6-[bis(4-chlorophenyl)methyl]-4-([[3-(trifluoromethyl)phenyl]methyl]amino)quinazolin-2-yl]oxy)ethoxy]propanoate as a yellow solid. The resulting residue was used in the next step without further purification. (ES (m/z) 726 [M+H]+

Step 2: 3-(2-(6-(Bis(4-chlorophenyl)methyl)-4-(3-(trifluoromethyl)benzylamino)quinazolin-2-yloxy)ethoxy)propanoic acid Into a 250-mL round-bottom flask purged and maintained with an inert atmosphere of nitrogen, was placed a solution of tert-butyl 3-[2-([6-[bis(4-chlorophenyl)methyl]-4-([[3-(trifluoromethyl)phenyl]methyl]amino)quinazolin-2-yl]oxy)ethoxy]propanoate (962.6 mg, 1.32 mmol, 1.00 equiv) in dichloromethane (50 mL). This was followed by the addition of trifluoroacetic acid (2.02 mL, 20.00 equiv) dropwise with stirring. The resulting solution was stirred overnight at room temperature. The reaction was then quenched by the addition of sat. NH$_4$Cl (50 mL). The resulting solution was extracted with ethyl acetate (2×100 mL) and the organic layers combined, dried over anhydrous sodium sulfate and concentrated under vacuum. The residue was applied onto a silica gel column with ethyl acetate/petroleum ether (85:15). The resulting residue was purified by re-crystallization from n-hexane, to yield 3-[2-([6-[bis(4-chlorophenyl)methyl]-4-([[3-(trifluoromethyl)phenyl]methyl]amino)quinazolin-2-yl]oxy)ethoxy]propanoic acid as a light yellow solid. LCMS (ES, m/z) 670 [M+H]$^+$ $^1$H-NMR (300 MHz, DMSO-d$_6$) δ 8.86 (br, 1H), 8.07 (s, 1H), 7.70-7.53 (m, 4H), 7.48-7.38 (m, 6H), 7.17 (d, J=8.4 Hz, 4H), 5.73 (s, 1H), 4.80-4.78 (m, 2H), 4.34-4.33 (m, 2H), 3.66-3.60 (m, 4H), 2.46-2.42 (m, 2H).

Example 65

3-(2-((6-(bis(4-chlorophenyl)methyl)-4-((3-(trifluoromethyl)benzyl)amino)quinazolin-2-yl)oxy)ethoxy)propanenitrile (Compound #50)

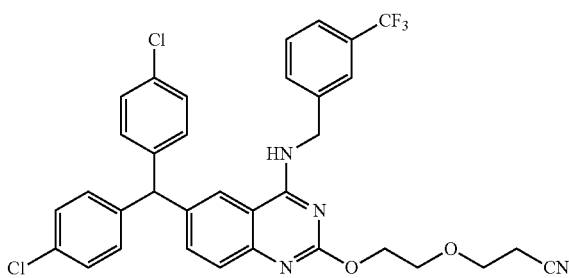 [SMILES: OCCOCCOc1nc(NCc2cccc(C(F)(F)F)c2)c2cc(C(c3ccc(Cl)cc3)c3ccc(Cl)cc3)ccc2n1]

Into a 50-mL round-bottom flask, was placed a solution of 2-([6-[bis(4-chlorophenyl)methyl]-4-([[3-(trifluoromethyl)phenyl]methyl]amino)quinazolin-2-yl]oxy)ethan-1-ol (1 g, 1.67 mmol, 1.00 equiv) in 1,4-dioxane (10 mL), prop-2-enenitrile (133 mg, 2.51 mmol, 1.50 equiv), potassium hydroxide (47 mg, 0.84 mmol, 0.50 equiv) and water (0.118 mL). The resulting solution was stirred overnight at room temperature. The reaction was then quenched by the addition of sat. NH$_4$Cl (30 mL). The resulting solution was extracted with ethyl acetate (2×20 mL) and the organic layers combined. The resulting solution was extracted with DCM (2×20 mL) and the organic layers combined, dried over anhydrous sodium sulfate and concentrated under vacuum. The resulting residue was purified by Prep-TLC with 1:1 EA/PE as eluent, to yield 3-[2-([6-[bis(4-chlorophenyl)methyl]-4-([[3-(trifluoromethyl)phenyl]methyl]amino)quinazolin-2-yl]oxy)ethoxy]propanenitrile as a white solid. LCMS (ES, m/z) 651 [M+H]$^+$ $^1$H-NMR (400 MHz, DMSO-d$_6$) δ 8.23 (s, 1H), 7.79 (s, 1H), 7.72-7.66 (m, 3H), 7.62-7.58 (m, 1H), 7.54 (d, J=8.4 Hz, 1H), 7.41 (d, J=8.8 Hz, 4H), 7.17 (d, J=8.4 Hz, 4H), 5.80 (s, 1H), 4.93 (s, 2H), 4.61 (s, 2H), 3.75-3.73 (m, 2H), 3.63 (t, J=6.0 Hz, 2H), 2.72 (t, J=6.0 Hz, 2H).

Example 66

4-((6-(bis(4-chlorophenyl)methyl)-4-((3-(trifluoromethyl)benzyl)amino)quinazolin-2-yl)oxy)butan-1-ol (Compound #53)

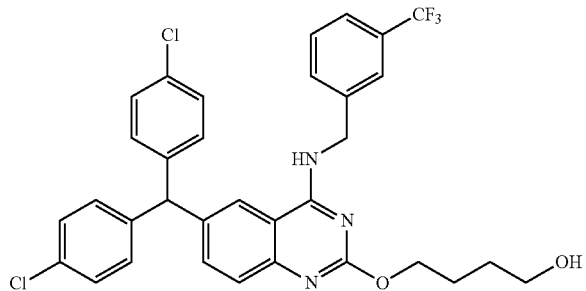 [SMILES: OCCCCOc1nc(NCc2cccc(C(F)(F)F)c2)c2cc(C(c3ccc(Cl)cc3)c3ccc(Cl)cc3)ccc2n1]

Into a 500-mL round-bottom flask purged and maintained with an inert atmosphere of nitrogen, was placed a solution of butane-1,4-diol (62 mL, 200.00 equiv) in tetrahydrofuran (200 mL). This was followed by the addition of sodium hydride (4.2 g, 175.00 mmol, 30.00 equiv), in portions. The resulting solution was stirred for 20 min at room temperature. To the resulting mixture was added 6-[bis(4-chlorophenyl)methyl]-2-chloro-N-[[3-(trifluoromethyl)phenyl]methyl]quinazolin-4-amine (2 g, 3.49 mmol, 1.00 equiv), in portions. The resulting solution was allowed to react overnight at 70° C. with stirring. The reaction was then quenched by the addition of sat. sodium bicarbonate (200 mL). The resulting solution was extracted with ethyl acetate (2×200 mL) and the organic layers combined, dried over anhydrous sodium sulfate and concentrated under vacuum. The residue was applied onto a silica gel column with ethyl acetate/petroleum ether (15:85), to yield 4-([6-[bis(4-chlorophenyl)methyl]-4-([[3-(trifluoromethyl)phenyl]methyl]amino)quinazolin-2-yl]oxy)butan-1-ol as a yellow solid. LCMS (ES, m/z) 626[M+H]$^+$ $^1$H-NMR (300 MHz, DMSO-d$_6$) δ 8.85 (br, 1H), 8.05 (s, 1H), 7.71 (s, 1H), 7.64-7.52 (m, 3H), 7.47-7.38 (m, 6H), 7.17 (d, J=8.4 Hz, 4H), 5.72 (s, 1H), 4.78-4.76 (m, 2H), 4.42-4.33 (m, 1H), 4.25-4.20 (m, 2H), 3.44-3.35 (m, 2H), 1.75-1.63 (m, 2H), 1.54-1.46 (m, 2H).

Example 67

2-(((6-(bis(4-chlorophenyl)methyl)-4-((3-(trifluoromethyl)benzyl)amino)quinazolin-2-yl)oxy)methyl)propane-1,3-diol (Compound #49)

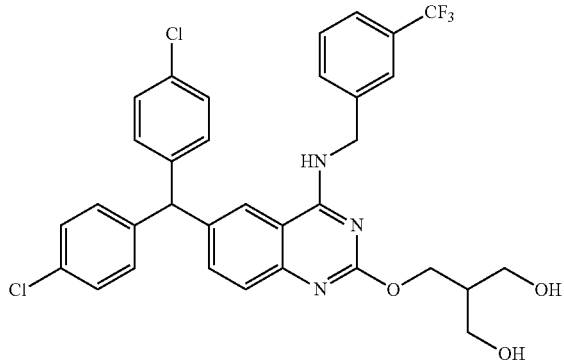 [SMILES: OCC(CO)COc1nc(NCc2cccc(C(F)(F)F)c2)c2cc(C(c3ccc(Cl)cc3)c3ccc(Cl)cc3)ccc2n1]

Into a 30-mL round-bottom flask, was placed a solution of 6-[bis(4-chlorophenyl)methyl]-2-chloro-N-[[3-(trifluoromethyl)phenyl]methyl]quinazolin-4-amine (200 mg, 0.35 mmol, 1.00 equiv) in tetrahydrofuran (10 mL), 2-(hydroxymethyl)propane-1,3-diol (371 mg, 3.50 mmol, 10.00 equiv) and sodium hydride (140 mg, 5.83 mmol, 10.00 equiv). The resulting solution was stirred overnight at 120° C. The reaction was then quenched by the addition of of sat. sodium bicarbonate (50 mL). The resulting solution was extracted with ethyl acetate (2×50 mL) and the organic layers combined, dried over anhydrous sodium sulfate and concentrated under vacuum. The resulting residue was purified by Prep-TLC with ethyl acetate as eluent, to yield 2-[([6-[bis(4-chlorophenyl)methyl]-4-([[3-(trifluoromethyl)phenyl]methyl]amino)quinazolin-2-yl]oxy)methyl]propane-1,3-diol as an off-white solid. LC-MS (ES, m/z): 642 [M+H]$^+$ $^1$H-NMR (DMSO-$d_6$, 300 MHz): δ 8.82 (s, 1H), 8.06 (s, 1H), 7.73-7.23 (m, 10H), 7.17 (d, J=8.4 Hz, 4H), 5.72 (s, 1H), 4.79-4.78 (m, 2H), 4.49-4.46 (m, 2H), 4.26-4.24 (m, 2H), 3.50-3.46 (m, 4H), 1.96-1.90 (m, 1H).

Example 68

2-(((6-(bis(4-chlorophenyl)methyl)-4-((3-(trifluoromethyl)benzyl)amino)quinazolin-2-yl)oxy)methyl)-2-(hydroxymethyl)propane-1,3-diol (Compound #54)

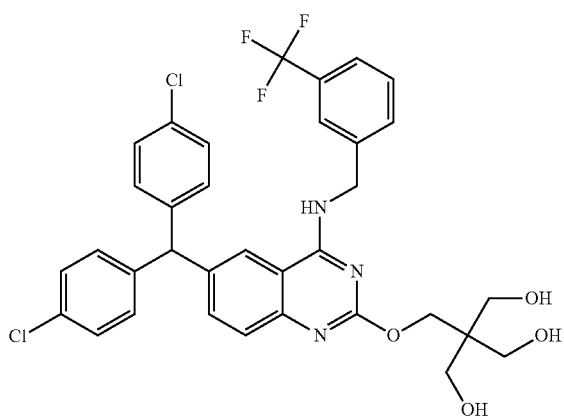 [SMILES: OCC(CO)(CO)COc1nc(NCc2cccc(C(F)(F)F)c2)c2cc(C(c3ccc(Cl)cc3)c3ccc(Cl)cc3)ccc2n1]

Into a 150-mL sealed tube, was placed a solution of 2,2-bis(hydroxymethyl)propane-1,3-diol (14.24 g, 104.59 mmol, 30.00 equiv) in tetrahydrofuran (70 mL). This was followed by the addition of sodium hydride (2.09 g, 87.08 mmol, 15.00 equiv) in several batches. The resulting solution was stirred for 20 min at room temperature. To the resulting mixture was added 6-[bis(4-chlorophenyl)methyl]-2-chloro-N-[[3-(trifluoromethyl)phenyl]methyl]quinazolin-4-amine (2 g, 3.49 mmol, 1.00 equiv), in portions. The resulting solution was allowed to react, with stirring, for an additional 3 days at 120° C. The reaction was then quenched by the addition of sat. sodium bicarbonate (100 mL). The resulting solution was extracted with ethyl acetate (2×200 mL) and the organic layers combined, dried over anhydrous sodium sulfate and concentrated under vacuum. The residue was applied onto a silica gel column with ethyl acetate, to yield 2-[([6-[bis(4-chlorophenyl)methyl]-4-([[3-(trifluoromethyl)phenyl]methyl]amino)quinazolin-2-yl]oxy)methyl]-2-(hydroxymethyl)propane-1,3-diol as an off-white solid. LCMS (ES, m/z) 672[M+H]$^+$ $^1$H-NMR (400 MHz, DMSO) δ 8.82 (br, 1H), 8.06 (s, 1H), 7.75 (s, 1H), 7.67-7.54 (m, 3H), 7.48-7.39 (m, 6H), 7.17 (d, J=8.4 Hz, 4H), 5.72 (s, 1H), 4.80-4.79 (m, 2H), 4.41-4.38 (m, 3H), 4.21 (s, 2H), 3.44-3.43 (m, 6H).

Example 69

2-(4-aminobutoxy)-6-(bis(4-chlorophenyl)methyl)-N-(3-(trifluoromethyl)benzyl)quinazolin-4-amine (Compound #31)

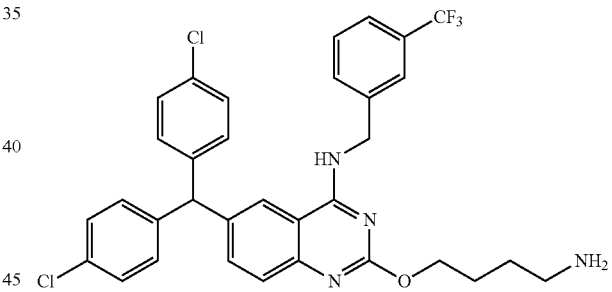

Step 1: 4-Hydroxybutyl 4-methylbenzenesulfonate

Into a 500-mL round-bottom flask purged and maintained with an inert atmosphere of nitrogen, was placed butane-1,4-diol (68.02 mL, 5.90 equiv), 4-dimethylaminopyridine (158 mg, 1.29 mmol, 0.01 equiv), pyridine (41.5 mL) and dichloromethane (215 mL). This was followed by the addition of 4-methylbenzene-1-sulfonyl chloride (24.38 g, 127.88 mmol, 1.00 equiv) in several batches at −10° C. in 30 min. The resulting solution was stirred for 5 h at −10° C. The reaction was then quenched by the addition of water/ice (200 mL). The resulting solution was extracted with DCM (3×100 mL) and the organic layers combined. The organic phase was washed with 3M HCl (150 mL), sat. sodium bicarbonate (200 mL) and brine (200 mL). The resulting mixture was dried over anhydrous sodium sulfate and concentrated under vacuum. The residue was applied onto a silica gel column with ethyl acetate/petroleum ether (1:1), to yield 4-[[(4-methylbenzene)sulfonyl]oxy]butan-1-ol as colorless oil.

Step 2: 4-Azidobutan-1-ol

Into a 250-mL round-bottom flask purged and maintained with an inert atmosphere of nitrogen, was placed a solution of 4-[[(4-methylbenzene)sulfonyl]oxy]butan-1-ol (20.15 g, 82.48 mmol, 1.00 equiv) in N,N-dimethylformamide (100 mL). This was followed by the addition of $NaN_3$ (10.74 g, 165.21 mmol, 2.00 equiv) in several batches. The resulting solution was stirred for 24 h at 80° C. The resulting solution was diluted with diethyl ether (100 mL). The solids were filtered out and washed with diethyl ether (100 mL). The organic phase was washed with brine (100 mL). The organic solution was dried over anhydrous sodium sulfate and concentrated under vacuum, to yield 4-azidobutan-1-ol as yellow oil. $^1$H-NMR (300 MHz, $CDCl_3$) δ 7.970 (s, 1H), 4.080-4.041 (m, 2H), 3.639-3.622 (m, 2H), 2.930-2.839 (m, 4H).

Step 3: 2-(4-Azidobutoxy)-6-(bis(4-chlorophenyl)methyl)-N-(3-(trifluoromethyl)benzyl)quinazolin-4-amine Into a 250-mL round-bottom flask purged and maintained with an inert atmosphere of nitrogen, was placed a solution of 4-azidobutan-1-ol (8.05 g, 69.92 mmol, 50.00 equiv) in tetrahydrofuran (140 mL). This was followed by the addition of sodium hydride (840 mg, 35.00 mmol, 15.00 equiv) in several batches. The resulting solution was stirred for 30 min at room temperature. To the resulting mixture was added 6-[bis(4-chlorophenyl)methyl]-2-chloro-N-[[3-(trifluoromethyl)phenyl]methyl]quinazolin-4-amine (800 mg, 1.40 mmol, 1.00 equiv), in portions. The resulting solution was stirred overnight at 70° C. The reaction was then quenched by the addition of sat. sodium bicarbonate (1000 mL). The resulting solution was extracted with ethyl acetate (100 mL) and the organic layers combined, dried over anhydrous sodium sulfate and concentrated under vacuum. The resulting solution was stirred with hydrogen chloride.$Et_2O$ (50 mL) for 30 min. The resulting mixture was concentrated under vacuum. The product was precipitated by the addition of ethyl acetate. The solids were collected by filtration and washed with ethyl acetate. The residue was dissolved in sat. sodium bicarbonate (50 mL) and extracted with ethyl acetate (100 mL) and the organic layers combined, dried over anhydrous sodium sulfate and concentrated under vacuum, to yield 2-(4-azidobutoxy)-6-[bis(4-chlorophenyl)methyl]-N-[[3-(trifluoromethyl)phenyl]methyl]quinazolin-4-amine as a white solid.

Step 4: 2-(4-Aminobutoxy)-6-(bis(4-chlorophenyl)methyl)-N-(3-(trifluoromethyl)benzyl)quinazolin-4-amine Into a 25-mL round-bottom flask purged and maintained with an inert atmosphere of nitrogen, was placed 2-(4-azidobutoxy)-6-[bis(4-chlorophenyl)methyl]-N-[[3-(trifluoromethyl)phenyl]methyl]quinazolin-4-amine (600 mg, 0.92 mmol, 1.00 equiv), $PPh_3$ (289 mg, 1.10 mmol, 1.20 equiv), sodium hydroxide (1.2 mL, 0.1 M) and tetrahydrofuran (16 mL). The resulting solution was stirred overnight at 50° C. The resulting solution was diluted with water (30 mL). The resulting solution was extracted with ethyl acetate (2×50 mL) and the organic layers combined, dried over anhydrous sodium sulfate and concentrated under vacuum. The resulting residue was purified by Prep-TLC with methanol/DCM=1/4 as eluent, to yield 2-(4-aminobutoxy)-6-[bis(4-chlorophenyl)methyl]-N-[[3-(trifluoromethyl)phenyl]methyl]quinazolin-4-amine as a white solid. LCMS (ES, m/z) 625[M+H]$^+$ $^1$H-NMR (300 MHz, DMSO-$d_6$) δ 8.85 (br, 1H), 8.06 (s, 1H), 7.71 (s, 1H), 7.65-7.53 (m, 3H), 7.47-7.38 (m, 6H), 7.17 (d, J=8.7 Hz, 4H), 5.72 (s, 1H), 4.77 (s, 2H), 4.22 (t, J=6.6 Hz, 2H), 2.60-2.56 (m, 2H), 1.72-1.65 (m, 2H), 1.49-1.39 (m, 2H).

Example 70

4-((4-((6-(bis(4-chlorophenyl)methyl)quinazolin-4-yl)amino)piperidin-1-yl)sulfonyl)benzimidamide (Compound #47)

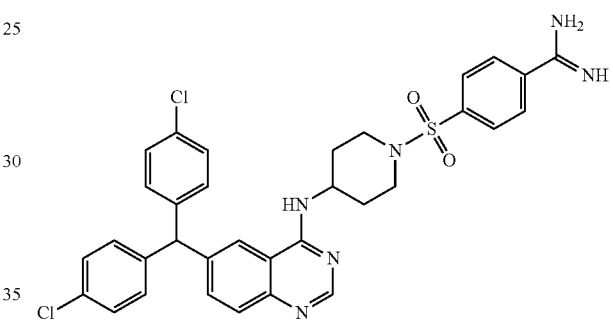

Step 1: 4-(4-(6-(Bis(4-chlorophenyl)methyl)quinazolin-4-ylamino)piperidin-1-ylsulfonyl)benzonitrile Into a 25-mL round-bottom flask, was placed 6-[bis(4-chlorophenyl)methyl]-N-(piperidin-4-yl)quinazolin-4-amine (200 mg, 0.43 mmol, 1.00 equiv), dichloromethane (4 mL, 40.00 equiv) and triethylamine (133 mg, 1.31 mmol, 3.00 equiv). The resulting solution was stirred for 15 mins at room temperature. 4-Cyanobenzene-1-sulfonyl chloride (104 mg, 0.52 mmol, 1.20 equiv) was then added to the mixture. The resulting solution was stirred for 2 h at 25° C. The resulting mixture was concentrated under vacuum, to yield 4-[4-([6-[bis(4-chlorophenyl)methyl]quinazolin-4-yl]amino)piperidine-1-sulfonyl]benzonitrile as a white solid. (ES, m/z) 628 [M+H]+

Step 2: 4-(4-(6-(Bis(4-chlorophenyl)methyl)quinazolin-4-ylamino)piperidin-1-ylsulfonyl)benzimidamide Into a 100-mL round-bottom flask, was placed 4-[4-([6-[bis(4-chlorophenyl)methyl]quinazolin-4-yl]amino)piperidine-1-sulfonyl]benzonitrile (100 mg, 0.16 mmol, 1.00 equiv). This was followed by the addition of methanol (25 mL). The reaction mixture was then charged with HCl (g) for 1 h at 0° C. The resulting solution was stirred overnight at room temperature. To the resulting mixture was added NH₄Cl (34 mg). To the mixture was then added ammonia (25 mL) dropwise with stirring at 0° C. The resulting solution was stirred overnight at 25° C. The resulting mixture was concentrated under vacuum. The resulting solution was diluted with methanol (50 mL). The solids were filtered out. The resulting mixture was concentrated under vacuum. The residue was applied onto a silica gel column with dichloromethane:CH₃OH (5:1), to yield 4-[4-([6-[bis (4-chlorophenyl)methyl]quinazolin-4-yl]amino)piperidine-1-sulfonyl]benzene-1-carboximidamide as a white solid. LC-MS (ES, m/z): 645 [M+H]⁺

¹H-NMR (300 MHz, DMSO+D₂O, ppm) δ 8.375 (s, 1H), 8.179 9s, 1h), 7.955-8.030 (m, 4H), 7.638 (d, J=8.4 Hz, 1H), 7.501 (d, J=8.7 Hz, 1H), 7.399-7.370 (m, 4H), 7.157-7.128 (m, 4H), 5.747 (s, 1H), 4.094 (br, 1H), 3.802-3.765 (m, 2H), 2.371-2.448 (m, 2H), 2.024-1.987 (m, 2H), 1.691-1.661 (m, 2H)

Example 71

4-((4-((6-(bis(4-chlorophenyl)methyl)quinazolin-4-yl)amino)piperidin-1-yl)sulfonyl)benzonitrile (Compound #52)

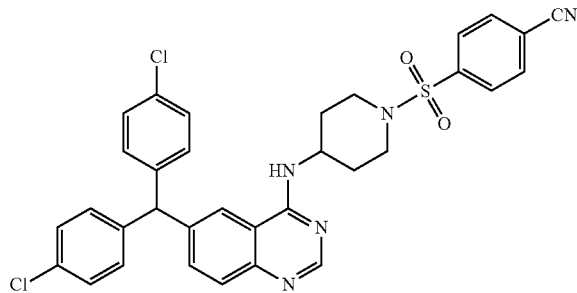 [SMILES: N#Cc1ccc(S(=O)(=O)N2CCC(Nc3ncnc4ccc(C(c5ccc(Cl)cc5)c5ccc(Cl)cc5)cc34)CC2)cc1]

Into a 25-mL round-bottom flask, was placed 6-[bis(4-chlorophenyl)methyl]-N-(piperidin-4-yl)quinazolin-4-amine (100 mg, 0.22 mmol, 1.00 equiv), dichloromethane (4 mL), triethylamine (66 mg, 3.00 equiv) and 4-cyanobenzene-1-sulfonyl chloride (52 mg, 1.20 equiv). The resulting solution was stirred overnight at room temperature. The reaction was then quenched by the addition of water (30 mL). The resulting solution was extracted with ethyl acetate (3×30 mL) and the organic layers combined and dried over anhydrous sodium sulfate. The solid was filtered out. The resulting mixture was concentrated under vacuum. The resulting residue was re-crystallized from EA: n-hexane in the ratio of 1:20, to yield 4-[4-((6-[bis(4-chlorophenyl) methyl]quinazolin-4-yl]amino)piperidine-1-sulfonyl]benzonitrile as a white solid. LC-MS (ES, m/z): 628 [M+H]⁺

¹H-NMR (DMSO-d₆, 300 MHz) δ 8.40 (s, 1H), 8.19-8.13 (m, 3H), 8.00-7.93 (m, 3H), 7.64 (d, J=8.4 Hz, 1H), 7.47-7.39 (m, 5H), 7.15 (d, J=8.4 Hz, 4H), 5.76 (s, 1H), 4.18-4.16 (m, 1H), 3.77-3.73 (m, 2H), 2.57-2.50 (m, 2H), 2.02-1.99 (m, 2H), 1.69-1.58 (m, 1H).

Example 72

4-(4-((6-(bis(4-chlorophenyl)methyl)quinazolin-4-yl)amino)piperidine-1-carbonyl)-N-(2-hydroxyethyl) benzenesulfonamide (Compound #45)

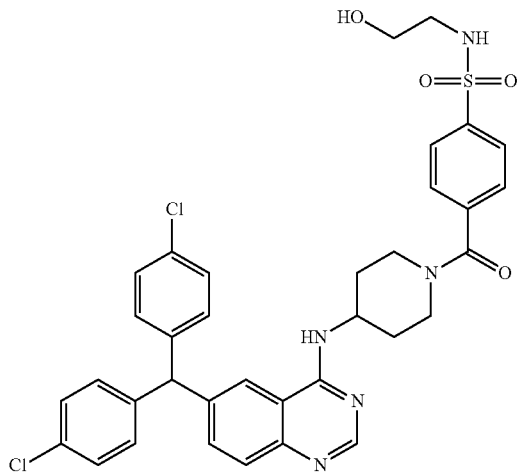 [SMILES: O=C(c1ccc(S(=O)(=O)NCCO)cc1)N1CCC(Nc2ncnc3ccc(C(c4ccc(Cl)cc4)c4ccc(Cl)cc4)cc23)CC1]

Step 1: 4-(2-Hydroxyethylsulfonyl)benzoic acid

Into a 100-mL 3-necked round-bottom flask, was placed 4-(chlorosulfonyl)benzoic acid (200 mg, 0.91 mmol, 1.00 equiv), dichloromethane (20 mL) and triethylamine (0.3 mL). This was followed by the addition of 2-aminoethan-1-ol (110 mg, 1.80 mmol, 2.00 equiv) dropwise with stirring at 0° C. The resulting solution was stirred for 5 h at 25° C. The resulting solution was diluted with DCM (50 mL). The resulting mixture was washed with water (2×30 mL). The mixture was dried over anhydrous sodium sulfate. The solids were filtered out. The resulting mixture was concentrated under vacuum, to yield 4-[(2-hydroxyethyl)sulfamoyl]benzoic acid as light yellow oil.

Step 2: 4-(4-(6-(Bis(4-chlorophenyl)methyl)quinazolin-4-ylamino)piperidine-1-carbonyl)-N-(2-hydroxyethyl)benzenesulfonamide Into a 25 mL round-bottom flask, was placed 6-[bis(4-chlorophenyl)methyl]-N-(piperidin-4-yl)quinazolin-4-amine (100 mg, 0.22 mmol, 1.00 equiv), 4-[(2-hydroxyethyl)sulfamoyl]benzoic acid (64 mg, 0.26 mmol, 1.20 equiv), N,N-dimethylformamide (10 mL), HATU (123 mg, 0.32 mmol, 1.50 equiv) and DIPEA (0.2 mL). The resulting solution was stirred overnight at 25° C. The resulting solution was diluted with water (150 mL). The solids were collected by filtration. The residue was applied onto a silica gel column with dichloromethane/methanol (10:1), to yield S-(4-[[4-([6-[bis(4-chlorophenyl)methyl]quinazolin-4-yl] amino)piperidin-1-yl]carbonyl]phenyl)-2-hydroxyethane-1-sulfonamido as a white solid. LC-MS (ES, m/z) 690 [M+H]⁺

¹H-NMR (300 MHz, DMSO, ppm) δ 8.442 (s, 1H), 8.210 (s, 1H), 7.948-7.985 (m, 3H), 7.717-7.566 (m, 4H), 7.475-7.389 (m, 5H), 7.176-7.148 (m, 4H), 5.762 (s, 1H), 4.710-4.673 (m, 1H), 4.691-4.509 (m, 2H), 3.567-3.537 (m, 1H), 3.404-3.307 (m, 2H), 3.284-3.232 (m, 1H), 3.050-2.970 (m, 1H), 2.820-2.723 (m, 2H), 2.068-1.899 (m, 2H), 1.587-1.544 (m, 2H).

Example 73

4-((4-((6-(bis(4-chlorophenyl)methyl)-2-methoxy-quinazolin-4-yl)amino)piperidin-1-yl)sulfonyl)benzoic acid (Compound #46)

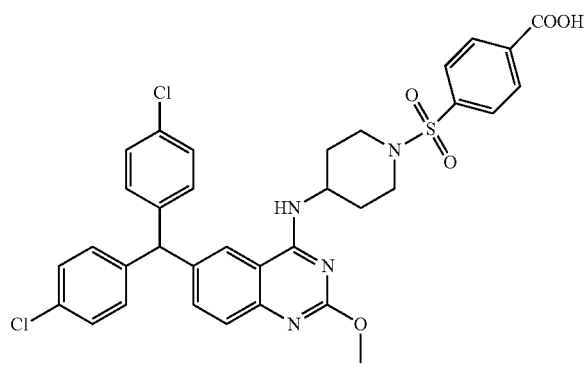 [SMILES: COc1nc(NC2CCN(S(=O)(=O)c3ccc(C(=O)O)cc3)CC2)c2cc(C(c3ccc(Cl)cc3)c3ccc(Cl)cc3)ccc2n1]

Step 1: tert-Butyl 4-(6-bromo-2-chloroquinazolin-4-ylamino)piperidine-1-carboxylate Into a 250-mL round-bottom flask purged and maintained with an inert atmosphere of nitrogen, was placed a solution of 6-bromo-2,4-dichloroquinazoline (3 g, 10.79 mmol, 1.00 equiv) in tetrahydrofuran (83 mL). This was followed by the addition of DIPEA (8.7 mL, 5.00 equiv) dropwise with stirring at 0° C. To the resulting mixture was added tert-butyl 4-aminopiperidine-1-carboxylate (2.4 g, 11.98 mmol, 1.20 equiv, dissolved in a minimum volume of THF) dropwise with stirring at 0° C. The resulting solution was stirred overnight at room temperature. The resulting solution was diluted with water (100 mL). The resulting solution was extracted with ethyl acetate (2×200 mL) and the organic layers combined, dried over anhydrous sodium sulfate and concentrated under vacuum. The residue was applied onto a silica gel column with ethyl acetate/petroleum ether (15:85), to yield tert-butyl 4-[(6-bromo-2-chloroquinazolin-4-yl)amino]piperidine-1-carboxylate as a light yellow solid. (ES, m/z) 442 [M+H]+

Step 2: tert-Butyl 4-(6-(bis(4-chlorophenyl)(hydroxy)methyl)-2-chloroquinazolin-4-ylamino)piperidine-1-carboxylate Into a 1000-mL 3-necked round-bottom flask purged and maintained with an inert atmosphere of nitrogen, was placed a solution of tert-butyl 4-[(6-bromo-2-chloroquinazolin-4-yl)amino]piperidine-1-carboxylate (3.85 g, 8.72 mmol, 1.00 equiv) in tetrahydrofuran (523 mL). This was followed by the addition of LiHMDS (21.8 mL, 2.50 equiv, 1 M) dropwise with stirring at 0° C. The resulting solution was stirred for 20 min at 0° C. To the resulting mixture was added n-BuLi (19 mL, 3.50 equiv, 1.6M) dropwise with stirring at −78° C. To the mixture was then added bis(4-chlorophenyl)methanone (7.66 g, 30.50 mmol, 3.50 equiv dissolved in a minimum volume of THF) dropwise with stirring at −78° C. The reaction was then warmed to room temperature slowly and quenched by the addition of sat. sodium bicarbonate (200 mL). The resulting solution was extracted with ethyl acetate (2×200 mL) and the organic layers combined, dried over anhydrous sodium sulfate and concentrated under vacuum. The residue was applied onto a silica gel column with ethyl acetate/petroleum ether (20:80). The resulting residue was purified by re-crystallization from DCM, to yield tert-butyl 4-([6-[bis(4-chlorophenyl)(hydroxy)methyl]-2-chloroquinazolin-4-yl]amino)piperidine-1-carboxylate as a white solid. (ES, m/z) 614 [M+H]+

Step 3: tert-Butyl 4-(6-(bis(4-chlorophenyl)(hydroxy)methyl)-2-methoxyquinazolin-4-ylamino)piperidine-1-carboxylate Into a 50-mL round-bottom flask purged and maintained with an inert atmosphere of nitrogen, was placed a solution of tert-butyl 4-([6-[bis(4-chlorophenyl)(hydroxy)methyl]-2-chloroquinazolin-4-yl]amino)piperidine-1-carboxylate (200 mg, 0.33 mmol, 1.00 equiv) in methanol (30 mL). This was followed by the addition of sodium hydride (396 mg, 16.50 mmol, 30.00 equiv), in portions. The resulting solution was heated to reflux overnight. The reaction was then quenched by the addition of sat. sodium bicarbonate (50 mL). The resulting solution was extracted with ethyl acetate (2×100 mL) and the organic layers combined, dried over anhydrous sodium sulfate and concentrated under vacuum, to yield bis(4-chlorophenyl)([2-methoxy-4-[(piperidin-4-yl)amino]quinazolin-6-yl])methanol as a yellow solid, which was used in the next step without further purification.

Step 4: 6-(Bis(4-chlorophenyl)methyl)-2-methoxy-N-(piperidin-4-yl)quinazolin-4-amine Into a 25-mL round-bottom flask purged and maintained with an inert atmosphere of nitrogen, was placed a solution of tert-butyl 4-([6-[bis(4-chlorophenyl)(hydroxy)methyl]-2-methoxyquinazolin-4-yl]amino)piperidine-1-carboxylate (200 mg, 0.33 mmol, 1.00 equiv) in dichloromethane (15 mL). This was followed by the addition of Et$_3$SiH (0.21 mL, 4.00 equiv) dropwise with stirring at 0° C. To the resulting mixture was added trifluoroacetic acid (0.632 mL, 25.00 equiv) dropwise with stirring at 0° C. The resulting solution was stirred for 2 h at 0° C. The resulting solution was allowed to react, with stirring, for an additional 3 h at room temperature. The reaction was then quenched by the addition of sat. sodium bicarbonate (20 mL). The resulting solution was extracted with DCM (2×50 mL) and the organic layers combined and dried over anhydrous sodium sulfate. The resulting residue was re-crystallized from EA/HEX in the ratio of 10:90, to yield 6-[bis(4-chlorophenyl)methyl]-2-methoxy-N-(piperidin-4-yl)quinazolin-4-amine as a gray solid. (ES, m/z) 493 [M+H]+

Step 5: 4-(4-(6-(Bis(4-chlorophenyl)methyl)-2-methoxyquinazolin-4-ylamino)piperidin-1-ylsulfonyl)benzoic acid Into a 25-mL round-bottom flask purged and maintained with an inert atmosphere of nitrogen, was placed a solution of 6-[bis(4-chlorophenyl)methyl]-2-methoxy-N-(piperidin-4-yl)quinazolin-4-amine (141 mg, 0.29 mmol, 1.00 equiv) in dichloromethane (10 mL). This was followed by the addition of triethylamine (0.081 mL, 2.00 equiv) dropwise with stirring at 0° C. To the resulting mixture was added 4-(chlorosulfonyl)benzoic acid (71 mg, 0.32 mmol, 1.10 equiv), in portions at 0° C. The resulting solution was stirred for 2 h at room temperature. The reaction was then quenched by the addition of sat. NH$_4$Cl (30 mL). The resulting solution was extracted with DCM (2×30 mL) and the organic layers combined and dried over anhydrous sodium sulfate. The resulting residue was purified by Prep-TLC with 10% methanol/DCM as eluent, to yield 4-[4-([6-[bis(4-chlorophenyl)methyl]-2-methoxyquinazolin-4-yl]amino)piperidine-1-sulfonyl]benzoic acid as a white solid. LCMS (ES, m/z) 677[M+H]+

$^1$H-NMR (300 MHz, DMSO-d$_6$) δ 8.18-8.11 (m, 3H), 7.96-7.86 (m, 3H), 7.46-7.34 (m, 6H), 7.14 (d, J=8.4 Hz, 4H), 5.69 (s, 1H), 4.05 (br, 1H), 3.80-3.72 (m, 5H), 2.02-1.98 (m, 2H), 1.65-1.61 (m, 2H).

Example 74

4-((4-(((6-(bis(4-chlorophenyl)methyl)-2-(2-hydroxyethoxy)quinazolin-4-yl)amino)piperidin-1-yl)sulfonyl)benzoic acid (Compound #39)

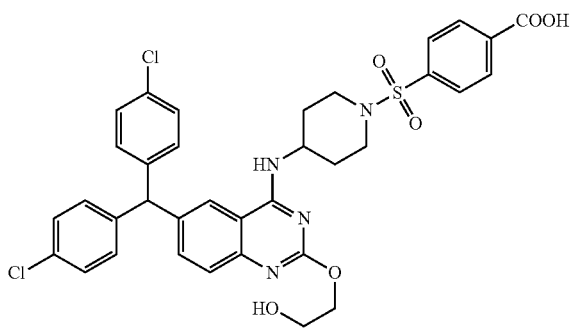 [SMILES: O=C(O)c1ccc(S(=O)(=O)N2CCC(Nc3nc(OCCO)nc4ccc(C(c5ccc(Cl)cc5)c5ccc(Cl)cc5)cc34)CC2)cc1]

Step 1: tert-Butyl 4-(6-(bis(4-chlorophenyl)(hydroxy)methyl)-2-(2-hydroxyethoxy)quinazolin-4-ylamino)piperidine-1-carboxylate Into a 100-mL round-bottom flask purged and maintained with an inert atmosphere of nitrogen, was placed a solution of ethane-1,2-diol (8.06 g, 129.86 mmol, 200.00 equiv) in tetrahydrofuran (31 mL). This was followed by the addition of sodium hydride (780 mg, 32.50 mmol, 30.00 equiv) in several batches. The resulting solution was stirred for 20 min at room temperature. To the resulting mixture was added tert-butyl 4-([6-[bis(4-chlorophenyl)(hydroxy)methyl]-2-chloroquinazolin-4-yl]amino)piperidine-1-carboxylate (400 mg, 0.65 mmol, 1.00 equiv), in portions. The resulting solution was allowed to react, with stirring, for an additional 2 days under reflux. The reaction was then quenched by the addition of sat. sodium bicarbonate (100 mL). The resulting solution was extracted with ethyl acetate (2×200 mL) and the organic layers combined and concentrated under vacuum. The resulting solution was diluted with water (100 mL). The resulting solution was extracted with DCM (100 mL) and the organic layers combined and concentrated under vacuum. The resulting residue was re-crystallized from methanol/H$_2$O in the ratio of 1:10, to yield tert-butyl 4-([6-[bis(4-chlorophenyl)(hydroxy)methyl]-2-(2-hydroxyethoxy)quinazolin-4-yl]amino)piperidine-1-carboxylate as a yellow solid, which was used in the next step without further purification. (ES, m/z) 693 [M+H]+

Step 2: 2-(6-(Bis(4-chlorophenyl)methyl)-4-(piperidin-4-ylamino)quinazolin-2-yloxy)ethanol Into a 50-mL round-bottom flask purged and maintained with an inert atmosphere of nitrogen, was placed a solution of tert-butyl 4-([6-[bis(4-chlorophenyl)(hydroxy)methyl]-2-(2-hydroxyethoxy)quinazolin-4-yl]amino)piperidine-1-carboxylate (200 mg, 0.31 mmol, 1.00 equiv) in dichloromethane (15 mL). This was followed by the addition of Et$_3$SiH (0.198 mL, 4.00 equiv) dropwise with stirring at 0° C. To the resulting mixture was added trifluoroacetic acid (0.549 mL, 25.00 equiv) dropwise with stirring at 0° C. The resulting solution was stirred for 3 h at room temperature. The reaction was then quenched by the addition of sat. sodium bicarbonate (30 mL). The resulting solution was extracted with DCM (2×50 mL) and the organic layers combined, dried over anhydrous sodium sulfate and concentrated under vacuum. The resulting residue was re-crystallized from EA/HEX in the ratio of 5:95, to yield 2-([6-[bis(4-chlorophenyl)methyl]-4-[(piperidin-4-yl)amino]quinazolin-2-yl]oxy)ethan-1-ol as a yellow solid. (ES, m/z) 523 [M+H]+

Step 3: 4-(4-(6-(Bis(4-chlorophenyl)methyl)-2-(2-hydroxyethoxy)quinazolin-4-ylamino)piperidin-1-ylsulfonyl)benzoic acid Into a 25-mL round-bottom flask purged and maintained with an inert atmosphere of nitrogen, was placed a solution of 2-([6-[bis(4-chlorophenyl)methyl]-4-[(piperidin-4-yl)amino]quinazolin-2-yl]oxy)ethan-1-ol (52 mg, 0.10 mmol, 1.00 equiv) in dichloromethane (10 mL). This was followed by the addition of triethylamine (0.028 mL, 2.00 equiv) dropwise with stirring at −40° C. To the resulting mixture was added 4-(chlorosulfonyl)benzoic acid (22.1 mg, 0.10 mmol, 1.00 equiv), in portions at −40° C. This solution was then warmed to room temperature slowly in 2 hours. The resulting solution was stirred for 2 h at room temperature. The reaction was then quenched by the addition of sat. NH$_4$Cl (20 mL). The resulting solution was extracted with DCM (2×30 mL) and the organic layers combined, dried over anhydrous sodium sulfate and concentrated under vacuum. The resulting residue was purified by Prep-TLC with methanol/DCM=4/6 as eluent, to yield 4-[4-([6-[bis(4-chlorophenyl)methyl]-2-(2-hydroxyethoxy)quinazolin-4-yl]amino)piperidine-1-sulfonyl]benzoic acid as a white solid. LCMS (ES, m/z) 707[M+H]+

$^1$H-NMR (300 MHz, DMSO-d$_6$) δ 8.16-8.11 (m, 3H), 7.95-7.82 (m, 3H), 7.43-7.29 (m, 6H), 7.13 (d, J=8.4 Hz, 4H), 5.69 (s, 1H), 4.78 (br, 1H), 4.24-4.21 (m, 2H), 4.05 (br, 1H), 3.75-3.64 (m, 4H), 2.00-1.97 (m, 2H), 1.64-1.61 (m, 2H).

Example 75

4-((4-((6-(bis(4-chlorophenyl)methyl)-2-(2-(methylsulfonamido)ethoxy)quinazolin-4-yl)amino)piperidin-1-yl)sulfonyl)benzoic acid (Compound #33)

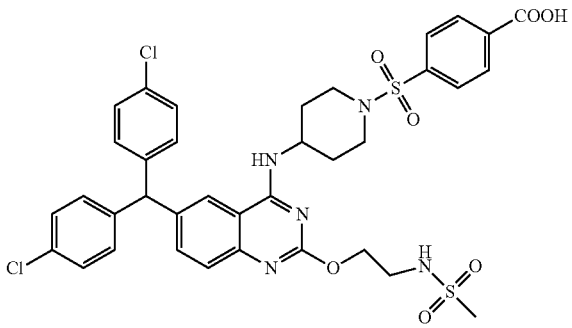 [SMILES: CS(=O)(=O)NCCOc1nc(NC2CCN(S(=O)(=O)c3ccc(C(=O)O)cc3)CC2)c2cc(C(c3ccc(Cl)cc3)c3ccc(Cl)cc3)ccc2n1]

Step 1: tert-Butyl 4-(2-(2-azidoethoxy)-6-(bis(4-chlorophenyl)(hydroxy)methyl)quinazolin-4-ylamino)piperidine-1-carboxylate Into a 100-mL round-bottom flask purged and maintained with an inert atmosphere of nitrogen, was placed a solution of 2-azidoethan-1-ol (5.67 g, 65.11 mmol, 40.00 equiv) in tetrahydrofuran (60 mL). This was followed by the addition of sodium hydride (1.30 g, 54.17 mmol, 20.00 equiv) in several batches. The resulting solution was stirred for 20 min at room temperature. To the resulting mixture was added tert-butyl 4-([6-[bis(4-chlorophenyl)(hydroxy)methyl]-2-chloroquinazolin-4-yl]amino)piperidine-1-carboxylate (1 g, 1.63 mmol, 1.00 equiv), in portions. The resulting solution was allowed to react, with stirring, for an additional 2 h while the temperature was maintained at reflux. The reaction was then quenched by the addition of sat. sodium bicarbonate (100 mL). The resulting solution was extracted with ethyl acetate (3×100 mL) and the organic layers combined, dried over anhydrous sodium sulfate and concentrated under vacuum. The residue was applied onto a silica gel column with ethyl acetate/petroleum ether (15:85), to yield tert-butyl 4-[[2-(2-azidoethoxy)-6-[bis(4-chlorophenyl)(hydroxy)methyl]quinazolin-4-yl]amino]piperidine-1-carboxylate as a yellow solid. (ES, m/z) 664 [M+H]+

Step 2: tert-Butyl 4-(2-(2-aminoethoxy)-6-(bis(4-chlorophenyl)(hydroxy)methyl)quinazolin-4-ylamino)piperidine-1-carboxylate Into a 25-mL round-bottom flask purged and maintained with an inert atmosphere of nitrogen, was placed a solution of 4-(4-[[2-(2-azidoethoxy)-6-[bis(4-chlorophenyl)methyl]quinazolin-4-yl]amino]piperidine-1-sulfonyl)benzoic acid (280 mg, 0.38 mmol, 1.00 equiv) in tetrahydrofuran (8 mL), $PPh_3$ (121 mg, 0.46 mmol, 1.20 equiv) and sodium hydroxide (0.6 mL, 0.1 M). The resulting solution was stirred overnight at 50° C. The resulting mixture was concentrated under vacuum. The resulting residue was purified by Prep-TLC with methanol/DCM (1/1) as eluent, to yield 4-(4-[[2-(2-aminoethoxy)-6-[bis(4-chlorophenyl)methyl]quinazolin-4-yl]amino]piperidine-1-sulfonyl)benzoic acid as a white solid. (ES, m/z) 638 [M+H]+

Step 3: tert-Butyl 4-(6-(bis(4-chlorophenyl)(hydroxy)methyl)-2-(2-(methylsulfonamido)ethoxy)quinazolin-4-ylamino)piperidine-1-carboxylate Into a 25-mL round-bottom flask purged and maintained with an inert atmosphere of nitrogen, was placed a solution of tert-butyl 4-[[2-(2-aminoethoxy)-6-[bis(4-chlorophenyl)(hydroxy)methyl]quinazolin-4-yl]amino]piperidine-1-carboxylate (320 mg, 0.50 mmol, 1.00 equiv) in dichloromethane (10 mL). This was followed by the addition of triethylamine (0.139 mL, 2.00 equiv) dropwise with stirring at −40° C. To the resulting mixture was added MsCl (0.035 mL, 0.90 equiv) dropwise with stirring at −40° C. The resulting solution was stirred for 30 min at −40° C. The solution was warmed to 0° C. slowly and stirred for additional 1 hr. The reaction was then quenched by the addition of sat. sodium bicarbonate (30 mL). The resulting solution was extracted with ethyl acetate (2×50 mL) and the organic layers combined and dried in an oven under reduced pressure. and concentrated under vacuum. The residue was applied onto a silica gel column with ethyl acetate/petroleum ether (1:1), to yield tert-butyl 4-([6-[bis(4-chlorophenyl)(hydroxy)methyl]-2-(2-methanesulfonamidoethoxy)quinazolin-4-yl]amino)piperidine-1-carboxylate as a yellow solid. (ES, m/z) 716 [M+H]+

Step 4: N-(2-(6-(bis(4-chlorophenyl)methyl)-4-(piperidin-4-ylamino)quinazolin-2-yloxy)ethyl)methanesulfonamide Into a 25-mL round-bottom flask, was placed a solution of tert-butyl 4-([6-[bis(4-chlorophenyl)(hydroxy)methyl]-2-(2-methanesulfonamidoethoxy)quinazolin-4-yl]amino)piperidine-1-carboxylate (390 mg, 0.54 mmol, 1.00 equiv) in dichloromethane (10 mL). This was followed by the addition of $Et_3SiH$ (0.344 mL, 4.00 equiv) dropwise with stirring at 0° C. To the resulting mixture was added trifluoroacetic acid (1.03 mL, 25.00 equiv) dropwise with stirring at 0° C. The resulting solution was stirred for 3 h at room temperature. The reaction was then quenched by the addition of sat. sodium bicarbonate (30 mL). The resulting solution was extracted with ethyl acetate (3×50 mL) and the organic layers combined, dried over anhydrous sodium sulfate and concentrated under vacuum. The resulting residue was re-crystallized from EA/PE in the ratio of 10:90, to yield N-[2-([6-[bis(4-chlorophenyl)methyl]-4-[(piperidin-4-yl)amino]quinazolin-2-yl]oxy)ethyl]methanesulfonamide as an off-white solid.

Step 5: 4-(4-(6-(Bis(4-chlorophenyl)methyl)-2-(2-(methylsulfonamido)ethoxy)quinazolin-4-ylamino)piperidin-1-ylsulfonyl)benzoic acid Into a 25-mL round-bottom flask purged and maintained with an inert atmosphere of nitrogen, was placed a solution of N-[2-([6-[bis(4-chlorophenyl)methyl]-4-[(piperidin-4-yl)amino]quinazolin-2-yl]oxy)ethyl]methanesulfonamide (134.5 mg, 0.22 mmol, 1.00 equiv) in dichloromethane (10 mL). This was followed by the addition of triethylamine (0.061 mL, 2.00 equiv) dropwise with stirring at −40° C. To the resulting mixture was added 4-(chlorosulfonyl)benzoic acid (53 mg, 0.24 mmol, 1.10 equiv) in several batches at −40° C. The resulting solution was stirred for 1 h at −40° C. Then the temperature was raised to 0° C. and the solution was stirred at this temperature for another 1 hour. The reaction was then quenched by the addition of sat. $NH_4Cl$ (30 mL). The resulting solution was extracted with ethyl acetate (4×50 mL) and the organic layers combined, dried over anhydrous sodium sulfate and concentrated under vacuum. The resulting residue was purified by Prep-TLC with methanol/DCM=1/4 as eluent, to yield 4-[4-([6-[bis(4-chlorophenyl)methyl]-2-(2-methanesulfonamidoethoxy)quinazolin-4-yl]amino)piperidine-1-sulfonyl]benzoic acid as an off-white solid. LCMS (ES, m/z) 784[M+H]+

$^1$H-NMR (400 MHz, DMSO-$d_6$) δ 8.15 (s, 1H), 8.04-8.05 (m, 3H), 7.65 (d, J=8.0 Hz, 2H), 7.44-7.32 (m, 6H), 7.22 (s, 1H), 7.14 (d, J=8.4 Hz, 4H), 5.70 (s, 1H), 4.29-4.28 (m, 2H), 4.05 (br, 1H), 3.73-3.70 (m, 2H), 3.30-3.29 (m, 2H), 2.92 (s, 3H), 2.44-2.38 (m, 2H), 2.00-1.97 (m, 2H), 1.70-1.59 (m, 2H).

Example 76

3-((4-((6-(bis(4-chlorophenyl)methyl)quinazolin-4-yl)amino)piperidin-1-yl)methyl)benzoic acid (Compound #37)

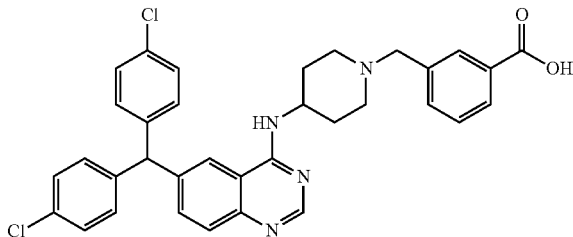 [SMILES: O=C(O)c1cccc(CN2CCC(Nc3ncnc4ccc(C(c5ccc(Cl)cc5)c5ccc(Cl)cc5)cc34)CC2)c1]

Step 1: Methyl 3-((4-(6-(bis(4-chlorophenyl)methyl)quinazolin-4-ylamino)piperidin-1-yl)methyl)benzoate Into a 100-mL round-bottom flask, was placed 6-[bis(4-chlorophenyl)methyl]-N-(piperidin-4-yl)quinazolin-4-amine (100 mg, 0.22 mmol, 1.00 equiv), N,N-dimethylformamide (20 mL), potassium carbonate (90 mg, 0.65 mmol, 3.00 equiv) and methyl 3-(bromomethyl)benzoate (60 mg, 0.26 mmol, 1.20 equiv). The resulting solution was stirred for 5 h at 25° C. The resulting solution was diluted with water (150 mL). The solids were collected by filtration. The residue was applied onto a silica gel column with dichloromethane:CH$_3$OH (20:1), to yield methyl 3-[[4-([6-[bis(4-chlorophenyl)methyl]quinazolin-4-yl]amino)piperidin-1-yl]methyl]benzoate as a white solid. (ES, m/z) 611 [M+H]+

Step 2: 3-((4-(6-(Bis(4-chlorophenyl)methyl)quinazolin-4-ylamino)piperidin-1-yl)methyl)benzoic acid Into a 100-mL round-bottom flask, was placed methyl 3-[[4-([6-[bis(4-chlorophenyl)methyl]quinazolin-4-yl]amino)piperidin-1-yl]methyl]benzoate (100 mg, 0.16 mmol, 1.00 equiv), methanol (20 mL) and 1M NaOH (20 mL). The resulting solution was stirred overnight at 50° C. The pH value of the solution was adjusted to pH 5-6 with 10% HCl. The solids were collected by filtration, to yield 3-[[4-([6-[bis(4-chlorophenyl)methyl]quinazolin-4-yl]amino)piperidin-1-yl]methyl]benzoic acid as a white solid. LC-MS (ES, m/z): [M−H]− 595

$^1$H-NMR (300 MHz, DMSO, ppm) δ 8.649 (s, 1H), 8.453 (s, 1H), 8.173 (m, 1H), 8.039 (d, J=7.8 Hz, 1H), 7.867 (d, J=7.7 Hz, 1H), 7.744 (d, J=8.6 Hz, 1H), 7.686-7.569 (m, 2H), 7.470-7.356 (m, 4H), 7.170 (d, J=8.2 Hz, 4H), 5.803 (s, 1H), 4.481 (br m, 1H), 4.391 (br s, 2H), 3.45-3.39 (br m, 3H), 3.161 (br m, 1H), 2.155 (br m, 2H), 2.073-1.960 (br m, 2H).

Example 77

3-((4-((6-(bis(4-chlorophenyl)methyl)quinazolin-4-yl)amino)piperidin-1-yl)methyl)benzamide (Compound #36)

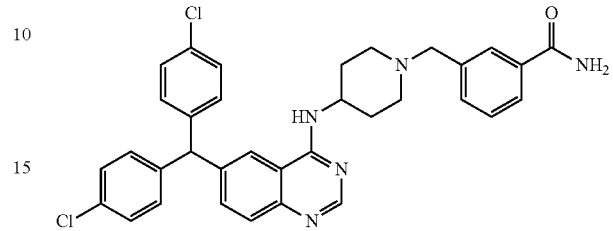

Into a 25-mL round-bottom flask, was placed 3-[[4-([6-[bis(4-chlorophenyl)methyl]quinazolin-4-yl]amino)piperidin-1-yl]methyl]benzoic acid (100 mg, 0.17 mmol, 1.00 equiv), NH$_4$Cl (54 mg, 1.01 mmol, 6.00 equiv), HATU (95 mg, 0.25 mmol, 1.50 equiv) and N,N-dimethylformamide (10 mL), DIPEA (0.3 mL). The resulting solution was stirred overnight at 25° C. The resulting solution was diluted with water (100 mL). The solids were collected by filtration. The residue was applied onto a silica gel column with dichloromethane/methanol (10:1), to yield 3-[[4-([6-[bis(4-chlorophenyl)methyl]quinazolin-4-yl]amino)piperidin-1-yl]methyl]benzamide as a white solid. LC-MS (ES, m/z): 596 [M+H]+

$^1$H-NMR (300 MHz, DMSO, ppm) δ 8.413 (s, 1H), 8.223 (s, 1H), 7.948-7.736 (overlapping m, 4H), 7.618 (d, J=8.7 Hz, 1H), 7.327-7.452 (m, 7H), 7.141-7.169 (m, 4H), 5.748 (s, 1H), 4.178 (br m, 1H), 3.525 (m, 2H), 2.857 (m, 2H), 2.039-2.109 (m, 2H), 1.871-1.903 (m, 2H), 1.598-1.704 (m, 2H).

Example 78

Methyl 4-((4-((6-(bis(4-chlorophenyl)methyl)quinazolin-4-yl)amino)piperidin-1-yl)methyl)benzoate (Compound #43)

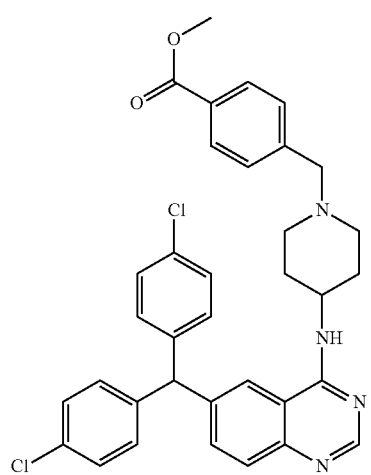 [SMILES: COC(=O)c1ccc(CN2CCC(Nc3ncnc4ccc(C(c5ccc(Cl)cc5)c5ccc(Cl)cc5)cc34)CC2)cc1]

Step 1: Methyl 4-((4-(tert-butoxycarbonylamino) piperidin-1-yl)methyl)benzoate Into a 250-mL 3-necked round-bottom flask, was placed tert-butyl N-(piperidin-4-yl)carbamate (5 g, 24.97 mmol, 1.00 equiv), N,N-dimethylformamide (100 mL), potassium carbonate (7 g, 50.65 mmol, 2.00 equiv) and methyl 4-(bromomethyl)benzoate (7.4 g, 32.30 mmol, 1.30 equiv). The resulting solution was stirred for 5 h at 25° C. The resulting solution was diluted with water (300 mL). The resulting solution was extracted with ethyl acetate (3×100 mL) and the organic layers combined and dried over anhydrous sodium sulfate. The solids were filtered out. The resulting mixture was concentrated under vacuum. The residue was applied onto a silica gel column with ethyl acetate/petroleum ether (1:5), to yield methyl 4-[(4-[[(tert-butoxy)carbonyl] amino]piperidin-1-yl)methyl]benzoate as a light yellow solid.

Step 2: Methyl 4-((4-aminopiperidin-1-yl)methyl)benzoate

Into a 250-mL round-bottom flask, was placed methyl 4-[(4-[[(tert-butoxy)carbonyl]amino]piperidin-1-yl)methyl] benzoate (5 g, 14.35 mmol, 1.00 equiv) and hydrogen chloride/CH$_3$OH (100 mL). The resulting solution was stirred overnight at 25° C. The resulting mixture was concentrated under vacuum. The resulting solution was diluted with ethyl acetate (80 mL). The solids were collected by filtration, to yield methyl 4-[(4-aminopiperidin-1-yl)methyl] benzoate dihydrochloride as a white solid.

Step 3: Methyl 4-((4-(6-(bis(4-chlorophenyl)methyl) quinazolin-4-ylamino)piperidin-1-yl)methyl)benzoate Into a 50-mL round-bottom flask, was placed 6-[bis(4-chlorophenyl)methyl]-4-chloroquinazoline (300 mg, 0.75 mmol, 1.00 equiv), propan-2-ol (20 mL), methyl 4-[(4-aminopiperidin-1-yl)methyl]benzoate dihydrochloride (313 mg, 0.97 mmol, 1.30 equiv) and triethylamine (1 mL). The resulting solution was stirred overnight at 30° C. The resulting mixture was concentrated under vacuum. The residue was applied onto a silica gel column with dichloromethane:CH$_3$OH (20:1), to yield methyl 4-[[4-([6-[bis(4-chlorophenyl)methyl]quinazolin-4-yl]amino)piperidin-1-yl] methyl]benzoate as a white solid. LC-MS (ES, m/z): 611 [M+H]$^+$ $^1$H-NMR (300 MHz, DMSO, ppm) δ: 8.411 (s, 1H), 8.218 (s, 1H), 7.968-7.809 (m, 3H), 7.619 (d, J=8.7 Hz, 1H), 7.526-7.383 (m, 6H), 7.239-7.144 (m, 4H), 5.750 (s, 1H), 4.170 (br m, 1H), 3.875 (s, 3H), 3.567 (br s, 2H), 2.856-2.831 (m, 2H), 2.092-2.055 (m, 2H), 1.871-1.813 (m, 2H), 1.756-1.639 (m, 2H)

Example 79

3-((4-((6-(bis(4-chlorophenyl)methyl)quinazolin-4-yl)amino)piperidin-1-yl)methyl)phenol (Compound #28)

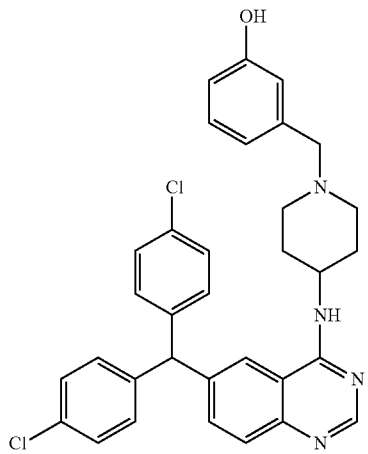 [SMILES: Oc1cccc(CN2CCC(Nc3ncnc4ccc(C(c5ccc(Cl)cc5)c5ccc(Cl)cc5)cc34)CC2)c1]

Step 1: tert-Butyl 1-(3-hydroxybenzyl)piperidin-4-ylcarbamate

Into a 100-mL 3-necked round-bottom flask, was placed a solution of 3-hydroxybenzaldehyde (610 mg, 5.00 mmol, 1.00 equiv) in dichloromethane (50 ml), tert-butyl N-(piperidin-4-yl)carbamate (1 g, 4.99 mmol, 1.00 equiv), acetic acid (5 mL) and NaBH(OAc)$_3$ (3.2 g, 15.09 mmol, 3.00 equiv). The resulting solution was stirred overnight at 25° C. The resulting solution was diluted with DCM (100 mL). The resulting mixture was washed with water (3×100 mL). The mixture was dried over anhydrous sodium sulfate. The solids were filtered out. The resulting mixture was concentrated under vacuum, to yield tert-butyl N-[1-[(3-hydroxyphenyl) methyl]piperidin-4-yl]carbamate as a white solid.

Step 2: 3-[(4-Aminopiperidin-1-yl)methyl]phenol dihydrochloride

Into a 100-mL round-bottom flask, was placed tert-butyl N-[1-[(3-hydroxyphenyl)methyl]piperidin-4-yl]carbamate (1 g, 3.26 mmol, 1.00 equiv) and hydrogen chloride/CH$_3$OH (50 mL). The resulting solution was stirred overnight at 25° C. The resulting mixture was concentrated under vacuum. The resulting solution was diluted with ethyl acetate (80 mL). The solids were collected by filtration, to yield 3-[(4-aminopiperidin-1-yl)methyl]phenol dihydrochloride as a white solid.

Step 3: 3-((4-(6-(Bis(4-chlorophenyl)methyl)quinazolin-4-ylamino)piperidin-1-yl)methyl)phenol Into a 25-mL round-bottom flask, was placed 6-[bis(4-chlorophenyl)methyl]-4-chloroquinazoline (100 mg, 0.25 mmol, 1.00 equiv), 3-[(4-aminopiperidin-1-yl)methyl]phenol dihydrochloride (90 mg, 0.32 mmol, 1.30 equiv), propan-2-ol (10 mL) and triethylamine (0.1 mL). The resulting solution was stirred overnight at 30° C. The resulting mixture was concentrated under vacuum. The residue was applied onto a silica gel column with dichloromethane:CH$_3$OH (20:1), to yield 3-[[4-([6-[bis(4-chlorophenyl) methyl]quinazolin-4-yl]amino)piperidin-1-yl]methyl]phenol as a white solid. LC-MS (ES, m/z): 569 [M+H]$^+$ $^1$H-NMR (300 MHz, DMSO, ppm) δ: 9.287 (s, 1H), 8.424 (s, 1H), 8.237 (m, 1H), 7.901 (m, 1H), 7.630 (d, J=8.4 Hz, 1H), 7.461-7.300 (m, 5H), 7.178-7.077 (m, 5H), 6.729-6.626 (m, 3H), 5.761 (s, 1H), 4.186 (m, 1H), 3.393 (m, 2H), 2.868-2.842 (m, 2H), 2.149-1.877 (m, 4H), 1.662-1.628 (m, 2H).

Example 80

4-(4-((6-(bis(4-chlorophenyl)methyl)quinazolin-4-yl)amino)piperidin-1-yl)phenol (Compound #32)

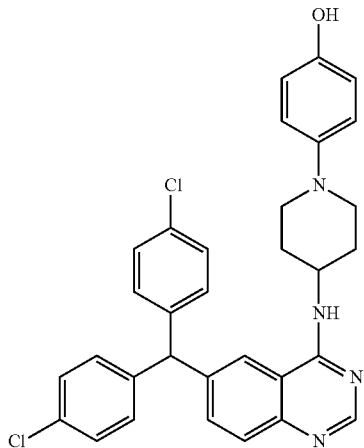 [SMILES: Oc1ccc(N2CCC(Nc3ncnc4ccc(C(c5ccc(Cl)cc5)c5ccc(Cl)cc5)cc34)CC2)cc1]

Step 1: tert-Butyl N-[1-(4-methoxyphenyl)piperidin-4-yl]carbamate

Into a 500-mL 3-necked round-bottom flask purged and maintained with an inert atmosphere of nitrogen, was placed tert-butyl N-(piperidin-4-yl)carbamate (20 g, 99.86 mmol, 1.00 equiv), 1-bromo-4-methoxybenzene (22.5 g, 120.30 mmol, 1.20 equiv), 1,4-dioxane (300 mL), (tert-butoxy) potassium (22.4 g, 199.62 mmol, 2.00 equiv), Pd$_2$(dba)$_3$ (4.5 g, 4.91 mmol, 0.05 equiv) and X-PHOS (2.4 g, 5.03 mmol, 0.05 equiv). The resulting solution was stirred overnight at 100° C. The reaction mixture was cooled with a water/ice bath. The resulting solution was diluted with ethyl acetate (500 mL). The resulting mixture was washed with water (3×500 mL). The mixture was dried over anhydrous sodium sulfate. The resulting mixture was concentrated under vacuum. The residue was applied onto a silica gel column with ethyl acetate:petroleum ether (1:3), to yield tert-butyl N-[1-(4-methoxyphenyl)piperidin-4-yl]carbamate as a light yellow solid.

Step 2: 1-(4-Methoxyphenyl)piperidin-4-amine dihydrochloride

Into a 250-mL 3-necked round-bottom flask, was placed tert-butyl N-[1-(4-methoxyphenyl)piperidin-4-yl]carbamate (6 g, 19.58 mmol, 1.00 equiv) and hydrogen chloride/CH$_3$OH (100 mL). The resulting solution was stirred overnight at 25° C. The resulting mixture was concentrated under vacuum. The resulting solution was diluted with ethyl acetate (100 mL). The solids were collected by filtration, to yield 1-(4-methoxyphenyl)piperidin-4-amine dihydrochloride as a light yellow solid.

Step 3: 6-(Bis(4-chlorophenyl)methyl)-N-(1-(4-methoxyphenyl)piperidin-4-yl)quinazolin-4-amine Into a 100-mL round-bottom flask, was placed 6-[bis(4-chlorophenyl)methyl]-4-chloroquinazoline (500 mg, 1.25 mmol, 1.00 equiv), 1-(4-methoxyphenyl)piperidin-4-amine dihydrochloride (460 mg, 1.65 mmol, 1.30 equiv), propan-2-ol (50 mL) and triethylamine (1 mL). The resulting solution was stirred overnight at 30° C. The resulting mixture was concentrated under vacuum. The residue was applied onto a silica gel column with dichloromethane:CH$_3$OH (20:1), to yield 6-[bis(4-chlorophenyl)methyl]-N-[1-(4-methoxyphenyl)piperidin-4-yl]quinazolin-4-amine as a light yellow solid.

Step 4: 4-(4-(6-(Bis(4-chlorophenyl)methyl)quinazolin-4-ylamino)cyclohexyl)phenol Into a 250-mL 3-necked round-bottom flask, was placed 6-[bis(4-chlorophenyl)methyl]-N-[1-(4-methoxyphenyl)piperidin-4-yl]quinazolin-4-amine (550 mg, 0.97 mmol, 1.00 equiv) and dichloromethane (100 mL). This was followed by the addition of BBr$_3$ (1 g, 4.00 mmol, 4.00 equiv) dropwise with stirring at −78° C. The resulting solution was stirred overnight at 25° C. The reaction was then quenched by the addition of water/ice (100 mL). The solids were collected by filtration. The residue was applied onto a silica gel column with dichloromethane/methanol (10:1), to yield 4-[4-([6-[bis(4-chlorophenyl)methyl]quinazolin-4-yl]amino)piperidin-1-yl]phenol as an orange solid. LC-MS (ES, m/z) 555 [M+H]$^+$ $^1$H-NMR (300 MHz, DMSO+D$_2$O, ppm) δ 8.960 (s, 1H), 8.673 (s, 1H), 7.841-7.763 (m, 2H), 7.714-7.575 (m, 2H), 7.443-7.414 (m, 4H), 7.185-7.157 (m, 4H), 6.905 (d, J=9.0 Hz, 2H), 5.877 (s, 1H), 4.794-4.761 (br m, 1H), 3.686-3.568 (br m, 4H), 2.402-2.258 (br m, 4H).

Example 81

((Isopropoxycarbonyl)oxy)methyl 4-((4-((6-(bis(4-chlorophenyl)methyl)quinazolin-4-yl)amino)piperidin-1-yl)sulfonyl)benzoate (Compound #64)

A suspension of 4-((4-((6-(bis(4-chlorophenyl)methyl)quinazolin-4-yl)amino)piperidin-1-yl)sulfonyl)benzoic acid (250 mg, 0.386 mmol), chloromethyl isopropyl carbonate (88.4 mg, 0.579 mmol) and TEA (0.082 mL, 0.579 mmol) in 1 mL of CH$_3$CN containing enough DMF to form a solution was heated to 50° C. After 4h, the resulting mixture was cooled to room temperature and concentrated to remove CH$_3$CN. The resulting residue was diluted with water and CH$_2$Cl$_2$, and the layers were separated. The aqueous phase was extracted with CH$_2$Cl$_2$ twice, then washed with brine, dried over Na$_2$SO$_4$, and concentrated. The resulting residue was purified on a Isco (CH$_2$Cl$_2$—CH$_3$OH; product elutes @~3% MeOH) to yield ((isopropoxycarbonyl)oxy)methyl 4-((4-((6-(bis(4-chlorophenyl)methyl)quinazolin-4-yl)amino)piperidin-1-yl)sulfonyl)benzoate.

$^1$H NMR (DMSO-d6) δ: 8.39 (s, 1H), 8.18-8.28 (m, 3H), 8.00 (m, 1H), 7.95 (d, J=8.3 Hz, 2H), 7.64 (d, J=8.6 Hz, 1H), 7.46 (d, J=8.8 Hz, 1H), 7.40 (d, J=8.6 Hz, 4H), 7.15 (d, J=8.3 Hz, 4H), 5.99 (s, 2H), 5.77 (s, 1H), 4.84 (dt, J=12.5, 6.2 Hz, 1H), 4.02-4.28 (m, 1H), 3.76 (d, J=11.0 Hz, 2H), 2.47 (m, 2H), 1.99 (m, 2H), 1.56-1.73 (m, 2H), 1.25 (d, J=6.1 Hz, 6H).

Example 82

5-((4-((6-(bis(4-chlorophenyl)methyl)quinazolin-4-yl)amino)piperidin-1-yl)sulfonyl)thiophene-2-carboxylic acid (Compound #25)

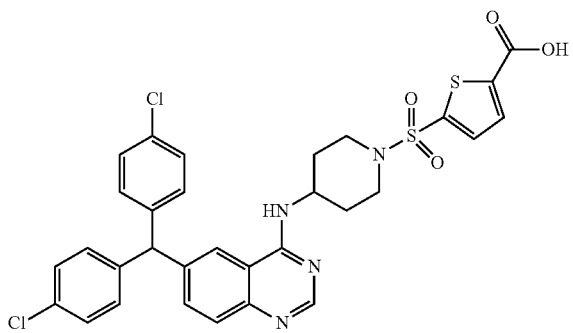 [SMILES: O=C(O)c1ccc(S(=O)(=O)N2CCC(Nc3ncnc4ccc(C(c5ccc(Cl)cc5)c5ccc(Cl)cc5)cc34)CC2)s1]

Step 1: Methyl 5-[4-([6-[bis(4-chlorophenyl)methyl]quinazolin-4-yl]amino)piperidine-1-sulfonyl]thiophene-2-carboxylate Into a 100-mL 3-necked round-bottom flask, was placed 6-[bis(4-chlorophenyl)methyl]-N-(piperidin-4-yl)quinazolin-4-amine (100 mg, 0.22 mmol, 1.00 equiv), dichloromethane (20 mL), triethylamine (0.1 mL) and methyl 5-(chlorosulfonyl)thiophene-2-carboxylate (57 mg, 0.24 mmol, 1.1equiv). The resulting solution was stirred for 3 h at 25° C. The resulting mixture was concentrated under vacuum, to yield methyl 5-[4-([6-[bis(4-chlorophenyl)methyl]quinazolin-4-yl]amino)piperidine-1-sulfonyl]thiophene-2-carboxylate as a yellow solid.

Step 2: 5-[4-([6-[Bis(4-chlorophenyl)methyl]quinazolin-4-yl]amino)piperidine-1-sulfonyl]thiophene-2-carboxylic acid; trifluoroacetic acid Into a 100-mL 3-necked round-bottom flask, was placed methyl 5-[4-([6-[bis(4-chlorophenyl)methyl]quinazolin-4-yl]amino)piperidine-1-sulfonyl]thiophene-2-carboxylate (120 mg, 0.18 mmol, 1.00 equiv), 1M NaOH (20 mL), methanol (20 mL). The resulting solution was stirred overnight at 50° C. The pH value of the solution was adjusted to pH 5-6 with 10% HCl. The solids were collected by filtration. The resulting residue (mL) was purified by Prep-HPLC with the following conditions water with 0.05% TFA and MeOH (60% MeOH up to 85% in 10 min, hold 95% in 1 min, down to 60% in 1 min), to yield 5-[4-([6-[bis(4-chlorophenyl)methyl]quinazolin-4-yl]amino)piperidine-1-sulfonyl]thiophene-2-carboxylic acid; trifluoroacetic acid as a white solid. LC-MS (ES, m/z) 653 [M+H]$^+$ $^1$H-NMR (300 MHz, DMSO, ppm) δ 14.381-13.889 (brs, 1H), 8.644 (br s, 1H) 8.578 (s, 1H), 8.301 (s, 1H), 7.824-7.816 (m, 1H), 7.754-7.680 (m, 2H), 7.575-7.546 (m, 1H), 7.430-7.313 (m, 4H), 7.268-7.145 (m, 4H), 5.806 (s, 1H), 4.303-4.191 (brs, 1H), 3.773-3.738 (m, 2H), 2.729-2.603 (m, 2H), 2.192-2.029 (m, 2H), 1.739-1.484 (m, 2H).

Example 83

4-((4-((6-(bis(4-chlorophenyl)methyl)quinazolin-4-yl)amino)piperidin-1-yl)sulfonyl)-2-chlorobenzoic acid (Compound #23)

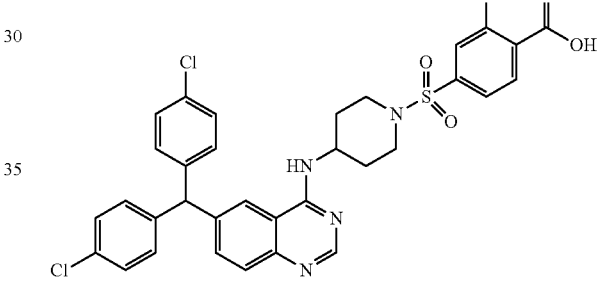

Step 1: Methyl 4-[4-([6-[bis(4-chlorophenyl)methyl]quinazolin-4-yl]amino)piperidine-1-sulfonyl]-2-chlorobenzoate Into a 100-mL 3-necked round-bottom flask, was placed 6-[bis(4-chlorophenyl)methyl]-N-(piperidin-4-yl)quinazolin-4-amine (100 mg, 0.22 mmol, 1.00 equiv), dichloromethane (20 mL) and triethylamine (0.1 mL). This was followed by the addition of methyl 2-chloro-4-(chlorosulfonyl)benzoate (64 mg, 0.24 mmol, 1.10 equiv) dropwise with stirring at 0° C. The resulting solution was stirred for 3 h at 25° C. The resulting mixture was concentrated under vacuum, to yield methyl 4-[4-([6-[bis(4-chlorophenyl)methyl]quinazolin-4-yl]amino)piperidine-1-sulfonyl]-2-chlorobenzoate as a light yellow solid.

Step 2: 4-[4-([6-[Bis(4-chlorophenyl)methyl]quinazolin-4-yl]amino)piperidine-1-sulfonyl]-2-chlorobenzoic acid Into a 100-mL round-bottom flask, was placed methyl 4-[4-([6-[bis(4-chlorophenyl)methyl]quinazolin-4-yl]amino)piperidine-1-sulfonyl]-2-chlorobenzoate (120 mg, 0.17 mmol, 1.00 equiv), methanol (20 mL) and 1M NaOH (20 mL). The resulting solution was stirred overnight at 50° C. The pH value of the solution was adjusted to pH 5-6 with 10% HCl. The solids were collected by filtration, to yield 4-[4-([6-[bis(4-chlorophenyl)methyl]quinazolin-4-yl]amino)piperidine-1-sulfonyl]-2-chlorobenzoic acid as a white solid. LC-MS (ES, m/z) 683 [M+H]+

$^{1}$H-NMR (300 MHz, DMSO, ppm) δ 8.390 (s, 1H), 8.204 (s, 1H), 7.963 (d, J=8.1 Hz, 2H), 7.833 (d, J=1.5 Hz, 1H), 7.780 (dd, J=8.1 Hz, J=1.5 Hz, 2H), 7.636 (d, J=8.4 Hz, 1H), 7.466-7.389 (overlapping m, 5H), 7.154 (d, J=8.7 Hz, 4H), 5.762 (s, 1H), 4.208 (br s, 1H), 3.754 (d, J=11.4 Hz, 2H), 2.611-2.495 (m, 2H), 2.018 (d, J=9.9 Hz, 2H), 1.656-1.627 (m, 2H).

Example 84

4-((4-((6-(bis(4-chlorophenyl)methyl)quinazolin-4-yl)amino)piperidin-1-yl)sulfonyl)-2-methoxybenzoic acid (Compound #22)

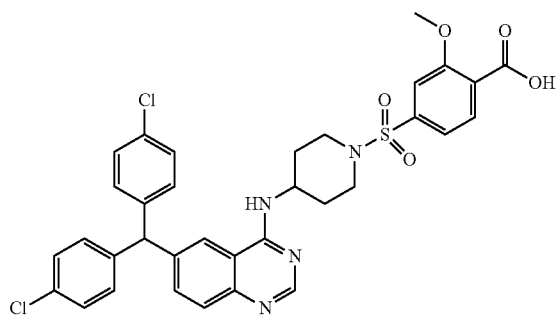 [SMILES: COc1cc(S(=O)(=O)N2CCC(Nc3ncnc4ccc(C(c5ccc(Cl)cc5)c5ccc(Cl)cc5)cc34)CC2)ccc1C(=O)O]

Step 1: Methyl 4-[4-([6-[bis(4-chlorophenyl)methyl]quinazolin-4-yl]amino)piperidine-1-sulfonyl]-2-methoxybenzoate Into a 100-mL 3-necked round-bottom flask, was placed 6-[bis(4-chlorophenyl)methyl]-N-(piperidin-4-yl)quinazolin-4-amine (100 mg, 0.22 mmol, 1.00 equiv), dichloromethane (20 mL) and triethylamine (0.1 mL). This was followed by the addition of methyl 4-(chlorosulfonyl)-2-methoxybenzoate (64 mg, 0.24 mmol, 1.10 equiv) dropwise with stirring at 0° C. The resulting solution was stirred for 3 h at 25° C. The resulting mixture was concentrated under vacuum, to yield methyl 4-[4-([6-[bis(4-chlorophenyl)methyl]quinazolin-4-yl]amino)piperidine-1-sulfonyl]-2-methoxybenzoate as a light yellow solid.

Step 2: 4-[4-([6-[Bis(4-chlorophenyl)methyl]quinazolin-4-yl]amino)piperidine-1-sulfonyl]-2-methoxybenzoic acid Into a 100-mL round-bottom flask, was placed methyl 4-[4-([6-[bis(4-chlorophenyl)methyl]quinazolin-4-yl]amino)piperidine-1-sulfonyl]-2-methoxybenzoate (120 mg, 0.17 mmol, 1.00 equiv), methanol (20 mL) and 1M NaOH (20 mL). The resulting solution was stirred overnight at 50° C. The pH value of the solution was adjusted to pH 5-6 with 10% HCl. The solids were collected by filtration, to yield 4-[4-([6-[bis(4-chlorophenyl)methyl]quinazolin-4-yl]amino)piperidine-1-sulfonyl]-2-methoxybenzoic acid as a white solid. LC-MS (ES, m/z) 678 [M+H]+

$^{1}$H-NMR (300 MHz, DMSO, ppm) δ: 13.202 (br s, 1H), 9.876 (br s, 1H), 8.819 (s, 1H), 8.597 (s, 1H), 7.827 (d, J=8.1 Hz, 2H), 7.739 (d, J=8.7 Hz, 1H), 7.441-7.333 (overlapping m, 6H), 7.169 (d, J=8.7 Hz, 4H), 5.844 (s, 1H), 4.400 (br s, 1H), 3.927 (s, 3H), 3.809 (d, J=11.7 Hz, 2H), 2.588-2.507 (m, 2H), 2.018-1.983 (m, 2H), 1.821-1.779 (m, 2H).

Example 85

6-((4-bromophenyl)(4-chlorophenyl)methyl)-N-(1-((trifluoromethyl)sulfonyl)piperidin-4-yl)quinazolin-4-amine (Compound #20)

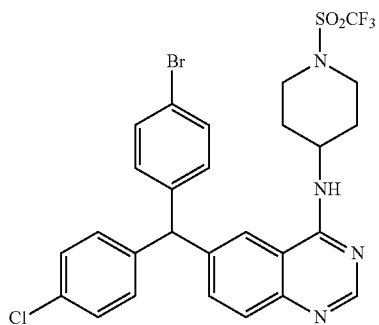

Step 1: Methyl 8-[[1-(trifluoromethane)sulfonylpiperidin-4-yl]amino]naphthalene-2-carboxylate Into a 100-mL 3-necked round-bottom flask, was placed 1-(trifluoromethane)sulfonylpiperidin-4-amine dihydrochloride (800 mg, 2.62 mmol, 1.00 equiv), methyl 4-chloroquinazoline-6-carboxylate (1.42 g, 6.38 mmol, 1.30 equiv), propan-2-ol (30 mL) and triethylamine (2.5 mL). The resulting solution was stirred overnight at 30° C. The resulting mixture was concentrated under vacuum. The residue was applied onto a silica gel column with ethyl acetate/petroleum ether (1:5), to yield methyl 8-[[1-(trifluoromethane)sulfonylpiperidin-4-yl]amino]naphthalene-2-carboxylate as a light yellow solid. (ES, m/z) 419 [M+H]+

Step 2: 4-[[1-(trifluoromethane)sulfonylpiperidin-4-yl]amino]quinazoline-6-carboxylic acid Into a 100-mL 3-necked round-bottom flask, was placed methyl 4-[[1-(trifluoromethane)sulfonylpiperidin-4-yl]amino]quinazoline-6-carboxylate (850 mg, 2.03 mmol, 1.00 equiv), methanol (30 mL) and 1M NaOH (20 mL). The resulting solution was stirred overnight at 30° C. The pH value of the solution was adjusted to pH 2-3 with 10% HCl solution. The solids were collected by filtration, to yield 4-[[1-(trifluoromethane)sulfonylpiperidin-4-yl]amino]quinazoline-6-carboxylic acid as a light yellow solid. (ES, m/z) 405 [M+H]+

Step 3: N-methoxy-N-methyl-4-[[1-(trifluoromethane)sulfonylpiperidin-4-yl]amino]quinazoline-6-carboxamide Into a 100-mL 3-necked round-bottom flask, was placed 4-[[1-(trifluoromethane)sulfonylpiperidin-4-yl]amino]quinazoline-6-carboxylic acid (700 mg, 1.73 mmol, 1.00 equiv), methoxy(methyl)amine hydrochloride (340 mg, 3.49 mmol, 2.00 equiv), HATU (850 mg, 2.24 mmol, 1.50 equiv), N,N-dimethylformamide (50 mL) and triethylamine (1 mL). The resulting solution was stirred overnight at 25° C. The resulting solution was diluted with water (150 mL). The solids were collected by filtration. The mixture was dried over anhydrous sodium sulfate, to yield N-methoxy-N-methyl-4-[[1-(trifluoromethane)sulfonylpiperidin-4-yl]amino]quinazoline-6-carboxamide as a light yellow solid.

Step 4: 6-[(4-Chlorophenyl)carbonyl]-N-[1-(trifluoromethane)sulfonylpiperidin-4-yl]quinazolin-4-amine Into a 100-mL 3-necked round-bottom flask, was placed N-methoxy-N-methyl-4-[[1-(trifluoromethane)sulfonylpiperidin-4-yl]amino]quinazoline-6-carboxamide (700 mg, 1.56 mmol, 1.00 equiv) and tetrahydrofuran (50 mL). This was followed by the addition of bromo(4-chlorophenyl)magnesium (7.8 mL, 5.00 equiv) dropwise with stirring. The resulting solution was stirred overnight at 25° C. The reaction was then quenched by the addition of water (80 mL). The resulting solution was extracted with ethyl acetate (3×80 mL) and the organic layers combined and dried over anhydrous sodium sulfate. The solids were filtered out. The resulting mixture was concentrated under vacuum, to yield 6-[(4-chlorophenyl)carbonyl]-N-[1-(trifluoromethane)sulfonylpiperidin-4-yl]quinazolin-4-amine as a light yellow solid. (ES, m/z) 499 [M+H]+

Step 5: (4-Bromophenyl)(4-chlorophenyl)(4-[[1-(trifluoromethane)sulfonylpiperidin-4-yl]amino]quinazolin-6-yl)methanol Into a 50-mL round-bottom flask purged and maintained with an inert atmosphere of nitrogen, was placed a solution of 6-[(4-chlorophenyl)carbonyl]-N-[1-(trifluoromethane)sulfonylpiperidin-4-yl]quinazolin-4-amine (570 mg, 1.14 mmol, 1.00 equiv) in tetrahydrofuran (20 mL). This was followed by the addition of 1M LiHMDS (2.3 mL, 2.00 equiv) dropwise with stirring at −20° C. The resulting solution was stirred for 10 min at −20° C. and then cooled to −78° C. Into another flame-dried 25 mL round-bottom flask was placed a solution of 1,4-dibromobenzene (540 mg, 2.29 mmol, 2.00 equiv) in tetrahydrofuran (15 mL). To this solution was added n-BuLi (1.2 mL, 1.6 equiv) dropwise with stirring at −78° C. under nitrogen atmosphere and stirred for an additional 10 min at −78° C. The resulting solution was then transferred into the former formed mixture at −78° C. The reaction was then warmed to 10° C. slowly and stirred for an additional 1 h. The resulting solution was diluted with water (50 mL). The resulting solution was extracted with ethyl acetate (3×80 mL) and the organic layers combined and dried over anhydrous sodium sulfate. The solids were filtered out. The resulting mixture was concentrated under vacuum, to yield (4-bromophenyl)(4-chlorophenyl)(4-[[1-(trifluoromethane)sulfonylpiperidin-4-yl]amino]quinazolin-6-yl)methanol as a yellow solid.

Step 6: 6-[(4-Bromophenyl)(4-chlorophenyl)methyl]-N-[1-(trifluoromethane)sulfonylpiperidin-4-yl]quinazolin-4-amine Into a 100-mL 3-necked round-bottom flask, was placed a solution of (4-bromophenyl)(4-chlorophenyl)(4-[[1-(trifluoromethane)sulfonylpiperidin-4-yl]amino]quinazolin-6-yl)methanol (700 mg, 1.07 mmol, 1.00 equiv) in dichloromethane (20 mL) and Et₃SiH (500 mg, 4.31 mmol, 4.00 equiv). This was followed by the addition of trifluoroacetic acid (2 mL) dropwise with stirring at 0° C. The resulting solution was stirred overnight at 25° C. The resulting solution was diluted with DCM (80 mL). The resulting mixture was washed with sodium bicarbonate(aq) (3×80 mL). The mixture was dried over anhydrous sodium sulfate. The solids were filtered out. The resulting mixture was concentrated under vacuum, to yield 6-[(4-bromophenyl)(4-chlorophenyl)methyl]-N-[1-(trifluoromethane)sulfonylpiperidin-4-yl]quinazolin-4-amine as an off-white solid. LC-MS (ES, m/z) 641 [M+H]+

¹H-NMR (300 MHz, DMSO, ppm) δ: 8.458 (s, 1H), 8.208 (s, 1H), 7.986 (d, J=7.8 Hz, 1H), 7.661 (d, J=8.7 Hz, 1H), 7.541 (d, J=8.4 Hz, 2H), 7.482-7.395 (overlapping m, 5H), 7.162 (d, J=8.4 Hz, 2H), 7.100 (d, J=8.4 Hz, 2H), 5.756 (s, 1H), 4.482 (br s, 1H), 3.874 (d, J=13.2 Hz, 2H), 3.443-3.361 (m, 2H), 2.080 (d, J=10.5 Hz, 2H), 1.707-1.599 (m, 2H).

Example 86

4-((4-chlorophenyl)(4-((1-(((trifluoromethyl)sulfonyl)piperidin-4-yl)amino)quinazolin-6-yl)methyl)benzonitrile (Compound #19)

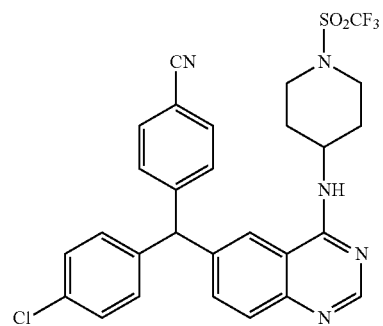

Step 1: 4-[(4-Chlorophenyl)(hydroxy)(4-[[1-(trifluoromethane)sulfonylpiperidin-4-yl]amino]quinazolin-6-yl)methyl]benzonitrile Into a 10-mL round-bottom flask purged and maintained with an inert atmosphere of nitrogen, was placed 6-[(4-chlorophenyl)carbonyl]-N-[1-(trifluoromethane)sulfonylpiperidin-4-yl]quinazolin-4-amine (71 mg, 0.14 mmol, 1.00 equiv), tetrahydrofuran (3 mL) and 1M LiHMDS (0.3 mL, 2.00 equiv). The resulting "mixture A" was stirred for 5 min at −20° C. Into a separate 10-mL round-bottom flask purged and maintained with an inert atmosphere of nitrogen, was placed 4-bromobenzonitrile (52 mg, 0.29 mmol, 1.00 equiv) and tetrahydrofuran (2 mL). To this mixture was then added 1.6M n-BuLi (0.15 mL, 0.80 equiv) dropwise with stirring at −100° C. The resulting solution was stirred for 10 min at −100° C. and then dropwise, canulated to "mixture A" (prepared as described above), at −78° C. The resulting solution was allowed to react, with stirring, for an additional 15 min at −78° C. The reaction was then quenched by the addition of water (15 mL). The resulting solution was extracted with ethyl acetate (3×50 mL) and the organic layers combined and dried over anhydrous sodium sulfate. The solids were filtered out. The resulting mixture was concentrated under vacuum, to yield 4-[(4-chlorophenyl)(hydroxy)(4-[[1-(trifluoromethane)sulfonylpiperidin-4-yl]amino]quinazolin-6-yl)methyl]benzonitrile as a yellow solid.

Step 2: 4-[(4-Chlorophenyl)(4-[[1-(trifluoromethane)sulfonylpiperidin-4-yl]amino]quinazolin-6-yl)methyl]benzonitrile Into a 100-mL round-bottom flask, was placed 4-[(4-chlorophenyl)(hydroxy)(4-[[1-(trifluoromethane)sulfonylpiperidin-4-yl]amino]quinazolin-6-yl)methyl]benzonitrile (90 mg, 0.15 mmol, 1.00 equiv), dichloromethane (20 mL), Et$_3$SiH (70 mg, 0.60 mmol, 4.00 equiv) and trifluoroacetic acid (2 mL). The resulting solution was stirred overnight at 25° C. The resulting mixture was concentrated under vacuum. The residue was applied onto a silica gel column with dichloromethane/methanol (20:1), to yield 4-[(4-chlorophenyl)(4-[[1-(trifluoromethane)sulfonylpiperidin-4-yl]amino]quinazolin-6-yl)methyl]benzonitrile as a white solid. LC-MS (ES, m/z) 587 [M+H]$^+$ $^1$H-NMR (300 MHz, DMSO, ppm) δ 8.478 (s, 1H), 8.211 (s, 1H), 8.043 (d, J=7.2 Hz, 1H), 7.818 (d, J=8.4 Hz, 2H), 7.670 (d, J=8.7 Hz, 1H), 7.482 (dd, J=8.7 Hz, J=1.5 Hz, 1H), 7.420 (d, J=8.4 Hz, 2H), 7.348 (d, J=8.4 Hz, 2H), 7.168 (d, J=8.4 Hz, 2H), 5.883 (s, 1H), 4.498 (br s, 1H), 3.871 (d, J=13.2 Hz, 2H), 3.440-3.356 (m, 2H), 2.072 (d, 7.420 J=10.8 Hz, 2H), 1.718-1.584 (m, 2H).

Example 87

4-((4-chlorophenyl)(4-((1-((trifluoromethyl)sulfonyl)piperidin-4-yl)amino)quinazolin-6-yl)methyl)benzoic acid (Compound #16)

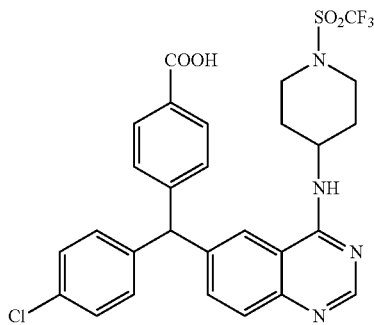

Into a 50-mL 3-necked round-bottom flask purged and maintained with an inert atmosphere of nitrogen, was placed 6-[(4-bromophenyl)(4-chlorophenyl)methyl]-N-[1-(trifluoromethane)sulfonylpiperidin-4-yl]quinazolin-4-amine (200 mg, 0.31 mmol, 1.00 equiv) and tetrahydrofuran (20 mL). This was followed by the addition of 1M LiHMDS (0.78 mL, 2.50 equiv) dropwise with stirring at −20° C. The resulting solution was stirred for 10 min at −20° C. To the resulting mixture was added 1.6M n-BuLi (0.6 mL, 3.00 equiv) dropwise with stirring at −78° C. The resulting solution was allowed to react, with stirring, for an additional 30 min at −78° C. To the mixture was then added CO$_2$(s) (10 g). The resulting solution was allowed to react, with stirring, overnight at 25° C. The reaction was then quenched by the addition of water (10 mL). The pH value of the solution was adjusted to pH 2-3 with 10% HCl. The resulting solution was extracted with ethyl acetate (3×50 mL) and the organic layers combined and dried over anhydrous sodium sulfate. The solids were filtered out. The resulting mixture was concentrated under vacuum. The residue was applied onto a silica gel column with chloroform/methanol (5:1), to yield 4-[(4-chlorophenyl)(4-[[1-(trifluoromethane)sulfonylpiperidin-4-yl]amino]quinazolin-6-yl)methyl]benzoic acid as an off-white solid. LC-MS (ES, m/z) 605 [M+H]$^+$ $^1$H-NMR (300 MHz, DMSO, ppm) δ 8.452 (s, 1H), 8.245 (s, 1H), 8.029 (d, J=7.2 Hz, 1H), 7.836 (d, J=8.1 Hz, 2H), 7.648 (d, J=8.7 Hz, 1H), 7.479 (d, J=7.2 Hz, 1H), 7.390 (d, J=8.7 Hz, 2H), 7.164 7.420 (d, J=8.4 Hz, 2H), 7.103 (d, J=8.1 Hz, 2H), 5.764 (s, 1H), 4.470 (s, 1H), 3.874 (d, J=13.5 Hz, 2H), 3.441-3.324 (m, 2H), 2.080 (d, J=10.5 Hz, 2H), 1.724-1.653 (m, 2H).

Example 88

6-((4-chlorophenyl)(4-((2-methoxyethyl)amino)phenyl)methyl)-N-(1-((trifluoromethyl)sulfonyl)piperidin-4-yl)quinazolin-4-amine (Compound #15)

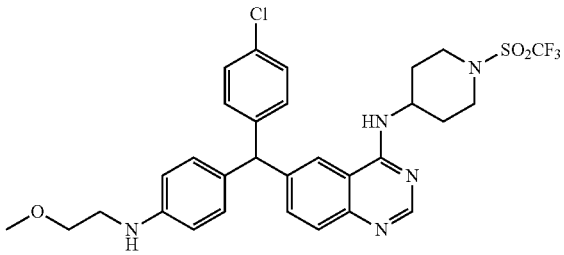

Into a 10-mL round-bottom flask, was placed 6-[(4-bromophenyl)(4-chlorophenyl)methyl]-N-[1-(trifluoromethane)sulfonylpiperidin-4-yl]quinazolin-4-amine (100 mg, 0.16 mmol, 1.00 equiv), 2-methoxyethan-1-amine (24 mg, 0.32 mmol, 2.00 equiv), 1,4-dioxane (2 mL), Cs$_2$CO$_3$ (77 mg, 0.24 mmol, 1.50 equiv), Pd$_2$(dba)$_3$ (16 mg, 0.02 mmol, 0.10 equiv) and XantPhos (27 mg, 0.30 equiv). The resulting solution was stirred overnight at 75° C. The resulting solution was diluted with water (20 mL). The resulting solution was extracted with ethyl acetate (3×30 mL) and the organic layers combined and dried over anhydrous sodium sulfate. The solids were filtered out. The resulting mixture was concentrated under vacuum. The residue was applied onto a silica gel column with dichloromethane/methanol (20:1), to yield 6-[(4-chlorophenyl)([4-[(2-methoxyethyl)amino]phenyl])methyl]-N-[1-(trifluoromethane)sulfonylpiperidin-4-yl]quinazolin-4-amine as an off-white solid. LC-MS (ES, m/z) 635 [M+H]$^+$ $^1$H-NMR (300 MHz, DMSO, ppm) δ 8.442 (s, 1H), 8.182 (s, 1H), 7.940 (d, J=7.2 Hz, 1H), 7.631 (d, J=8.4 Hz, 1H), 7.450 (d, J=7.2 Hz, 1H), 7.364 (d, J=8.4 Hz, 2H), 7.132 (d, J=8.7 Hz, 2H), 6.836 (d, J=8.4 Hz, 2H), 6.549 (d, J=8.7 Hz, 2H), 5.552 (s, 1H), 5.530 (m, 1H), 4.498 (br s, 1H), 3.870 (d, J=13.2 Hz, 2H), 3.473-3.312 (overlapping m, 4H), 3.259 (s, 3H), 3.156-3.137 (m, 2H), 2.090 (d, J=10.5 Hz, 2H), 1.740-1.590 (m, 2H).

Example 89

4-((4-((6-(bis(4-chlorophenyl)methyl)quinazolin-4-yl)amino)piperidin-1-yl)sulfonyl)-N-(3-(4-(chloromethyl)phenoxy)propyl)benzamide (Compound #30)

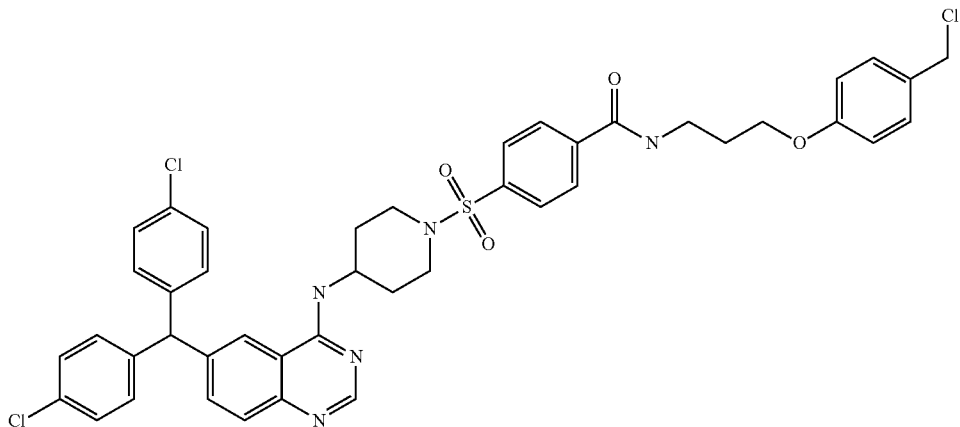 [SMILES: O=C(NCCCOc1ccc(CCl)cc1)c1ccc(S(=O)(=O)N2CCC(Nc3ncnc4ccc(C(c5ccc(Cl)cc5)c5ccc(Cl)cc5)cc34)CC2)cc1]

Step 1: (4-(3-aminopropoxy)phenyl)methanol hydrochloride salt

To a suspension of 4-(hydroxymethyl)phenol (0.5 g, 4.03 mmol) and $Cs_2CO_3$ (1.58 g, 4.83 mmol) in DMF (10 mL) was added tert-butyl(3-bromopropyl)carbamate (1.05 g, 4.43 mmol). The resulting mixture was heated to 90° C. for 3 hr and then cooled to room temperature. The resulting mixture was then diluted with $CH_2Cl_2$ and water. The organics were washed with water and concentrated. The resulting residue was purified by silica gel column (55-65% EtOAc/hexanes) to yield tert-butyl (3-(4-(hydroxymethyl)phenoxy)propyl)carbamate. (ES, m/z) 304.0 [M+Na]⁺. The tert-butyl (3-(4-(hydroxymethyl)phenoxy)propyl)carbamate was then treated with 4M HCl (5 mL) in 1,4-dioxane to yield (4-(3-aminopropoxy)phenyl)methanol hydrochloride salt. (ES, m/z) 182.1 [M+Na]

Step 2: 4-((4-((6-(Bis(4-chlorophenyl)methyl)quinazolin-4-yl)amino)piperidin-1-yl)sulfonyl)-N-(3-(4-(chloromethyl)phenoxy)propyl)benzamide A mixture of (4-(3-aminopropoxy)phenyl)methanol hydrochloride salt (32 mg, 0.147 mmol), 4-((4-((6-(bis(4-chlorophenyl)methyl)quinazolin-4-yl)amino)piperidin-1-yl)sulfonyl)benzoic acid (126.8 mg, 0.196 mmol), HATU (96.8 mg, 0.255 mmol) and TEA (0.109 mL, 0.78 mmol) in DMF (0.8 mL) was stirred at room temperature for 3 hr. The resulting mixture was diluted with EtOAc and washed with water. The organic layer was concentrated and purified by silica column (0-3% MeOH/EtOAc) to yield 4-((4-((6-(Bis(4-chlorophenyl)methyl)quinazolin-4-yl)amino)piperidin-1-yl)sulfonyl)-N-(3-(4-(chloromethyl)phenoxy)propyl)benzamide. (ES, m/z) 825.2, 826.2, 827.1 [M+H]⁺

Example 90

4-((4-((6-(bis(4-chlorophenyl)methyl)quinazolin-4-yl)amino)piperidin-1-yl)sulfonyl)-N-(3-(4-(hydroxymethyl)phenoxy)propyl)benzamide (Compound #26)

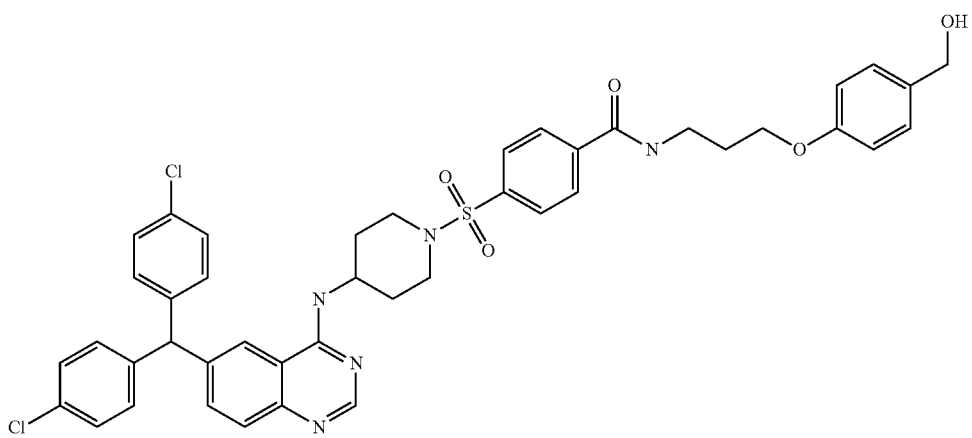 [SMILES: O=C(NCCCOc1ccc(CO)cc1)c1ccc(S(=O)(=O)N2CCC(Nc3ncnc4ccc(C(c5ccc(Cl)cc5)c5ccc(Cl)cc5)cc34)CC2)cc1]

A solution of 4-((4-((6-(Bis(4-chlorophenyl)methyl)quinazolin-4-yl)amino)piperidin-1-yl)sulfonyl)-N-(3-(4-(chloromethyl)phenoxy)propyl)benzamide (108 mg, 0.13 mmol), NaOAc (106.8 mg, 1.3 mmol) and KI (10.8 mg, 0.065 mmol) in DMF (1 mL) was heated to 90° C. overnight under argon. The resulting mixture was cooled to 45° C. To the resulting mixture was then added 1N NaOH solution (0.26 mL) and the mixture stirred at 45° C. for 3 hr, then diluted with CH$_2$Cl$_2$ and water. The organic layer was washed with water and concentrated. The resulting residue was purified by silica column (5-8% MeOH/CH$_2$Cl$_2$) to yield 4-((4-((6-(bis(4-chlorophenyl)methyl)quinazolin-4-yl)amino)piperidin-1-yl)sulfonyl)-N-(3-(4-(hydroxymethyl)phenoxy)propyl)benzamide. (ES, m/z) 809.2, 810.2, 811.2 [M+H]$^+$;

$^1$H NMR (CHLOROFORM-d) δ: 8.49 (s, 1H), 7.91 (d, J=8.1 Hz, 2H), 7.77 (d, J=8.1 Hz, 2H), 7.73 (d, J=8.6 Hz, 1H), 7.54 (s, 1H), 7.43 (d, J=8.6 Hz, 1H), 7.29 (m, 1H), 7.23 (d, J=8.1 Hz, 4H), 6.94-7.02 (m, 5H), 6.86 (d, J=8.6 Hz, 2H), 5.86 (d, J=7.6 Hz, 1H), 5.58 (s, 1H), 4.62 (s, 2H), 4.14-4.19 (m, 3H), 3.86 (d, J=12.1 Hz, 2H), 3.72 (q, J=5.9 Hz, 2H), 2.44 (t, J=11.4 Hz, 2H), 2.11-2.22 (m, 4H), 1.67 (qd, J=12.1, 3.5 Hz, 2H)

Example 91

Ethyl 2-(4-((4-((6-(bis(4-chlorophenyl)methyl)quinazolin-4-yl)amino)piperidin-1-yl)sulfonyl)phenoxy)acetate (Compound #4)

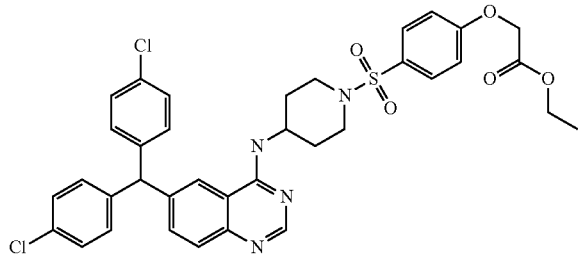 [SMILES: CCOC(=O)COc1ccc(S(=O)(=O)N2CCC(Nc3ncnc4ccc(C(c5ccc(Cl)cc5)c5ccc(Cl)cc5)cc34)CC2)cc1]

A mixture of 4-((4-((6-(bis(4-chlorophenyl)methyl)quinazolin-4-yl)amino)piperidin-1-yl)sulfonyl)phenol (30 mg, 0.048 mmol), ethyl 2-bromoacetate (9.7 mg, 0.058 mmol) and Cs$_2$CO$_3$ (23.7 mg, 0.073 mmol) in DMF (0.8 ml) was heated to 65° C. for 3 hr. The resulting mixture was diluted with EtOAc and water. The organics were washed with water and concentrated. The resulting residue was purified by silica column (100% CH$_2$Cl$_2$ to 5% MeOH/CH$_2$Cl$_2$) to yield ethyl 2-(4-((4-((6-(bis(4-chlorophenyl)methyl)quinazolin-4-yl)amino)piperidin-1-yl)sulfonyl)phenoxy)acetate. (ES, m/z) 705.2, 707.1 [M+H]$^+$ $^1$H NMR (CHLOROFORM-d) δ: 8.51 (s, 1H), 7.63-7.78 (m, 4H), 7.40 (d, J=10.1 Hz, 1H), 7.18 (d, J=8.6 Hz, 4H), 7.02 (d, J=8.6 Hz, 2H), 6.91 (d, J=8.6 Hz, 4H), 6.23 (d, J=7.6 Hz, 1H), 5.50 (s, 1H), 4.72 (s, 2H), 4.30 (q, J=7.1 Hz, 2H), 4.23 (m, 1H), 3.87 (d, J=11.6 Hz, 2H), 2.42 (t, J=11.1 Hz, 2H), 2.19 (d, J=10.6 Hz, 2H), 1.74-1.91 (m, 2H), 1.32 (t, J=7.1 Hz, 3H)

Example 92

Hexyl ((4-((4-((6-(bis(4-chlorophenyl)methyl)quinazolin-4-yl)amino)piperidin-1-yl)sulfonyl)phenyl)(imino)methyl)carbamate (Compound #7)

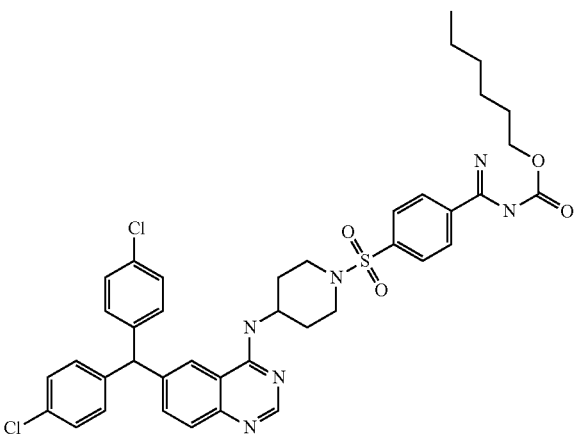 [SMILES: CCCCCCOC(=O)NC(=N)c1ccc(S(=O)(=O)N2CCC(Nc3ncnc4ccc(C(c5ccc(Cl)cc5)c5ccc(Cl)cc5)cc34)CC2)cc1]

4-((4-((6-(Bis(4-chlorophenyl)methyl)quinazolin-4-yl)amino)piperidin-1-yl)sulfonyl)benzimidamide (100 mg, 0.114 mmol) and TEA (0.024 mL, 0.143 mmol) were combined in DMF (2 mL) at 0° C., followed by addition of hexyl carbonochloridate (0.048 mL, 0.343 mmol) with stirring. The resulting mixture was warmed to room temperature overnight. The resulting mixture was partitioned between water and EtOAc. The organic layer was washed twice with brine, then dried over anhydrous Na$_2$SO$_4$ and concentrated. The resulting residue was purified on ISCO with EtOAc—CH$_2$Cl$_2$ (70% EtOAc/CH$_2$Cl$_2$) to yield hexyl ((4-((4-((6-(bis(4-chlorophenyl)methyl)quinazolin-4-yl)amino)piperidin-1-yl)sulfonyl)phenyl)(imino)methyl)carbamate. (ES, m/z) 774 [M+H]$^+$.

Example 93

5-((4-((6-(bis(4-chlorophenyl)methyl)quinazolin-4-yl)amino)piperidin-1-yl)methyl)thiophene-3-carboxylic acid (Compound #18)

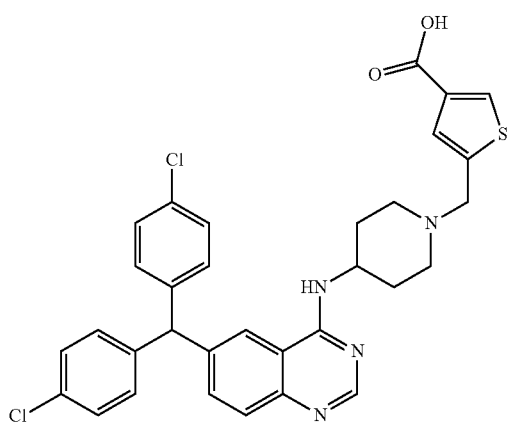 [SMILES: O=C(O)c1csc(CN2CCC(Nc3ncnc4ccc(C(c5ccc(Cl)cc5)c5ccc(Cl)cc5)cc34)CC2)c1]

Step 1: Methyl 5-((4-(6-(bis(4-chlorophenyl)methyl) quinazolin-4-ylamino)piperidin-1-yl)methyl)thiophene-3-carboxylate Into a 50-mL round-bottom flask, was placed 6-[bis(4-chlorophenyl)methyl]-N-(piperidin-4-yl)quinazolin-4-amine (100 mg, 0.22 mmol, 1.00 equiv), methyl 5-formyl-thiophene-3-carboxylate (55 mg, 0.32 mmol, 1.50 equiv), methanol (10 mL), NaBH$_3$CN (40 mg, 0.63 mmol, 3.00 equiv) and acetic acid (0.1 mL). The resulting solution was stirred overnight at 25° C. The resulting mixture was concentrated under vacuum. The resulting residue was applied onto a silica gel column with dichloromethane/methanol (20:1) to yield methyl 5-[[4-([6-[bis(4-chlorophenyl)methyl]quinazolin-4-yl]amino)piperidin-1-yl]methyl]thiophene-3-carboxylate as a yellow solid. LC-MS (ES, m/z) 617 [M+H]$^+$

Step 2: 5-((4-(6-(Bis(4-chlorophenyl)methyl)quinazolin-4-ylamino)piperidin-1-yl)methyl)thiophene-3-carboxylic acid Into a 100-mL round-bottom flask, was placed methyl 5-[[4-([6-[bis(4-chlorophenyl)methyl]quinazolin-4-yl] amino)piperidin-1-yl]methyl]thiophene-3-carboxylate (90 mg, 0.15 mmol, 1.00 equiv), methanol (20 mL) and sodium hydroxide (10 mL). The resulting solution was stirred overnight at 30° C. The resulting mixture was concentrated under vacuum. The pH value of the solution was adjusted to pH3-4 with 10% HCl. The resulting solids were collected by filtration to yield 5-[[4-([6-[bis(4-chlorophenyl)methyl]quinazolin-4-yl]amino)piperidin-1-yl]methyl]thiophene-3-carboxylic acid as a pink solid. LC-MS (ES, m/z): 601 [M–H]$^-$.

$^1$H-NMR (300 MHz, DMSO, ppm) δ 8.696 (s, 1H), 8.454 (br s, 1H) 8.395 (s, 1H), 7.758 (d, J=8.7 Hz, 1H), 7.674-7.646 (overlapping m, 2H), 7.420 (d, (d, J=8.4 Hz, 2H), 7.172 (d, (d, J=8.4 Hz, 2H), 5.816 (s, 1H), 4.600-4.420 (br m, 3H), 3.544-3.400 (br m, 3H), 3.126-3.103 (br m, 1H), 2.190-2.164 (m, 2H), 2.001-1.976 (m, 2H).

Example 94

6-(bis(4-chlorophenyl)methyl)-N-(1-phenethylpiperidin-4-yl)quinazolin-4-amine (Compound #11)

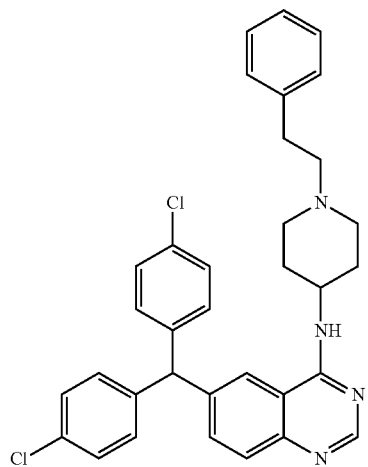 [SMILES: Clc1ccc(C(c2ccc(Cl)cc2)c2ccc3ncnc(NC4CCN(CCc5ccccc5)CC4)c3c2)cc1]

Into a 25-mL round-bottom flask, was placed 6-[bis(4-chlorophenyl)methyl]-N-(piperidin-4-yl)quinazolin-4-amine (100 mg, 0.22 mmol, 1.00 equiv), 2-phenylacetaldehyde (26 mg, 0.22 mmol, 1.00 equiv), methanol (10 mL), NaBH$_3$CN (41 mg, 0.65 mmol, 3.00 equiv) and acetic acid (0.1 mL). The resulting solution was stirred overnight at 25° C. The resulting mixture was then concentrated under vacuum. The resulting residue was applied onto a silica gel column with dichloromethane/methanol (20:1) to yield 6-[bis(4-chlorophenyl)methyl]-N-[1-(2-phenylethyl)piperidin-4-yl]quinazolin-4-amine as a off-white solid. LC-MS (ES, m/z) 567 [M+H]$^+$.

$^1$H-NMR (300 MHz, DMSO, ppm) δ 8.417 (s, 1H), 8.233 (s, 1H), 7.890 (d, (d, J=7.5 Hz, 1H), 7.620 (d, J=8.4 Hz, 1H), 7.451-7.381 (overlapping m, 5H), 7.291-7.187 (overlapping m, 5H), 7.154 (d, J=8.4 Hz, 4H), 5.747 (s, 1H), 4.227-4.096 (br m, 1H), 2.981 (m, 2H), 2.733 (m, 2H), 2.549-2.4.97 (m, 2H), 2.056 (m, 2H), 1.890 (m, 2H), 1.614 (m, 2H).

Example 95

4-(2-(4-((6-(bis(4-chlorophenyl)methyl)quinazolin-4-yl)amino)piperidin-1-yl)ethyl)benzoic acid (Compound #10)

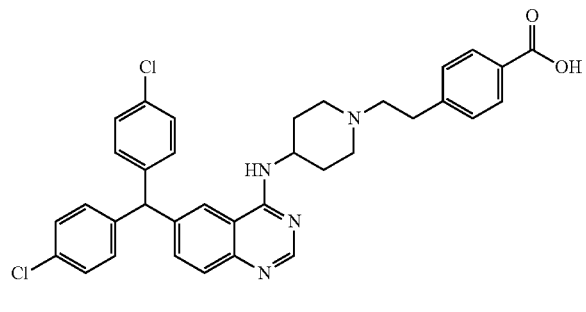 [SMILES: O=C(O)c1ccc(CCN2CCC(Nc3ncnc4ccc(C(c5ccc(Cl)cc5)c5ccc(Cl)cc5)cc34)CC2)cc1]

Step 1: Methyl 4-(2-(4-(6-(bis(4-chlorophenyl) methyl)quinazolin-4-ylamino)piperidin-1-yl)ethyl) benzoate Into a 50-mL round-bottom flask, was placed 6-[bis(4-chlorophenyl)methyl]-N-(piperidin-4-yl)quinazolin-4-amine (200 mg, 0.43 mmol, 1.00 equiv), methyl 4-(2-oxoethyl)benzoate (115 mg, 0.65 mmol, 1.20 equiv), methanol (20 mL), NaBH$_3$CN (136 mg, 2.12 mmol, 3.00 equiv) and acetic acid (0.1 mL). The resulting solution was stirred overnight at 25° C. The resulting mixture was concentrated under vacuum. The resulting residue was applied onto a silica gel column with dichloromethane/methanol (20:1) to yield methyl 4-[2-[4-([6-[bis(4-chlorophenyl) methyl]quinazolin-4-yl]amino)piperidin-1-yl]ethyl]benzoate as a white solid.

Step 2: 4-(2-(4-(6-(Bis(4-chlorophenyl)methyl)qui-
nazolin-4-ylamino)piperidin-1-yl)ethyl)benzoic acid Into a 100-mL round-bottom flask, was placed methyl 4-[2-[4-([6-[bis(4-chlorophenyl)methyl]quinazolin-4-yl]amino)piperidin-1-yl]ethyl]benzoate (90 mg, 0.14 mmol, 1.00 equiv), methanol (20 mL) and 1 M sodium hydroxide (20 mL). The resulting solution was stirred overnight at 50° C. The resulting mixture was concentrated under vacuum. The pH value of the solution was adjusted to pH4-5 with 10% HCl. The resulting solids were collected by filtration to yield 4-[2-[4-([6-[bis(4-chlorophenyl)methyl]quinazolin-4-yl]amino)piperidin-1-yl]ethyl]benzoic acid as a white solid. LC-MS (ES, m/z) 611 [M+H]⁺

¹H-NMR (300 MHz, DMSO, ppm) δ 8.418 (s, 1H), 8.227 (s, 1H), 7.901-7.833 (overlapping m, 3H), 7.621 (d, J=8.7 Hz, 1H), 7.486-7.310 (overlapping m, 7H), 7.153 (d, J=8.7 Hz, 4H), 5.746 (s, 1H), 4.170 (br s, 1H), 2.997 (m, 2H), 2.823 (m, 2H), 2.597 (br m, 2H), 2.105 (br m, 2H), 1.899 (m, 2H), 1.612 (m, 2H).

Example 96

4-((3-((6-(bis(4-chlorophenyl)methyl)quinazolin-4-yl)amino)pyrrolidin-1-yl)methyl)benzoic acid
(Compound #14)

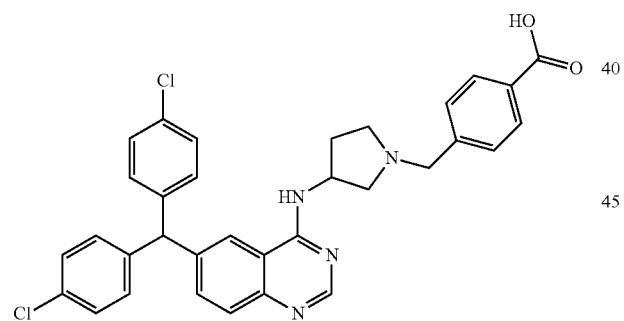

Step 1: Methyl 4-[[3-([6-[bis(4-chlorophenyl)methyl]quinazolin-4-yl]amino)pyrrolidin-1-yl]methyl]benzoate Into a 50-mL round-bottom flask, was placed 6-[bis(4-chlorophenyl)methyl]-N-(pyrrolidin-3-yl)quinazolin-4-amine (100 mg, 0.22 mmol, 1.00 equiv), methyl 4-formylbenzoate (71 mg, 0.43 mmol, 2.00 equiv), methanol (20 mL), NaBH₃CN (68 mg, 1.08 mmol, 5.00 equiv) and acetic acid (0.1 mL). The resulting solution was stirred overnight at 25° C. The resulting mixture was concentrated under vacuum. The resulting residue was applied onto a silica gel column with dichloromethane/methanol (20:1) to yield methyl 4-[[3-([6-[bis(4-chlorophenyl)methyl]quinazolin-4-yl]amino)pyrrolidin-1-yl]methyl]benzoate as a white solid. LC-MS (ES, m/z) 597 [M+H]⁺

Step 2: 4-[[3-([6-[Bis(4-chlorophenyl)methyl]quinazolin-4-yl]amino)pyrrolidin-1-yl]methyl]benzoic acid Into a 100-mL round-bottom flask, was placed methyl 4-[[3-([6-[bis(4-chlorophenyl)methyl]quinazolin-4-yl]amino)pyrrolidin-1-yl]methyl]benzoate (95 mg, 0.16 mmol, 1.00 equiv), methanol (20 mL) and 1M sodium hydroxide (20 mL). The resulting solution was stirred overnight at 50° C. The resulting mixture was concentrated under vacuum. The pH value of the solution was adjusted to pH 5-6 with 10% HCl. The resulting solids were collected by filtration to yield 4-[[3-([6-[bis(4-chlorophenyl)methyl]quinazolin-4-yl]amino)pyrrolidin-1-yl]methyl]benzoic acid as a white solid. LC-MS (ES, m/z) 583 [M+H]⁺.

¹H-NMR (300 MHz, DMSO, ppm) 68.506 (s, 1H), 8.105-7.999 (m, 3H), 7.705 (d, J=8.7 Hz, 1H), 7.649-7.545 (m, 3H), 7.317 (d, J=8.1 Hz, 4H), 7.109 (d, J=8.4 Hz, 4H), 5.761 (s, 1H), 4.352 (ABq, J=13.2 Hz, 2H), 3.683-3.492 (m, 2H), 3.398-3.202 (overlapping m, 3H), 2.601 (m, 1H), 2.257 (m 1H).

Example 97

N-(1-(6-(bis(4-chlorophenyl)methyl)quinazolin-4-yl)pyrrolidin-3-yl)trifluoromethanesulfonamide (Compound #9)

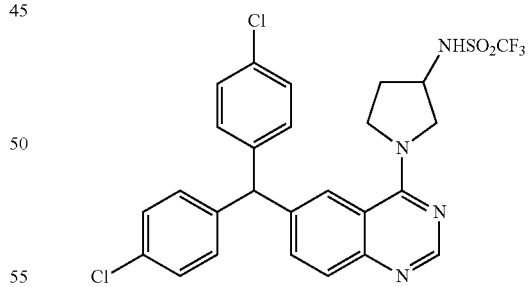

Into a 25-mL round-bottom flask, was placed 6-[bis(4-chlorophenyl)methyl]-4-chloroquinazoline (100 mg, 0.25 mmol, 1.00 equiv), 1,1,1-trifluoro-N-(pyrrolidin-3-yl)methanesulfonamide hydrochloride (73 mg, 0.33 mmol, 1.30 equiv), propan-2-ol (0.2 mL) and TEA (10 mL). The resulting solution was stirred overnight at 30° C. The resulting mixture was concentrated under vacuum. The residue was applied onto a silica gel column with dichloromethane/methanol (20:1) to yield N-(1-[6-[bis(4-chlorophenyl)methyl]quinazolin-4-yl]pyrrolidin-3-yl)-1,1,1-trifluoromethanesulfonamide as an off-white solid. LC-MS (ES, m/z) 581 [M+H]⁺.

¹H-NMR (300 MHz, DMSO, ppm) δ 9.972 (br s, 1H), 8.464 (s, 1H), 7.811 (s, 1H), 7.693 (d, J=8.4 Hz, 1H), 7.553 (dd, J=8.4 Hz, J=1.5 Hz, 1H), 7.395 (d, J=8.1 Hz, 4H), 7.161 (dd, J=8.4 Hz, J=1.8 Hz, 4H), 5.914 (s, 1H), 4.201 (m, 1H), 4.018-3.700 (overlapping m, 3H), 3.612 (m, 1H), 2.222 (m, 1H), 1.971 (m, 1H).

Example 98

4-(2-((6-(bis(4-chlorophenyl)methyl)quinazolin-4-yl)amino)ethyl)thiomorpholine 1,1-dioxide (Compound #6)

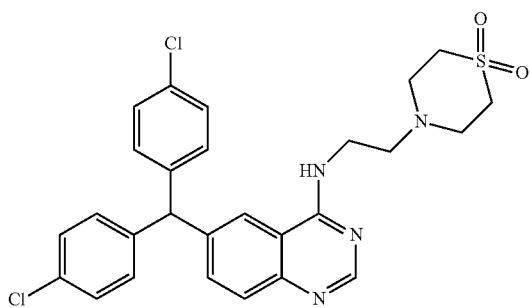 [SMILES: O=S1(=O)CCN(CCNc2ncnc3ccc(C(c4ccc(Cl)cc4)c4ccc(Cl)cc4)cc23)CC1]

Into a 25-mL round-bottom flask, was placed 6-[bis(4-chlorophenyl)methyl]-4-chloroquinazoline (100 mg, 0.25 mmol, 1.00 equiv), 4-(2-aminoethyl)-1ˆ[6],4-thiomorpholine-1,1-dione (58 mg, 0.33 mmol, 1.30 equiv), propan-2-ol (10 mL) and triethylamine (0.1 mL). The resulting solution was stirred overnight at 30° C. The resulting mixture was concentrated under vacuum. The resulting residue was applied onto a silica gel column with dichloromethane:methanol (20:1) to yield 4-[2-([6-[bis(4-chlorophenyl)methyl]quinazolin-4-yl]amino)ethyl]-1ˆ[6],4-thiomorpholine-1,1-dione as a white solid. LC-MS (ES, m/z) 541 [M+H]⁺

¹H-NMR (400 MHz, DMSO, ppm) 68.449 (s, 1H), 8.210-8.183 (m, 1H), 8.048 (s, 1H), 7.657 (d, J=8.8 Hz, 1H), 7.513 (d, d, J=8.8 Hz, 1H), 7.420 (d, J=8.4 Hz, 4H) 7.189 (d, (d, J=8.4 Hz, 4H), 5.794 (s, 1H), 3.658-3.612 (m, 2H), 3.078-3.004 (m, 8H), 2.776-2.742 (m, 2H).

Example 99

6-(bis(4-chlorophenyl)methyl)-N-phenethylquinazolin-4-amine (Compound #12)

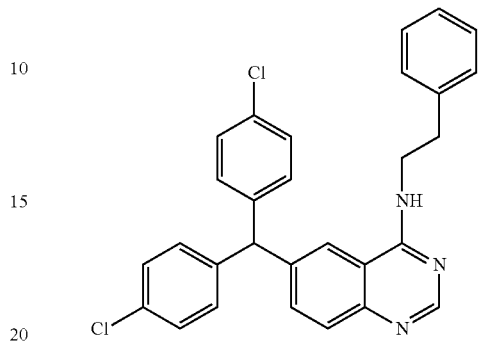

Into a 25-mL round-bottom flask, was placed 6-[bis(4-chlorophenyl)methyl]-4-chloroquinazoline (80 mg, 0.20 mmol, 1.00 equiv), 2-phenylethan-1-amine (32 mg, 0.26 mmol, 1.30 equiv), propan-2-ol (10 mL) and triethylamine (0.1 mL). The resulting solution was stirred overnight at 30° C. The resulting mixture was concentrated under vacuum. The resulting residue was applied onto a silica gel column with dichloromethane:methanol (20:1) to yield 6-[bis(4-chlorophenyl)methyl]-N-(2-phenylethyl)quinazolin-4-amine as a white solid. LC-MS (ES, m/z) 485 [M+H]⁺

¹H-NMR (300 MHz, DMSO, ppm) δ: 8.464 (s, 1H), 8.320 (m, 1H), 8.045 (s, 1H), 7.643 (d, J=8.4 Hz, 1H), 7.511 (dd, J=8.4 Hz, J=1.5 Hz, 1H), 7.408 (d, J=8.4 Hz, 4H), 7.306-7.225 (overlapping m, 5H), 7.181 (d, J=8.7 Hz, 4H), 5.771 (s, 1H), 3.739-3.671 (m, 2H), 2.954-2.904 (m, 2H).

Example 100

4-((4-((6-(bis(4-chlorophenyl)methyl)methyl)quinazolin-4-yl)amino)piperidin-1-yl)sulfonyl)phenol (Compound #8)

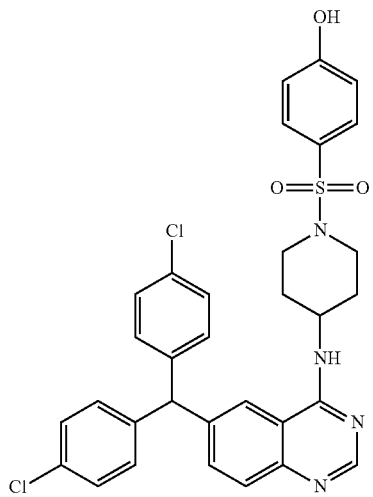 [SMILES: O=S(=O)(c1ccc(O)cc1)N1CCC(Nc2ncnc3ccc(C(c4ccc(Cl)cc4)c4ccc(Cl)cc4)cc23)CC1]

Into a 100-mL round-bottom flask, was placed 6-[bis(4-chlorophenyl)methyl]-N-(piperidin-4-yl)quinazolin-4- amine (300 mg, 0.65 mmol, 1.00 equiv), dichloromethane (50 mL), TEA (0.5 mL) and 4-hydroxybenzene-1-sulfonyl chloride (125 mg, 0.65 mmol, 1.00 equiv). The resulting solution was stirred for 2 h at 25° C. The resulting mixture was concentrated under vacuum. The resulting residue was applied onto a silica gel column with dichloromethane/methanol (20:1) to yield 4-[4-([6-[bis(4-chlorophenyl)methyl]quinazolin-4-yl]amino)piperidine-1-sulfonyl]phenol as a off-white solid. LC-MS (ES, m/z) 619 [M+H]$^+$ $^1$H-NMR (300 MHz, DMSO, ppm) δ 10.520 (s, 1H), 8.370 (s, 1H), 8.189 (s, 1H), 7.932 (d, J=7.2 Hz, 1H), 7.681-7.558 (m, 3H), 7.452-7.379 (overlapping m, 5H), 7.143 (d, J=8.4 Hz, 4H), 6.955 (d, J=8.7 Hz, 2H), 5.750 (s, 1H), 4.071 (br m, 1H), 3.654 (d, J=12.0 Hz, 2H), 2.361-2.261 (m, 2H), 2.065-1.972 (m, 2H), 1.682-1.575 (m, 2H).

Example 101

3-(2-((6-(bis(4-chlorophenyl)methyl)quinazolin-4-yl)amino)ethyl)benzoic acid (Compound #2)

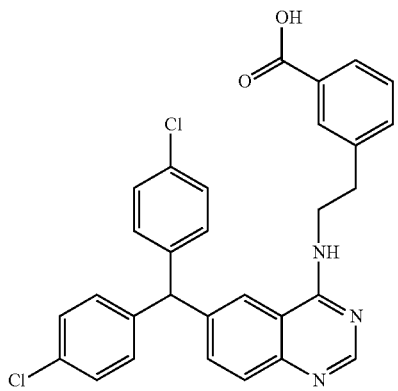 [SMILES: O=C(O)c1cccc(CCNc2ncnc3ccc(C(c4ccc(Cl)cc4)c4ccc(Cl)cc4)cc23)c1]

Step 1: Methyl 3-(2-(6-(bis(4-chlorophenyl)methyl)quinazolin-4-ylamino)ethyl)benzoate Into a 25-mL round-bottom flask, was placed 6-[bis(4-chlorophenyl)methyl]-4-chloroquinazoline (100 mg, 0.25 mmol, 1.00 equiv), methyl 3-(2-aminoethyl)benzoate hydrochloride (70 mg, 0.32 mmol, 1.30 equiv), propan-2-ol (10 mL) and TEA (0.2 mL). The resulting solution was stirred overnight at 30° C. The resulting mixture was concentrated under vacuum. The resulting residue was applied onto a silica gel column with dichloromethane/methanol (20:1) to yield methyl 3-[2-([6-[bis(4-chlorophenyl)methyl]quinazolin-4-yl]amino)ethyl]benzoate as a white solid. LC-MS (ES, m/z) 542 [M+H]$^+$ Step 2: 3-(2-(6-(Bis(4-chlorophenyl)methyl)quinazolin-4-ylamino)ethyl)benzoic acid Into a 100-mL round-bottom flask, was placed methyl 3-[2-([6-[bis(4-chlorophenyl)methyl]quinazolin-4-yl]amino)ethyl]benzoate (80 mg, 0.15 mmol, 1.00 equiv), methanol (20 mL) and 1M sodium hydroxide (20 mL). The resulting solution was stirred overnight at 50° C. The resulting mixture was concentrated under vacuum. The pH value of the solution was adjusted to pH 4-5 with 10% HCl. The resulting solids were collected by filtration to yield 3-[2-([6-[bis(4-chlorophenyl)methyl]quinazolin-4-yl]amino)ethyl]benzoic acid as a white solid. LC-MS (ES, m/z): 529 [M+H]$^+$ $^1$H-NMR (300 MHz, DMSO, ppm) δ 12.879 (s, 1H), 8.474 (s, 1H), 8.368 (s, 1H), 8.032 (s, 1H), 7.832-7.771 (m, 1H), 7.655-7.627 (m, 1H), 7.523-7.367 (m, 7H), 7.178-7.150 (m, 4H), 5.762 (s, 1H), 3.757-3.692 (m, 2H), 3.155-2.972 (m, 2H).

Example 102 tert-Butyl 4-((6-(bis(4-chlorophenyl)methyl)quinazolin-4-yl)amino)piperidine-1-carboxylate (Compound #1)

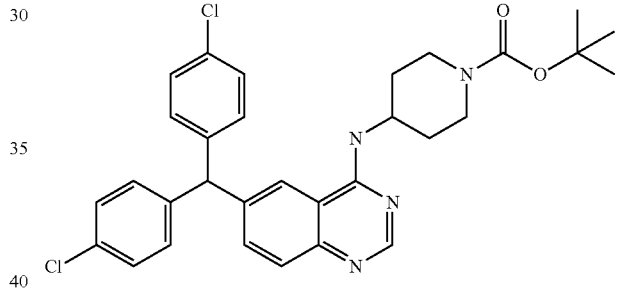

A solution of 6-(bis(4-chlorophenyl)methyl)-4-chloroquinazoline (800 mg, 2.00 mmol), tert-butyl 4-aminopiperidine-1-carboxylate (481 mg, 2.40 mmol) and triethyl amine (0.835 mL, 6.00 mmol) in isopropanol (16 mL) was heated to 80° C. for 6 hr. The resulting mixture was then cooled to room temperature and concentrated. To the resulting residue was then added CH$_2$Cl$_2$ and water. The aqueous layer was extracted with CH$_2$Cl$_2$. The combined organics were washed with water and brine and concentrated. The resulting residue was recrystallized from EtOAc/heptane to yield tert-butyl 4-((6-(bis(4-chlorophenyl)methyl)quinazolin-4-yl)amino)piperidine-1-carboxylate as a white solid LCMS (ES, m/z) 563.0, 565.0 [M+H]$^+$ Additional representative compound of formula (I) of the present invention were prepared according to the procedures as described in the Schemes and Examples above, selecting and substituting suitably substituted reactants, as would be readily recognized by those skilled in the art. Table 4, below lists the additional compounds prepared, along with structure, name and, where applicable, measured physical properties.

TABLE 4

Representative Compounds of Formula (I)

| ID No. | Structure and Name | Measured Analytical Data |
|---|---|---|
| 3 | 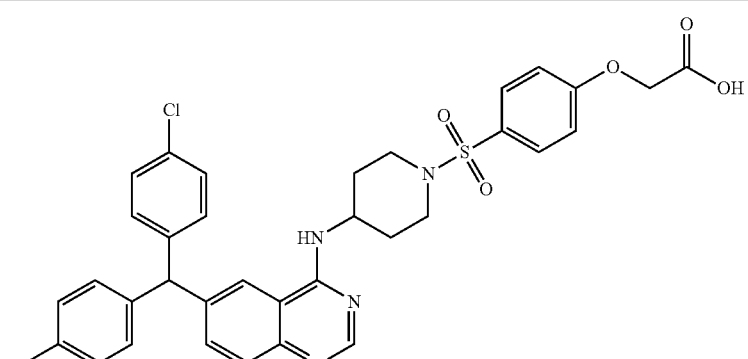<br>2-(4-((4-((6-(bis(4-chlorophenyl)methyl)quinazolin-4-yl)amino)piperidin-1-yl)sulfonyl)phenoxy)acetic acid | (ES, m/z) 677.1, 679.0 [M + H] + |
| 5 | 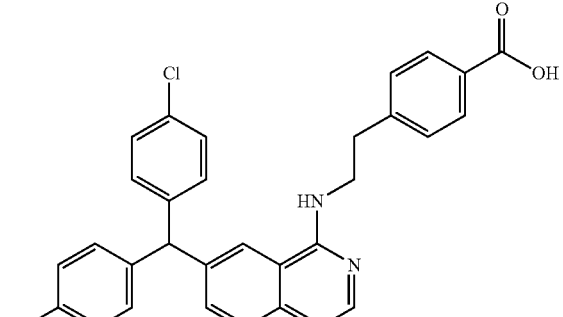<br>4-(2-(6-(bis(4-chlorophenyl)methyl)quinazolin-4-ylamino)ethyl)benzoic acid | LC-MS (ES, m/z): 529 [M + H] +.<br>$^1$H-NMR (300 MHz, DMSO + D2O, ppm) δ: 12.881 (brs, 1H), 10.174 (brs, 1H), 8.873 (s, 1H), 8.336 (s, 1H), 7.883-7.780 (m, 4H), 7.442-7.363 (m, 6H), 7.200-7.171 (m, 4H), 5.859 (s, 1H), 3.946-3.880 (m, 2H), 3.086-3.039 (m, 2H). |
| 13 | 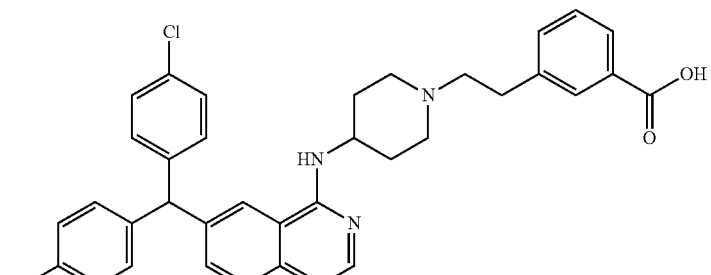<br>3-(2-(4-(6-(bis(4-chlorophenyl)methyl)quinazolin-4-ylamino)piperidin-1-yl)ethyl)benzoic acid | LC-MS (ES, m/z) 611 [M + H] +<br>$^1$H-NMR (300 MHz, DMSO + D2O, ppm) δ: 8.460 (s, 1H), 8.270 (s, 1H), 7.886-7.825 (m, 2H), 7.679-7.651 (m, 1H), 7.564-7.385 (m, 7H), 7.168-7.140 (m, 4H), 5.761 (s, 1H), 4.359 (brm, 1H), 3.508-3.435 (m, 2H), 3.221-3.069 (m, 6H), 2.154-2.119 (m, 2H), 1.917-1.811 (m, 2H). |

TABLE 4-continued

Representative Compounds of Formula (I)

| ID No. | Structure and Name | Measured Analytical Data |
|---|---|---|
| 17 | 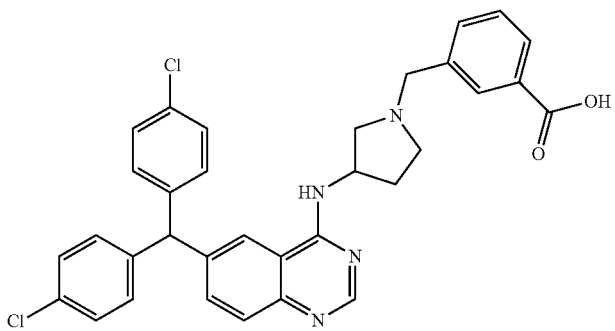 [SMILES: O=C(O)c1cccc(CN2CCC(Nc3ncnc4ccc(C(c5ccc(Cl)cc5)c5ccc(Cl)cc5)cc34)C2)c1]<br>3-((3-(6-(bis(4-chlorophenyl)methyl)quinazolin-4-ylamino)pyrrolidin-1-yl)methyl)benzoic acid | LC-MS (ES, m/z) 583 [M + H] +<br>$^1$H-NMR (300 MHz, CD3OD, ppm) δ 8.531 (s, 1H), 8.324 (s, 1H), 8.085-8.032 (m, 2H), 7.695-7.646 (m, 2H), 7.593-7.558 (m, 1H), 7.510-7.458 (m, 1H), 7.306-7.258 (m, 4H), 7.085 (d, J = 8.7 Hz, 2H), 7.022 (d, J = 8.4 Hz, 2H), 5.690 (s, 1H), 4.988-4.952 (m, 2H), 4.467-4.368 (m, 2H), 3.707-3.489 (m, 3H), 2.687-2.641 (m, 1H), 2.398-2.336 (m, 1H) |
| 21 | 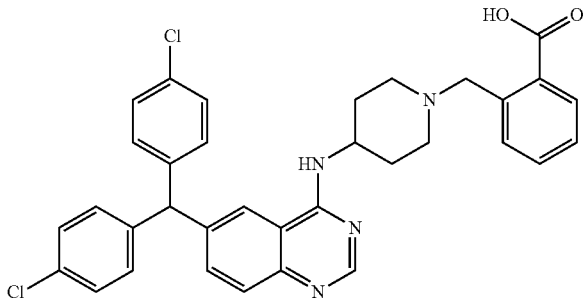 [SMILES: O=C(O)c1ccccc1CN1CCC(Nc2ncnc3ccc(C(c4ccc(Cl)cc4)c4ccc(Cl)cc4)cc23)CC1]<br>2-((4-(6-(bis(4-chlorophenyl)methyl)quinazolin-4-ylamino)piperidin-1-yl)methyl)benzoic acid | (ES, m/z) 597 [M + H] +<br>$^1$H NMR (300 MHz, DMSO, ppm) δ 8.450 (s, 1H), 8.208 (s, 1H), 8.015 (m, 1H), 7.884 (d, J = 8.6 Hz, 1H), 7.664-7.635 (m, 1H), 7.475-7.337 (m, 8H), 7.172-7.144 (m, 4H), 5.760 (s, 1H), 4.416 (br, 1H), 4.031 (m, 2H), 3.092-3.053 (m, 2H), 2.782-2.705 (m, 2H), 2.064-1.990 (m, 2H), 1.786-1.671 (m, 2H). |
| 27 | 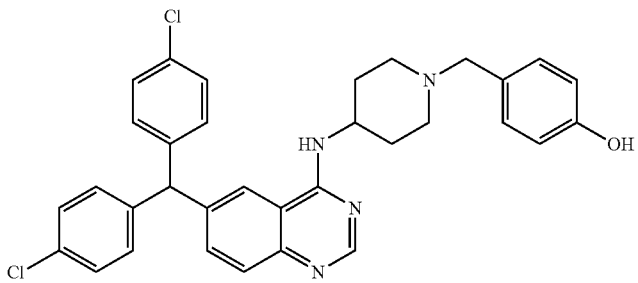 [SMILES: Oc1ccc(CN2CCC(Nc3ncnc4ccc(C(c5ccc(Cl)cc5)c5ccc(Cl)cc5)cc34)CC2)cc1]<br>4-((4-(6-(bis(4-chlorophenyl)methyl)quinazolin-4-ylamino)piperidin-1-yl)methyl)phenol | (ES, m/z): 569 [M + H] +<br>$^1$H NMR (300 MHz, DMSO, ppm) δ 9.251 (s, 1H), 8.421 (s, 1H), 8.233 (s, 1H), 7.962-7.872 (br m, 1H), 7.629 (d, J = 8.4 Hz, 1H), 7.458-7.388 (m, 5H), 7.242-7.070 (m, 6H), 6.942-6.697 (m, 2H), 5.756 (s, 1H), 4.292 (brm, 1H), 3.319 (s, 2H), 2.823-2.728 (m, 2H), 2.205-1.857 (m, 4H), 1.634-1.604 (m, 2H) |

TABLE 4-continued

Representative Compounds of Formula (I)

| ID No. | Structure and Name | Measured Analytical Data |
|---|---|---|
| 34 | 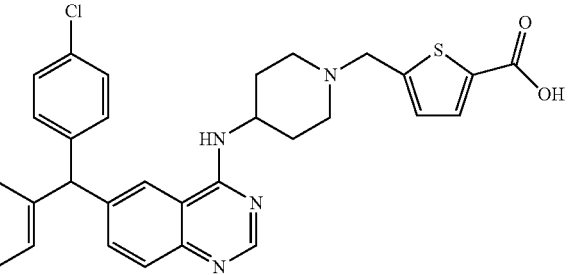<br>5-((4-(6-(bis(4-chlorophenyl)methyl)quinazolin-4-ylamino)piperidin-1-yl)methyl)thiophene-2-carboxylic acid | (ES, m/z) 603 [M + H] +<br>$^1$H NMR (300 MHz, DMSO, ppm) δ 12.993 (brs, 1H), 8.427 (s, 1H), 8.238 (s, 1H), 7.935 (d, J = 8.3 Hz, 1H), 7.646-7.594 (m, 2H), 7.582-7.394 (m, 5H), 7.182-7.125 (m, 4H), 7.033 (d, J = 3.6 Hz, 1H), 5.762 (s, 1H), 4.216 (brm, 1H), 3.747-3.666 (m, 2H), 2.960-2.925 (m, 2H), 2.153-2.075 (m, 2H), 1.927-1.817 (m, 2H), 1.724-1.651 (m, 2H) |
| 38 | 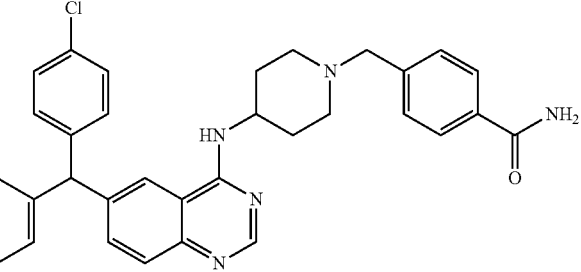<br>4-((4-(6-(bis(4-chlorophenyl)methyl)quinazolin-4-ylamino)piperidin-1-yl)methyl)benzamide | (ES, m/z): 596 [M + H] +<br>$^1$H NMR (300 MHz, DMSO, ppm) δ: 8.414 (s, 1H), 8.229 (s, 1H), 7.906-7.814 (m, 4H), 7.625 (d, J = 8.6 Hz, 1H), 7.454-7.299 (m, 8H), 7.172-7.144 (m, 4H), 5.715 (s, 1H), 4.187 br(m, 1H), 3.531 (s, 2H), 2.862-2.825 (m, 2H), 2.109-2.034 (m, 2H), 1.904-1.871 (m, 2H), 1.702-1.634 (m, 2H) |
| 42 | 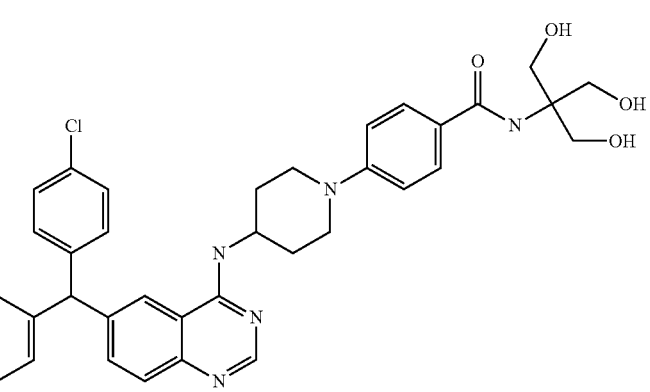<br>4-(4-((6-(bis(4-chlorophenyl)methyl)quinazolin-4-yl)amino)piperidin-1-yl)-N-(1,3-dihydro-2-(hydroxymethyl)propan-2-yl)benzamide | (ES, m/z) 686.1, 688.2 [M + H]$^+$<br>$^1$H NMR (CH$_3$OD) d: 8.43 (s, 1H), 8.09 (s, 1H), 7.67-7.75 (d, J = 9.1 Hz, 2H), 7.65 (d, J = 8.6 Hz, 1H), 7.52 (dd, J = 8.6, 2.0 Hz, 1H), 7.30 (d, J = 8.1 Hz, 4H), 7.10 (d, J = 8.1 Hz, 4H), 6.90-7.03 (m, J = 9.1 Hz, 2H), 5.73 (s, 1H), 4.32-4.56 (m, 1H), 3.95 (d, J = 13.1 Hz, 2H), 3.82 (s, 6H), 2.97 (t, J = 11.6 Hz, 2H), 2.09 (d, J = 10.1 Hz, 2H), 1.75 (qd, J = 12.1, 3.5 Hz, 2H). |

TABLE 4-continued

Representative Compounds of Formula (I)

| ID No. | Structure and Name | Measured Analytical Data |
|---|---|---|
| 44 | 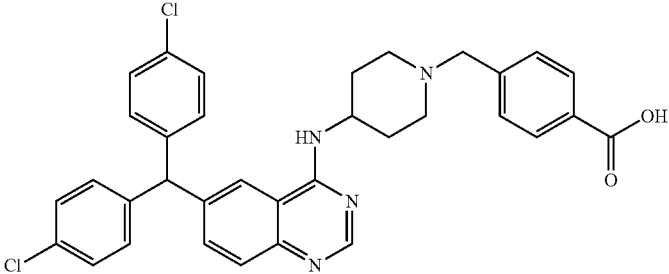 [SMILES: O=C(O)c1ccc(CN2CCC(Nc3ncnc4ccc(C(c5ccc(Cl)cc5)c5ccc(Cl)cc5)cc34)CC2)cc1]<br>4-((4-(6-(bis(4-chlorophenyl)methyl)quinazolin-4-ylamino)piperidin-1-yl)methyl)benzoic acid | (ES, m/z) 597 [M + H] +<br>$^1$H NMR (300 MHz, DMSO, ppm) δ 8.409 (s, 1H), 8.258 (s, 1H), 7.955 (d, J = 7.5 Hz, 1H), 7.866 (d, J = 7.8 hz, 2H), 7.628-7.599 (m, 1H), 7.451-7.315 (m, 7H), 7.172-7.143 (m, 4H), 5.765 (s, 1H), 4.191 (brm, 1H), 3.517 (s, 2H), 2.865-2.829 (m, 2H), 2.101-2.027 (m, 2H), 1.896-1.861 (m, 2H), 1.714-1.609 (m, 2H). |
| 56 | 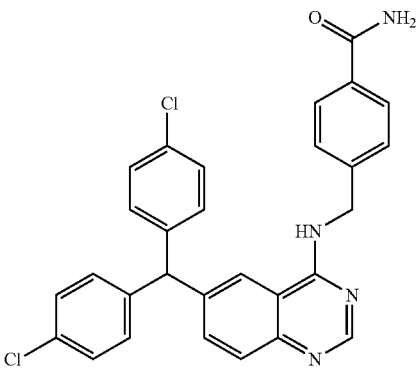 [SMILES: NC(=O)c1ccc(CNc2ncnc3ccc(C(c4ccc(Cl)cc4)c4ccc(Cl)cc4)cc23)cc1]<br>4-((6-(bis(4-chlorophenyl)methyl)quinazolin-4-ylamino)methyl)benzamide | (ES, m/z): 513 [M + H] + |
| 60 | 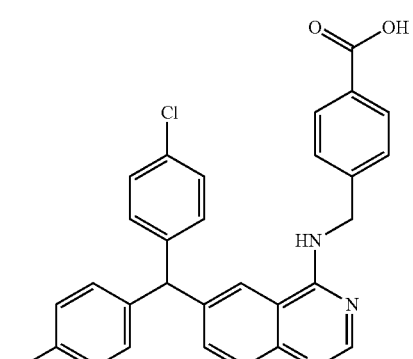<br>4-((6-(bis(4-chlorophenyl)methyl)quinazolin-4-ylamino)methyl)benzoic acid | (ES, m/z): 514 [M + H] + |

TABLE 4-continued

Representative Compounds of Formula (I)

| ID No. | Structure and Name | Measured Analytical Data |
|---|---|---|
| 61 | 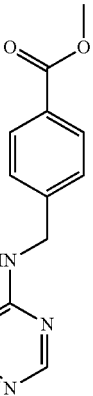<br>methyl 4-((6-(bis(4-chlorophenyl)methyl)quinazolin-4-ylamino)methyl)benzoate | (ES, m/z): 528 [M + H] + |
| 63 | 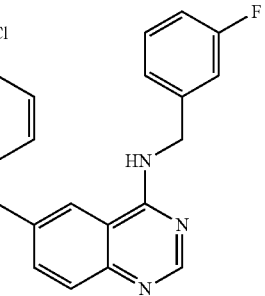<br>6-(bis(4-chlorophenyl)methyl)-N-(3-fluorobenzyl)quinazolin-4-amine | (ES, m/z): 488 [M + H] +<br>$^1$H NMR (300 MHz, DMSO, ppm) δ 8.816 (brs, 1H), 8.431 (s, 1H), 8.149 (s, 1H), 7.684-7.655 (m, 1H), 7.540-7.535 (m, 1H), 7.512-7.308 (m, 5H), 7.193-7.017 (m, 7H), 5.787 (s, 1H), 4.753 (d, J = 5.4 Hz, 2H). |
| 65 | 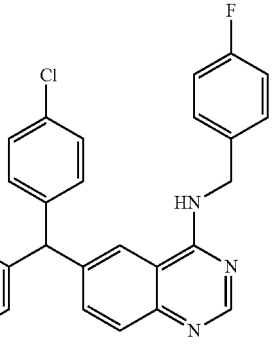<br>6-(bis(4-chlorophenyl)methyl)-N-(4-fluorobenzyl)quinazolin-4-amine | (ES, m/z): 588 [M + H] +<br>$^1$H NMR (300 MHz, DMSO, ppm) δ: 8.792 (t, J = 5.7 Hz, 1H), 8.429 (s, 1H), 8.143 (d, J = 1.5 Hz, 1H), 7.673-7.644 (m, 1H), 7.528-7.499 (m, 1H), 7.410-7.345 (m, 6H), 7.184-7.096 (m, 6H), 5.775 (s, 1H), 4.719 (d, J = 5.1 Hz, 2H). |

TABLE 4-continued

Representative Compounds of Formula (I)

| ID No. | Structure and Name | Measured Analytical Data |
|---|---|---|
| 82 | 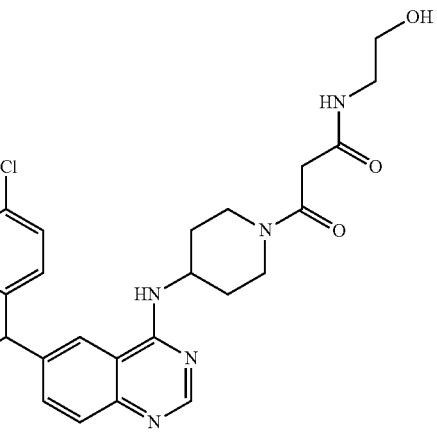<br>3-(4-(6-(bis(4-chlorophenyl)methyl)quinazolin-4-ylamino)piperidin-1-yl)-N-(2-hydroxyethyl)-3-oxopropanamide | (ES, m/z): 592. [M + H] +<br>$^1$H NMR (300 MHz, DMSO, ppm) δ: 8.461 (s, 1H), 8.249 (s, 1H), 8.050-7.978 (m, 2H), 7.650 (d, J = 8.7 Hz, 1H), 7.484-7.398 (m, 5H), 7.179-7.158 (m, 4H), 5.761 (s, 1H), 4.657 (t, J = 4.2 Hz, 1H), 4.444-4.413 (m, 2H), 3.962-3.913 (m, 1H), 3.435-3.095 (overlapping m, 7H), 2.736-2.2.672 (m, 1H), 1.951-1.921 (m, 2H), 1.676-1.625 (m, 1H), 1.447-1.396 (m, 1H). |
| 83 | 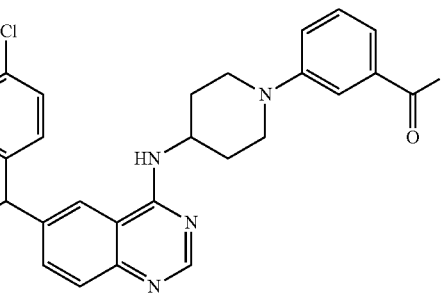<br>3-(4-(6-(bis(4-chlorophenyl)methyl)quinazolin-4-ylamino)piperidin-1-yl)-N-(2-hydroxyethyl)benzamide | (ES, m/z): 626. [M + H] +<br>$^1$H NMR (300 MHz, DMSO, ppm) δ: 8.466 (s, 1H), 8.371-8.343 (m, 1H), 8.239 (s, 1H), 7.959-7.940 (m, 1H), 7.660-7.638 (m, 1H), 7.475-7.391 (m, 6H), 7.302-7.227 (m, 2H), 7.172-7.103 (m, 5H), 5.750 (s, 1H), 4.712 (t, J = 4.2 Hz, 1H), 4.453-4.415 (m, 1H), 3.906-3.875 (m, 2H), 3.543-3.504 (m, 2H), 3.347-3.302 (m, 2H), 2.943-2.882 (m, 2H), 2.009-1.982 (m, 2H), 1.764-1.682 (m, 2H). |
| 87 | 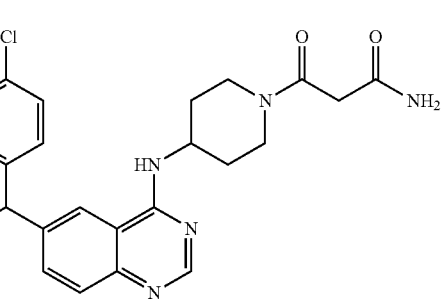<br>3-(4-(6-(bis(4-chlorophenyl)methyl)quinazolin-4-ylamino)piperidin-1-yl)-3-oxopropanamide | (ES, m/z): 548 [M + H] +<br>$^1$H NMR (400 MHz, DMSO, ppm) δ: 8.451 (s, 1H), 8.241 (s, 1H), 7.954 (d, J = 7.5 Hz, 1H), 7.646 (d, J = 8.6 Hz, 1H), 7.476-7.395 (m, 6H), 7.167 (d, J = 8.0 hz, 4H), 6.988 (s, 1H), 5.758 (s, 1H), 4.438 (dd, J = 11.7, 4.6 Hz, 2H), 3.942 (d, J = 13.32 Hz, 1H), 3.373-3.099 (overlapping m, 3H), 2.757-2.644 (m, 1H), 2.018-1.899 (m, 2H), 1.667-1.587 (m, 1H), 1.479-1.388 (m, 1H), |

TABLE 4-continued

Representative Compounds of Formula (I)

| ID No. | Structure and Name | Measured Analytical Data |
|---|---|---|
| 88 | 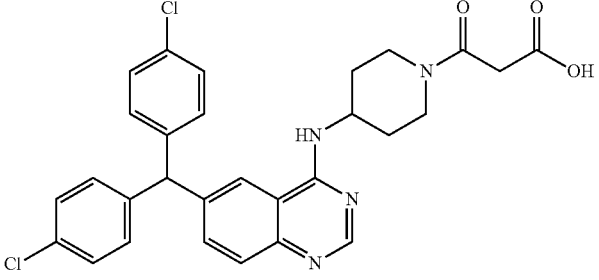 [SMILES: O=C(O)CC(=O)N1CCC(Nc2ncnc3ccc(C(c4ccc(Cl)cc4)c4ccc(Cl)cc4)cc23)CC1]<br>3-(4-(6-(bis(4-chlorophenyl)methyl)quinazolin-4-ylamino)piperidin-1-yl)-3-oxopropanoic acid | (ES, m/z): 549 [M + H] +<br>$^1$H NMR (300 MHz, DMSO, ppm) δ: 8.445 (s, 1H), 8.251 (s, 1H), 7.984-7.965 (m, 1H), 7.652-7.630 (m, 1H), 7.474-7.392 (m, 5H), 7.179-7.158 (m, 4H), 5.757 (s, 1H), 4.439-4.416 (m, 2H), 3.945-3.912 (m, 1H), 3.315-3.104 (m, 2H), 2.712-2.650 (m, 2H), 2.028-1.910 (m, 2H), 1.661-1.633 (m, 1H), 1.466-1.440 (m, 1H) |
| 89 | 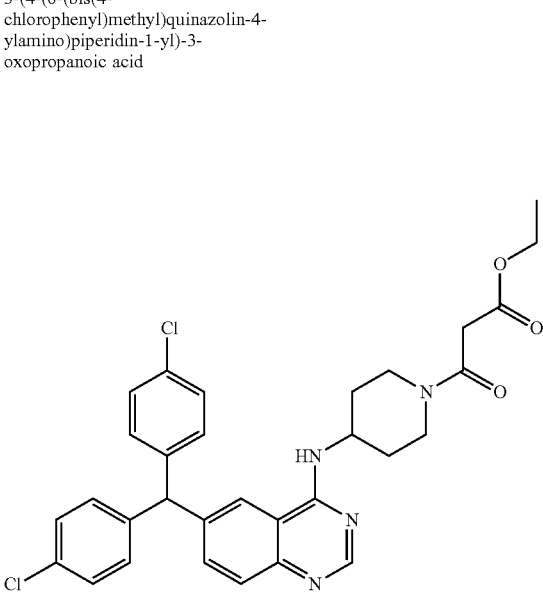<br>ethyl 3-(4-(6-(bis(4-chlorophenyl)methyl)quinazolin-4-ylamino)piperidin-1-yl)-3-oxopropanoate | (ES, m/z): 577 [M + H] +<br>$^1$H NMR (300 MHz, DMSO, ppm) δ: 8.456 (s, 1H), 8.233 (s, 1H), 7.994 (d, J = 7.2 Hz, 1H), 7.666-7.637 (m, 1H), 7.488-7.391 (m, 5H), 7.176-7.148 (m, 4H), 5.764 (s, 1H), 4.473-4.393 (m, 2H), 4.138-4.067 (m, 2H), 3.851-3.805 (m, 1H), 3.623-3.495 (m, 2H), 3.320-3.132 (m, 1H), 2.771-2.693 (m, 1H), 1.971-1.936 (m, 2H), 1.614-1.422 (m, 2H), 1.226-1.178 (m, 3H). |
| 95 | 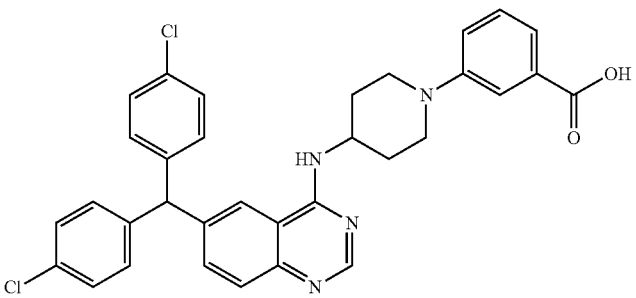 [SMILES: O=C(O)c1cccc(N2CCC(Nc3ncnc4ccc(C(c5ccc(Cl)cc5)c5ccc(Cl)cc5)cc34)CC2)c1]<br>3-(4-(6-(bis(4-chlorophenyl)methyl)quinazolin-4-ylamino)piperidin-1-yl)benzoic acid | (ES, m/z): 583 [M + H] +<br>$^1$H NMR (400 MHz, DMSO, ppm) δ: 9.860 (brs, 1H), 8.874 (s, 1H), 8.643 (s, 1H), 7.874 (d, J = 8.7 Hz, 1H), 7.756 (dd, J = 8.7, 1.8 Hz, 1H), 7.515 (d, J = 2.3 Hz, 1H), 7.432-7.410 (m, 4H), 7.358-7.324 (m, 2H), 7.222-7.168 (m, 5H), 5.832 (s, 1H), 4.645 (brm, m, 1H), 3.900 (d, J = 12.7 Hz, 2H), 2.942 (t, J = 12.3 Hz, 2H), 1.992-1.866 (m, 4H). |

TABLE 4-continued

Representative Compounds of Formula (I)

| ID No. | Structure and Name | Measured Analytical Data |
|---|---|---|
| 96 | 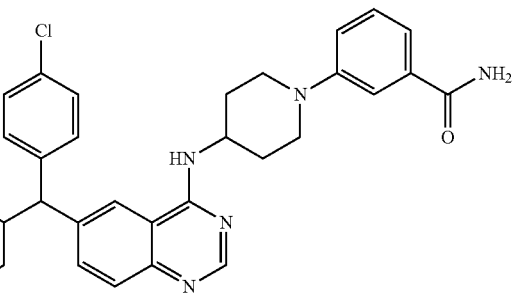<br>3-(4-(6-(bis(4-chlorophenyl)methyl)quinazolin-4-ylamino)piperidin-1-yl)benzamide | (ES, m/z): 582 [M + H] +<br>$^1$H NMR (400 MHz, DMSO, ppm) δ: 8.465 (s, 1H), 8.237 (s, 1H), 7.960-7.910 (m, 2H), 7.659-7.637 (m, 1H), 7.478-7.409 (m, 6H), 7.298-7.2520 (m, 3H), 7.173-7.123 (m, 5H), 5.750 (s, 1H), 4.44 (brm, 1H), 3.908-3.876 (m, 2H), 2.942-2.882 (m, 2H), 1.998-1.970 (m, 2H), 1.768-1.728 (m, 2H). |
| 97 | 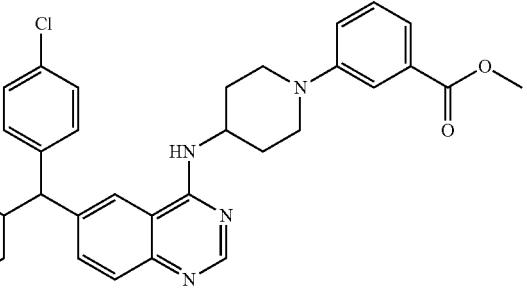<br>methyl 3-(4-(6-(bis(4-chlorophenyl)methyl)quinazolin-4-ylamino)piperidin-1-yl)benzoate | (ES, m/z): 597 [M + H] +<br>$^1$H NMR (300 MHz, DMSO, ppm) δ: 8.458 (s, 1H), 8.225 (s, 1H), 7.981-7.886 (m, 1H), 7.644 (d, J = 8.6 Hz, 1H), 7.526-7.227 (m, 9H), 7.155 (d, J = 8.4 Hz, 4H), 5.745 (s, 1H), 4.431 (brm, 1H), 3.838 (m, 5H), 2.937 (t, J = 12.3 Hz, 2H), 1.993 (d, J = 11.6 Hz, 2H), 1.800-1.654 (m, 2H). |
| 101 | 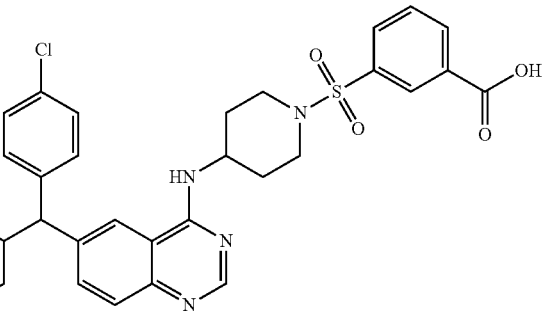<br>3-(4-(6-(bis(4-chlorophenyl)methyl)quinazolin-4-ylamino)piperidin-1-ylsulfonyl)benzoic acid | (ES, m/z): 647 [M + H] +<br>$^1$H NMR (400 MHz, DMSO, ppm) δ 8.369 (s, 1H), 8.281-8.153 (m, 3H), 8.005-7.985 (m, 2H), 7.793 (t, J = 7.8 Hz, 1H), 7.616 (d, J = 8.5 Hz, 1H), 7.474-7.340 (m, 5H), 7.169-7.090 (m, 4H), 5.741 (s, 1H), 4.125 (brm, 1H), 3.723 (d, J = 11.5 Hz, 2H), 2.482-2.427 (m, 2H), 1.997 (d, J = 11.8 Hz, 2H), 1.637 (m, 2H), 1 |

TABLE 4-continued

Representative Compounds of Formula (I)

| ID No. | Structure and Name | Measured Analytical Data |
|---|---|---|
| 109 | 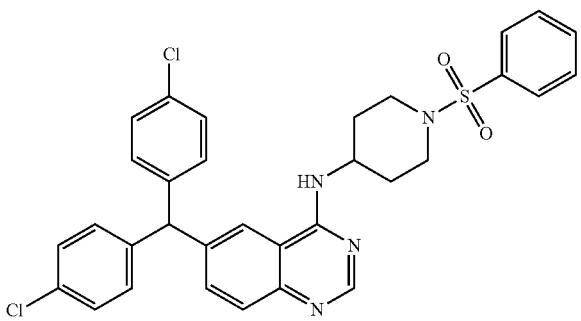 [SMILES: O=S(=O)(c1ccccc1)N1CCC(Nc2ncnc3ccc(C(c4ccc(Cl)cc4)c4ccc(Cl)cc4)cc23)CC1]<br>6-(bis(4-chlorophenyl)methyl)-N-(1-(phenylsulfonyl)piperidin-4-yl)quinazolin-4-amine | (ES, m/z): 603 [M + H] +<br>$^1$H NMR (400 MHz, DMSO, ppm) δ: 8.388 (s, 1H), 8.202 (s, 1H), 7.955 (d, J = 6.8 Hz, 1H), 7.785-7.626 (m, 6H), 7.463-7.397 (m, 5H), 7.168-7.147 (m, 4H), 5.764 (s, 1H), 4.127 (brm, 1H), 3.724-3.712 (m, 2H), 2.445-2.388 (m, 2H), 2.024-1.996 (m, 2H), 1.699-1.617 (m, 2H). |
| 111 | 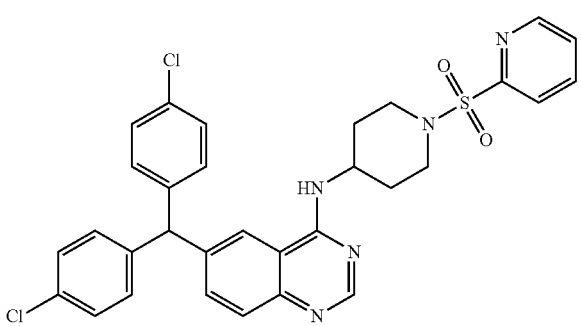 [SMILES: O=S(=O)(c1ccccn1)N1CCC(Nc2ncnc3ccc(C(c4ccc(Cl)cc4)c4ccc(Cl)cc4)cc23)CC1]<br>6-(bis(4-chlorophenyl)methyl)-N-(1-(pyridin-2-ylsulfonyl)piperidin-4-yl)quinazolin-4-amine | (ES, m/z): 604 [M + H] +<br>$^1$H NMR (300 MHz, DMSO, ppm) δ: 8.790 (d, J = 3.9 Hz, 1H), 8.411 (s, 1H), 8.212 9s, 1H), 8.160-8.102 (m, 1H), 7.954-7.928 (m, 2H), 7.750-7.725 (m, 2H), 7.470-7.420 (m, 5H), 7.172-7.144 (m, 4H), 5.765 (s, 1H), 4.423 (brm, 1H), 3.846-3.804 (m, 2H), 2.880-2.803 (m, 2H), 2.021-1.987 (m, 2H), 1.696-1.644 (m, 2H). |
| 115 | 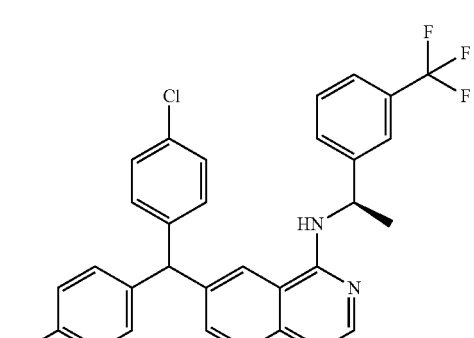<br>(R)-6-(bis(4-chlorophenyl)methyl)-N-(1-(3-(trifluoromethyl)phenyl)ethyl)quinazolin-4-amine | (ES, m/z): 552 [M + H] +<br>$^1$H NMR (300 MHz, DMSO, ppm) δ 8.535 (d, J = 7.8 Hz, 1H), 8.402-8.384 (m, 2H), 7.744-7.506 (m, 7H), 7.483-7.406 (m, 4H), 7.208-7.180 (m, 4H), 5.812 (s, 1H), 5.660-5.636 (m, 1H), 1.595 (d, J = 6.9 Hz, 3H) |

TABLE 4-continued

Representative Compounds of Formula (I)

| ID No. | Structure and Name | Measured Analytical Data |
|---|---|---|
| 116 | 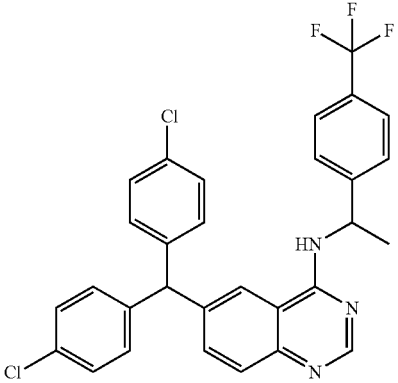 [SMILES: CC(Nc1ncnc2ccc(C(c3ccc(Cl)cc3)c3ccc(Cl)cc3)cc12)c1ccc(C(F)(F)F)cc1]<br>6-(bis(4-chlorophenyl)methyl)-N-(1-(4-(trifluoromethyl)phenyl)ethyl)quinazolin-4-amine | (ES, m/z) 552 [M + H] +<br>$^1$H NMR (400 MHz, DMSO, ppm) δ 8.536 (d, J = 7.2 Hz, 1H), 8.416 (s, 1H), 8.384 (s, 1H), 7.694-7.620 (m, 5H), 7.499-7.416 (m, 5H), 7.204-7.183 (m, 4H), 5.808 (s, 1H), 5.633-5.597 (m, 1H), 1.604 (d, J = 7.2 Hz, 3H). |
| 119 | 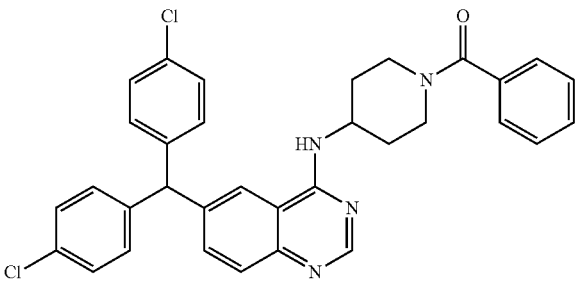 [SMILES: O=C(c1ccccc1)N1CCC(Nc2ncnc3ccc(C(c4ccc(Cl)cc4)c4ccc(Cl)cc4)cc23)CC1]<br>(4-(6-(bis(4-chlorophenyl)methyl)quinazolin-4-ylamino)piperidin-1-yl)(phenyl)methanone | (ES, m/z): 567 [M + H] +<br>$^1$H NMR (300 MHz, DMSO, ppm) δ 8.456 (s, 1H), 8.220 (s, 1H), 7.977 (d, J = 7.5 Hz, 1H), 7.652 (d, J = 8.7 Hz, 1H), 7.477-7.395 (m, 10H), 7.166 (d, J = 8.4 Hz, 4H), 5.768 (s, 1H), 4.516 (brm, 2H), 3.615 (brm, 1H), 3.2123 (brm, 1H), 2.970 (brm, 1H), 1.989-1.924 (m, 2H), 1.555 (brm, 2H). |
| 121 | 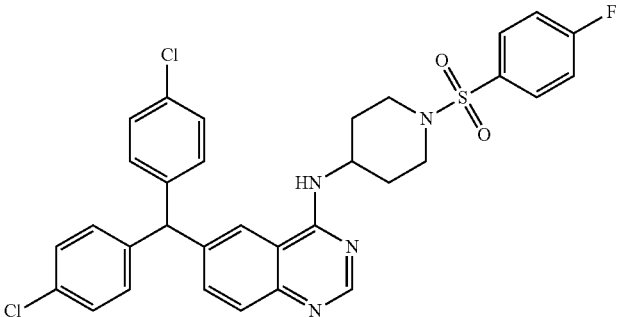 [SMILES: O=S(=O)(c1ccc(F)cc1)N1CCC(Nc2ncnc3ccc(C(c4ccc(Cl)cc4)c4ccc(Cl)cc4)cc23)CC1]<br>6-(bis(4-chlorophenyl)methyl)-N-(1-(4-fluorophenylsulfonyl)piperidin-4-yl)quinazolin-4-amine | (ES, m/z): 621 [M + H] +<br>$^1$H NMR (300 MHz, DMSO, ppm) δ 8.395 (s, 1H), 8.208 (s, 1H), 7.960 (d, J = 7.2 Hz, 1H), 7.872-7.865 (m, 2H), 7.7.642 9d, J = 8.7 Hz, 1H), 7.541-7.401 (m, 7H), 7.174-7.145 (m, 4H), 5.767 (s, 1H), 4.155-4.119 (m, 1H), 3.745-3.705 (m, 2H), 2.448-2.408 (m, 2H), 2.031-1.995 9m, (H) 1.723-1.630 (m, 2H). |

TABLE 4-continued

Representative Compounds of Formula (I)

| ID No. | Structure and Name | Measured Analytical Data |
|---|---|---|
| 124 | 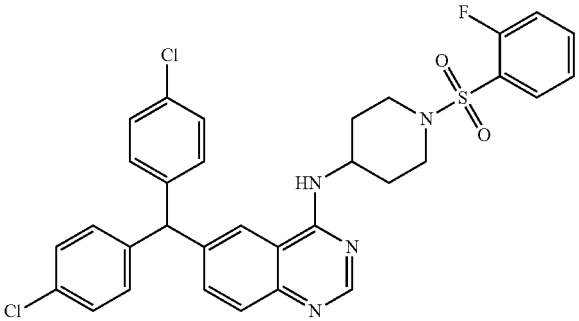 [SMILES: O=S(=O)(c1ccccc1F)N1CCC(Nc2ncnc3ccc(C(c4ccc(Cl)cc4)c4ccc(Cl)cc4)cc23)CC1]<br>6-(bis(4-chlorophenyl)methyl)-N-(1-(2-fluorophenylsulfonyl)piperidin-4-yl)quinazolin-4-amine | (ES, m/z): 621 [M + H] +<br>$^1$H NMR (300 MHz, DMSO, ppm) δ 8.415 (s, 1H), 8.216 (s, 1H), 7.993-7.963 (m, 1H), 7.845-7.746 (m, 2H), 7.650 (d, J = 8.7 Hz, 1H), 7.551-7.401 (m, 7H), 7.175-7.147 (m, 4H), 5.767 (s, 1H), 4.272 (brm, 1H), 3.797-3.756 (m, 2H), 2.797-2.750 (m, 2H), 2.508-2.496 (m, 2H), 1.692-1.652 (m, 2H). |
| 125 | 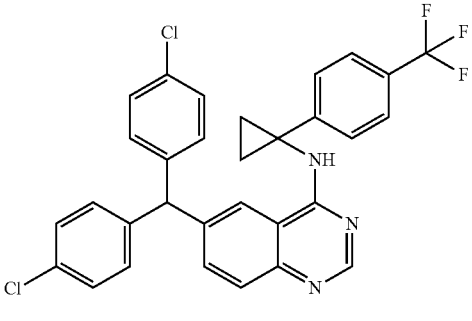 [SMILES: FC(F)(F)c1ccc(C2(Nc3ncnc4ccc(C(c5ccc(Cl)cc5)c5ccc(Cl)cc5)cc34)CC2)cc1]<br>6-(bis(4-chlorophenyl)methyl)-N-(1-(4-(trifluoromethyl)phenyl)cyclopropyl)quinazolin-4-amine | (ES, m/z): 564 [M + H] +<br>$^1$H NMR (300 MHz, DMSO, ppm) δ 9.051 (s, 1H), 8.385 (s, 1H), 8.312 (s, 1H), 7.682 (d, J = 8.4 Hz, 1H), 7.598-7.514 (m, 3H), 7.435-7.407 (m, 4H), 7.349-7.322 (m, 2H), 7.217-7.189 (m, 4H), 5.793 (s, 1H), 1.481-1.419 (m, 4H). |
| 126 | 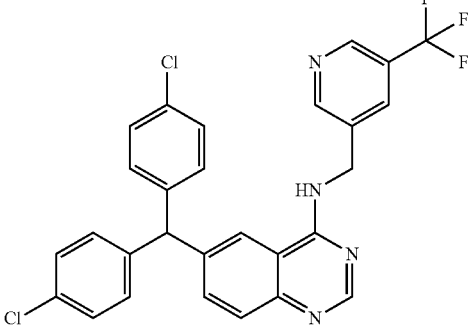<br>6-(bis(4-chlorophenyl)methyl)-N-((5-(trifluoromethyl)pyridin-3-yl)methyl)quinazolin-4-amine | (ES, m/z) 539 [M + H] +<br>$^1$H NMR (300 MHz, DMSO) δ 8.98-8.92 (m, 3H), 8.46 (s, 1H), 8.16-8.12 (m, 2H), 7.71-7.68 (m, 1H), 7.56-7.53 (m, 1H), 7.41 (d, J = 8.4 Hz, 4H), 7.19 (d, J = 8.4 Hz, 4H), 5.81 (s, 1H), 4.87-4.85 (m, 2H) |

TABLE 4-continued

Representative Compounds of Formula (I)

| ID No. | Structure and Name | Measured Analytical Data |
|---|---|---|
| 127 | 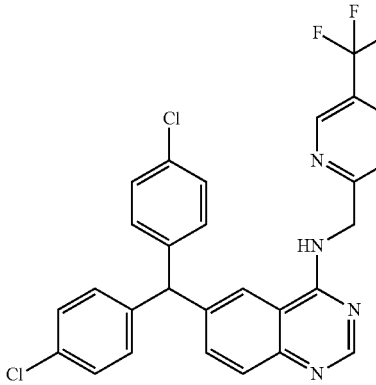<br>6-(bis(4-chlorophenyl)methyl)-N-((5-(trifluoromethyl)pyridin-2-yl)methyl)quinazolin-4-amine | 0 (ES, m/z) 539 [M + H] +<br>$^1$H NMR (300 MHz, DMSO) δ 8.98-8.92 (m, 2H), 8.41 (s, 1H), 8.20-8.13 (m, 2H), 7.73-7.70 (m, 1H), 7.60-7.54 (m, 2H), 7.44 (d, J = 8.4 Hz, 4H), 7.23 (d, J = 8.4 Hz, 4H), 5.84 (s, 1H), 4.93-4.91 (m, 2H) |
| 128 | 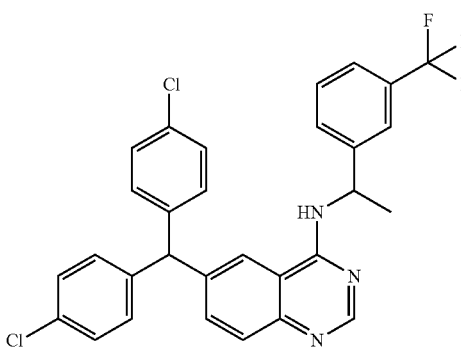<br>6-(bis(4-chlorophenyl)methyl)-N-(1-(3-(trifluoromethyl)phenyl)ethyl)quinazolin-4-amine | (ES, m/z) 552 [M + H] +<br>$^1$H NMR (300 MHz, DMSO) δ 8.54 (d, J = 7.8 Hz, 1H), 8.43-8.41 (m, 2H), 7.80-7.68 (m, 3H), 7.60-7.43 (m, 7H), 7.23-7.20 (m, 4H), 5.84 (s, 1H), 5.77-5.66 (m, 1H), 1.63 (d, J = 7.2 Hz, 3H) |
| 129 | 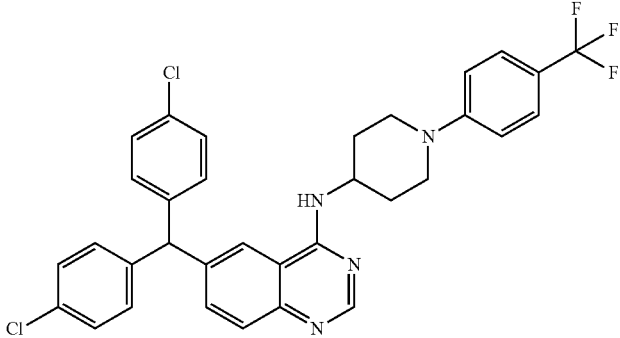 [SMILES: FC(F)(F)c1ccc(N2CCC(Nc3ncnc4ccc(C(c5ccc(Cl)cc5)c5ccc(Cl)cc5)cc34)CC2)cc1]<br>6-(bis(4-chlorophenyl)methyl)-N-(1-(4-(trifluoromethyl)phenyl)piperidin-4-yl)quinazolin-4-amine | (ES, m/z) 607 [M + H] +<br>$^1$H NMR (300 MHz, DMSO) δ 8.460 (s, 1H), 8.198-8.193 (m, 1H), 7.935-7.910 (m, 1H), 7.659-7.630 (m, 1H), 7.515-7.379 (m, 7H), 7.162-7.087 (m, 6H), 5.736 (s, 1H), 4.525-4.474 (m, 1H), 4.015-3.972 (m, 2H), 3.066-2.985 (m, 2H), 1.977-1.944 (m, 2H), 1.707-1.598 (m, 2H) |

TABLE 4-continued

Representative Compounds of Formula (I)

| ID No. | Structure and Name | Measured Analytical Data |
|---|---|---|
| 131 | 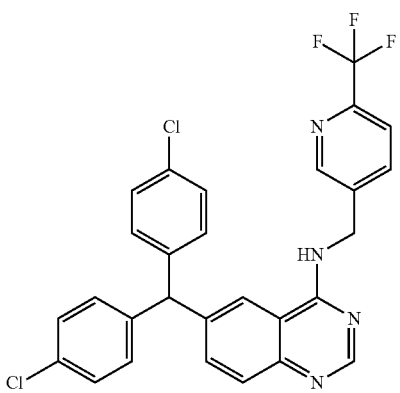 [SMILES: FC(F)(F)c1ccc(CNc2ncnc3ccc(C(c4ccc(Cl)cc4)c4ccc(Cl)cc4)cc23)cn1]<br>6-(bis(4-chlorophenyl)methyl)-N-((6-(trifluoromethyl)pyridin-3-yl)methyl)quinazolin-4-amine | (ES, m/z) 538 [M + H] +<br>$^1$H NMR (300 MHz, DMSO) δ 8.935 (brm, 1H), 8.808 (s, 1H), 8.473 (s, 1H), 8.159 (s, 1H), 8.041-8.015 (m, 1H), 7.883-7.856 (m, 1H), 7.734-7.705 (m, 1H), 7.588-7.560 (m, 1H), 7.452-7.425 (m, 4H), 7.227-7.200 (m, 4H), 5.834 (s, 1H), 4.871 (brm, 2H) |
| 135 | 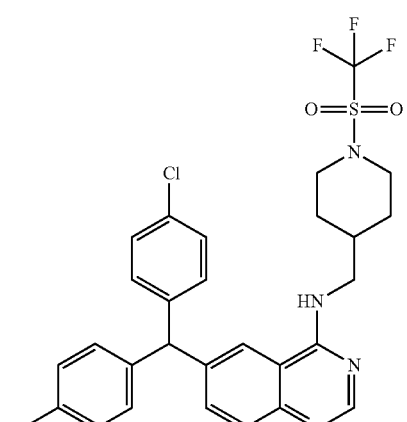<br>6-(bis(4-chlorophenyl)methyl)-N-((1-(trifluoromethylsulfonyl)piperidin-4-yl)methyl)quinazolin-4-amine | (ES, m/z) 609 [M + H] +<br>$^1$H NMR (300 MHz, DMSO) δ 8.441 (s, 1H), 8.358 (brm, 1H), 8.145 (s, 1H), 7.657-7.636 (m, 1H), 7.495-7.402 (m, 5H), 7.186-7.165 (m, 4H), 5.775 (s, 1H), 3.822-3.790 (m, 2H), 3.455-3.426 (m, 2H), 3.194-3.138 (m, 2H), 1.994 (brm, 1H), 1.856-1.825 (m, 2H), 1.336-1.196 (m, 2H) |
| 138 | 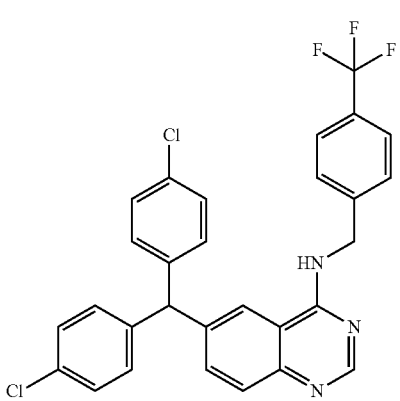 [SMILES: FC(F)(F)c1ccc(CNc2ncnc3ccc(C(c4ccc(Cl)cc4)c4ccc(Cl)cc4)cc23)cc1]<br>6-(bis(4-chlorophenyl)methyl)-N-(4-(trifluoromethyl)benzyl)quinazolin-4-amine | (ES, m/z) 538 [M + H] +<br>$^1$H NMR (300 MHz, DMSO) δ 8.883 (brm, 1H), 8.422 (s, 1H), 8.165 (s, 1H), 7.695-7.669 (m, 3H), 7.554-7.533 (m, 3H), 7.427-7.406 (m, 4H), 7.204-7.183 (m, 4H), 5.806 (s, 1H), 4.834-4.821 (m, 2H) |

TABLE 4-continued

Representative Compounds of Formula (I)

| ID No. | Structure and Name | Measured Analytical Data |
|---|---|---|
| 140 | 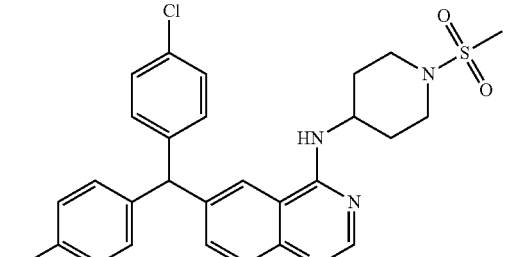<br>6-(bis(4-chlorophenyl)methyl)-N-(1-(methylsulfonyl) piperidin-4-yl) quinazolin-4-amine | (ES, m/z) 541 [M + H] +<br>$^1$H NMR (300 MHz, DMSO) δ 8.464 (s, 1H), 8.239 (s, 1H), 8.041-8.024 (m, 1H), 7.767-7.650 (m, 1H), 7.478-7.402 (m, 5H), 7.178-7.157 (m, 4H), 5.782 (s, 1H), 4.327-4.310 (m, 1H), 3.649-3.620 (m, 2H), 2.904-2.859 (m, 5H), 2.053-2.024 (m, 2H), 1.703-1.621 (m, 2H) |
| 141 | 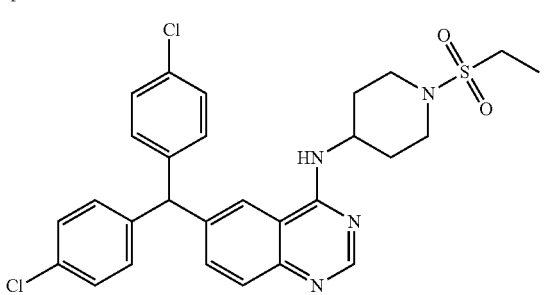<br>6-(bis(4-chlorophenyl)methyl)-N-(1-(ethylsulfonyl) piperidin-4-yl) quinazolin-4-amine | (ES, m/z) 555 [M + H] +;<br>$^1$H NMR (300 MHz, DMSO) δ 8.468 (s, 1H), 8.248 (s, 1H), 8.021-7.996 (m, 1H), 7.686-7.658 (m, 1H), 7.492-7.415 (m, 5H), 7.197-7.169 (m, 4H), 5.792 (s, 1H), 4.349 (brm, 1H), 3.713-3.673 (m, 2H), 3.134-2.953 (m, 4H), 2.041-2.002 (m, 2H), 1.698-1.619 (m, 2H), 1.272-1.223 (m, 3H) |

BIOLOGICAL ASSAYS $CB_1$ and $CB_2$ receptors are Gi-coupled GPCR. Activation of $CB_1$ and $CB_2$ receptors results in a decrease in cAMP production. An inverse agonist of the $CB_1$ or $CB_2$ receptor results in the opposite effect, an increase of cAMP production. The principle of this assay is based on HTRF® technology (Homogeneous Time-Resolved Fluorescence). The method is a competitive immunoassay between native cAMP produced by cells and the cAMP labeled with the fluorophore d2. The tracer binding is quantified by a Mab anti-cAMP labeled with Eu3+TBP-NHS Cryptate (supplied as part of the assay kit). The specific signal (i.e. energy transfer) is inversely proportional to the concentration of cAMP in the standard or sample.

Biological Example 1

CB-1 and CB-2 In Vitro Assay

Preparation of Cells

Human $CB_1R$ (Cannabanoid receptor 1) was stably transfected in HEK-293 cells (DiscoveRx, cat: 93-0200C1). Human $CB_2R$ (Cannabanoid receptor 2) was stably transfected in HEK-293 cells (DiscoveRx, cat: 93-0201C1). Cell cultures were maintained in media: DMEM (Invitrogen Cat#12430-054) supplemented with 10% HI FBS (Invitrogen Cat#16140-071), 1% L-glutamine (Invitrogen Cat#25030-081), 0.2 mg/ml Hygromycin B (Invitrogen Cat#10687-010), 600 μg/mL G418 (Invitrogen Cat#10131-035), and 1× Penn/Strep (Invitrogen 15140-122). After cell expansion, aliquots were cryo-stored in media containing 5% DMSO (Pierce Cat#20684).

Plating Cells from Cryostore

One day prior to experiments media was warmed to 37° C. and the cryo-stored cells were thawed in a 37° C. water bath. The cells were then added to media (10× volume) and the mixture was centrifugated at 1000 RPM for 5 min. The supernate was removed and the cells were re-suspended in media. A sample of the cell suspension was evaluated on a Cedex XS automated cell counter (Innovatis Systems) to determine viable cells/ml. Additional media was added to the cells to achieve a final cell density of 4E5 cells/mL. The cells were then plated into 384 well PDL white solid bottom plates (Greiner, Cat#781945) at 20 μL per well using a Multidrop (Thermo Scientific). Cells were removed from Row P (location of cAMP standards). Two columns of cells were plated into a clear bottom 384 well PDL coated plate (Greiner, Cat#781944) to view confluence the day of the assay. The cell plates were lidded and stored for 15 minutes in a hood, then transferred to an incubator (37° C., 5% $CO_2$, 95% humidity) overnight.

Preparation of Compound Plates

DMSO was added to all wells of 384 well V bottom polystyrene plate (Greiner, Cat#781280) except to columns 1 and 13, rows O and P and wells M13-M23 and N13-N23. Test compounds (60 μL, 10 mM) were added to Column 1 and 13 (A1 through N1 and A13 through L13). Test compounds were serially diluted 1/3 by transferring and mixing 20 μl sample with 40 μL DMSO. This process resulted in a plate of 26 compounds, 11 doses per compound, 10 mM to 0.5 μM.

Preparation of Control Plate

DMSO (40 µL) was added to wells of 384 well V bottom polystyrene plate: O2 through O11, M14 through M23, N14 through N23, and O14 through O23. AM630 (also known as [6-iodo-2-methyl-1-[2-(4-morpholinyl)ethyl]-1H-indol-3-yl](4-methoxyphenyl)-methanone, Cayman Chemical, Cat#10006974) (60 µL, 10 mM) was added to O1; and 1-(2,4-dichlorophenyl)-7-[(4-fluorophenyl)methylene]-4,5,6,7-tetrahydro-N-1-piperidinyl-1H-indazole-3-carboxamide (60 µL, 10 mM) was added to N13. The control was serially diluted 1/3 by transferring and mixing 20 µl sample with 40 µL DMSO. This process resulted 11 doses per control, 10 mM to 0.5 µM.

cAMP Assay Protocol

Cells plated the day prior to the assay in clear bottom plates were viewed on an inverse microscope to ensure confluency in the range of 60-75%.

The following mixtures and buffer solutions were prepared: (a) Buffer 1: HBSS (Mediatech Cat#21-023-CV) with 5 mM HEPES (1 mM stock, Gibco BRL Cat#15630-056) and 0.1% BSA (7.5% stock, Invitrogen Cat#15260-037); (b) Buffer 2: 0.5 mM IBMX (200 mM stock in DMSO, Sigma 15879) in Buffer 1; (c) 1 µM cAMP Standard (50 µM stock, Perkin Elmer Cat#AD0262) diluted in Buffer 2 and serially diluted in Buffer 2, 12 doses @1/2 dilutions resulting in a dose range of 1 µM to 0.5 nM; (d) d2 labelled cAMP (CisBio HTRF Detection Kit Cat #62AM4PEB reconstituted with 6 ml dH$_2$O) diluted 1/20 with lysis buffer (CisBio HTRF Detection Kit Cat #62AM4PEB); (e) anti-cAMP (CisBio HTRF Detection Kit Cat #62AM4PEB reconstituted with 5 ml dH$_2$O) diluted 1/20 with lysis buffer (CisBio HTRF Detection Kit Cat #62AM4PEB); and (f) Forskolin (Sigma Cat#F6886, 10 mM in DMSO) diluted first in DMSO to 1 mM and then to 1.5 µM in Buffer 2.

A FLEXDROP (Perkin Elmer) was cleaned with ethanol then water, and primed with Buffer 2. A 384 well V bottom polypropylene plate containing d2 labelled cAMP and a second 384 well V bottom polypropylene plate containing anti-cAMP was prepared (50 µl per well). Media as "dumped" from the cell plate and 30 µL Buffer 1 was added to each well using a Multidrop. The content of the cell plate was again "dumped" and 10 µL Buffer 2 was added to each well using a Flexdrop. 12.5 nL test compound dilutions or control compound dilutions (10 mM to 0.5 µM) were added to the cell plate using an ECHO 555 (Labcyte). The cell plate was mixed (Speed 6, Lab-Line Instruments Titer Plate Shaker) and centrifugated (1000 RPMs, 1 min). Using the Flexdrop, 2 µl additions were made into the cell plate: Buffer 2 was added to Column 24; and, 1.5 µM Forskolin was added to columns 1 through 23. Final volume of the cell plate was 12 µl with 250 nM Forskolin in all wells except column 12, and serial dilutions of test compound or control ranging from 10 µM to 0.5 nM. The cell plate was again mixed (speed 6) and centrifugated (1000 RPMs, 1 min). The cell plate was incubated for 30 minutes at room temperature (~27° C.). The contents of row P were removed and the cAMP standard dilutions were added in duplicate to Row P (P1-12 and P13-24). After incubation, 6 µL d2 labelled cAMP and 6 µL of Anti-cAMP were added to all wells of the cell plate using a BioMek FX (Beckman Coulter). The cell plate was again mixed (speed 6) and centrifugated (1000 RPMs, 1 min) and was incubated for 60 minutes in the dark at room Temp (~27° C.).

After this final incubation, the cell plate was read in HTRF mode (fluorescence at 665 nm and 620 nm) on an Envision plate Reader (Perkin Elmer). The Envision reader outputs a ratio of channel 1/channel 2 fluorescence×10,000 (Normalized signal (NS)). Amount of cAMP in nM was calculated for each well (based on NS) from a cAMP standard curve located on each plate (at P1-12 and P13-24). $EC_{50}$ values were determined from a 4-point fit (Hill equation) of a single 11-point compound dosing. Hill slope was fixed at 1.0. The bottom of the dose response curve was fixed because it was always the same as that of the control wells containing vehicle (DMSO) instead of compound. The top of the dose response curve was floated unless a plateau was not reached.

Representative compounds of formula (I) of the present invention were tested for activity against the CB-1 and CB-2 receptors, according to assay protocol as outlined in Biological Example 1, with $EC_{50}$ results (in micromolar) as listed in Tables 5, below. Where a compound was tested more than once, the result presented below represents a mean of the individual measurements.

TABLE 5

CB-1 & CB-2 Biological Activity

| ID No | CB-1 $EC_{50}$ (µM) | CB-2 $EC_{50}$ (µM) |
|---|---|---|
| 2 | 0.325 | 1.055 |
| 3 | 0.098 | 3.432 |
| 4 | 0.009 | 0.170 |
| 5 | 3.199 | 0.265 |
| 6 | 0.035 | 0.455 |
| 7 | 0.072 | >42 |
| 8 | 0.008 | 0.248 |
| 9 | 0.191 | 0.150 |
| 10 | 0.894 | 0.998 |
| 11 | 0.124 | >10 |
| 12 | 0.012 | 0.808 |
| 13 | 1.241 | 3.049 |
| 14 | 1.124 | 8.700 |
| 15 | 0.029 | 0.268 |
| 16 | 0.343 | >10 |
| 17 | 4.000 | 7.635 |
| 18 | 0.165 | 6.260 |
| 19 | 0.006 | 0.157 |
| 20 | 0.017 | 0.218 |
| 21 | 4.815 | 4.714 |
| 22 | 0.023 | 0.280 |
| 23 | 0.019 | 0.434 |
| 25 | 0.009 | 0.278 |
| 26 | 0.020 | >10 |
| 27 | 0.120 | >10 |
| 28 | 0.069 | >10 |
| 30 | 0.446 | >10 |
| 31 | 0.077 | 4.123 |
| 32 | 0.015 | 0.371 |
| 33 | 0.227 | 0.917 |
| 34 | 0.176 | >10 |
| 36 | 0.014 | 3.642 |
| 37 | 0.146 | 6.764 |
| 38 | 0.191 | 3.566 |
| 39 | 0.041 | 0.514 |
| 40 | 0.010 | 1.671 |
| 41 | 0.008 | 1.470 |
| 42 | 0.180 | 0.216 |
| 43 | 0.059 | >10 |
| 44 | 0.580 | >10 |
| 45 | 0.222 | 1.196 |
| 46 | 0.031 | 0.616 |
| 47 | 0.010 | 3.917 |
| 48 | 0.067 | 0.806 |
| 49 | 0.004 | 1.934 |
| 50 | 0.011 | >10 |
| 51 | 0.583 | 3.340 |
| 52 | 0.012 | >10 |
| 53 | 0.042 | 3.700 |
| 54 | 0.021 | 4.459 |
| 55 | 0.013 | 4.445 |
| 56 | 0.446 | 9.099 |
| 57 | 0.215 | 4.948 |

TABLE 5-continued

CB-1 & CB-2 Biological Activity

| ID No | CB-1 EC$_{50}$ (μM) | CB-2 EC$_{50}$ (μM) |
|---|---|---|
| 58 | 0.0005 | 0.067 |
| 59 | 4.428 | >10 |
| 60 | 5.299 | >10 |
| 61 | 0.020 | >10 |
| 62 | 0.014 | 8.078 |
| 63 | 0.010 | 1.200 |
| 64 | 0.015 | >10 |
| 65 | 0.004 | 2.940 |
| 66 | 0.008 | 0.845 |
| 67 | 0.001 | 1.149 |
| 68 | 0.950 | >10 |
| 69 | 0.098 | >10 |
| 71 | 0.019 | >10 |
| 72 | 0.051 | >10 |
| 73 | 0.014 | 4.428 |
| 74 | 0.082 | 0.178 |
| 75 | 0.005 | >10 |
| 76 | 4.389 | >10 |
| 77 | 0.297 | 3.288 |
| 78 | 0.016 | 9.399 |
| 79 | 0.004 | 0.173 |
| 80 | 6.048 | >10 |
| 81 | 0.002 | 0.452 |
| 82 | 5.754 | >10 |
| 83 | 0.085 | 3.499 |
| 84 | 0.026 | 0.326 |
| 85 | 0.010 | >10 |
| 86 | 2.465 | 8.999 |
| 87 | 2.915 | >10 |
| 88 | 0.799 | >10 |
| 89 | 0.025 | 1.803 |
| 90 | 0.034 | 0.461 |
| 91 | 0.030 | >10 |
| 92 | 0.695 | 0.195 |
| 93 | 0.014 | 0.323 |
| 94 | 0.004 | 0.068 |
| 95 | 0.818 | 3.164 |
| 96 | 0.023 | 0.218 |
| 97 | 0.083 | >10 |
| 98 | 0.232 | 7.900 |
| 99 | 0.001 | 8.492 |
| 100 | 0.432 | >10 |
| 101 | 0.106 | 3.883 |
| 102 | 0.010 | >10 |
| 103 | 0.004 | >10 |
| 104 | 0.068 | >10 |
| 106 | 0.070 | 5.700 |
| 107 | 0.075 | >10 |
| 108 | 0.008 | >10 |
| 109 | 0.004 | >10 |
| 110 | 0.041 | 3.217 |
| 111 | 0.015 | 2.738 |
| 112 | 0.010 | 4.703 |
| 113 | 0.254 | >10 |
| 114 | 0.032 | 5.687 |
| 115 | 0.034 | 8.200 |
| 116 | 0.008 | 2.500 |
| 118 | 0.011 | 0.196 |
| 119 | 0.005 | 0.910 |
| 120 | 0.004 | 2.146 |
| 121 | 0.003 | 2.142 |
| 122 | 0.052 | >10 |
| 123 | 0.002 | 0.490 |
| 124 | 0.002 | 1.934 |
| 125 | 0.044 | 5.937 |
| 126 | 0.025 | 1.180 |
| 127 | 0.030 | 1.725 |
| 128 | 0.009 | 10.399 |
| 129 | 0.003 | 0.072 |
| 130 | 0.002 | 0.154 |
| 131 | 0.016 | 1.269 |
| 132 | 0.173 | >13.9991 |
| 133 | 0.007 | 2.214 |
| 134 | 0.194 | >10 |
| 135 | 0.008 | 2.853 |
| 136 | 0.003 | >10 |
| 137 | 0.002 | 0.280 |
| 138 | 0.011 | >10 |
| 139 | 0.002 | 0.771 |
| 140 | 0.024 | 2.450 |
| 141 | 0.032 | 5.007 |
| 142 | 0.574 | >10 |
| 143 | 0.091 | >10 |
| 144 | 0.163 | 2.746 |
| 145 | 0.005 | 0.801 |
| 146 | 0.008 | 0.978 |
| 200 | 0.009 | 6.500 |

Biological Example 2

CB-1 & CB-2 Receptor Binding Assay

Experimental Procedure CB-1 Membrane Binding

Into Greiner V bottom polypropylene plates, hCB1-CHO-K1 membranes (2 μg/well final concentration) in assay buffer (50 mM Tris-HCl pH 7.4, 5 mM MgCl$_2$ and 0.5 mg/ml (0.05%) Ultra fatty acid free BSA) were dispensed. Membranes were purchased from Perkin Elmer. Test compounds were then added to each well and then [$^3$H] CP 55, 940 (0.4 nM final well concentration) in assay buffer (50 mM Tris-HCl pH 7.4, 5 mM MgCl$_2$ and 0.5 mg/ml (0.05%) Ultra fatty acid free BSA) was added. Samples were mixed and incubated for 90 min at 30° C. in the Greiner V Bottom Polypropylene plate. After incubation, assay reagents were transferred to a blocked 384 well polypropylene filter plates. The binding reaction was stopped by filtration and washed seven times with ice cold rinse buffer. Filter plates were then dried overnight at room temperature. The next day, plate bottoms were sealed with plate tape and 15 μl MicroScint 20 was added to each well. Plates were incubated for 2h and radioactivity was measured by Topcount.

Experimental Procedure CB-2

Membrane Binding—Prophetic Example

Into Greiner V bottom polypropylene plates, hCB2-HEK293 membranes (2 μg/well final concentration) in assay buffer (50 mM Tris-HCl pH 7.4, 5 mM MgCl$_2$ and 0.5 mg/ml (0.05%) Ultra fatty acid free BSA) are dispensed. Membranes are prepared as described in FELDER, C. C., et al., *Molecular Pharmacology*, 1992, pp 838-845, Vol. 42. Test compounds are then added to each well and then [$^3$H] CP 55, 940 (0.5 nM final well concentration) in assay buffer (50 mM Tris-HCl pH 7.4, 5 mM MgCl$_2$ and 0.5 mg/ml (0.05%) Ultra fatty acid free BSA) is added. Samples are mixed and incubated for 90 min at 30° C. in the Greiner V Bottom Polypropylene plate. After incubation, assay reagents are transferred to a blocked 384 well polypropylene filter plates. The binding reaction is stopped by filtration and washed nine times with ice cold rinse buffer. Filter plates are then dried overnight at room temperature. The next day, plate bottoms are sealed with plate tape and 15 ul MicroScint 20 is added to each well. Plates are incubated for 2h and radioactivity is measured by Topcount.

Total Binding:

Total Binding levels were achieved by combining membrane, DMSO, and [$^3$H] CP-55,940 (also known as 5-(1,1-dimethylheptyl)-2-[(1R,2R,5R)-5-hydroxy-2-(3-hydroxypropyl)cyclohexyl]-phenol).

Non-Specific Binding (NSB):

Non-Specific Binding (NSB) levels were achieved by combining membrane, 10 μM final concentration WIN-55,212 (also known as (R)-(+)-[2,3-dihydro-5-methyl-3[(4-morpholinyl)methyl]pyrrolo[1,2,3-de]-1,4-benzoxazinyl]-(1-naphthalenyl)methanone mesylate, Tocris Biosciences Cat#1038), and [$^3$H] CP-55,940 (also known as 5-(1,1-dimethylheptyl)-2-[(1R,2R,5R)-5-hydroxy-2-(3-hydroxypropyl)cyclohexyl]-phenol).

Data Analysis:

Top Count raw data files were used for data analysis as follows:

Non-specific binding (NSB=10 μM WIN-55,212+Membrane+[$^3$H] CP-55,940) was used as the negative control, while the Total Binding (TB=DMSO+Membrane+[$^3$H] CP-55,940) was used as the positive control.

Excel data file reports were generated by the PE TopCount and imported into Excel for calculations or were imported into a macro driven Excel template maintained by Lead Generation—Biology.

IC$_{50}$ data was calculated using raw CPM values. Curves were fitted individually from singlet 11 point dosing curves+ 1% DMSO Control. IC$_{50}$ values were fit appropriately and calculated using the following equation:

$$v = V_{min} + \frac{V_0 - V_{min}}{1 + ([I]/IC_{50})^h}$$

$V_{min}$, CPM at maximum inhibition; $V_o$, CPM at zero inhibition; IC$_{50}$, inhibitor concentration at 50% inhibition; h, Hill coefficient.

Maximal compound % inhibition of control treated wells was also noted since some compounds exhibited values suitable for calculating IC$_{50}$'s.

% Inhibition of Total Binding=(1−(CPM Compound Treated Well/CPM Control Treated Well))*100

Compound #140 was tested according to the procedure as described above, for binding to the CB-1 membrane, with calculated IC$_{50}$ of 0.074 μM.

In Vivo Biological Assays

Animals, Diets and Test Compound:

Male 14-20-week old diet-induced obese mice were ordered from Taconic. Mice were started on a 60% fat diet (D12492, Research Diets, New Brunswick, N.J.) at 6 weeks of age. Mice were single-housed.

Male Sprague Dawley rats were ordered from Charles River (225-250 gm upon arrival). They were fed standard chow diet (Purina 5001) and housed 2 per cage. Male C57bl/6j mice were ordered from Charles River at 22-25 g and housed 3 per cage. They were fed standard chow (Purina 5001). All animals were housed in a temperature-controlled room with 12-hour light/dark cycle. Animals were given food and water ad libitum, except as noted.

Test compounds were formulated in 10% PEG400 and 10% solutol. Test compounds were administered by oral gavage (5 ml kg$^{-1}$).

Biological Example 3

Mouse Fast PK/BBB

Male C57bl/6j mice were dosed with test compounds at 30 mg/kg. Plasma was collected via retro-orbital bleeding at 1 hr and 4 hrs after dosing. Whole brain without cerebellum was collected at 4 hrs after dosing. Wet brain weight was recorded before freezing. Brains were homogenized in saline and sent for analysis for determination of concentration of test compound.

Tables 6A and 6B below present results for representative compounds of the present invention, tested according to the procedure as described above. Each compound was tested in three animals (N=3) and administered PO at 20 mg/kg or 30 mg/kg.

TABLE 6A

Mouse Fast PK/BBB Results

| ID No. | Dose (mg/kg) | Time | PLASMA Mean Conc. (ng/mL) ± Std. Dev (ng/mL) | BRAIN Mean Conc. (ng/mL) ± Std. Dev (ng/mL) |
|---|---|---|---|---|
| 47 | 30 | 1 hr | 7.83 ± 1.08 | BLOQ ± NA |
| | 30 | 4 hr | BLOQ ± NA | BLOQ ± NA |
| 54 | 30 | 1 hr | 946 ± 99.4 | BLOQ ± NA |
| | 30 | 4 hr | 1303 ± 155 | BLOQ ± NA |
| 163 | 20 | 1 hr | 3963 ± 205 | 9.32 ± NA |
| | 20 | 4 hr | 2303 ± 693 | 19.5 ± NA |
| 138 | 20 | 1 hr | 3299 ± 537 | 61.7 ± 22.6 |
| | 20 | 4 hr | 3794 ± 743 | 192 ± 14.0 |

BLOQ = below level of quantitation;
NA = Not applicable

TABLE 6B

Mouse Fast PK/BBB Results

| ID No. | DOSE (mg/kg) | Formulation | Time | PLASMA Range of Conc. (ng/mL) | BRAIN Range of Conc. (ng/mL) |
|---|---|---|---|---|---|
| 93 | 20 | 10% PEG400 and 10% Solutol in water | 1 hr | ND, BLOQ, ND | ND, ND, ND |
| | | | 4 hr | 17.155, 6.427, 16.050 | ND, ND, ND |
| 93 | 30 | 5% NMP and 20% HPβCD ~pH8 in water | 1 hr | 280, 9.10, 9.00 | BLOQ, BLOQ, BLOQ |
| | | | 4 hr | BLOQ, BLOQ, BLOQ | BLOQ, BLOQ, BLOQ |

BLOQ = below level of quantitation;
ND = Not detectable

Biological Example 4

Chronic DIO Mouse—Prophetic Example

The test compound is formulated in 10% PEG400 and 10% solutol. DIO mice receive vehicle, test compound (@1, 3 and 10 mg/kg) daily for 26 days. At the end of the experiment, the mice are euthanized and blood and tissues are collected.

Body weight and food weight (food intake) are monitored daily for days 1-5 and twice weekly thereafter. Fed blood glucose is measured weekly. An insulin tolerance test (0.5 U/kg Humulin, ip) is performed on day 19 after a 4 hour food removal. Blood glucose is measured at 0, 15, 30, 60 and 120 minutes after insulin. After an overnight fast, an oral glucose tolerance test (2 g/kg glucose) is performed on day 23. Blood glucose is measured at 0, 30, 60 and 120 minutes after glucose challenge. Blood glucose is measured from the tail vein with a Lifescan glucometer. Plasma insulin is measured with an ELISA or HTRF kit (Cisbio). Plasma parameters are measured with an Olympus clinical chemistry analyzer.

Biological Example 5

Open Field Locomotor Activity in Rats (CNS Activity)—Prophetic Example

Male SD rats are weighed and transferred to the Activity Chambers with access to water. After a 2-hr acclimation period, the rats are dosed with vehicle or test compound (@3 and 10 mg/kg). The Activity Chamber monitoring software program is initiated and automatically records rat activity in each chamber for a period of 4 hours. At the end of the 4 hour monitoring period, the software is stopped and the rats are removed from the activity chambers. The rats are anesthetized and blood samples are obtained via retro-orbital puncture to determine plasma concentration of compounds. The rats are immediately euthanized with $CO_2$ and the brains are removed, washed with PBS, frozen on dry ice and stored at −80° C. for receptor occupancy (RO) analysis.

Satellite groups of 3 rats are dosed with test compound at 3 mg/kg and 10 mg/kg respectively. Four hours later, the rats are anesthetized. Blood is collected from these rats and then perfused with 400 ml heparinized saline through the left ventricle of the heart. The brains are removed and homogenized in PBS (4 ml/gm tissue). The samples are submitted for determination of plasma and brain compound levels.

Formulation Example 1

Solid, Oral Dosage Form—Prophetic Example

As a specific embodiment of an oral composition, 100 mg of the Compound 44, prepared as in Example 2, is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of formula (I)

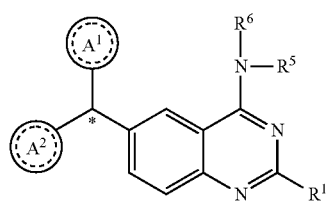

(I)

wherein

is selected from the group consisting of phenyl, furyl, thienyl, thiazolyl, pyridyl, benzothiazolyl and benzo[d][1,3]dioxolyl;

wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and $NR^A R^B$; wherein $R^A$ and $R^B$ are each independently selected from the group consisting of hydrogen, $C_{1-4}$alkyl and —($C_{2-4}$alkyl)-O—($C_{1-4}$alkyl); provided that each substituent is bound to a carbon atom of the ring;

is selected from the group consisting of phenyl, furyl, thienyl, thiazolyl, pyridyl, benzothiazolyl and benzo[d][1,3]dioxolyl;

wherein the phenyl, furyl, thienyl, thiazolyl, pyridyl, benzothiazolyl or benzo[d][1,3]dioxolyl is optionally substituted with one or more substituents independently selected from the group consisting of halogen, hydroxy, $C_{1-4}$alkyl, fluorinated $C_{1-4}$alkyl, $C_{1-4}$alkoxy, fluorinated $C_{1-4}$alkoxy, cyano, —C(O)OH, C(O)O—$C_{1-4}$alkyl and $NR^C R^D$; wherein $R^C$ and $R^D$ are each independently selected from the group consisting of hydrogen, $C_{1-4}$alkyl and —($C_{2-4}$alkyl)-O—($C_{1-4}$alkyl); provided that each substituent is bound to a carbon atom of the ring;

$R^1$ is selected from the group consisting of hydrogen, $C_{1-6}$alkyl, —CH=CH—($C_{1-4}$alkyl)-OH, —CH=CH—($C_{0-3}$alkyl)-$CO_2$H, —CH=CH—($C_{0-3}$alkyl)-C(O)O—($C_{1-4}$alkyl), —CH=CH—($C_{1-4}$alkyl)-$NH_2$, —$CH_2CH_2$—($C_{1-4}$alkyl)-OH, —$CH_2CH_2$—($C_{0-3}$alkyl)-$CO_2$H, —$CH_2CH_2$—($C_{0-3}$alkyl)-C(O)O—($C_{1-4}$alkyl), —$CH_2CH_2$—($C_{1-4}$alkyl)-$NH_2$, cyclopropyl, cyclobutyl, —$OR^2$ and —$NR^3 R^4$;

$R^2$ is selected from the group consisting of hydrogen, —$C_{1-12}$alkyl, —$CH_2$-(hydroxy substituted $C_{1-11}$alkyl), —($C_{1-12}$alkyl)-$N_3$, —($C_{2-12}$alkyl)-$NR^E R^F$, —($C_{2-12}$alkyl)-O—($C_{1-12}$alkyl), —($C_{2-12}$alkyl)-O—($C_{1-12}$alkyl)-OH, —($C_{2-12}$alkyl)-O—($C_{1-12}$alkyl)-CN, —($C_{2-12}$alkyl)-O—($C_{1-12}$alkyl)-$CO_2$H, —($C_{2-12}$alkyl)-O—($C_{1-12}$alkyl)-C(O)—O—($C_{1-6}$alkyl), —($C_{2-12}$alkyl)-O—($C_{1-12}$alkyl)-C(O)—$NR^E R^F$, —($C_{1-12}$alkyl)-$CO_2$H, —($C_{1-12}$alkyl)-C(O)—O—($C_{1-6}$alkyl), —($C_{2-12}$alkyl)-OC(O)—($C_{1-6}$alkyl), —($C_{2-12}$alkyl)-OC(O)—$NR^E R^F$, —($C_{1-12}$alkyl)-C(O)—$NR^E R^F$, —($C_{2-12}$alkyl)-$NR^E$—C(O)—($C_{1-6}$alkyl), —($C_{2-12}$alkyl)-$NR^E$—C(O)—($C_{1-12}$alkyl)-OH and —($C_{2-12}$alkyl)-$NR^E$—$SO_2$—($C_{1-6}$alkyl); wherein $R^E$ and $R^F$ are each independently selected from the group consisting of hydrogen, $C_{1-6}$alkyl and —$CH_2$-(hydroxy substituted $C_{1-5}$alkyl);

$R^3$ is selected from the group consisting of hydrogen and $C_{1-4}$alkyl;

$R^4$ is selected from the group consisting of hydrogen, —$C_{1-12}$alkyl, —$CH_2$-(hydroxy substituted $C_{1-11}$ alkyl), —($C_{1-12}$alkyl)-$N_3$, —($C_{2-12}$alkyl)-$NR^G R^H$, —($C_{2-12}$alkyl)-O—($C_{1-12}$alkyl), —($C_{2-12}$alkyl)-O—($C_{1-12}$alkyl)-OH, —($C_{2-12}$alkyl)-O—($C_{1-12}$alkyl)-CN, —($C_{2-12}$alkyl)-O—($C_{1-12}$alkyl)-$CO_2$H, —($C_{2-12}$alkyl)-

O—($C_{1-12}$alkyl)-C(O)—O—($C_{1-6}$alkyl), —($C_{2-12}$alkyl)-O—($C_{1-12}$alkyl)-C(O)—$NR^GR^H$, —($C_{1-12}$alkyl)-$CO_2H$, —($C_{1-12}$alkyl)-C(O)O—($C_{1-6}$alkyl), —($C_{2-12}$alkyl)-OC(O)—($C_{1-6}$alkyl), —($C_{2-12}$alkyl)-OC(O)—$NR^GR^H$, —($C_{1-12}$alkyl)-C(O)—$NR^GR^H$, —($C_{2-12}$alkyl)-$NR^G$—C(O)—($C_{1-6}$alkyl), —($C_{2-12}$alkyl)-$NR^G$—C(O)—($C_{1-12}$alkyl)-OH, —($C_{2-12}$alkyl)-$NR^G$—$SO_2$—($C_{1-6}$alkyl), —C(O)—($C_{1-4}$alkyl), —$SO_2$—($C_{1-4}$alkyl) and —$SO_2$-(halogenated $C_{1-6}$alkyl); wherein $R^G$ and $R^H$ are each independently selected from the group consisting of hydrogen, $C_{1-6}$alkyl and —$CH_2$-(hydroxy substituted $C_{1-5}$alkyl);

$R^5$ is selected from the group consisting of hydrogen and $C_{1-4}$alkyl;

$R^6$ is selected from the group consisting of

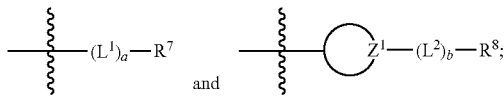
and a is an integer from 0 to 1;

$L^1$ is selected from the group consisting of —$CH_2$—, —$CH(CH_3)$—, —$CH_2CH_2$— and cycloprop-1,1-diyl;

$R^7$ is selected from the group consisting of azetidin-3-yl, pyrrolidin-3-yl, piperidin-4-yl, piperazin-1-yl, morpholin-4-yl, thiomorpholin-4-yl, thiomorpholin-4-yl-1-oxide, thiomorpholin-4-yl-1,1-dioxide, phenyl, pyridin-2-yl, pyridin-3-yl, pyridin-4-yl, thien-2-yl, thien-3-yl, furan-2-yl, furan-3-yl, pyrimidin-2-yl, pyrazin-2-yl, cyclopropyl, cyclobutyl, cyclopentyl and cyclohexyl;

wherein any of the $R^7$ ring structures is optionally substituted with one substituent selected from the group consisting of halogen, hydroxy, cyano, $C_{1-4}$alkyl, halogenated $C_{1-4}$alkyl, hydroxy substituted $C_{1-12}$alkyl, $C_{1-4}$alkoxy, halogenated $C_{1-4}$alkoxy, —($C_{1-4}$alkyl)-O—($C_{1-4}$alkyl), —($C_{1-4}$alkyl)-$CO_2H$, —($C_{1-4}$alkyl)-C(O)O—($C_{1-4}$alkyl), —($C_{1-4}$alkyl)-C(O)—$NR^JR^K$, —O—($C_{1-4}$alkyl)-O—($C_{1-4}$alkyl), —O—($C_{1-4}$alkyl)-$CO_2H$, —O—($C_{1-4}$alkyl)-C(O)O—($C_{1-4}$alkyl), —O—($C_{1-4}$alkyl)-C(O)—$NR^JR^K$, —C(O)—($C_{1-4}$alkyl), —C(O)-(halogenated $C_{1-4}$alkyl), —C(O)—($C_{1-4}$alkyl)-$CO_2H$, —C(O)—($C_{1-4}$alkyl)-C(O)O—($C_{1-4}$alkyl), —C(O)—$NR^JR^K$, —C(O)—($C_{1-4}$alkyl)-C(O)—$NR^JR^K$, —$CO_2H$, —C(O)O—($C_{1-4}$alkyl), —C(O)O—($C_{1-4}$alkyl)-OC(O)O—($C_{1-4}$alkyl), —C(=$NR^J$)—$NR^K$—C(O)O—($C_{1-4}$alkyl), —C(=NH)—$NH_2$, —C(=N-Boc)-NH(Boc), —$NR^JR^K$, —$NR^J$—C(O)—($C_{1-4}$alkyl), —$NR^J$—$SO_2$—($C_{1-4}$alkyl), —$SO_2$—($C_{1-4}$alkyl), —$SO_2$-(halogenated $C_{1-4}$alkyl), —$SO_2$—($C_{1-4}$alkyl)-OH, —$SO_2$—($C_{1-4}$alkyl)-C(O)O—($C_{1-4}$alkyl), —$SO_2$—$NR^JR^K$ and —$SO_2$—($C_{1-4}$alkyl)-C(O)—$NR^JR^K$; and wherein $R^J$ and $R^K$ are each independently selected from the group consisting of hydrogen, $C_{1-4}$alkyl and ($C_{2-4}$alkyl)-OH;

and wherein $R^7$ is phenyl; the phenyl is further optionally substituted with an additional substituent selected from the group consisting of halogen, hydroxy, cyano, $C_{1-4}$alkyl, halogenated $C_{1-4}$alkyl, $C_{1-4}$alkoxy and halogenated $C_{1-4}$alkoxy;

provided that when a is 0 ($L^1$ Is absent), then $R^7$ is other than piperazin-1-yl, morpholin-4-yl, thiomorpholin-4-yl or thiomorpholin-4-yl-1-oxide provided further that when the substituent group on the $R^7$ ring structure is selected from the group consisting of $C_{1-4}$alkoxy, halogenated $C_{1-4}$alkoxy, —O—($C_{1-4}$alkyl)-O—($C_{1-4}$alkyl), —O—($C_{1-4}$alkyl)-$CO_2H$, —O—($C_{1-4}$alkyl)-C(O)O—($C_{1-4}$alkyl), —O—($C_{1-4}$alkyl)-C(O)—$NR^JR^K$, —$NR^JR^K$, —$NR^J$—C(O)—($C_{1-4}$alkyl) and —$NR^J$—$SO_2$—($C_{1-4}$alkyl), then said substitutent group is bound to a carbon atom on the $R^7$ ring structure;

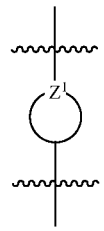

is selected from the group consisting of

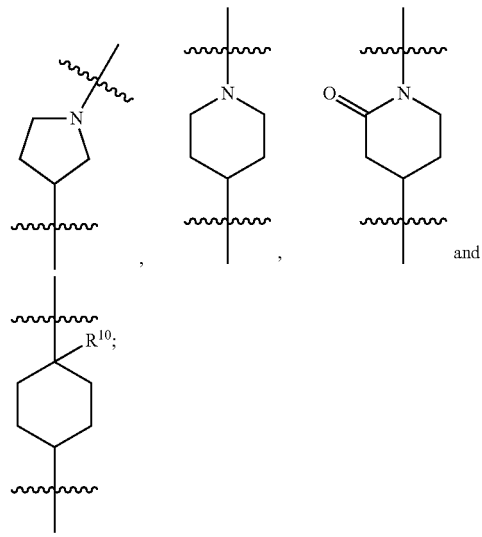

wherein $Z^1$ is selected from the group consisting of N and CH;

b is an integer from 0 to 1;

$L^2$ is selected from the group consisting of —$CH_2$—, —$CH_2CH_2$—, —$CH(CH_3)$—, —$CH(CH_2CH_3)$—, —C(O)— and —$SO_2$—;

$R^8$ is selected from the group consisting of azetidin-3-yl, pyrrolidin-1-yl, piperidin-4-yl, piperazin-1-yl, morpholin-4-yl, phenyl, pyridin-2-yl, pyridin-3-yl, pyridin-4-yl, thien-2-yl, thien-3-yl, furan-2-yl, furan-3-yl, pyrimidin-2-yl, pyrazin-2-yl, cyclopropyl, cyclobutyl, cyclopentyl and cyclohexyl;

wherein any of the $R^8$ ring structures is optionally substituted with one substituent selected from the group consisting of halogen, hydroxy, cyano, $C_{1-4}$alkyl, halogenated $C_{1-4}$alkyl, hydroxy substituted $C_{1-12}$alkyl, $C_{1-4}$alkoxy, halogenated $C_{1-4}$alkoxy, —($C_{1-4}$alkyl)-O—($C_{1-4}$alkyl), —($C_{1-4}$alkyl)-$CO_2H$, —($C_{1-4}$alkyl)-C(O)O—($C_{1-4}$alkyl), —($C_{1-4}$alkyl)-C(O)—$NR^PR^Q$, —O—($C_{1-4}$alkyl)-O—($C_{1-4}$alkyl), —O—($C_{1-4}$alkyl)-$CO_2H$, —O—($C_{1-4}$alkyl)-C(O)O—($C_{1-4}$alkyl), —O—($C_{1-4}$alkyl)-C(O)—$NR^PR^Q$, —C(O)—($C_{1-4}$alkyl), —C(O)-(halogenated $C_{1-4}$alkyl), —C(O)—($C_{1-4}$alkyl)-$CO_2H$, —C(O)—($C_{1-4}$alkyl)-C(O)O—($C_{1-4}$alkyl), —C(O)—$NR^PR^Q$, —C(O)$NR^P$—($C_{2-4}$alkyl)-O—$R^{11}$, —C(O)—($C_{1-4}$alkyl)-C(O)—$NR^PR^Q$, —$CO_2H$, —C(O)O—($C_{1-4}$alkyl), —C(O)O—($C_{1-4}$alkyl)-OC(O)

O—(C$_{1-4}$alkyl), —C(=NR$^P$)—NR$^Q$—C(O)O—(C$_{1-6}$alkyl), —C(=NH)—NH$_2$, —C(=N-Boc)-NH(Boc), —NR$^P$R$^Q$, —NR$^P$—C(O)—(C$_{1-4}$alkyl), —NR$^Q$—SO$_2$—(C$_{1-4}$alkyl), —SO$_2$—(C$_{1-4}$alkyl), —SO$_2$-(halogenated C$_{1-4}$alkyl), —SO$_2$—(C$_{1-4}$alkyl)-OH, —SO$_2$—(C$_{1-4}$alkyl)-C(O)O—(C$_{1-4}$alkyl), —SO$_2$—NR$^P$R$^Q$ and —SO$_2$—(C$_{1-4}$alkyl)-C(O)—NR$^P$R$^Q$;

wherein R$^{11}$ is phenyl; wherein the phenyl is optionally substituted at the 4-position with a substituents selected from the group consisting of halogen, hydroxymethyl, methyl, ethyl, trifluoromethyl and cyano;

and wherein R$^P$ and R$^Q$ are each independently selected from the group consisting of hydrogen, C$_{1-4}$alkyl, and —CH$_2$-(hydroxy substituted C$_{1-5}$alkyl);

and wherein R$^8$ is phenyl; the phenyl is further optionally substituted with an additional substituent selected from the group consisting of halogen, hydroxy, cyano, C$_{1-4}$alkyl, halogenated C$_{1-4}$alkyl, C$_{1-4}$alkoxy and halogenated C$_{1-4}$alkoxy;

R$^{10}$ is selected from the group consisting of hydrogen, hydroxy and cyano;

provided that when

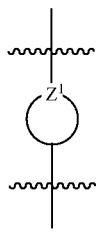

is selected from the group consisting of

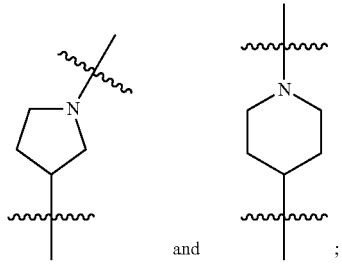 [SMILES: *C1CCN(*)C1 ; *C1CCN(*)CC1]

and the R$^8$ ring structure is bound through a nitrogen ring atom; then b is 1 and L$^2$ is selected from the group consisting of —C(O)— and —SO$_2$—;

provided further that when

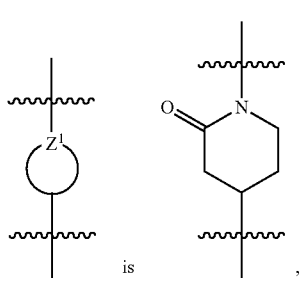

then R$^8$ is phenyl, wherein the phenyl is optionally substituted with one to two substituents independently selected from the group consisting of F, Cl, methyl, ethyl, cyano, trifluoromethyl, methoxy and ethoxy;

alternatively, R$^5$ and R$^6$ are taken together with the nitrogen atom to which they are bound to form a ring structure selected from the group consisting of

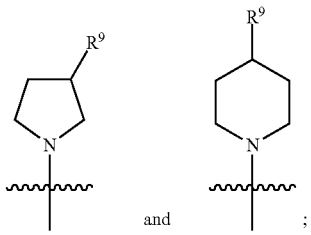

R$^9$ is selected from the group consisting of C$_{1-4}$alkyl, trifluoromethyl, cyclopropyl and —NR$^S$R$^T$; wherein R$^S$ is selected from the group consisting of hydrogen, methyl and ethyl; and R$^T$ is selected from the group consisting of —C(O)—(C$_{1-4}$alkyl), —SO$_2$—(C$_{1-4}$alkyl) and —SO$_2$-(halogenated C$_{1-4}$alkyl);

or a stereoisomer, tautomer or pharmaceutically acceptable salt thereof.

2. A compound as in claim 1, of the formula (I-A)

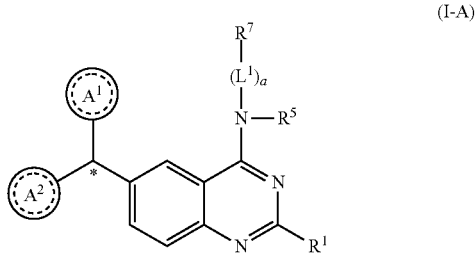

(I-A)

or a stereoisomer, tautomer or pharmaceutically acceptable salt thereof.

3. A compound as in claim 2, wherein

is selected from the group consisting of phenyl and thiazolyl;

wherein the phenyl or thiazolyl is optionally substituted with one or more substituents independently selected from the group consisting of halogen, hydroxy, C$_{1-2}$alkyl, trifluoromethyl, C$_{1-2}$alkoxy, trifluoromethoxy, cyano, —C(O)OH, C(O)O—C$_{1-2}$alkyl and NR$^A$R$^B$; wherein R$^A$ and R$^B$ are each independently selected from the group consisting of hydrogen, C$_{1-2}$alkyl and —(C$_{2-4}$alkyl)-O—(C$_{1-4}$alkyl); provided that each substituent is bound to a carbon atom of the ring;

is selected from the group consisting of phenyl and thiazolyl;
wherein the phenyl or thiazolyl is optionally substituted with one or more substituents independently selected from the group consisting of halogen, hydroxy, $C_{1-2}$alkyl, trifluoromethyl, $C_{1-2}$alkoxy, trifluoromethoxy, cyano, —C(O)OH, C(O)O—$C_{1-2}$alkyl and NR$^A$R$^B$; wherein R$^A$ and R$^B$ are each independently selected from the group consisting of hydrogen, $C_{1-2}$alkyl and —($C_{2-4}$alkyl)-O—($C_{1-4}$alkyl); provided that each substituent is bound to a carbon atom of the ring;

$R^1$ is selected from the group consisting of hydrogen, $C_{1-2}$alkyl, —CH=CH—($C_{1-2}$alkyl)-OH, —CH=CH—($C_{0-1}$alkyl)-$CO_2$H, —CH=CH—($C_{0-1}$alkyl)-C(O)O—($C_{1-4}$alkyl), —$CH_2CH_2$—($C_{1-2}$alkyl)-OH, —$CH_2CH_2$—($C_{0-1}$alkyl)-$CO_2$H, —$CH_2CH_2$—($C_{0-1}$alkyl)-C(O)O—($C_{1-4}$alkyl), cyclopropyl, —OR$^2$ and —NR$^3$R$^4$;

$R^2$ is selected from the group consisting of hydrogen, —$C_{1-6}$alkyl, —$CH_2$-(hydroxy substituted $C_{1-6}$alkyl), —($C_{1-4}$alkyl)-$N_3$, —($C_{2-4}$alkyl)-NR$^E$R$^F$, —($C_{2-4}$alkyl)-O—($C_{1-4}$alkyl), —($C_{2-4}$alkyl)-O—($C_{1-6}$alkyl)-OH, —($C_{2-4}$alkyl)-O—($C_{1-6}$alkyl)-CN, —($C_{2-4}$alkyl)-O—($C_{1-12}$alkyl)-$CO_2$H, —($C_{1-4}$alkyl)-C(O)—NR$^E$R$^F$, —($C_{2-4}$alkyl)-NR$^E$—C(O)—($C_{1-6}$alkyl) and —($C_{2-4}$alkyl)-NR$^E$—$SO_2$—($C_{1-6}$alkyl); wherein R$^E$ and R$^F$ are each independently selected from the group consisting of hydrogen, $C_{1-2}$alkyl and —$CH_2$-(hydroxy substituted $C_{1-2}$alkyl);

$R^3$ is selected from the group consisting of hydrogen and $C_{1-2}$alkyl;

$R^4$ is selected from the group consisting of hydrogen, —$C_{1-6}$alkyl, —$CH_2$-(hydroxy substituted $C_{1-4}$alkyl), —($C_{1-4}$alkyl)-$N_3$, —($C_{2-4}$alkyl)-NR$^G$R$^H$, —($C_2$alkyl)-O—($C_{1-4}$alkyl), —($C_{2-4}$alkyl)-O—($C_{1-4}$alkyl)-OH, —($C_{2-4}$alkyl)-O—($C_{1-4}$alkyl)-$CO_2$H, —($C_{1-4}$alkyl)-$CO_2$H, —($C_{1-4}$alkyl)-C(O)O—($C_{1-4}$alkyl), —C(O)—($C_{1-4}$alkyl), —$SO_2$—($C_{1-4}$alkyl) and —$SO_2$-(halogenated $C_{1-2}$alkyl); wherein R$^G$ and R$^H$ are each independently selected from the group consisting of hydrogen, $C_{1-2}$alkyl and —$CH_2$-(hydroxy substituted $C_{1-2}$alkyl);

$R^5$ is selected from the group consisting of hydrogen and $C_{1-4}$alkyl;

a is an integer from 0 to 1;

$L^1$ is selected from the group consisting of —$CH_2$—, —CH($CH_3$)—, —$CH_2CH_2$—, and cycloprop-1,1-diyl;

$R^7$ is selected from the group consisting of piperidin-4-yl, piperazin-1-yl, morpholin-4-yl, thiomorpholin-4-yl, thiomorpholin-4-yl-1-oxide, thiomorpholin-4-yl-1,1-dioxide, phenyl, pyridin-2-yl, pyridin-3-yl, pyridin-4-yl, pyrimidin-2-yl and pyrazin-2-yl;
wherein any of the R$^7$ ring structures is optionally substituted with one substituent selected from the group consisting of halogen, hydroxy, cyano, $C_{1-4}$alkyl, halogenated $C_{1-2}$alkyl, hydroxy substituted $C_{1-4}$alkyl, —($C_{1-2}$alkyl)-O—($C_{1-4}$alkyl), —($C_{1-2}$alkyl)-$CO_2$H, —($C_{1-2}$alkyl)-C(O)O—($C_{1-4}$alkyl), —C(O)-(halogenated $C_{1-2}$alkyl), —C(O)—($C_{1-4}$alkyl)-$CO_2$H, —C(O)—($C_{1-4}$alkyl)-C(O)O—($C_{1-4}$alkyl), —C(O)—NR$^J$R$^K$, —C(O)—($C_{1-2}$alkyl)-C(O)—NR$^J$R$^K$, —$CO_2$H, —C(O)O—($C_{1-4}$alkyl), —C(=NR$^J$)—NR$^K$—C(O)O—($C_{1-4}$alkyl), —C(=NH)—$NH_2$, —C(=N-Boc)-NH(Boc), —$SO_2$—($C_{1-4}$alkyl), —$SO_2$-(halogenated $C_{1-2}$alkyl), —$SO_2$—($C_{1-4}$alkyl)-OH, —$SO_2$—($C_{1-4}$alkyl)-C(O)O—($C_{1-4}$alkyl) and —$SO_2$—($C_{1-4}$alkyl)-C(O)—NR$^J$R$^K$; and wherein R$^J$ and R$^K$ are each independently selected from the group consisting of hydrogen, $C_{1-2}$alkyl and ($C_{2-4}$alkyl)-OH;

and wherein R$^7$ is phenyl; the phenyl is further optionally substituted with an additional substituent selected from the group consisting of halogen, cyano, $C_{1-4}$alkyl and halogenated $C_{1-4}$alkyl;

provided that when a is 0 (i.e. $L^1$ is absent), then R$^7$ is other than piperazin-1-yl, morpholin-4-yl, thiomorpholin-4-yl or thiomorpholin-4-yl-1-oxide;

or a stereoisomer, tautomer or pharmaceutically acceptable salt thereof.

4. A compound as in claim 2, wherein

is phenyl; wherein the phenyl is substituted with a substituent selected from the group consisting of halogen, cyano and carboxy;

is selected from the group consisting phenyl and thiazol-2-yl; wherein the phenyl is substituted with a substituent selected from the group consisting of halogen, cyano, carbonyl and —NH—($C_2$alkyl)-O—($C_{1-2}$alkyl);

$R^1$ is selected from the group consisting of hydrogen, cyclopropyl, —OR$^2$ and —NR$^3$R$^4$;

$R^2$ is selected from the group consisting of hydrogen, $C_{1-2}$alkyl, —($C_{1-2}$alkyl)-$CO_2$H, —$CH_2$-(hydroxy substituted $C_{1-4}$alkyl), —$C_{1-2}$alkyl)-$N_3$, —($C_2$alkyl)-O—($C_{1-2}$alkyl), —($C_2$-alkyl)-O—($C_2$alkyl)-OH, —($C_2$alkyl)-O—($C_2$alkyl)-$CO_2$H, —($C_2$-alkyl)-O—($C_2$alkyl)-CN, —($C_{2-4}$alkyl)-$NH_2$, —($C_{1-4}$alkyl)-C(O)—NR$^E$R$^F$ and —($C_2$alkyl)-NH—C(O)—($C_{1-4}$alkyl); wherein R$^E$ and R$^F$ are each independently selected from the group consisting of hydrogen and —$CH_2CH_2$—OH;

$R^3$ is hydrogen;

$R^4$ is selected from the group consisting of $C_{1-2}$alkyl, —C(O)—$C_{1-2}$alkyl and —$SO_2$—$C_{1-2}$alkyl;

$R^5$ is selected from the group consisting of hydrogen and $C_{1-2}$alkyl;

a is an integer from 0 to 1;

$L^1$ is selected from the group consisting of —$CH_2$—, —$CH_2CH_2$—, —CH($CH_3$)— and cycloprop-1,1-diyl;

$R^7$ is selected from the group consisting of phenyl, piperidin-4-yl, pyridin-2-yl, pyridin-3-yl and thiomorpholin-2-yl-1,1-dioxide;
wherein any of the R$^7$ ring structures is optionally substituted with one substituent selected from the group consisting of halogen, carboxy, halogenated $C_{1-2}$alkyl, —C(O)O—($C_{1-4}$alkyl), —C(O)—($C_{1-2}$alkyl)-$CO_2$H, —C(O)-(halogenated $C_{1-2}$alkyl), —C(O)—($C_{1-2}$alkyl)-C(O)O—($C_{1-2}$alkyl), —C(O)—$NH_2$, —C(O)—($C_{1-2}$alkyl)-C(O)—$NH_2$, —C(O)—($C_{1-2}$alkyl)-C(O)—NH—($C_2$alkyl)-OH, —$SO_2$—($C_{1-4}$alkyl), —$SO_2$-(halogenated $C_{1-2}$alkyl), —$SO_2$—($C_{1-2}$alkyl)-OH, —$SO_2$—($C_{1-2}$alkyl)-C(O)O—($C_{1-2}$alkyl) and —$SO_2$—($C_{1-2}$alkyl)-C(O)—$NH_2$;

and wherein R$^7$ is phenyl; the phenyl is further optionally substituted with an additional substituent selected from the group consisting of halogen and halogenated $C_{1-2}$alkyl;

provided that when a is 0 (i.e. L¹ is absent), then R⁷ is other than thiomorpholin-4-yl-1,1-dioxide;

or a stereoisomer, tautomer or pharmaceutically acceptable salt thereof.

5. A compound as in claim 2, wherein

is 4-chlorophenyl;

is selected from the group consisting of 4-chlorophenyl, 4-bromophenyl, 4-carboxyphenyl, 4-cyanophenyl, 4-(2-methoxy-ethyl-amino)phenyl and thiazol-2-yl;

$R^1$ is selected from the group consisting of hydrogen, —OH, —OCH₃, —O—CH₂—CO₂H, —O—CH₂CH₂—OH, —O—CH₂CH₂—OCH₃, —O—(CH₂)₄—OH, —O—CH₂CH₂—O—CH₂CH₂—OH, —O—CH₂—CH(CH₂OH)₂, —O—CH₂—C(CH₂OH)₃, —O—CH₂CH₂—O—CH₂CH₂—CO₂H, —O—CH₂CH₂—O—CH₂CH₂—CN, —O—CH₂CH₂—N₃, —O—CH₂CH₂—NH₂, —O—(CH₂)₄—NH₂, —O—(CH₂)₃—C(O)—NH₂, —O—CH₂—C(O)—NH—CH₂CH₂—OH, —O—CH₂CH₂—NH—C(O)—CH₃, —NH₂, —NH—CH₃, —NH—C(O)—CH₃, —NH—SO₂—CH₃, and cyclopropyl;

$R^5$ is selected from the group consisting of hydrogen and methyl;

a is an integer from 0 to 1;

$L^1$ is selected from the group consisting of —CH₂—, —CH₂CH₂—, —CH(CH₃)—CH(R*—CH₃)—, —CH(S*—CH₃)— and cycloprop-1,1-diyl;

$R^7$ is selected from the group consisting of phenyl, 3-fluoro-phenyl, 4-fluoro-phenyl, 3-carboxy-phenyl, 4-carboxy-phenyl, 3-trifluoromethyl-phenyl, 4-trifluoromethyl-phenyl, 3-(methoxy-carbonyl)-phenyl, 4-(methoxy-carbonyl)-phenyl, 3-(amino-carbonyl)-phenyl, 4-(amino-carbonyl)-phenyl, 4-(trifluoromethyl-sulfonyl)-phenyl, 3-chloro-4-trifluoromethyl-phenyl, 1-(2,2,2-trifluoroethyl)-piperidin-4yl, 1-(t-butoxycarbonyl)-piperidin-4-yl, 1-(trifluoromethyl-sulfonyl)-piperidin-4-yl, 1-(methyl-sulfonyl)-piperidin-4-yl, 1-(ethyl-sulfonyl)-piperidin-4-yl, 1-(2,2,2-trifluoroethyl-carbonyl)-piperidin-4-yl, 1-((2-hydroxyethyl)-amino-carbonyl-ethyl-carbonyl)-piperidin-4-yl, 1-((2-hydroxyethyl)-sulfonyl)-piperidin-4-yl, 1-((2-carboxy-methyl)-carbonyl)-piperidin-4-yl, 1-((2-carboxy-ethyl)-carbonyl)-piperidin-4-yl, 1-(ethoxy-carbonyl-methyl-carbonyl)-piperidin-4-yl, 1-((2-ethoxy-carbonyl-ethyl)-carbonyl)-piperidin-4-yl, 1-((2-hydroxyethyl)-amino-carbonyl-methyl-carbonyl)-piperidin-4-yl, 1-(methoxy-carbonyl-methyl-sulfonyl)-piperidin-4-yl, 1-(amino-carbonyl-methyl-carbonyl)-piperidin-4-yl, 1-(amino-carbonyl-ethyl-carbonyl)-piperidin-4-yl, 1-(amino-carbonyl-methyl-sulfonyl)-piperidin-4-yl, 5-trifluoromethyl-pyridin-2-yl, 5-trifluoromethyl-pyridin-3-yl, 6-trifluoromethyl-pyridin-3-yl, and thiomorpholin-4-yl-1,1-dioxide;

provided that when a is 0 (i.e. L¹ is absent), then R⁷ is other than thiomorpholin-4-yl-1,1-dioxide;

or a stereoisomer, tautomer or pharmaceutically acceptable salt thereof.

6. A compound as in claim 5, wherein

is 4-chlorophenyl;

is selected from the group consisting of 4-chlorophenyl, 4-bromophenyl, 4-carboxyphenyl, 4-cyanophenyl, 4-(2-methoxy-ethyl-amino)-phenyl and thiazol-2-yl;

$R^1$ is selected from the group consisting of hydrogen, —OH, —OCH₃, —O—CH₂CH₂—OH, —O—CH₂CH₂—OCH₃, —O—(CH₂)₄—OH, —O—CH₂—CH(CH₂OH)₂, —O—CH₂—C(CH₂OH)₃, —O—CH₂CH₂—O—CH₂CH₂—CO₂H, —O—CH₂CH₂—O—CH₂CH₂—CN, —O—CH₂CH₂—N₃, —O—CH₂CH₂—NH₂, —O—(CH₂)₄—NH₂, —O—(CH₂)₃—C(O)—NH₂, —O—CH₂—C(O)—NH—CH₂CH₂—OH, —O—CH₂CH₂—NH—C(O)—CH₃, —NH₂, —NH—C(O)—CH₃ and cyclopropyl;

$R^5$ is selected from the group consisting of hydrogen and methyl;

a is an integer from 0 to 1;

$L^1$ is selected from the group consisting of —CH₂—, —CH₂CH₂—, —CH(CH₃)—CH(R*—CH₃)—, —CH(S*—CH₃)— and cycloprop-1,1-diyl;

$R^7$ is selected from the group consisting of phenyl, 3-fluoro-phenyl, 4-fluoro-phenyl, 3-trifluoromethyl-phenyl, 4-trifluoromethyl-phenyl, 3-(methoxy-carbonyl)-phenyl, 4-(methoxy-carbonyl)-phenyl, 4-(trifluoromethyl-sulfonyl)-phenyl, 3-chloro-4-trifluoromethyl-phenyl, 1-(2,2,2-trifluoroethyl)-piperidin-4yl, 1-(trifluoromethyl-sulfonyl)-piperidin-4-yl, 1-(methyl-sulfonyl)-piperidin-4-yl, 1-(ethyl-sulfonyl)-piperidin-4-yl, 1-(2,2,2-trifluoroethyl-carbonyl)-piperidin-4-yl, 1-((2-hydroxyethyl)-sulfonyl)-piperidin-4-yl, 1-(ethoxy-carbonyl-methyl-carbonyl)-piperidin-4-yl, 1-((2-ethoxy-carbonyl-ethyl)-carbonyl)-piperidin-4-yl, 1-(methoxy-carbonyl-methyl-sulfonyl)-piperidin-4-yl, 5-trifluoromethyl-pyridin-2-yl, 5-trifluoromethyl-pyridin-3-yl, 6-trifluoromethyl-pyridin-3-yl, and thiomorpholin-4-yl-1,1-dioxide;

provided that when a is 0 (i.e. L¹ is absent), then R⁷ is other than thiomorpholin-4-yl-1,1-dioxide;

or a stereoisomer, tautomer or pharmaceutically acceptable salt thereof.

7. A compound as in claim 5, wherein

is 4-chlorophenyl;

is selected from the group consisting of 4-chlorophenyl, 4-bromophenyl, 4-carboxyphenyl, 4-cyanophenyl, 4-(2-methoxy-ethyl-amino)-phenyl and thiazol-2-yl;

$R^1$ is selected from the group consisting of hydrogen, —OH, —OCH$_3$, —O—CH$_2$CH$_2$—OH, —O—CH$_2$CH$_2$—OCH$_3$, —O—(CH$_2$)$_4$—OH, —O—CH$_2$—CH(CH$_2$OH)$_2$, —O—CH$_2$—C(CH$_2$OH)$_3$, —O—CH$_2$CH$_2$—O—CH$_2$CH$_2$—CO$_2$H, —O—CH$_2$CH$_2$—O—CH$_2$CH$_2$—CN, —O—CH$_2$CH$_2$—N$_3$, —O—(CH$_2$)$_3$—C(O)—NH$_2$, —O—CH$_2$—C(O)—NH—CH$_2$CH$_2$—OH and cyclopropyl;

$R^5$ is hydrogen;

a is an integer from 0 to 1;

$L^1$ is selected from the group consisting of —CH$_2$—, —CH$_2$CH$_2$—, —CH(CH$_3$)—CH(R*—CH$_3$)—, —CH(S*—CH$_3$)— and cycloprop-1,1-diyl;

$R^7$ is selected from the group consisting of phenyl, 3-fluoro-phenyl, 4-fluoro-phenyl, 3-trifluoromethyl-phenyl, 4-trifluoromethyl-phenyl, 3-(methoxy-carbonyl)-phenyl, 4-(methoxy-carbonyl)-phenyl, 3-chloro-4-trifluoromethyl-phenyl, 1-(2,2,2-trifluoroethyl)-piperidin-4yl, 1-(trifluoromethyl-sulfonyl)-piperidin-4-yl, 1-(methyl-sulfonyl)-piperidin-4-yl, 1-(ethyl-sulfonyl)-piperidin-4-yl, 1-(2,2,2-trifluoroethyl-carbonyl)-piperidin-4-yl, 1-((2-hydroxyethyl)-sulfonyl)-piperidin-4-yl, 1-(ethoxy-carbonyl-methyl-carbonyl)-piperidin-4-yl, 1-((2-ethoxy-carbonyl-ethyl)-carbonyl)-piperidin-4-yl, 1-(methoxy-carbonyl-methyl-sulfonyl)-piperidin-4-yl, 5-trifluoromethyl-pyridin-2-yl, 5-trifluoromethyl-pyridin-3-yl, 6-trifluoromethyl-pyridin-3-yl and thiomorpholin-4-yl-1,1-dioxide;

provided that when a is 0 (i.e. $L^1$ is absent), then $R^7$ is other than thiomorpholin-4-yl-1,1-dioxide;

or a stereoisomer, tautomer or pharmaceutically acceptable salt thereof.

8. A compound as in claim 5, wherein

is 4-chlorophenyl;

is selected from the group consisting of 4-chlorophenyl and thiazol-2-yl;

$R^1$ is selected from the group consisting of hydrogen, —OCH$_3$, —O—CH$_2$—CH(CH$_2$OH)$_2$, —O—CH$_2$CH$_2$—N$_3$, —O—(CH$_2$)$_3$—C(O)—NH$_2$, —O—CH$_2$—C(O)—NH—CH$_2$CH$_2$—OH and cyclopropyl;

$R^5$ is hydrogen;

a is an integer from 0 to 1;

$L^1$ is selected from the group consisting of —CH$_2$—, —CH(CH$_3$)— and —CH(S*—CH$_3$)—;

$R^7$ is selected from the group consisting of phenyl, 3-fluoro-phenyl, 4-fluoro-phenyl, 3-trifluoromethyl-phenyl, 4-trifluoromethyl-phenyl, 1-(2,2,2-trifluoroethyl)-piperidin-4yl, 1-(trifluoromethyl-sulfonyl)-piperidin-4-yl, 1-(2,2,2-trifluoroethyl-carbonyl)-piperidin-4-yl and 1-((2-ethoxy-carbonyl-ethyl)-carbonyl)-piperidin-4-yl;

or a stereoisomer, tautomer or pharmaceutically acceptable salt thereof.

9. A compound as in claim 5, wherein

is 4-chlorophenyl;

is 4-chlorophenyl; $R^1$ is selected from the group consisting of hydrogen and —O—CH$_2$—CH(CH$_2$OH)$_2$; $R^5$ is hydrogen; a is an integer from 0 to 1; $L^1$ is —CH$_2$—; and $R^7$ is selected from the group consisting of 3-trifluoromethyl-phenyl, 4-trifluoromethyl-phenyl and 1-(2,2,2-trifluoroethyl)-piperidin-4-yl;

or a stereoisomer, tautomer or pharmaceutically acceptable salt thereof.

10. A compound as in claim 1, of the formula (I-B)

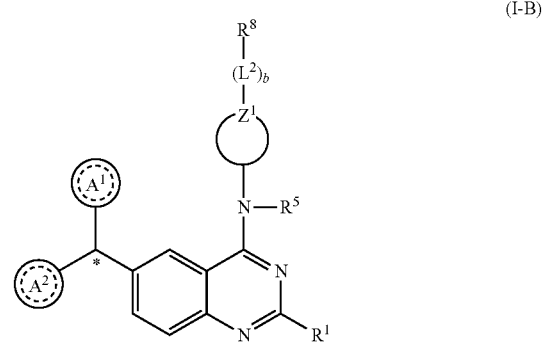

(I-B)

or a stereoisomer, tautomer or pharmaceutically acceptable salt thereof.

11. A compound as in claim 10, wherein

is selected from the group consisting of phenyl and thiazolyl;

wherein the phenyl or thiazolyl is optionally substituted with one or more substituents independently selected from the group consisting of halogen, hydroxy, $C_{1-2}$alkyl, trifluoromethyl, $C_{1-2}$alkoxy, trifluoromethoxy, cyano, —C(O)OH, C(O)O—$C_{1-2}$alkyl and NR$^A$R$^B$; wherein R$^A$ and R$^B$ are each independently selected from the group consisting of hydrogen, $C_{1-2}$alkyl and —(C$_{2-4}$ alkyl)-O—(C$_{1-4}$alkyl); provided that each substituent is bound to a carbon atom of the ring;

is selected from the group consisting of phenyl and thiazolyl;
wherein the phenyl or thiazolyl is optionally substituted with one or more substituents independently selected from the group consisting of halogen, hydroxy, $C_{1-2}$alkyl, trifluoromethyl, $C_{1-2}$alkoxy, trifluoromethoxy, cyano, —C(O)OH, C(O)O—$C_{1-2}$alkyl and $NR^AR^B$; wherein $R^A$ and $R^B$ are each independently selected from the group consisting of hydrogen, $C_{1-2}$alkyl and —($C_{2-4}$alkyl)-O—($C_{1-4}$alkyl); provided that each substituent is bound to a carbon atom of the ring;

$R^1$ is selected from the group consisting of hydrogen, $C_{1-2}$alkyl, —CH=CH—($C_{1-2}$alkyl)-OH, —CH=CH—($C_{0-1}$alkyl)-$CO_2$H, —CH=CH—($C_{0-1}$alkyl)-C(O)O—($C_{1-4}$alkyl), —$CH_2CH_2$—($C_{1-2}$alkyl)-OH, —$CH_2CH_2$—($C_{0-1}$ alkyl)-$CO_2$H, —$CH_2CH_2$—($C_{0-1}$ alkyl)-C(O)O—($C_{1-4}$alkyl), cyclopropyl, —$OR^2$ and —$NR^3R^4$;

$R^2$ is selected from the group consisting of hydrogen, —$C_{1-6}$alkyl, —$CH_2$-(hydroxy substituted $C_{1-6}$alkyl), —($C_{1-4}$alkyl)-$N_3$, —($C_{2-4}$alkyl)-$NR^ER^F$, —($C_{2-4}$alkyl)-O—($C_{1-4}$alkyl), —($C_{2-4}$alkyl)-O—($C_{1-6}$alkyl)-OH, —($C_{2-4}$alkyl)-O—($C_{1-6}$alkyl)-CN, —($C_{2-4}$alkyl)-O—($C_{1-4}$alkyl)-$CO_2$H, —($C_{1-12}$alkyl)-$CO_2$H, —($C_{1-12}$alkyl)-$CO_2$H, —($C_{1-4}$alkyl)-C(O)—$NR^ER^F$, —($C_{2-4}$alkyl)-$NR^E$—C(O)—($C_{1-6}$alkyl) and —($C_{2-4}$alkyl)-$NR^E$—$SO_2$—($C_{1-6}$alkyl); wherein $R^E$ and $R^F$ are each independently selected from the group consisting of hydrogen, $C_{1-2}$alkyl and —$CH_2$-(hydroxy substituted $C_{1-2}$alkyl);

$R^3$ is selected from the group consisting of hydrogen and $C_{1-2}$alkyl;

$R^4$ is selected from the group consisting of hydrogen, —$C_{1-6}$alkyl, —$CH_2$-(hydroxy substituted $C_{1-4}$alkyl), —($C_{1-4}$alkyl)-$N_3$, —($C_{2-4}$alkyl)-$NR^GR^H$, —($C_{2}$alkyl)-O—($C_{1-4}$alkyl), —($C_{2-4}$alkyl)-O—($C_{1-4}$alkyl)-OH, —($C_{2-4}$alkyl)-O—($C_{1-4}$alkyl)-$CO_2$H, —($C_{1-4}$alkyl)-$CO_2$H, —($C_{1-4}$alkyl)-C(O)O—($C_{1-4}$alkyl), —C(O)—($C_{1-4}$alkyl), —$SO_2$—($C_{1-4}$alkyl) and —$SO_2$-(halogenated $C_{1-2}$alkyl); wherein $R^G$ and $R^H$ are each independently selected from the group consisting of hydrogen, $C_{1-2}$alkyl and —$CH_2$-(hydroxy substituted $C_{1-2}$alkyl);

$R^5$ is selected from the group consisting of hydrogen and $C_{1-2}$alkyl;

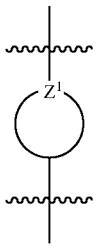

is selected from the group consisting of

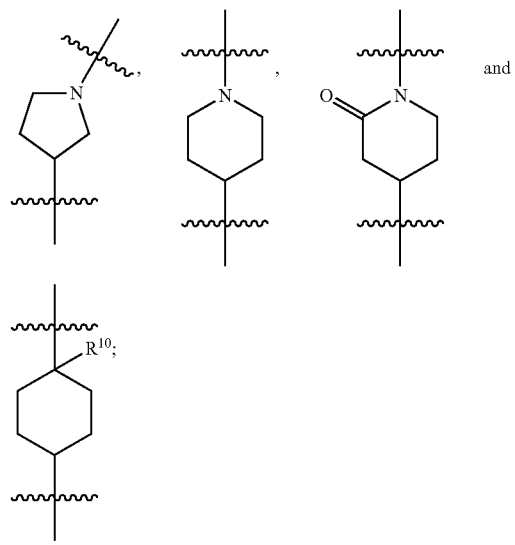

wherein $Z^1$ is selected from the group consisting of N and CH; and wherein $R^{10}$ is selected from the group consisting of hydroxy and cyano;

b is an integer from 0 to 1;

$L^2$ is selected from the group consisting of —$CH_2$—, —$CH_2CH_2$—, CH($CH_3$)—, —C(O)— and —$SO_2$—;

$R^8$ is selected from the group consisting of azetidin-3-yl, pyrrolidin-1-yl, piperidin-4-yl, piperazin-1-yl, phenyl, pyridin-2-yl, pyridin-3-yl, pyridin-4-yl, thien-2-yl, thien-3-yl, furan-2-yl, furan-3-yl, pyrimidin-2-yl and pyrazin-2-yl;

wherein any of the $R^8$ ring structures is optionally substituted with one substituent selected from the group consisting of halogen, hydroxy, cyano, halogenated $C_{1-4}$alkyl, hydroxy substituted $C_{1-4}$alkyl, —($C_{1-4}$alkyl)-$CO_2$H, —($C_{1-2}$alkyl)-C(O)O—($C_{1-4}$alkyl), —($C_{1-4}$alkyl)-C(O)—$NR^PR^Q$, —O—($C_{1-2}$alkyl)-O—($C_{1-4}$alkyl), —O—($C_{1-4}$alkyl)-$CO_2$H, —O—($C_{1-4}$alkyl)-C(O)O—($C_{1-4}$alkyl), —C(O)—($C_2$alkyl), —C(O)-(halogenated $C_{1-2}$alkyl), —C(O)—($C_{1-4}$alkyl)-$CO_2$H, —C(O)—($C_{1-2}$alkyl)-C(O)—O—($C_{1-4}$alkyl), —C(O)—$NR^PR^Q$, —C(O)—$NR^P$—($C_{2-4}$alkyl)-O—$R^{11}$, —C(O)—($C_{1-4}$alkyl)-C(O)—$NR^PR^Q$, —$CO_2$H, —C(O)O—($C_{1-4}$alkyl), —C(O)O—($C_{1-2}$alkyl)-OC(O)O—($C_{1-4}$alkyl), —C(=$NR^P$)—$NR^Q$—C(O)O—($C_{1-6}$alkyl), —C(=NH)—$NH_2$, —C(=N-Boc)-NH(Boc), —$SO_2$—($C_{1-2}$alkyl), —$SO_2$-(halogenated $C_{1-2}$alkyl), —$SO_2$—$NR^PR^Q$ and —$SO_2$—($C_{1-4}$alkyl)-C(O)—C(O)—$NR^PR^Q$; wherein $R^P$ and $R^Q$ are each independently selected from the group consisting of hydrogen, $C_{1-2}$alkyl and —$CH_2$-(hydroxy substituted $C_{1-5}$alkyl);

and wherein $R^{11}$ is phenyl; wherein the phenyl is optionally substituted at the 4-position with a substituent selected from the group consisting of halogen, hydroxymethyl, methyl and trifluoromethyl;

and wherein $R^8$ is phenyl; the phenyl is further optionally substituted with an additional substituent selected from the group consisting of halogen, hydroxy, $C_{1-2}$alkyl, trifluoromethyl, $C_{1-2}$alkoxy and trifluoromethoxy;
provided that when

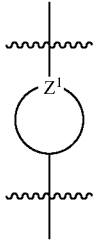

is selected from the group consisting of

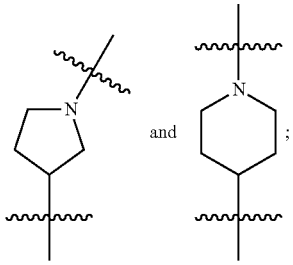 [SMILES: *C1CCN(*)C1 ; *C1CCN(*)CC1]

and the $R^8$ is selected from the group consisting of pyrrolidin-1-yl and piperazin-1-yl, then b is 1 and $L^2$ is selected from the group consisting of —C(O)— and —SO$_2$—;
provided further that when

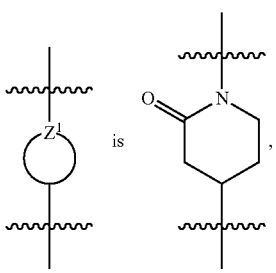

then $R^8$ is phenyl, wherein the phenyl is optionally substituted with one to two substituents independently selected from the group consisting of F, Cl, cyano and trifluoromethyl;
or a stereoisomer, tautomer or pharmaceutically acceptable salt thereof.

12. A compound as in claim 10, wherein

is phenyl; wherein the phenyl is optionally substituted with a halogen;

is phenyl, wherein the phenyl is optionally substituted with a substituent selected from the group consisting of halogen and $C_{1-2}$alkoxy;
  $R^1$ is selected from the group consisting of hydrogen and —OR$^2$;
  $R^2$ is selected from the group consisting of $C_{1-2}$alkyl, —CH$_2$-(hydroxy substituted $C_{1-2}$alkyl) and —(C$_2$alkyl)-NH—SO$_2$—(C$_{1-2}$alkyl);
  $R^5$ is hydrogen;

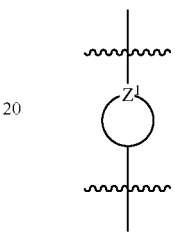

is selected from the group consisting of

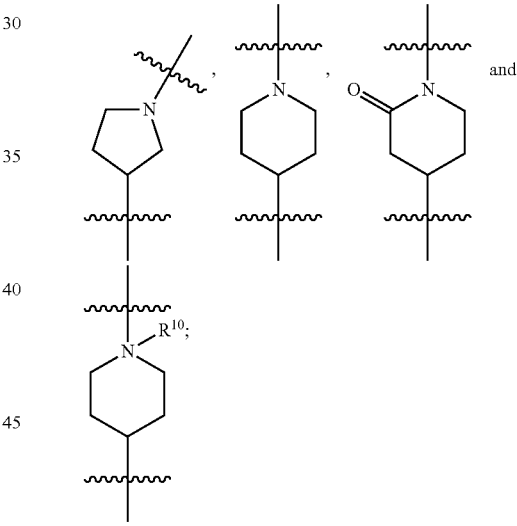

wherein $Z^1$ is selected from the group consisting of N and CH; and wherein $R^{10}$ is selected from the group consisting of hydroxy and cyano;
  b is an integer from 0 to 1;
  $L^2$ is selected from the group consisting of —CH$_2$—, —CH$_2$CH$_2$—, —C(O)— and —SO$_2$—;
  $R^8$ is selected from the group consisting of phenyl, pyrrolidiny-1-yl, piperidin-4-yl, thien-2-yl, pyridin-2-yl and pyrimidin-2-yl;
  wherein any of the $R^8$ ring structures is optionally substituted with one substituent selected from the group consisting of halogen, hydroxy, cyano, halogenated $C_{1-12}$alkyl, —O—(C$_{1-2}$alkyl)-CO$_2$H, —O—(C$_{1-2}$alkyl)-C(O)O—(C$_{1-12}$alkyl), —CO$_2$H, —(C$_{1-2}$alkyl)-CO$_2$H, —(C$_{1-2}$alkyl)-C(O)O—(C$_{1-2}$alkyl), —(C$_{1-2}$alkyl)-C(O)—NH$_2$, —C(O)O—(C$_{1-2}$alkyl), —C(O)O—(C$_{1-2}$alkyl)-OC(O)—O—(C$_{1-4}$alkyl), —C(O)—

NR$^P$R$^Q$, —C(O)—NH—(C$_{1-4}$alkyl)-O—R$^{11}$, —C(O)—NH—CH$_2$-(hydroxy substituted C$_{1-5}$alkyl), —C(=NH)—NH$_2$, —C(=NH)—NH—C(O)O—(C$_{1-6}$alkyl), and —SO$_2$—NH—CH$_2$-(hydroxy substituted C$_{1-2}$alkyl); wherein R$^P$ and R$^Q$ are each independently selected from the group consisting of hydrogen and —CH$_2$-(hydroxy substituted C$_{1-2}$alkyl); and wherein R$^{11}$ is phenyl; wherein the phenyl is optionally substituted at the 4-position with a substituent selected from the group consisting of halogen and hydroxymethyl;

and wherein R$^8$ is phenyl; the phenyl is further optionally substituted with an additional substituent selected from the group consisting of halogen and C$_{1-2}$alkoxy;

provided that when

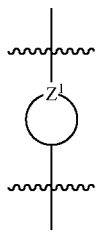

is selected from the group consisting of

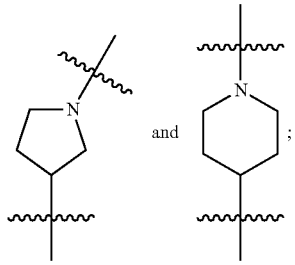

and the R$^8$ is pyrrolidin-1-yl, then b is 1 and L$^2$ is selected from the group consisting of —C(O)— and —SO$_2$—;

provided further that when

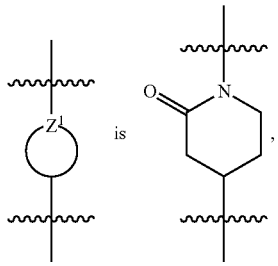

then R$^8$ is phenyl, wherein the phenyl is optionally substituted with one to two substituents independently selected from the group consisting of F, Cl, cyano and trifluoromethyl;

or a stereoisomer, tautomer or pharmaceutically acceptable salt thereof.

13. A compound as in claim 10, wherein

is selected from the group consisting of 4-chlorophenyl and 4-fluorophenyl;

is selected from the group consisting of 4-chlorophenyl, 4-fluorophenyl and 4-methoxyphenyl;
R$^1$ is selected from the group consisting of hydrogen, methoxy, —O—CH$_2$CH—OH and —O—CH$_2$CH$_2$—NH—SO$_2$—CH$_3$;
R$^5$ is hydrogen;

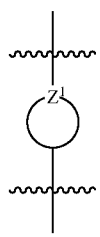

is selected from the group consisting of

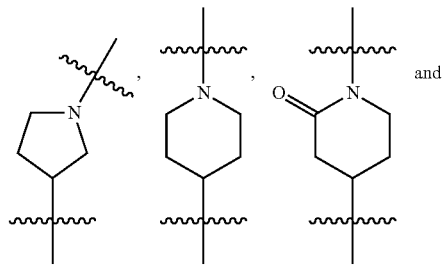

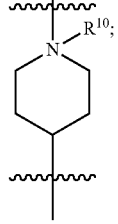

wherein Z$^1$ is selected from the group consisting of N and CH; and wherein R$^{10}$ is selected from the group consisting of hydroxy and cyano;
b is an integer from 0 to 1;
L$^2$ is selected from the group consisting of —CH$_2$—, —CH$_2$CH$_2$—, —C(O)— and —SO$_2$—;
R$^8$ is selected from the group consisting of phenyl, 3-hydroxyphenyl, 4-hydroxyphenyl, 2-fluorophenyl, 4-fluorophenyl, 4-trifluoromethyl-phenyl, 2-carboxyphenyl, 3-carboxyphenyl, 4-carboxyphenyl, 3-chloro- 4-carboxy-phenyl, 3-methoxy-4-carboxy-phenyl, 4-(carboxy-methyl)-phenyl, 3-(methoxy-carbonyl)-phenyl, 4-(methoxy-carbonyl)-phenyl, 4-(methoxy-carbonyl-methyl)-phenyl, 4-cyanophenyl, 3-(amino-carbonyl)-phenyl, 4-(amino-carbonyl)-phenyl, 4-(amino-carbonyl-methyl)-phenyl, 4-(carboxy-methoxy)-phenyl, 4-(ethoxycarbonyl-methoxy)-phenyl, 4-amidino-phenyl, 4-(n-hexyloxy-carbonyl-amidino)-phenyl, 4-((4-hydroxymethyl)-phenyloxy-n-propyl-amino-carbonyl)-phenyl, 4-((4-chloromethyl)-phenyloxy-n-propyl-amino-carbonyl)-phenyl, 4-(isopropyloxy-carbonyl-oxy-methoxy-carbonyl)-phenyl, 4-(1,3-dihydroxy-2-hydroxy-methyl)-propan-2-yl-amino-carbonyl)-phenyl, 4-((2-hydroxy-ethyl)-amino-sulfonyl)-phenyl, 3-((2-hydroxy-ethyl)-amino-carbonyl)-phenyl, 4-((2-hydroxy-ethyl)-amino-carbonyl)-phenyl, pyrrolidin-1-yl, 4-carboxy-thien-2-yl, 5-carboxy-thien-2-yl, pyridin-2-yl and pyrimidin-2-yl;

provided that when

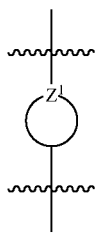

is selected from the group consisting of

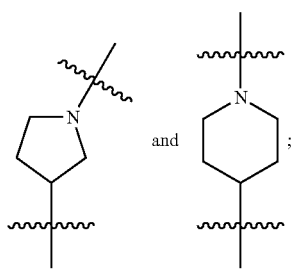 [SMILES: *C1CCN(*)C1 ; *C1CCN(*)CC1]

and $R^8$ is pyrrolidin-1-yl, then b is 1 and $L^2$ is selected from the group consisting of —C(O)— and —SO$_2$—;

provided further that when

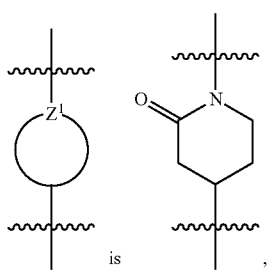

then $R^8$ is selected from the group consisting of phenyl, 2-fluorophenyl, 4-fluorophenyl and 4-trifluoromethyl-phenyl;

or a stereoisomer, tautomer or pharmaceutically acceptable salt thereof.

14. A compound as in claim 13, wherein

is selected from the group consisting of 4-chlorophenyl and 4-fluorophenyl;

is selected from the group consisting of 4-chlorophenyl, 4-fluorophenyl and 4-methoxyphenyl;

$R^1$ is selected from the group consisting of hydrogen, methoxy and —O—CH$_2$CH—OH;

$R^5$ is hydrogen;

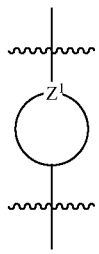

is selected from the group consisting of

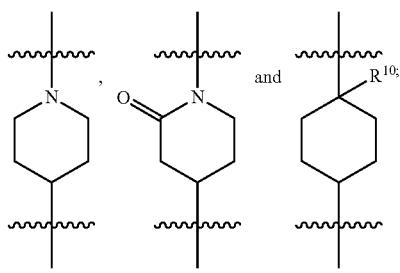

wherein $Z^1$ is selected from the group consisting of N and CH; and wherein $R^{10}$ is selected from the group consisting of hydroxy and cyano;

b is an integer from 0 to 1;

$L^2$ is selected from the group consisting of —CH$_2$—, —CH$_2$CH$_2$—, —C(O)— and —SO$_2$—;

R⁸ is selected from the group consisting of phenyl, 3-hydroxyphenyl, 4-hydroxyphenyl, 2-fluorophenyl, 4-fluorophenyl, 4-trifluoromethyl-phenyl, 4-carboxyphenyl, 3-chloro-4-carboxy-phenyl, 3-methoxy-4-carboxy-phenyl, 3-(methoxy-carbonyl)-phenyl, 4-(methoxy-carbonyl)-phenyl, 4-(methoxy-carbonyl-methyl)-phenyl, 4-cyanophenyl, 4-amidino-phenyl, 3-(amino-carbonyl)-phenyl, 4-(amino-carbonyl)-phenyl, 4-(ethoxycarbonyl-methoxy)-phenyl, 4-(n-hexyloxy-carbonyl-amidino)-phenyl, 4-((4-hydroxymethyl)-phenyloxy-n-propyl-amino-carbonyl)-phenyl, 4-(isopropyloxy-carbonyl-oxy-methoxy-carbonyl)-phenyl, 4-(1,3-dihydroxy-2-hydroxy-methyl)-propan-2-yl-amino-carbonyl)-phenyl, 3-((2-hydroxy-ethyl)-amino-carbonyl)-phenyl, 4-((2-hydroxy-ethyl)-amino-carbonyl)-phenyl, pyrrolidin-1-yl, 4-carboxy-thien-2-yl, 5-carboxy-thien-2-yl, pyridin-2-yl and pyrimidin-2-yl;

provided that when is

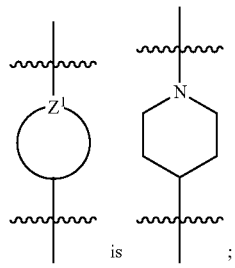

is ;

and R⁸ is pyrrolidin-1-yl, then b is 1 and L² is selected from the group consisting of —C(O)— and —SO₂—;

provided further that when is

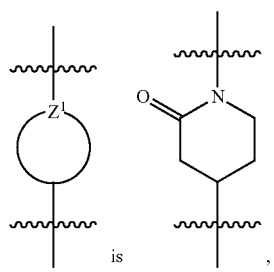

is , then R⁸ is selected from the group consisting of phenyl, 2-fluorophenyl, 4-fluorophenyl and 4-trifluoromethyl-phenyl;

or a stereoisomer, tautomer or pharmaceutically acceptable salt thereof.

15. A compound as in claim 13, wherein

is selected from the group consisting of 4-chlorophenyl and 4-fluorophenyl;

is selected from the group consisting of 4-chlorophenyl, 4-fluorophenyl and 4-methoxyphenyl;

R¹ is selected from the group consisting of hydrogen and methoxy;

R⁵ is hydrogen;

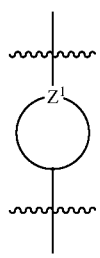

is selected from the group consisting of

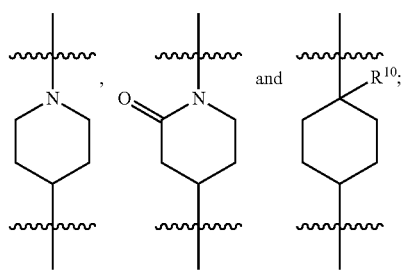

wherein Z¹ is selected from the group consisting of N and CH; and wherein R¹⁰ is selected from the group consisting of hydroxy and cyano;

b is an integer from 0 to 1;

L² is selected from the group consisting of —CH₂—, —C(O)— and —SO₂—;

R⁸ is selected from the group consisting of phenyl, 3-hydroxyphenyl, 4-hydroxyphenyl, 2-fluorophenyl, 4-fluorophenyl, 4-trifluoromethyl-phenyl, 4-carboxyphenyl, 3-chloro-4-carboxy-phenyl, 3-methoxy-4-carboxy-phenyl, 4-(methoxy-carbonyl)-phenyl, 4-(methoxy-carbonyl-methyl)-phenyl, 4-cyanophenyl, 4-amidino-phenyl, 3-(amino-carbonyl)-phenyl, 4-(amino-carbonyl)-phenyl, 4-(ethoxycarbonyl-methoxy)-phenyl, 4-(n-hexyloxy-carbonyl-amidino)-phenyl, 4-((4-hydroxymethyl)-phenyloxy-n-propyl-amino-carbonyl)-phenyl, 4-(isopropyloxy-carbonyl-oxy-methoxy-carbonyl)-phenyl, 4-(1,3-dihydroxy-2-hydroxy-methyl)-propan-2-yl-amino-carbonyl)-phenyl, 4-((2-hydroxy-ethyl)-amino-carbonyl)-phenyl, pyrrolidin-1-yl, 5-carboxy-thien-2-yl, pyridin-2-yl and pyrimidin-2-yl;

provided that when

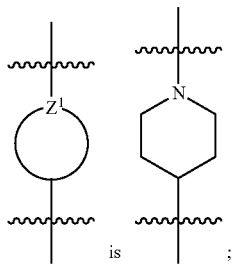

is and R⁸ is pyrrolidin-1-yl, then b is 1 and L² is selected from the group consisting of —C(O)— and —SO₂—;
provided further that when

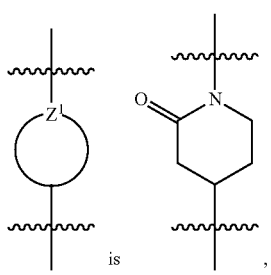

is then R⁸ is selected from the group consisting of phenyl, 2-fluorophenyl, 4-fluorophenyl and 4-trifluoromethyl-phenyl;
or a stereoisomer, tautomer or pharmaceutically acceptable salt thereof.

16. A compound as in claim 13, wherein

is selected from the group consisting of 4-chlorophenyl and 4-fluorophenyl;

is selected from the group consisting of 4-chlorophenyl and 4-fluorophenyl;
R¹ is hydrogen;
R⁵ is hydrogen;

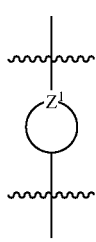

is selected from the group consisting of

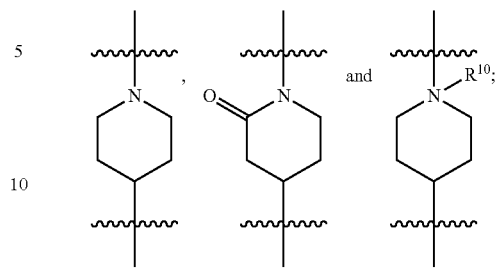

wherein Z¹ is selected from the group consisting of N and CH; and
wherein R¹⁰ is hydroxy;
b is an integer from 0 to 1;
L² is selected from the group consisting of —C(O)— and —SO₂—;
R⁸ is selected from the group consisting of phenyl, 4-hydroxyphenyl, 2-fluorophenyl, 4-fluorophenyl, 4-trifluoromethyl-phenyl, 4-(methoxy-carbonyl)-phenyl, 4-(methoxy-carbonyl-methyl)-phenyl, 4-amidino-phenyl, 4-(ethoxycarbonyl-methoxy)-phenyl4-(1,3-dihydroxy-2-hydroxy-methyl)-propan-2-yl-amino-carbonyl)-phenyl, pyrrolidin-1-yl, 5-carboxy-thien-2-yl, pyridin-2-yl and pyrimidin-2-yl;
provided that when

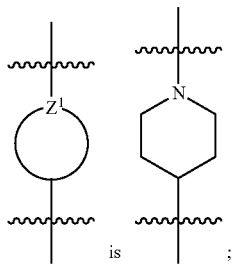

is and R⁸ is pyrrolidin-1-yl, then b is 1 and L² is selected from the group consisting of —C(O)— and —SO₂—;
provided further that when

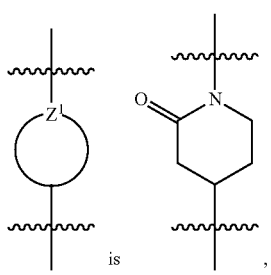

is then R⁸ is selected from the group consisting of phenyl, 2-fluorophenyl, 4-fluorophenyl and 4-trifluoromethyl-phenyl;
or a stereoisomer, tautomer or pharmaceutically acceptable salt thereof.

17. A compound as in claim 13, wherein

is 4-chlorophenyl;

is 4-chlorophenyl; $R^1$ is hydrogen; $R^5$ is hydrogen;

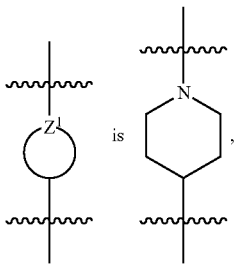

wherein $Z^1$ is N; b is an integer from 0 to 1; $L^2$ is —$SO_2$—; and $R^8$ is selected from the group consisting of phenyl, 4-fluorophenyl, 4-carboxy-phenyl, 4-amidino-phenyl, pyrrolidin-1-yl; and pyridin-2-yl;

provided that when

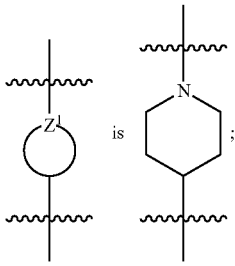

and $R^8$ is pyrrolidin-1-yl, then b is 1 and $L^2$ is —$SO_2$—;

or a stereoisomer, tautomer or pharmaceutically acceptable salt thereof.

18. A compound as in claim 1, of the formula (I-C)

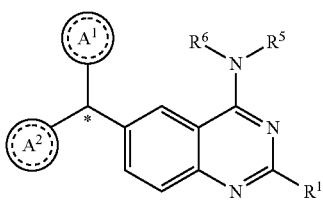
(I-C)

wherein $R^5$ and $R^6$ are taken together with the nitrogen atom to which they are bound to form a ring structure selected from the group consisting of

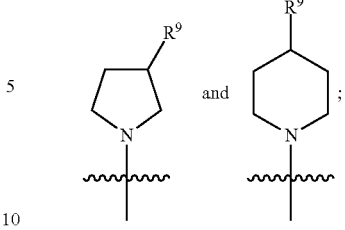

and $R^9$ is selected from the group consisting of $C_{1-4}$alkyl, trifluoromethyl, cyclopropyl and —$NR^SR^T$; wherein $R^S$ is selected from the group consisting of hydrogen, methyl and ethyl; and $R^T$ is selected from the group consisting of —C(O)—($C_{1-4}$alkyl), —$SO_2$—($C_{1-4}$alkyl) and —$SO_2$-(halogenated $C_{1-4}$alkyl);

or stereoisomer, tautomer or pharmaceutically acceptable salt thereof.

19. A compound as in claim 18, wherein

is selected from the group consisting of phenyl and thiazolyl;

wherein the phenyl or thiazolyl is optionally substituted with one or more substituents independently selected from the group consisting of halogen, hydroxy, $C_{1-2}$alkyl, trifluoromethyl, $C_{1-2}$alkoxy, trifluoromethoxy, cyano, —C(O)OH, C(O)O—$C_{1-2}$alkyl and $NR^AR^B$; wherein $R^A$ and $R^B$ are each independently selected from the group consisting of hydrogen, $C_{1-2}$alkyl and —($C_{2-4}$alkyl)-O—($C_{1-4}$alkyl); provided that each substituent is bound to a carbon atom of the ring;

is selected from the group consisting of phenyl and thiazolyl;

wherein the phenyl or thiazolyl is optionally substituted with one or more substituents independently selected from the group consisting of halogen, hydroxy, $C_{1-2}$alkyl, trifluoromethyl, $C_{1-2}$alkoxy, trifluoromethoxy, cyano, —C(O)OH, C(O)O—$C_{1-2}$alkyl and $NR^AR^B$; wherein $R^A$ and $R^B$ are each independently selected from the group consisting of hydrogen, $C_{1-2}$alkyl and —($C_{2-4}$alkyl)-O—($C_{1-4}$alkyl); provided that each substituent is bound to a carbon atom of the ring;

$R^1$ is selected from the group consisting of hydrogen, $C_{1-2}$alkyl, —CH=CH—($C_{1-2}$alkyl)-OH, —CH=CH—($C_{0-1}$alkyl)-$CO_2$H, —CH=CH—($C_{0-1}$alkyl)-C(O)O—($C_{1-4}$alkyl), —$CH_2CH_2$—($C_{1-2}$alkyl)-OH, —$CH_2CH_2$—($C_{0-1}$ alkyl)-$CO_2$H, —$CH_2CH_2$—($C_{0-1}$ alkyl)-C(O)O—($C_{1-4}$alkyl), cyclopropyl, —$OR^2$ and —$NR^3R^4$;

$R^2$ is selected from the group consisting of hydrogen, —$C_{1-6}$alkyl, —$CH_2$-(hydroxy substituted $C_{1-6}$alkyl), —($C_{1-4}$alkyl)-$N_3$, —($C_{2-4}$alkyl)-$NR^ER^F$, —(C$_{2-4}$alkyl)-O—(C$_{1-4}$alkyl), —(C$_{2-4}$alkyl)-O—(C$_{1-6}$alkyl)-OH, —(C$_{2-4}$alkyl)-O—(C$_{1-6}$alkyl)-CN, —(C$_{2-4}$alkyl)-O—(C$_{1-4}$alkyl)-CO$_2$H, —(C$_{1-12}$alkyl)-CO$_2$H, (C$_{1-4}$alkyl)-C(O)—NR$^E$R$^F$, —(C$_{2-4}$alkyl)-NR$^E$—C(O)—(C$_{1-6}$alkyl) and —(C$_{2-4}$alkyl)-NR$^E$—SO$_2$—(C$_6$alkyl); wherein R$^E$ and R$^F$ are each independently selected from the group consisting of hydrogen, C$_{1-2}$alkyl and —CH$_2$-(hydroxy substituted C$_{1-2}$alkyl);

R$^3$ is selected from the group consisting of hydrogen and C$_{1-2}$alkyl;

R$^4$ is selected from the group consisting of hydrogen, —C$_{1-6}$alkyl, —CH$_2$-(hydroxy substituted C$_{1-4}$alkyl), —(C$_{1-4}$alkyl)-N$_3$, —(C$_{2-4}$alkyl)-NR$^G$R$^H$, —(C$_2$alkyl)-O—(C$_{1-4}$alkyl), —(C$_{2-4}$alkyl)-O—(C$_{1-4}$alkyl)-OH, —(C$_{2-4}$alkyl)-O—(C$_{1-4}$alkyl)-CO$_2$H, —(C$_{1-4}$alkyl)-CO$_2$H, —(C$_{1-4}$alkyl)-C(O)O—(C$_{1-4}$alkyl), —C(O)—(C$_{1-4}$alkyl), —SO$_2$—(C$_{1-4}$alkyl) and —SO$_2$-(halogenated C$_{1-2}$alkyl); wherein R$^G$ and R$^H$ are each independently selected from the group consisting of hydrogen, C$_{1-2}$alkyl and —CH$_2$-(hydroxy substituted C$_{1-2}$alkyl);

R$^5$ and R$^6$ are taken together with the nitrogen atom to which they are bound to form a ring structure selected from the group consisting of

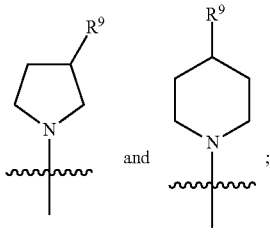

and R$^9$ is selected from the group consisting of —NR$^S$R$^T$; wherein R$^S$ is selected from the group consisting of hydrogen, methyl and ethyl; and wherein R$^T$ is —SO$_2$-(halogenated C$_{1-2}$alkyl);

or a stereoisomer, tautomer or pharmaceutically acceptable salt thereof.

20. A compound as in claim 18, wherein

is 4-chlorophenyl;

is 4-chlorophenyl; R$^1$ is hydrogen; R$^5$ and R$^6$ are taken together with the nitrogen atom to which they are bound to form a ring structure selected from the group consisting of

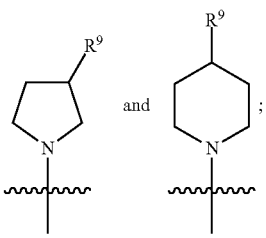

and R$^9$ is trifluoromethyl-sulfonyl-amino;

or a stereoisomer, tautomer or pharmaceutically acceptable salt thereof.

21. A pharmaceutical composition comprising a pharmaceutically acceptable carrier and a compound of claim 1.

22. A pharmaceutical composition made by mixing a compound of claim 1 and a pharmaceutically acceptable carrier.

23. A process for making a pharmaceutical composition comprising mixing a compound of claim 1 and a pharmaceutically acceptable carrier.

24. A compound as in claim 1 for use as a medicament.

* * * * *